United States Patent

Müller et al.

Patent Number: 5,965,587
Date of Patent: Oct. 12, 1999

[54] PYRIDYLACETIC ACID DERIVATIVES, THEIR PREPARATION, INTERMEDIATES FOR THEIR PREPARATION AND COMPOSITIONS CONTAINING THEM

[75] Inventors: Bernd Müller, Frankenthal; Hubert Sauter; Herbert Bayer, both of Mannheim; Wassilios Grammenos, Ludwigshafen; Thomas Grote, Schifferstadt; Reinhard Kirstgen, Neustadt; Klaus Oberdorf, Heidelberg; Franz Röhl, Schifferstadt; Norbert Götz, Worms; Michael Rack, Heidelberg; Ruth Müller, Friedelsheim; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 09/068,002

[22] PCT Filed: Oct. 28, 1996

[86] PCT No.: PCT/EP96/04676

§ 371 Date: Apr. 29, 1998

§ 102(e) Date: Apr. 29, 1998

[87] PCT Pub. No.: WO97/17328

PCT Pub. Date: May 15, 1997

[30] Foreign Application Priority Data

Nov. 3, 1995 [DE] Germany ............... 19540989

[51] Int. Cl.[6] .......... C07D 213/54; A01N 43/40
[52] U.S. Cl. .......... 514/354; 514/357; 546/314; 546/323; 546/334; 546/335
[58] Field of Search .............. 546/334, 335, 546/314, 323; 514/357, 354, 277

[56] References Cited

FOREIGN PATENT DOCUMENTS

| | | |
|---|---|---|
| 2182407 | 8/1995 | Canada . |
| 2182529 | 8/1995 | Canada . |
| 95/18789 | 7/1995 | WIPO . |
| 96/11183 | 4/1996 | WIPO . |

*Primary Examiner*—Zinna Northington Davis
*Attorney, Agent, or Firm*—Keil & Weinkauf

[57] ABSTRACT

Pyridylacetic acid compounds of the formula I

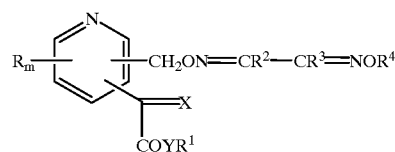

where
X is $NOCH_3$. $CHOCH_3$, $CHCH_3$ or $CHCH_2CH_3$; and
Y is oxygen or NR', and salts thereof,
processes and intermediates for their preparation and compositions containing them which are used for controlling animal pests and fungi.

20 Claims, No Drawings

PYRIDYLACETIC ACID DERIVATIVES, THEIR PREPARATION, INTERMEDIATES FOR THEIR PREPARATION AND COMPOSITIONS CONTAINING THEM

This application is a 371 of PCT/EP 96/04676 filed Oct. 18, 1996.

The present invention relates to pyridylacetic acid derivatives of the formula I

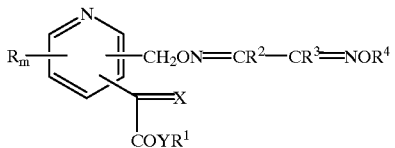

where

X is $NOCH_3$, $CHOCH_3$, $CHCH_3$ or $CHCH_2CH_3$;

Y is oxygen or NR';

R' is hydrogen or $C_1$–$C_4$-alkyl;

R is cyano, nitro, trifluoromethyl, halogen, $C_1$–$C_4$-alkyl or $C_1$–$C_4$-alkoxy;

m is 0, 1 or 2, and the radicals R may be different when m is 2;

$R^1$ is hydrogen or $C_1$–$C_4$-alkyl;

$R^2$ is hydrogen, cyano, nitro, hydroxyl, amino, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino or di-$C_1$–$C_4$-alkylamino;

$R^3$ is hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N-$C_2$–$C_6$-alkenyl-N-$C_1$–$C_6$-alkylamino, $C_2$–$C_6$-alkynyl, $C_2$–$C_6$-alkynyloxy, $C_2$–$C_6$-alkenylthio, $C_2$–$C_6$-alkynylamino or N-$C_2$–$C_6$-alkynyl-N-$C_1$–$C_6$-alkylamino, where the hydrocarbon radicals of these groups may be partly or completely halogenated or may carry from one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio or hetaryl-$C_1$–$C_4$-alkylthio, where the cyclic radicals in turn may be partially or completely halogenated and/or may carry from one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(\pm NOR^a)$—$A_n$—$R^b$;

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalkyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamina or N-hetaryl-N-$C_1$–$C_6$-alkylamino, where the cyclic radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^a)$—$A_n$—$R^b$ or $NR^f$—CO—D—$R^g$;

$R^4$ is hydrogen, $C_1$–$C_{10}$alkyl, $C_2$–$C_{10}$alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkenylcarbonyl or $C_1$–$C_{10}$alkylsulfonyl, where these radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkyl-5 amino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy or hetarylthio, where the cyclic groups in turn may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^a)$—$A_n$—$R^b$;

$C_3$–$C_6$-cycloalkyl, aryl, arylcarbonyl, arylsulfonyl, hetaryl, hetarylcarbonyl or hetarylsulfonyl, where these radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^a)$—$A_n$—$R^b$ or $NR^f$—CO—D—$R^g$;

A is oxygen, sulfur or nitrogen and the nitrogen carries hydrogen or $C_1$–$C_6$-alkyl;

D is a direct bond, oxygen or $NR^h$;

n is 0 or 1;

$R^a$ and $R^b$ are each hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy or $C_1$–$C_6$-alkoxycarbonyl;

$R^g$, $R^h$ independently of one another, are each hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl or hetaryl-$C_1$–$C_6$-alkyl;

and salts thereof.

The present invention furthermore relates to processes and intermediates for the preparation of these compounds and to compositions which contain them and are used for controlling animal pests and harmful fungi.

The literature discloses phenylacetic acid derivatives for pest control (EP-A 422 597; EP-A 463 488; EP-A 370 629; EP-A 460 575; EP-A 472 300; WO-A 90/07,493; WO-A 92/13,830; WO-A 92/18,487; WO-A 95/18,789; WO-A 95/21,153; WO-A 95/21,154; WO-A 95/21,156).

It is an object of the present invention to provide novel compounds having improved activity.

We have found that this object is achieved by the pyridylacetic acid derivatives I defined at the outset. We have also found processes and intermediates for their preparation and compositions which contain them and are used for controlling animal pests and harmful fungi and their use in this context.

The compounds I are obtainable in various ways by processes known per se in the literature.

In the synthesis of the compounds I, it is in principle unimportant as to whether —C(X)—CO$_2$R$^1$ or —CH$_2$ON=C(R$^2$)—C(R$^3$)=NOR$^4$ is synthesized first.

The synthesis of —C(X)—CO$_2$R$^1$ is disclosed, for example, in the literature cited at the outset.

The method of synthesis of the —CH$_2$ON=C(R$^2$)—C(R$^3$)=NOR$^4$ side chain depends essentially on the type of substituents R$^2$ and R$^3$.

1. Where R$^2$ and R$^3$ are not halogen, —CH$_2$ON=C(R$^2$)—C(R$^3$)=NOR$^4$ is generally synthesized by reacting a benzyl derivative of the formula II with a hydroximine of the formula III.

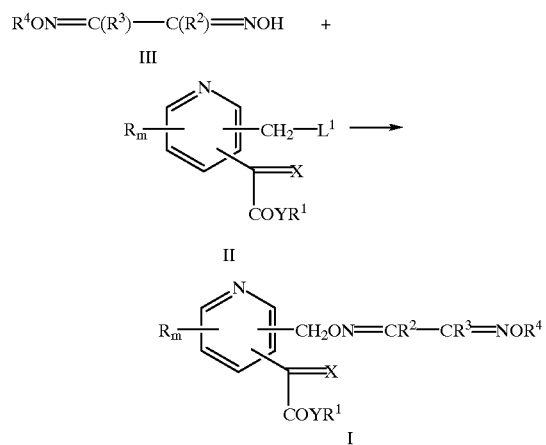

In formula II, L$^1$ is a nucleophilically substitutable leaving group, for example halogen or sulfonate, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate or triethylamine, by the methods described in Houben-Weyl, Vol. E 14b, page 370 et seq., and Houben-Weyl, Vol. 10/1, page 1189 et seq.

The required hydroximine III is obtained, for example, by reacting a corresponding dihydroximine IV with a nucleophilically substituted reagent VI

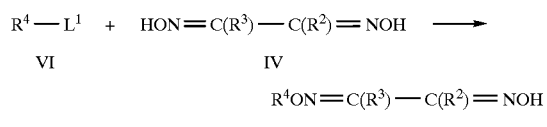

In formula VI, L$^2$ is a nucleophilically substitutable leaving group, for example halogen or sulfonate, preferably chlorine, bromine, iodine, mesylate, tosylate or triflate.

The reaction is carried out in a manner known per se in an inert organic solvent in the presence of a base, eg. potassium carbonate, potassium hydroxide, sodium hydride, pyridine or triethylamine, by the methods described in Houben-Weyl, Vol. E 14b, page 307 et seq., page 370 et seq. and page 385 et seq., Houben-Weyl, Vol. 10/4, page 55 et seq., page 180 et seq. and page 217 et seq., and Houben-Weyl, Vol. E 5, page 780 et seq.

1.1 Alternatively, the compounds I may also be obtained by first converting the benzyl derivative II with a dihydroximino derivative IV into a corresponding benzyloxime of the formula V, V then being reacted with the nucleophilically substituted reagent VI to give I.

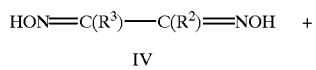

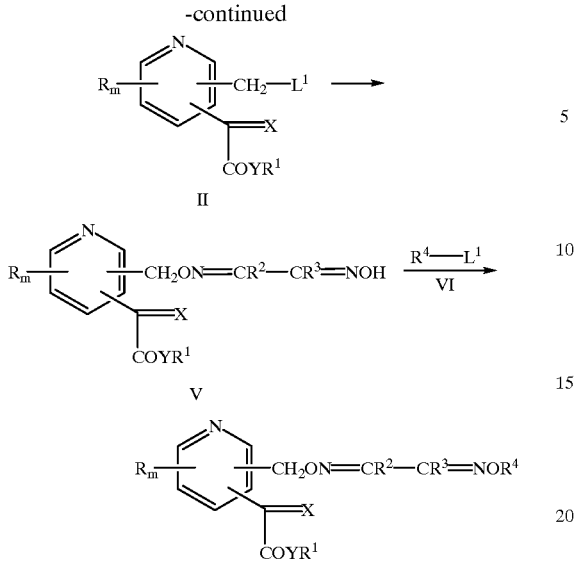

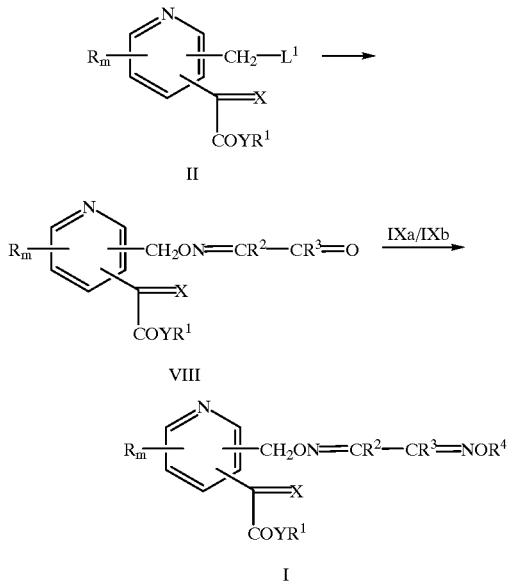

The reaction is carried out in a manner known per se in an inert organic solvent in the presence of a base, eg. potassium carbonate, potassium hydroxide, sodium hydride, pyridine or triethylamine, by the methods described in Houben-Weyl, Vol. 10/1, page 1189 et seq.; Houben-Weyl, Vol. E 14b, page 307 et seq., page 370 et seq. and page 385 et seq.; Houben-Weyl, Vol. 10/4, page 55 et seq., page 180 et seq. and page 217 et seq., and Houben-Weyl, Vol. E 5, page 780 et seq.

1.2 Similarly, it is also possible to prepare the required hydroximine of the formula III from a carbonylhydroximine VII by reaction with a hydroxylamine IXa or its salt IXb.

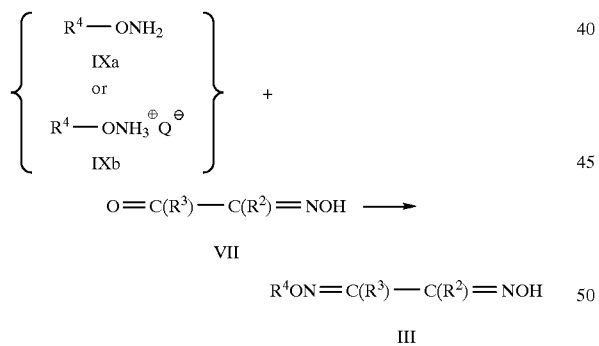

In the formula IXb, $Q^{\ominus}$ is an anion of an acid, in particular of an inorganic acid, for example halide, such as chloride.

The reaction is carried out in a manner known per se in an inert organic solvent by the methods described in EP-A 513 580 or Houben-Weyl, Vol. 10/4, page 73 et seq. or Houben-Weyl, Vol. E 14b, page 369 et seq. and page 385 et seq.

1.3 Alternatively, the compounds I may also be obtained by first converting the benzyl derivative II with the carbonylhydroximino derivative VII into a corresponding benzyloximine of the formula VIII, VIII then being reacted with the hydroxylamine IXa or its salt IXb to give I.

The reaction is carried out in a manner known per se in an inert organic solvent by the methods described in Houben-Weyl, Vol. E 14b, page 369 et seq.; Houben-Weyl, Vol. 10/1, page 1189 et seq., and Houben-Weyl, Vol. 10/4, page 73 et seq. or EP-A 513 580.

1.4 A further possibility for the preparation of the compounds I is the reaction of the benzyl derivative II with N-hydroxyphthalimide and subsequent hydrazinolysis to give the benzylhydroxylamine IIa and the further reaction of IIa with a carbonyl compound VIIa.

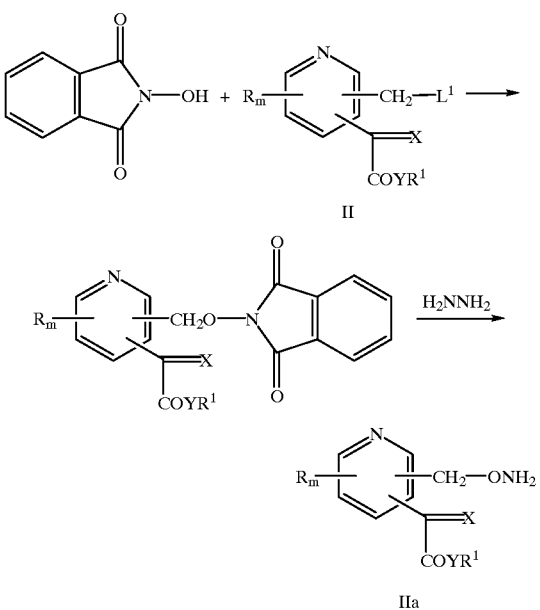

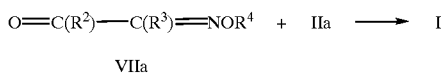

VIIa

The reaction is carried out in a manner known per se in an inert organic solvent by the methods described in EP-A 463 488, German Application No. 42 28 867.3.

The required carbonyl compound VIIa is obtained, for example, by reacting a corresponding hydroximinocarbonyl compound VII with a nucleophilically substituted reagent VI

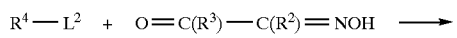

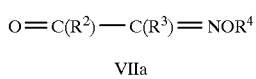

VIIa or by reacting a corresponding dicarbonyl compound VIIb with a hydroxylamine IXa or its salt IXb

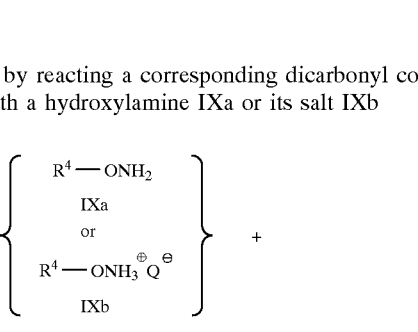

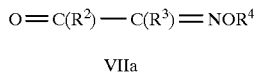

VIIa

The reactions are carried out in a manner known per se in an inert organic solvent by the methods described in EP-A 513 580, Houben-Weyl, Vol. 10/4, page 55 et seq., page 73 et seq., page 180 et seq. and page 217 et seq.; Houben-Weyl, Vol. E 14b, page 307 et seq. and 369 et seq. and Houben-Weyl, Vol. E 5, page 780 et seq.

1.5 Accordingly, the compounds I may also be obtained by first converting the benzylhydroxylamine IIa with the hydroximino derivative VII in the corresponding benzyloximino derivative of the formula V, V then being reacted with a nucleophilically substituted reagent VI as described above to give I.

$HON{=}C(R^3){-}C(R^2){=}O$  +

VII

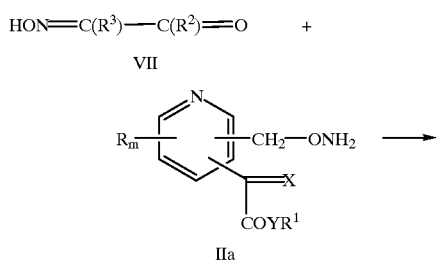

IIa

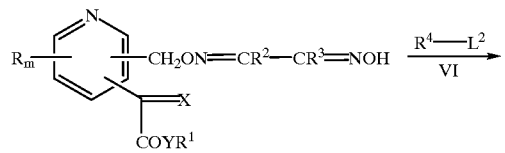

V

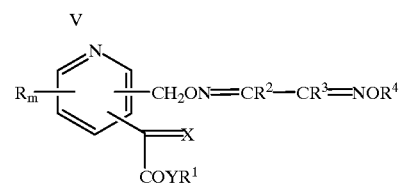

I 1.6 Similarly the compounds I can also be prepared by first converting the benzylhydroxylamine IIa with the dicarbonyl derivative of the formula VIIb into the benzyloximino derivative of the formula VIII and then reacting VIII with the hydroxylamine IXa or its salt IXb as described above to give I.

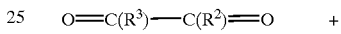

VIIb

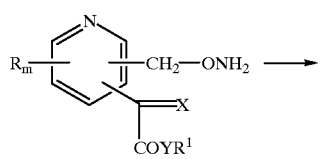

IIa

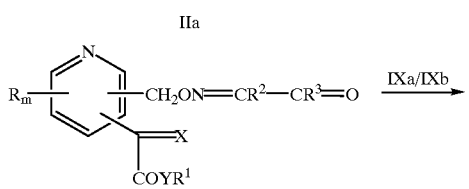

VIII

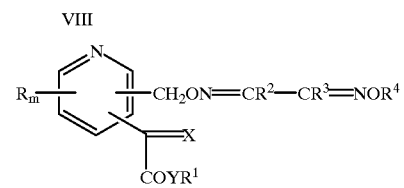

I

2. Compounds in which $R^2$ and/or $R^3$ are halogen are obtained from the corresponding intermediates in which the relevant radical is hydroxyl by methods known per se (cf. Houben-Weyl, Vol. E5, page 631; J. Org. Chem. 36 (1971), 233; J. Org. Chem. 57 (1992), 3245). The corresponding reactions to give the halogen derivative are preferably carried out at stages I and VIII.

3. Compounds in which $R^2$ and/or $R^3$ are bonded to the molecule skeleton via an O, S or N atom are obtained from the corresponding intermediates in which the relevant radical is halogen by methods known per se (cf. Houben-Weyl, Vol. E5, page 826 et seq. and 1280 et seq., J. Org. Chem. 36 (1971), 233, and J. Org. Chem. 46 (1981), 3623). The corresponding reactions of the halogen derivative are preferably carried out at stages I and VIII.

4. Compounds in which $R^2$ and/or $R^3$ are bonded to the molecule via an oxygen atom are also obtained from the corresponding intermediates in which the relevant radical is hydroxyl by methods known per se (cf. Houben-Weyl, Vol. E5, pages 826–829, Aust. J. Chem. 27 (1974), 1341–9). The corresponding reactions to give the alkoxy derivatives are preferably carried out at the stages I and VIII.

5. In a further process, the compounds I in which Y is oxygen (IA) are also obtained by converting a methylpyridinecarboxylate of the general formula X in a manner known per se into the corresponding methylenepyridinecarboxylate of the general formula XI where Hal is chlorine or bromine, then converting XI into the corresponding pyridinecarboxylate of the general formula XII by reaction with a hydroximine of the formula III, reducing XII to the alcohol XIII, oxidizing XIII to the pyridinaldehyde XIV, converting XIV in a manner known per se into the cyanohydrin XV, then hydrolyzing XV to the corresponding mandalate XVI, oxidizing XVI to the α-keto ester XVII and then converting XVII in a manner known per se, either a) with an O-methylhydroxylamine ($H_2NOCH_3$) or with an O-methylhydroxylammonium salt, or b) with an ethylene-Wittig or -Wittig-Horner reagent, or c) with a methoxy-Wittig or -Wittig-Horner reagent, into the corresponding pyridylacetate IA.

In the formula X, $R^x$ is $C_1$–$C_4$-alkyl, in particular methyl or ethyl.

In the formula XI, Hal is halogen, such as fluorine, chlorine, bromine or iodine, preferably chlorine or bromine, in particular bromine.

5a. This halogenation of X to give XI is usually carried out at from 20 to 160° C., preferably from 40 to 130° C., in an inert organic solvent with a halogenating agent in the presence of a free radical initiator or with exposure to high-energy light [cf. *Organikum,* 15th Edition, 1976, VEB Berlin, page 196].

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably chlorobenzene, methylene chloride, carbon tetrachloride and cyclohexane. Mixtures of the stated solvents may also be used.

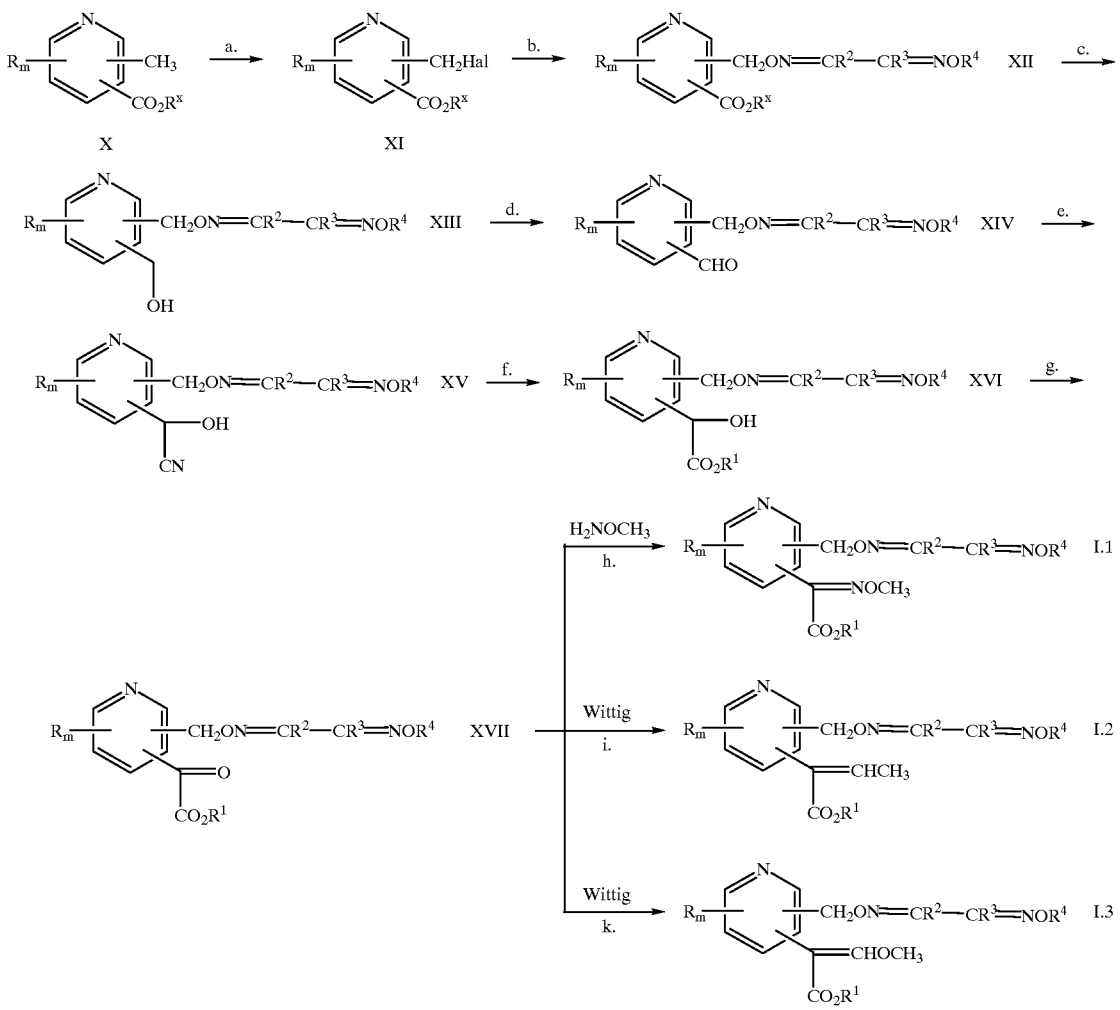

The halogenating agents generally used are inorganic compounds, such as chlorine, bromine and sulfuryl chloride. However, organic compounds, such as N-halides, in particular N-bromosuccinimide, are also particularly suitable.

The halogenating agents are generally used in equimolar amounts or in excess or, if required, as solvents.

It may be advantageous to carry out halogenation in the presence of a base. Suitable bases are in general inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and alkali metal and alkaline earth metal alcoholates, such as sodium methylate, sodium ethylate, potassium ethylate, potassium tert-butylate and dimethoxymagnesium, and in addition organic bases, for example tertiary amines, such as trimethylamine, triethylamine, triisopropylethylamine and N-methylpiperidine, pyridine, substituted pyridines, such as collidine, lutidine and 4-dimethylaminopyridine, and bicyclic amines. Sodium hydroxide, potassium hydroxide and pyridine are particularly preferred.

The bases are used in general in catalytic amounts but may also be used in equimolar amounts, in excess or, if required, as solvents.

The free radical initiators used are in general peroxides or azo compounds, particularly preferably dibenzoyl peroxide and azobisisobutyronitrile. The free radical initiators are usually used in catalytic amounts. In general, excess amounts of free radical initiators are not troublesome.

Depending on the halogenating agent used, UV light or light of a wavelength in the visible range may be used as high-energy light.

The starting materials II required for the preparation of the compounds I may be prepared by a process similar to that described in Section 5., starting from the nicotinates of the formula X, the synthesis of —C(=X)—COYR$^1$ preferably being effected first, followed by the halogenation.

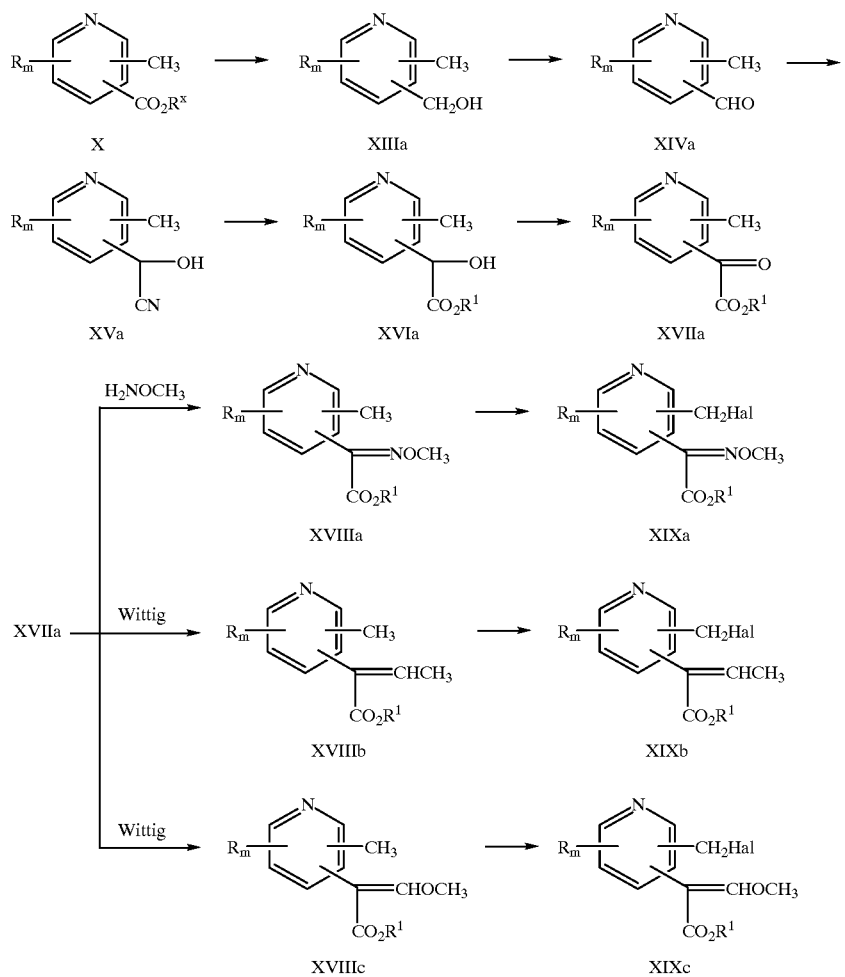

In addition, the compounds II may be prepared from the compounds I in which —ON=CR$^2$—CR$^3$=NOR$^4$ is eliminated (for example with HBr, HCl or BBr$_3$) by the benzyl ether cleavage method [cf. T. Greene, *Protective Groups in Organic Synthesis*, J. Wiley & Sons, 1981].

Furthermore, the compounds II may be prepared by the process described in Section 5., by starting in this process from derivatives in which the side chain is protected by an alkoxy, aryloxy or acyloxy protective group and the protective group is subsequently eliminated in the final process step by methods known from the literature [cf. T. Greene, Protective Groups in *Organic Synthesis*, J. Wiley & Sons, 1981].

5b. This reaction of XI with III to give XII is usually carried out at from 0 to 100° C., preferably from 20 to 60° C., in an inert organic solvent in the presence of a base.

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitrites, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably dimethylformamide, acetonitrile, tert-butyl methyl ether, toluene and water. Mixtures of the stated solvents may also be used.

Suitable bases are in general inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and alkali metal and alkaline earth metal alcoholates, such as sodium methylate, sodium ethylate, potassium ethylate, potassium tert-butylate and dimethoxymagnesium, and in addition organic bases, for example tertiary amines, such as trimethylamine, triethylamine, triisopropyl ethylamine and N-methylpiperidine, pyridine, substituted pyridines, such as collidine, lutidine and 4-dimethylaminopyridine, and bicyclic amines. Sodium hydride, potassium carbonate, sodium methylate and sodium ethylate are particularly preferred.

The bases are used in general in catalytic amounts but may also be used in equimolar amounts, in excess or, if required, as solvents.

5c. The reduction of XII to XIII is usually carried out at from −70 to 110° C., preferably from 0 to 60° C., in an inert organic solvent using a reducing agent.

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably toluene, tetrahydrofuran and tert-butyl methyl ether. Mixtures of the stated solvents may also be used.

The reducing agents generally used are metal hydrides. Lithium aluminum hydride and sodium borohydride are particularly suitable. The reducing agents may be used in general in equimolar amounts or in excess.

5d. The oxidation of XIII to XIV is usually carried out at from 0 to 60° C., preferably from 10 to 40° C., in an inert organic solvent using a conventional oxidizing agent [cf. *Organikum*, 15th Edition, 1976, pages 443–447, 604–607, VEB, Berlin], particularly preferably with sodium hypochlorite solution in the presence of tetramethylpyridine 1-oxide.

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably methylene chloride, toluene, tert-butyl methyl ether and water. Mixtures of the stated solvents may also be used.

5e. This reaction of XIV to give XV is usually carried out at from −10 to 50° C., preferably from 0 to 30° C., in an inert organic solvent using a cyanide in the presence of an acid.

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably diethyl ether, toluene, tert-butyl methyl ether and water. Mixtures of the stated solvents may also be used.

The cyanides generally used are inorganic compounds. Sodium cyanide and potassium cyanide are particularly suitable.

The cyanides may be used in general in at least equimolar amounts and are mostly used even in excess.

Acids and acidic catalysts used are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride, ammonium chloride and zinc(II) chloride, and organic acids, such as formic acid, acetic acid, propionic acid, oxalic acid, citric acid and trifluoroacetic acid. The acids are used in general in catalytic amounts but may also be used in equimolar amounts, in excess or, if required, as solvents.

5f. The hydrolysis of XV to give XVI is carried out via the imido ester XVa as an intermediate ($X^-$ is an anion, eg. halide or sulfate).

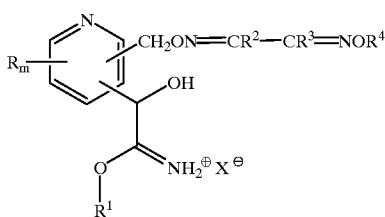

XVa

The conversion of XV to XVa is usually carried out at from −30 to 70° C., preferably from 0 to 30° C., in an inert organic solvent or in the alcohol $R^1$—OH in the presence of an acid.

Suitable solvents for the reaction of XV to give XVa are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably diethyl ether, toluene, methanol and ethanol.

Mixtures of the stated solvents may also be used.

Acids and acidic catalysts used are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and organic acids, such as formic acid, acetic acid, propionic acid, oxalic acid, citric acid and trifluoroacetic acid.

The acids are used in general in catalytic amounts but may also be used in equimolar amounts, in excess or, if required, as solvents.

The hydrolysis of XV to XVI is usually carried out at from 0 to 100° C., preferably from 40 to 100° C. in an inert organic solvent in the presence of an acid.

Suitable solvents are aliphatic hydrocarbons, such as pentane, hexane, cyclohexane and petroleum ether, aromatic hydrocarbons, such as toluene and o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and dimethyl sulfoxide and dimethylformamide, particularly preferably water, methanol, toluene and acetonitrile. Mixtures of the stated solvents may also be used.

Acids and acidic catalysts used are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and organic acids, such as formic acid, acetic acid, propionic acid, oxalic acid, citric acid and trifluoroacetic acid.

The acids are used in general in catalytic amounts but may also be used in equimolar amounts, in excess or, if required, as solvents.

In a particularly preferred embodiment, the imidoester hydrohalide is hydrolyzed in water without further addition of acids.

This oxidation of XVI to XVII is usually carried out by the processes stated in Section 5d.

5h. The reaction of the a-keto ester XVII with O-methylhydroxylamine ($H_2NOCH_3$) or with an O-methylhydroxylammonium salt is usually carried out at from 0 to 60° C., preferably from 20 to 40° C. [cf. EP-A 534 216].

5i. The reaction of the a-keto ester XVII with the ethylene-Wittig or -Wittig-Horner reagent is usually carried out at from −30 to 60° C. preferably from 10 to 40° C. according to EP-A 534 216, in an inert organic solvent in the presence of a base.

5k. The reaction of the a-keto ester XVII with a methoxy-Wittig or -Wittig-Horner reagent is usually carried out at from −30 to 60° C., preferably from 10 to 40° C., according to EP-A 534 216, in the presence of a base.

6. Compounds of the formula I in which Y is $NR^a$ (IB) are obtained from the corresponding compounds IA in a manner known per se, by reaction with an amine of the formula XVIII.

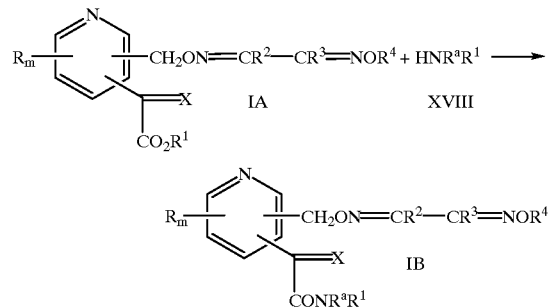

The reaction of the ester IA with the amine is usually carried out at from 0 to 80° C., preferably from 20 to 60° C., according to EP-A 534 216, in an inert organic solvent.

The reaction mixtures are worked up in a conventional manner, for example by mixing with water, separating the phases and, if required, purifying the crude products by chromatography. Some of the intermediates and end products are obtained in the form of colorless or slightly brownish, viscous oils which can be freed from volatile constituents or purified under reduced pressure and at moderately elevated temperatures. Where the intermediates and end products are obtained as solids, the purification may also be effected by recrystallization or digestion.

Owing to their C=C and C=N double bonds, compounds I may be obtained in the preparation as E/Z isomer mixtures, which can be separated into the individual compounds in a conventional manner, for example by crystallization or chromatography.

Where isomer mixtures are obtained in the synthesis, however, a separation is in general not essential since some of the individual isomers may be transformed into one another during the working up for use or during use (for example under the action of light, acid or base). Corresponding transformations may also occur after use, for example in the treatment of plants, in the treated plants or in the harmful fungi or animal pests to be controlled.

With regard to the C=X double bond, the E isomers of the compounds I are preferred in terms of their effectiveness (configuration based on the $OCH_3$ or $CH_3$ group in relation to the $COYR^1$ group.

With regard to the —N═CR²—CR³═N double bonds, the cis isomers of the compounds I (configuration based on R² or R³ in relation to the —OCH₂ or —OR⁴ group or based on R⁴ in relation to the —N═CR² group) are generally preferred in terms of their effectiveness.

In the case of the definitions of the compounds I stated at the outset, the collective terms used are in general representative of the following groups:

Halogen: fluorine, chlorine, bromine and iodine;

Alkyl: straight-chain or branched alkyl of 1 to 4, 6 or 10 carbon atoms, for example $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino which carries straight-chain or branched alkyl of 1 to 6 carbon atoms as stated above;

Dialkylamino: amino which carries two independent, straight-chain or branched alkyl groups, each of 1 to 6 carbon atoms, as stated above;

Alkylcarbonyl: straight-chain or branched alkyl of 1 to 10 carbon atoms which is bonded to the skeleton via carbonyl (—CO—);

Alkylsulfonyl: straight-chain or branched alkyl of 1 to 6 or 10 carbon atoms which is bonded to the skeleton via sulfonyl (—SO₂—);

Alkylsulfoxyl: straight-chain or branched alkyl of 1 to 6 carbon atoms which is bonded to the skeleton via sulfoxyl (—S(═O)—);

Alkylaminocarbonyl: alkylamino of 1 to 6 carbon atoms as stated above, which is bonded to the skeleton via carbonyl (—CO—);

Dialkylaminocarbonyl: dialkylamino where each alkyl radical is of 1 to 6 carbon atoms, as stated above, which is bonded to the skeleton via carbonyl (—CO—);

Alkylaminothiocarbonyl: alkylamino of 1 to 6 carbon atoms as stated above, which is bonded to the skeleton via thiocarbonyl (—CS—);

Dialkylaminothiocarbonyl: dialkylamino where each alkyl radical is of 1 to 6 carbon atoms, as stated above, which is bonded to the skeleton via thiocarbonyl (—CS—);

Haloalkyl: straight-chain or branched alkyl of 1 to 6 carbon atoms, where some or all of the hydrogen atoms in these groups may be replaced by halogen atoms as stated above, for example $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl of 1 to 4 or 6 carbon atoms as stated above, which is bonded to the skeleton via oxygen (—O—), for example $C_1$–$C_6$-alkoxy, such as methoxy, ethoxy, propyoxy, 1-methylethyoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

Alkoxycarbonyl: straight-chain or branched alkyl of 1 to 6 carbon atoms which is bonded to the skeleton via oxycarbonyl (—OC(═O)—);

Haloalkoxy: straight-chain or branched alkyl of 1 to 6 carbon atoms in which some or all of the hydrogen atoms may be replaced by halogen atoms as stated above and which may be bonded to the skeleton via oxygen;

Alkylthio: straight-chain or branched alkyl of 1 to 4 or 6 carbon atoms as stated above, which is bonded to the skeleton via sulfur (—S—), for example $C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl having 3 to 6 carbon ring members, eg. cyclopropyl, cyclobutyl, cyclopentyl and cyclohexyl;

Alkenyl: straight-chain or branched alkenyl having 2 to 6 or 10 carbon atoms and one double bond in any position, for example $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl having 2 to 6 carbon atoms and one double bond in any position, which is bonded to the skeleton via oxygen (—O—);

Alkenylthio or alkenylamino: straight-chain or branched alkenyl having 2 to 6 carbon atoms and one double bond in any position, which is bonded to the skeleton via sulfur (alkenylthio) or nitrogen (alkenylamino);

Alkenylcarbonyl: straight-chain or branched alkenyl having 2 to 10 carbon atoms and one double bond in any position, which is bonded to the skeleton via carbonyl (—CO—);

Alkynyl: straight-chain or branched alkynyl having 2 to 10 carbon atoms and one triple bond in any position, for example $C_2$–$C_6$-alkynyl, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alkynyloxy or alkenylthio and alkynylamino: straight-chain or branched alkynyl having 2 to 6 carbon atoms and one triple bond in any position, which is bonded to the skeleton via oxygen (alkynyloxy) or via sulfur (alkenylthio) or via nitrogen (alkynylamino);

Alkynylcarbonyl: straight-chain or branched alkynyl having 3 to 10 carbon atoms and one triple bond in any position, which is bonded to the skeleton via carbonyl (—CO—);

Cycloalkenyl or cycloalkenyloxy, cycloalkenylthio and cycloalkenylamino: monocyclic alkenyl having 3 to 6 carbon ring members which is bonded to the skeleton directly or via oxygen (cycloalkenyloxy) or sulfur (cycloalkenylthio) or nitrogen (cycloalkenylamino), eg. cyclopropenyl, cyclobutenyl, cyclopentenyl or cyclohexenyl.

Cycloalkoxy or cycloalkylthio and cycloalkylamino: monocyclic alkenyl having 3 to 6 carbon ring members, which is bonded to the skeleton via oxygen (cycloalkyloxy) or sulfur (cycloalkylthio) or nitrogen (cycloalkylamino), eg. cyclopropyl, cyclobutyl, cyclopentyl or cyclohexyl;

Heterocyclyl or heterocyclyloxy, heterocyclylthio and heterocyclylamino: three- to six-membered, saturated or partially unsaturated mono- or polycyclic heterocycles which contain from one to three hetero atoms selected from the group consisting of oxygen, nitrogen and sulfur and which are bonded to the skeleton directly or via oxygen (heterocyclyloxy) or sulfur (heterocyclylthio) or nitrogen (heterocyclylamino), eg. 2-tetrahydro-furanyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl or aryloxy, arylthio, arylcarbonyl and arylsulfonyl: aromatic mono- or polycyclic hydrocarbon radicals which are bonded to the skeleton directly via oxygen (—O—) (aryloxy) or sulfur (—S—) (arylthio) or carbonyl (—CO—) (arylcarbonyl) or sulfonyl (—SO$_2$—) (arylsulfonyl), eg. phenyl, naphthyl and phenanthrenyl or phenoxy, naphthyloxy and phenanthrenyloxy and the corresponding carbonyl and sulfonyl radicals;

Arylamino: aromatic mono- or polycyclic hydrocarbon radicals which are bonded to the skeleton via nitrogen;

Hetaryl or hetaryloxy, hetarylthio, hetarylcarbonyl and hetarylsulfonyl: aromatic mono- or polycyclic radicals which, in addition to carbon ring members may additionally contain from one to four nitrogen atoms or from one to three nitrogen atoms and one oxygen or one sulfur atom or one oxygen or one sulfur atom and which may be bonded to the skeleton directly or via oxygen (—O—) (hetaryloxy) or sulfur (—S—) (hetarylthio) or carbonyl (—CO—) (hetarylcarbonyl) or sulfonyl (—SO$_2$—) (hetarylsulfonyl), eg.

5-membered hetaryl containing from one to three nitrogen atoms: hetaryl which has a 5-membered ring and, in addition to carbon atoms, may contain from one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing from one to four nitrogen atoms or from one to three nitrogen atoms and one sulfur or oxygen atom or one oxygen or one sulfur atom: hetaryl which has a 5-membered ring and, in addition to carbon atoms, may contain from one to four nitrogen atoms or from one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzofused 5-membered hetaryl containing from one to three nitrogen atoms or one nitrogen atom and/or one oxygen or sulfur atom: hetaryl which has a 5-membered ring and, in addition to carbon atoms, may contain from one to four nitrogen atoms or from one to three nitrogen atoms and one sulfur or oxygen atom or one oxygen or one sulfur atom as ring members and in which two adjacent carbon ring members or one nitrogen and one adjacent carbon ring member may be bridged by a buta-1,3-diene-1,4-group;

5-membered hetaryl bonded via nitrogen and containing from one to four nitrogen atoms or benzofused 5-membered hetaryl bonded via nitrogen and containing from one to three nitrogen atoms: hetaryl which has a 5-membered ring and, in addition to carbon atoms, may contain from one to four nitrogen atoms or from one to three nitrogen atoms as ring members and in which two adjacent carbon ring members or one nitrogen and one adjacent carbon ring member may be bridged by a buta-1,3-diene-1,4-diyl group, these rings being bonded to the skeleton via one of the nitrogen ring members;

6-membered hetaryl containing from one to three or from one to four nitrogen atoms: hetaryl which has a 6-membered ring and, in addition to carbon atoms, may contain from one to three or from one to four nitrogen atoms as ring members, eg. 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 6-membered hetaryl containing from one to four nitrogen atoms: hetaryl which has a 6-membered ring and in which two adjacent carbon ring members may be bridged by a buta-1,3-diene-1,4-diyl group, eg. quinoline, isoquinoline, quinazoline and quinoxaline, or the corresponding oxy, thio, carbonyl or sulfonyl groups;

Hetarylamino: aromatic mono- or polycyclic radicals which, in addition to carbon ring members, may contain from one to four nitrogen atoms or from one to three nitrogen atoms and one oxygen or one sulfur atom and which are bonded to the skeleton via nitrogen.

The term "partially or completely halogenated" is intended to express the fact that, in groups characterized in this manner, some or all of the hydrogen atoms may be replaced via identical or different halogen atoms as stated above.

In view of their biological activity, compounds of the formula I in which m is 0 or 1, in particular 0, are preferred.

Where m is 1, compounds I in which R is chlorine or fluorine are preferred.

Particularly preferred compounds I are those in which X is NOCH$_3$ (formula I.1).

Compounds I in which X is CHCH$_3$ (formula I.2) are also preferred.

Other preferred compounds I are those in which X is CHOCH$_3$ (formula I.3).

Compounds I in which R$^1$ is methyl are also particularly preferred.

Further preferred compounds I are those in which Y is oxygen (formula IA).

Other preferred compounds I are those in which Y is NR', in particular NH (formula IB).

Furthermore, compounds I in which R$^2$ is C$_1$–C$_4$-alkyl, in particular methyl, are particularly preferred.

Other particularly preferred compounds I are those in which R$^2$ is trifluoromethyl.

Compounds I in which R$^2$ is cyclopropyl are also particularly preferred.

Further particularly preferred compounds I are those in which R$^2$ is C$_1$–C$_4$-alkoxy, in particular methoxy.

Compounds I in which R$^2$ is halogen, in particular chlorine, are also particularly preferred.

Other particularly preferred compounds I are those in which R$^3$ is aryl, in particular unsubstituted or substituted phenyl.

Compounds I in which R$^3$ is alkyl, in particular C$_1$–C$_6$-alkyl, are also particularly preferred.

Other particularly preferred compounds I are those in which R$^3$ is alkoxy, in particular C$_1$–C$_6$-alkoxy.

Compounds I in which R$^3$ is cycloalkyl, in particular C$_3$–C$_6$-cycloalkyl, are also particularly preferred.

Further particularly preferred compounds I are those in which R$^3$ is aryloxyalkyl, in particular phenoxy-C$_1$- or C$_2$-alkyl which is unsubstituted or substituted in the phenyl moiety.

Compounds I in which R$^3$ is hetaryl, in particular unsubstituted or substituted thienyl, isoxazolyl, pyrazolyl and pyridyl, are also particularly preferred.

Other particularly preferred compounds I are those in which R$^4$ is C$_1$–C$_6$-alkyl, in particular methyl.

Compounds I in which R$^4$ is C$_3$–C$_6$-alkenyl, in particular allyl, are also particularly preferred.

Other particularly preferred compounds I are those in which R$^4$ is C$_3$–C$_6$-alkynyl, in particular propargyl.

Compounds I in which R$^4$ is arylalkyl, in particular phenyl-C$_1$- or C$_2$-alkyl which is unsubstituted or substituted in the phenyl moiety, are also particularly preferred.

Further particularly preferred compounds I are those in which R$^4$ is haloalkenyl, in particular trans-chloroallyl.

Compounds I in which R$^4$ is alkoxyalkyl, in particular C$_1$- or C$_2$-alkoxy-C$_1$- or C$_2$-alkyl, are also particularly preferred.

Compounds I in which C(=X)-COYR$^1$ is bonded in the 2-position of the pyridyl ring are particularly preferred.

Compounds I in which C(=X)-COYR$^1$ is bonded in the 3-position of the pyridyl ring are also preferred.

Other preferred compounds I are those in which C(=X)-COYR$^1$ is bonded in the 4-position of the pyridyl ring.

Compounds I in which —CH$_2$ON=CR$^2$—CR$^3$=NOR$^4$ is bonded in the 2-position of the pyridyl ring are also particularly preferred.

Compounds I in which —CH$_2$ON=CR$^2$—CR$^3$=NOR$^4$ is bonded in the 3-position of the pyridyl ring are also preferred.

Other preferred compounds I are those in which —CH$_2$ON=CR$^2$—CR$^3$=NOR$^4$ is bonded in the 4-position of the pyridyl ring.

Particularly preferred compounds I are those in which C(=X)-COYR$^1$ is bonded in the 3-position and —CH$_2$ON=CR$^2$—CR$^3$=NOR$^4$ is bonded in the 2-position of the pyridyl ring.

TABLE 1

Compounds of the general formula IA.1 in which the combination of the substituents $R^2$, $R^3$ and $R^4$ for a compound corresponds in each case to a line in Table A

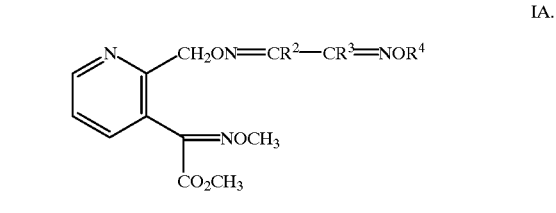

IA.1

TABLE 2

Compounds of the general formula IA.2 in which the combination of the substituents $R^2$, $R^3$ and $R^4$ for a compound corresponds in each case to a line in Table A

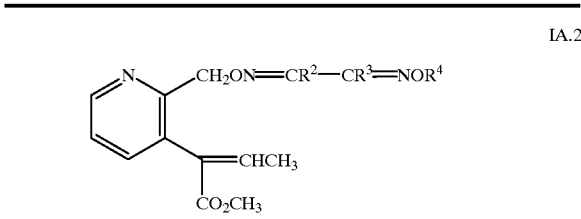

IA.2

TABLE 3

Compounds of the general formula IA.3 in which the combination of the substituents $R^2$, $R^3$ and $R^4$ for a compound corresponds in each case to a line in Table A

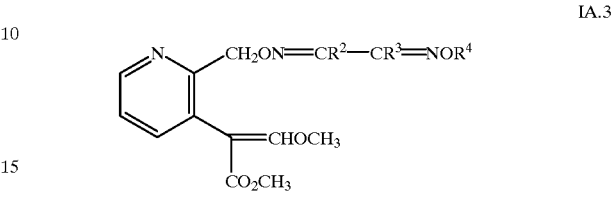

IA.3

TABLE 4

Compounds of the general formula IA.4 in which the combination of the substituents $R^2$, $R^3$ and $R^4$ for a compound corresponds in each case to a line in Table A

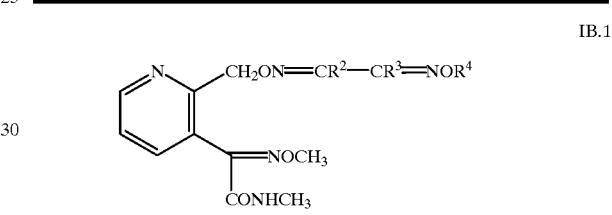

IB.1

TABLE A

| No. | $R^2$ | $R^3$ | $R^4$ |
|---|---|---|---|
| 1  | $CH_3$ | $CH_3$ | H |
| 2  | $CH_3$ | $CH_3$ | $CH_3$ |
| 3  | $CH_3$ | $CH_3$ | $C_2H_5$ |
| 4  | $CH_3$ | $CH_3$ | $n\text{-}C_3H_7$ |
| 5  | $CH_3$ | $CH_3$ | $i\text{-}C_3H_7$ |
| 6  | $CH_3$ | $CH_3$ | Cyclopropyl |
| 7  | $CH_3$ | $CH_3$ | $n\text{-}C_4H_9$ |
| 8  | $CH_3$ | $CH_3$ | $s\text{-}C_4H_9$ |
| 9  | $CH_3$ | $CH_3$ | $i\text{-}C_4H_9$ |
| 10 | $CH_3$ | $CH_3$ | $t\text{-}C_4H_9$ |
| 11 | $CH_3$ | $CH_3$ | $n\text{-}C_5H_{11}$ |
| 12 | $CH_3$ | $CH_3$ | $i\text{-}C_5H_{11}$ |
| 13 | $CH_3$ | $CH_3$ | $neo\text{-}C_5H_{11}$ |
| 14 | $CH_3$ | $CH_3$ | Cyclopentyl |
| 15 | $CH_3$ | $CH_3$ | $n\text{-}C_6H_{13}$ |
| 16 | $CH_3$ | $CH_3$ | Cyclohexyl |
| 17 | $CH_3$ | $CH_3$ | $n\text{-}C_8H_{17}$ |
| 18 | $CH_3$ | $CH_3$ | $CH_2CH_2Cl$ |
| 19 | $CH_3$ | $CH_3$ | $(CH_2)_4Cl$ |
| 20 | $CH_3$ | $CH_3$ | $CH_2CN$ |
| 21 | $CH_3$ | $CH_3$ | $CH_2CH_2CN$ |
| 22 | $CH_3$ | $CH_3$ | $(CH_2)_3CN$ |
| 23 | $CH_3$ | $CH_3$ | $(CH_2)_4CN$ |
| 24 | $CH_3$ | $CH_3$ | $(CH_2)_6CN$ |
| 25 | $CH_3$ | $CH_3$ | Cyclohexylmethyl |
| 26 | $CH_3$ | $CH_3$ | 2-Cyclohexyleth-1-yl |
| 27 | $CH_3$ | $CH_3$ | Cyclopropylmethyl |
| 28 | $CH_3$ | $CH_3$ | 2-Cyclopropyleth-1-yl |
| 29 | $CH_3$ | $CH_3$ | 2-Methoxyeth-1-yl |
| 30 | $CH_3$ | $CH_3$ | 2-Ethoxyeth-1-yl |
| 31 | $CH_3$ | $CH_3$ | 2-Isopropoxyeth-1-yl |
| 32 | $CH_3$ | $CH_3$ | 3-Methoxyprop-1-yl |

TABLE A-continued

| No. | R² | R³ | R⁴ |
|---|---|---|---|
| 33 | CH₃ | CH₃ | 3-Ethoxyprop-1-yl |
| 34 | CH₃ | CH₃ | 3-Isopropoxyprop-1-yl |
| 35 | CH₃ | CH₃ | 4-Methoxybut-1-yl |
| 36 | CH₃ | CH₃ | 4-Isopropoxybut-1-yl |
| 37 | CH₃ | CH₃ | Propen-3-yl |
| 38 | CH₃ | CH₃ | But-2-en-1-yl |
| 39 | CH₃ | CH₃ | 3-Methylbut-2-en-1-yl |
| 40 | CH₃ | CH₃ | 2-Vinyloxyeth-1-yl |
| 41 | CH₃ | CH₃ | Allyloxyeth-1-yl |
| 42 | CH₃ | CH₃ | 2-Trifluoromethoxyeth-1-yl |
| 43 | CH₃ | CH₃ | 3-Trifluoromethoxyprop-1-yl |
| 44 | CH₃ | CH₃ | 4-Difluoromethoxybut-1-yl |
| 45 | CH₃ | CH₃ | Hydroxycarbonylmethyl |
| 46 | CH₃ | CH₃ | Methoxycarbonylmethyl |
| 47 | CH₃ | CH₃ | Aminocarbonylmethyl |
| 48 | CH₃ | CH₃ | N-Methylaminocarbonylmethyl |
| 49 | CH₃ | CH₃ | N,N-Dimethylaminocarbonylmethyl |
| 50 | CH₃ | CH₃ | 2-Hydroxycarbonyleth-1-yl |
| 51 | CH₃ | CH₃ | 2-Methoxycarbonyleth-1-yl |
| 52 | CH₃ | CH₃ | 2-Aminocarbonyleth-1-yl |
| 53 | CH₃ | CH₃ | 2-N-Methylaminocarbonyleth-1-yl |
| 54 | CH₃ | CH₃ | 2-Dimethylaminocarbonyleth-1-yl |
| 55 | CH₃ | CH₃ | 2-Aminoeth-1-yl |
| 56 | CH₃ | CH₃ | 2-Aminoprop-1-yl |
| 57 | CH₃ | CH₃ | 4-Aminobut-1-yl |
| 58 | CH₃ | CH₃ | 3-Dimethylaminoprop-1-yl |
| 59 | CH₃ | CH₃ | 4-Aminothiocarbonylbut-1-yl |
| 60 | CH₃ | CH₃ | 2-Oxopropyl |
| 61 | CH₃ | CH₃ | Cyclohexyl |
| 62 | CH₃ | CH₃ | Cyclopropyl |
| 63 | CH₃ | CH₃ | Cyclopentyl |
| 64 | CH₃ | CH₃ | 2-Methoxyiminoprop-1-yl |
| 65 | CH₃ | CH₃ | 2-Methoxyiminoeth-1-yl |
| 66 | CH₃ | CH₃ | 6-Aminocarbonylhex-1-yl |
| 67 | CH₃ | CH₃ | 3-Aminothiocarbonylprop-1-yl |
| 68 | CH₃ | CH₃ | 2-Aminothiocarbonyleth-1-yl |
| 69 | CH₃ | CH₃ | Aminothiocarbonylmethyl |
| 70 | CH₃ | CH₃ | 4-(N,N-Dimethylamino)but-1-yl |
| 71 | CH₃ | CH₃ | 2-(Methylthio)eth-1-yl |
| 72 | CH₃ | CH₃ | 2-(Methylsulfonyl)eth-1-yl |
| 73 | CH₃ | CH₃ | 4-(Methylthio)prop-1-yl |
| 74 | CH₃ | CH₃ | 4-(Methylsulfonyl)prop-1-yl |
| 75 | CH₃ | CH₃ | Benzyl |
| 76 | CH₃ | CH₃ | 2-F-C₆H₄-CH₂ |
| 77 | CH₃ | CH₃ | 3-F-C₆H₄-CH₂ |
| 78 | CH₃ | CH₃ | 4-F-C₆H₄-CH₂ |
| 79 | CH₃ | CH₃ | 2,3-F₂-C₆H₃-CH₂ |
| 80 | CH₃ | CH₃ | 2,4-F₂-C₆H₃-CH₂ |
| 81 | CH₃ | CH₃ | 2,5-F₂-C₆H₃-CH₂ |
| 82 | CH₃ | CH₃ | 2,6-F₂-C₆H₃-CH₂ |
| 83 | CH₃ | CH₃ | 3,4-F₂-C₆H₃-CH₂ |
| 84 | CH₃ | CH₃ | 3,5-F₂-C₆H₃-CH₂ |
| 85 | CH₃ | CH₃ | 2-Cl-C₆H₄-CH₂ |
| 86 | CH₃ | CH₃ | 3-Cl-C₆H₄-CH₂ |
| 87 | CH₃ | CH₃ | 4-Cl-C₆H₄-CH₂ |
| 88 | CH₃ | CH₃ | 2,3-Cl₂-C₆H₃-CH₂ |
| 89 | CH₃ | CH₃ | 2,4-Cl₂-C₆H₃-CH₂ |
| 90 | CH₃ | CH₃ | 2,5-Cl₂-C₆H₃-CH₂ |
| 91 | CH₃ | CH₃ | 2,6-Cl₂-C₆H₃-CH₂ |
| 92 | CH₃ | CH₃ | 3,4-Cl₂-C₆H₃-CH₂ |
| 93 | CH₃ | CH₃ | 3,5-Cl₂-C₆H₃-CH₂ |
| 94 | CH₃ | CH₃ | 2,3,4-Cl₃-C₆H₂-CH₂ |
| 95 | CH₃ | CH₃ | 2,3,5-Cl₃-C₆H₂-CH₂ |
| 96 | CH₃ | CH₃ | 2,3,6-Cl₃-C₆H₂-CH₂ |
| 97 | CH₃ | CH₃ | 2,4,5-Cl₃-C₆H₂-CH₂ |
| 98 | CH₃ | CH₃ | 2,4,6-Cl₃-C₆H₂-CH₂ |
| 99 | CH₃ | CH₃ | 3,4,5-Cl₃-C₆H₂-CH₂ |
| 100 | CH₃ | CH₃ | 2-Br-H-C₆H₄-CH₂ |
| 101 | CH₃ | CH₃ | 3-Br-H-C₆H₄-CH₂ |
| 102 | CH₃ | CH₃ | 4-Br-H-C₆H₄-CH₂ |
| 103 | CH₃ | CH₃ | 2,3-Br₂-C₆H₃-CH₂ |
| 104 | CH₃ | CH₃ | 2,4-Br₂-C₆H₃-CH₂ |
| 105 | CH₃ | CH₃ | 2,5-Br₂-C₆H₃-CH₂ |
| 106 | CH₃ | CH₃ | 2,6-Br₂-C₆H₃-CH₂ |
| 107 | CH₃ | CH₃ | 3,4-Br₂-C₆H₃-CH₂ |
| 108 | CH₃ | CH₃ | 3,5-Br₂-C₆H₃-CH₂ |
| 109 | CH₃ | CH₃ | 2-F,3-Cl-C₆H₃-CH₂ |

TABLE A-continued

| No. | R² | R³ | R⁴ |
|---|---|---|---|
| 110 | CH₃ | CH₃ | 2-F,4-Cl-C₆H₃-CH₂ |
| 111 | CH₃ | CH₃ | 2-F,5-Cl-C₆H₃-CH₂ |
| 112 | CH₃ | CH₃ | 2-F,3-Br-C₆H₃-CH₂ |
| 113 | CH₃ | CH₃ | 2-F,4-Br-C₆H₃-CH₂ |
| 114 | CH₃ | CH₃ | 2-F,5-Br-C₆H₃-CH₂ |
| 115 | CH₃ | CH₃ | 2-Cl,3-Br-C₆H₃-CH₂ |
| 116 | CH₃ | CH₃ | 2-Cl,4-Br-C₆H₃-CH₂ |
| 117 | CH₃ | CH₃ | 2-Cl,5-Br-C₆H₃-CH₂ |
| 118 | CH₃ | CH₃ | 3-F,4-Cl-C₆H₃-CH₂ |
| 119 | CH₃ | CH₃ | 3-F,5-Cl-C₆H₃-CH₂ |
| 120 | CH₃ | CH₃ | 3-F,6-Cl-C₆H₃-CH₂ |
| 121 | CH₃ | CH₃ | 3-F,4-Br-C₆H₃-CH₂ |
| 122 | CH₃ | CH₃ | 3-F,5-Br-C₆H₃-CH₂ |
| 123 | CH₃ | CH₃ | 3-F,6-Br-C₆H₃-CH₂ |
| 124 | CH₃ | CH₃ | 3-Cl,4-Br-C₆H₃-CH₂ |
| 125 | CH₃ | CH₃ | 3-Cl,5-Br-C₆H₃-CH₂ |
| 126 | CH₃ | CH₃ | 3-Cl,6-Br-C₆H₃-CH₂ |
| 127 | CH₃ | CH₃ | 4-F,5-Cl-C₆H₃-CH₂ |
| 128 | CH₃ | CH₃ | 4-F,6-Cl-C₆H₃-CH₂ |
| 129 | CH₃ | CH₃ | 4-F,5-Br-C₆H₃-CH₂ |
| 130 | CH₃ | CH₃ | 4-F,6-Br-C₆H₃-CH₂ |
| 131 | CH₃ | CH₃ | 4-Cl,5-Br-C₆H₃-CH₂ |
| 132 | CH₃ | CH₃ | 5-F,6-Cl-C₆H₃-CH₂ |
| 133 | CH₃ | CH₃ | 5-F,6-Br-C₆H₃-CH₂ |
| 134 | CH₃ | CH₃ | 5-Cl,6-Br-C₆H₃-CH₂ |
| 135 | CH₃ | CH₃ | 3-Br,4-Cl,5-Br-C₆H₂-CH₂ |
| 136 | CH₃ | CH₃ | 2-CN-C₆H₄-CH₂ |
| 137 | CH₃ | CH₃ | 3-CN-C₆H₄-CH₂ |
| 138 | CH₃ | CH₃ | 4-CN-C₆H₄-CH₂ |
| 139 | CH₃ | CH₃ | 2-NO₂-C₆H₄-CH₂ |
| 140 | CH₃ | CH₃ | 3-NO₂-C₆H₄-CH₂ |
| 141 | CH₃ | CH₃ | 4-NO₂-C₆H₄-CH₂ |
| 142 | CH₃ | CH₃ | 2-CH₃-C₆H₄-CH₂ |
| 143 | CH₃ | CH₃ | 3-CH₃-C₆H₄-CH₂ |
| 144 | CH₃ | CH₃ | 4-CH₃-C₆H₄-CH₂ |
| 145 | CH₃ | CH₃ | 2,3-(CH₃)₂-C₆H₃-CH₂ |
| 146 | CH₃ | CH₃ | 2,4-(CH₃)₂-C₆H₃-CH₂ |
| 147 | CH₃ | CH₃ | 2,5-(CH₃)₂-C₆H₃-CH₂ |
| 148 | CH₃ | CH₃ | 2,6-(CH₃)₂-C₆H₃-CH₂ |
| 149 | CH₃ | CH₃ | 3,4-(CH₃)₂-C₆H₃-CH₂ |
| 150 | CH₃ | CH₃ | 3,5-(CH₃)₂-C₆H₃-CH₂ |
| 151 | CH₃ | CH₃ | 2-C₂H₅-C₆H₄-CH₂ |
| 152 | CH₃ | CH₃ | 3-C₂H₅-C₆H₄-CH₂ |
| 153 | CH₃ | CH₃ | 4-C₂H₅-C₆H₄-CH₂ |
| 154 | CH₃ | CH₃ | 2-i-C₃H₇-C₆H₄-CH₂ |
| 155 | CH₃ | CH₃ | 3-i-C₃H₇-C₆H₄-CH₂ |
| 156 | Ch₃ | Ch₃ | 4-i-C₃H₇-C₆H₄-CH₂ |
| 157 | CH₃ | CH₃ | 2-Cyclohexyl-C₆H₄-CH₂ |
| 158 | CH₃ | CH₃ | 3-Cyclohexyl-C₆H₄-CH₂ |
| 159 | CH₃ | CH₃ | 4-Cyclohexyl C₆H-CH₂ |
| 160 | CH₃ | CH₃ | 2-Vinyl-C₆H₄-CH₂ |
| 161 | CH₃ | CH₃ | 3-Vinyl-C₆H₄-CH₂ |
| 162 | CH₃ | CH₃ | 4-Vinyl-C₆H₄-CH₂ |
| 163 | CH₃ | CH₃ | 2-Allyl-C₆H₄-CH₂ |
| 164 | CH₃ | CH₃ | 3-Allyl-C₆H₄-CH₂ |
| 165 | CH₃ | CH₃ | 4-Allyl-C₆H₄-CH₂ |
| 166 | CH₃ | CH₃ | 2-C₆H₅-C₆H₄-CH₂ |
| 167 | CH₃ | CH₃ | 3-C₆H₅-C₆H₄-CH₂ |
| 168 | CH₃ | CH₃ | 4-C₆H₅-C₆H₄-CH₂ |
| 169 | CH₃ | CH₃ | 3-CH₃,5-t-C₄H₉-C₆H₃-CH₂ |
| 170 | CH₃ | CH₃ | 2-OH-C₆H₄-CH₂ |
| 171 | CH₃ | CH₃ | 3-OH-C₆H₄-CH₂ |
| 172 | CH₃ | CH₃ | 4-OH-C₆H₄-CH₂ |
| 173 | CH₃ | CH₃ | 2-OCH₃-C₆H₄-CH₂ |
| 174 | CH₃ | CH₃ | 3-OCH₃-C₆H₄-CH₂ |
| 175 | CH₃ | CH₃ | 4-OCH₃-C₆H₄-CH₂ |
| 176 | CH₃ | CH₃ | 2,3-(OCH₃)₂-C₆H₃-CH₂ |
| 177 | CH₃ | CH₃ | 2,4-(OCH₃)₂-C₆H₃-CH₂ |
| 178 | CH₃ | CH₃ | 2,5-(OCH₃)₂-C₆H₃-CH₂ |
| 179 | CH₃ | CH₃ | 3,4-(OCH₃)₂-C₆H₃-CH₂ |
| 180 | CH₃ | CH₃ | 3,5-(OCH₃)₂-C₆H₃-CH₂ |
| 181 | CH₃ | CH₃ | 3,4,5-(OCH₃)₃-C₆H₂-CH₂ |
| 182 | CH₃ | CH₃ | 2-OC₂H₅-C₆H₄-CH₂ |
| 183 | CH₃ | CH₃ | 3-OC₂H₅-C₆H₄-CH₂ |
| 184 | CH₃ | CH₃ | 4-OC₂H₅-C₆H₄-CH₂ |
| 185 | CH₃ | CH₃ | 2-O-(n-C₃H₇)-C₆H₄-CH₂ |
| 186 | CH₃ | CH₃ | 3-O-(n-C₃H₇)-C₆H₄-CH₂ |

TABLE A-continued

| No. | R² | R³ | R⁴ |
|---|---|---|---|
| 187 | CH₃ | CH₃ | 4-O-(n-C₃H₇)-C₆H₄-CH₂ |
| 188 | CH₃ | CH₃ | 2-O-(i-C₃H₇)-C₆H₄-CH₂ |
| 189 | CH₃ | CH₃ | 3-O-(i-C₃H₇)-C₆H₄-CH₂ |
| 190 | CH₃ | CH₃ | 4-O-(i-C₃H₇)-C₆H₄-CH₂ |
| 191 | CH₃ | CH₃ | 4-O-(n-C₄H₉)-C₆H₄-CH₂ |
| 192 | CH₃ | CH₃ | 3-O-(t-C₄H₉)-C₆H₄-CH₂ |
| 193 | CH₃ | CH₃ | 4-O-(n-C₆H₁₃)-C₆H₄-CH₂ |
| 194 | CH₃ | CH₃ | 2-O-Allyl-C₆H₄-CH₂ |
| 195 | CH₃ | CH₃ | 3-O-Allyl-C₆H₄-CH₂ |
| 196 | CH₃ | CH₃ | 4-O-Allyl-C₆H₄-CH₂ |
| 197 | CH₃ | CH₃ | 2-CF₃-C₆H₄-CH₂ |
| 198 | CH₃ | CH₃ | 3-CF₃-C₆H₄-CH₂ |
| 199 | CH₃ | CH₃ | 4-CF₃-C₆H₄-CH₂ |
| 200 | CH₃ | CH₃ | 2-Acetyl-C₆H₄-CH₂ |
| 201 | CH₃ | CH₃ | 3-Acetyl-C₆H₄-CH₂ |
| 202 | CH₃ | CH₃ | 4-Acetyl-C₆H₄-CH₂ |
| 203 | CH₃ | CH₃ | 2-Methoxycarbonyl-C₆H₄-CH₂ |
| 204 | CH₃ | CH₃ | 3-Methoxycarbonyl-C₆H₄-CH₂ |
| 205 | CH₃ | CH₃ | 4-Methoxycarbonyl-C₆H₄-CH₂ |
| 206 | CH₃ | CH₃ | 2-Aminocarbonyl-C₆H₄-CH₂ |
| 207 | CH₃ | CH₃ | 3-Aminocarbonyl-C₆H₄-CH₂ |
| 208 | CH₃ | CH₃ | 4-Aminocarbonyl-C₆H₄-CH₂ |
| 209 | CH₃ | CH₃ | 2-Dimethylaminocarbonyl-C₆H₄-CH₂ |
| 210 | CH₃ | CH₃ | 3-Dimethylaminocarbonyl-C₆H₄-CH₂ |
| 211 | CH₃ | CH₃ | 4-Dimethylaminocarbonyl-C₆H₄-CH₂ |
| 212 | CH₃ | CH₃ | 2-(N-Methylaminocarbonyl)-C₆H₄-CH₂ |
| 213 | CH₃ | CH₃ | 3-(N-Methylaminocarbonyl)-C₆H₄-CH₂ |
| 214 | CH₃ | CH₃ | 4-(N-Methylaminocarbonyl)-C₆H₄-CH₂ |
| 215 | CH₃ | CH₃ | 2-H₂N-C₆H₄-CH₂ |
| 216 | CH₃ | CH₃ | 3-H₂N-C₆H₄-CH₂ |
| 217 | CH₃ | CH₃ | 4-H₂N-C₆H₄-CH₂ |
| 218 | CH₃ | CH₃ | 2-Aminothiocarbonyl-C₆H₄-CH₂ |
| 219 | CH₃ | CH₃ | 3-Aminothiocarbonyl-C₆H₄-CH₂ |
| 220 | CH₃ | CH₃ | 4-Aminothiocarbonyl-C₆H₄-CH₂ |
| 221 | CH₃ | CH₃ | 2-Methoxyiminomethyl-C₆H₄-CH₂ |
| 222 | CH₃ | CH₃ | 3-Methoxyiminomethyl-C₆H₄-CH₂ |
| 223 | CH₃ | CH₃ | 4-Methoxyiminomethyl-C₆H₄-CH₂ |
| 224 | CH₃ | CH₃ | 2-Formyl-C₆H₄-CH₂ |
| 225 | CH₃ | CH₃ | 3-Formyl-C₆H₄-CH₂ |
| 226 | CH₃ | CH₃ | 4-Formyl-C₆H₄-CH₂ |
| 227 | CH₃ | CH₃ | 2-(1'-Methoxyiminoeth-1'-yl)-C₆H₄-CH₂ |
| 228 | CH₃ | CH₃ | 3-(1'-Methoxyiminoeth-1'-yl)-C₆H₄-CH₂ |
| 229 | CH₃ | CH₃ | 4-(1'-Methoxyiminoeth-1'-yl)-C₆H₄-CH₂ |
| 230 | CH₃ | CH₃ | 2-SCH₃-C₆H₄-CH₂ |
| 231 | CH₃ | CH₃ | 3-SCH₃-C₆H₄-CH₂ |
| 232 | CH₃ | CH₃ | 4-SCH₃-C₆H₄-CH₂ |
| 233 | CH₃ | CH₃ | 2-SO₂CH₃-C₆H₄-CH₂ |
| 234 | CH₃ | CH₃ | 3-SO₂CH₃-C₆H₄-CH₂ |
| 235 | CH₃ | CH₃ | 4-SO₂CH₃-C₆H₄-CH₂ |
| 236 | CH₃ | CH₃ | 2-OCF₃-C₆H₄-CH₂ |
| 237 | CH₃ | CH₃ | 3-OCF₃-C₆H₄-CH₂ |
| 238 | CH₃ | CH₃ | 4-OCF₃-C₆H₄-CH₂ |
| 239 | CH₃ | CH₃ | 2-OCHF₂-C₆H₄-CH₂ |
| 240 | CH₃ | CH₃ | 3-OCHF₂-C₆H₄-CH₂ |
| 241 | CH₃ | CH₃ | 4-OCHF₂-C₆H₄-CH₂ |
| 242 | CH₃ | CH₃ | 3-CF₃,4-OCF₃-C₆H₃-CH₂ |
| 243 | CH₃ | CH₃ | 1-Naphthyl-CH₂ |
| 244 | CH₃ | CH₃ | 2-Naphthyl-CH₂ |
| 245 | CH₃ | CH₃ | 2-Phenoxyeth-1-yl |
| 246 | CH₃ | CH₃ | 2-(2'-Chlorophenoxy)eth-1-yl |
| 247 | CH₃ | CH₃ | 2-(3'-Chlorophenoxy)eth-1-yl |
| 248 | CH₃ | CH₃ | 2-(4'-Chlorophenoxy)eth-1-yl |
| 249 | CH₃ | CH₃ | 2-(3',5'-Dichlorophenoxy)eth-1-yl |
| 250 | CH₃ | CH₃ | 2-(2'-Cyanophenoxy)eth-1-yl |
| 251 | CH₃ | CH₃ | 2-(3'-Cyanophenoxy)eth-1-yl |
| 252 | CH₃ | CH₃ | 2-(4'-Cyanophenoxy)eth-1-yl |
| 253 | CH₃ | CH₃ | 2-(2'-Methylphenoxy)eth-1-yl |
| 254 | CH₃ | CH₃ | 2-(3'-Methylphenoxy)eth-1-yl |
| 255 | CH₃ | CH₃ | 2-(4'-Methylphenoxy)eth-1-yl |
| 256 | CH₃ | CH₃ | 2-(3'-t-Butylphenoxy)eth-1-yl |
| 257 | CH₃ | CH₃ | 2-(4'-t-Butylphenoxy)eth-1-yl |
| 258 | CH₃ | CH₃ | 2-(2'-Nitrophenoxy)eth-1-yl |
| 259 | CH₃ | CH₃ | 2-(3'-Nitrophenoxy)eth-1-yl |
| 260 | CH₃ | CH₃ | 2-(4'-Nitrophenoxy)eth-1-yl |
| 261 | CH₃ | CH₃ | 2-(2'-Methoxyphenoxy)eth-1-yl |
| 262 | CH₃ | CH₃ | 2-(3'-Methoxyphenoxy)eth-1-yl |
| 263 | CH₃ | CH₃ | 2-(4'-Methoxyphenoxy)eth-1-yl |

TABLE A-continued

| No. | R² | R³ | R⁴ |
|---|---|---|---|
| 264 | CH₃ | CH₃ | 2-(2'-Trifluoromethylphenoxy)eth-1-yl |
| 265 | CH₃ | CH₃ | 2-(3'-Trifluoromethylphenoxy)eth-1-yl |
| 266 | CH₃ | CH₃ | 2-(4'-Trifluoromethylphenoxy)eth-1-yl |
| 267 | CH₃ | CH₃ | 2-(2'-Acetylphenoxy)eth-1-yl |
| 268 | CH₃ | CH₃ | 2-(3'-Acetylphenoxy)eth-1-yl |
| 269 | CH₃ | CH₃ | 2-(4'-Acetylphenoxy)eth-1-yl |
| 270 | CH₃ | CH₃ | 2-(2'-Methoxycarbonyl)eth-1-yl |
| 271 | CH₃ | CH₃ | 2-(3'-Methoxycarbonyl)eth-1-yl |
| 272 | CH₃ | CH₃ | 2-(4'-Methoxycarbonyl)eth-1-yl |
| 273 | CH₃ | CH₃ | 2-(2'-Dimethylaminocarbonyl)eth-1-yl |
| 274 | CH₃ | CH₃ | 2-(3'-Dimethylaminocarbonyl)eth-1-yl |
| 275 | CH₃ | CH₃ | 2-(4'-Dimethylaminocarbonyl)eth-1-yl |
| 276 | CH₃ | CH₃ | 2-(2'-Aminothiocarbonyl)eth-1-yl |
| 277 | CH₃ | CH₃ | 2-(3'-Aminothiocarbonyl)eth-1-yl |
| 278 | CH₃ | CH₃ | 2-(4'-Aminothiocarbonyl)eth-1-yl |
| 279 | CH₃ | CH₃ | 2-(2'-Methylsulfonyl)eth-1-yl |
| 280 | CH₃ | CH₃ | 2-(3'-Methylsulfonyl)eth-1-yl |
| 281 | CH₃ | CH₃ | 2-(4'-Methylsulfonyl)eth-1-yl |
| 282 | CH₃ | CH₃ | 3-Phenoxyprop-1-yl |
| 283 | CH₃ | CH₃ | 3-(2'-Chlorophenoxy)prop-1-yl |
| 284 | CH₃ | CH₃ | 3-(3'-Clorophenoxy)prop-1-yl |
| 285 | CH₃ | CH₃ | 3-(4'-Chlorophenoxy)prop-1-yl |
| 286 | CH₃ | CH₃ | 3-(3',5',Dichlorophenoxy)prop-1-yl |
| 287 | CH₃ | CH₃ | 3-(2'-Cyanophenoxy)prop-1-yl |
| 288 | CH₃ | CH₃ | 3-(3'-Cyanophenoxy)prop-1-yl |
| 289 | CH₃ | CH₃ | 3-(4'-Cyanophenoxy)prop-1-yl |
| 290 | CH₃ | CH₃ | 3-(2'-Methylphenoxy)prop-1-yl |
| 291 | CH₃ | CH₃ | 3-(3'-Methylphenoxy)prop-1-yl |
| 292 | CH₃ | CH₃ | 3-(4'-Methylphenoxy)prop-1-yl |
| 293 | CH₃ | CH₃ | 3-(2'-Methoxyphenoxy)prop-1-yl |
| 294 | CH₃ | CH₃ | 3-(3'-Methoxyphenoxy)prop-1-yl |
| 295 | CH₃ | CH₃ | 3-(4'-Methoxyphenoxy)prop-1-yl |
| 296 | CH₃ | CH₃ | 3-(2'-Trifluoromethylphenoxy)prop-1-yl |
| 297 | CH₃ | CH₃ | 3-(3'-Trifluoromethylphenoxy)prop-1-yl |
| 298 | CH₃ | CH₃ | 3-(4'-Trifluoromethylphenoxy)prop-1-yl |
| 299 | CH₃ | CH₃ | 4-Phenoxybut-1-yl |
| 300 | CH₃ | CH₃ | 2-Phenyleth-1-yl |
| 301 | CH₃ | CH₃ | 2-(2'-chlorophenyl)eth-1-yl |
| 302 | CH₃ | CH₃ | 2-(3'-chlorophenyl)eth-1-yl |
| 303 | CH₃ | CH₃ | 2-(4'-chlorophenyl)eth-1-yl |
| 304 | CH₃ | CH₃ | 2-(3',5'-Dichlorophenyl)eth-1-yl |
| 305 | CH₃ | CH₃ | 2-(2'-Cyanophenyl)eth-1-yl |
| 306 | CH₃ | CH₃ | 2-(3'-Cyanophenyl)eth-1-yl |
| 307 | CH₃ | CH₃ | 2-(4'-Cyanophenyl)eth-1-yl |
| 308 | CH₃ | CH₃ | 2-(2'-Methylphenyl)eth-1-yl |
| 309 | CH₃ | CH₃ | 2-(3'-Methylphenyl)eth-1-yl |
| 310 | CH₃ | CH₃ | 2-(4'-Methylphenyl)eth-1-yl |
| 311 | CH₃ | CH₃ | 2-(2'-Methoxyphenyl)eth-1-yl |
| 312 | CH₃ | CH₃ | 2-(3'-Methoxyphenyl)eth-1-yl |
| 313 | CH₃ | CH₃ | 2-(4'-Methoxyphenyl)eth-1-yl |
| 314 | CH₃ | CH₃ | 2-(2'-Trifluoromethylphenyl)eth-1-yl |
| 315 | CH₃ | CH₃ | 2-(3'-Trifluoromethylphenyl)eth-1-yl |
| 316 | CH₃ | CH₃ | 2-(4'-Trifluoromethylphenyl)eth-1-yl |
| 317 | CH₃ | CH₃ | 3-Phenylprop-1-yl |
| 318 | CH₃ | CH₃ | 3-(2'-Chlorophenyl)prop-1-yl |
| 319 | CH₃ | CH₃ | 3-(3'-Chlorophenyl)prop-1-yl |
| 320 | CH₃ | CH₃ | 3-(4'-Chlorophenyl)prop-1-yl |
| 321 | CH₃ | CH₃ | 3-(2'-Cyanophenyl)prop-1-yl |
| 322 | CH₃ | CH₃ | 3-(3'-Cyanophenyl)prop-1-yl |
| 323 | CH₃ | CH₃ | 3-(4'-Cyanophenyl)prop-1-yl |
| 324 | CH₃ | CH₃ | 3-(2'-Trifluoromethylphenyl)prop-1-yl |
| 325 | CH₃ | CH₃ | 4-Phenylbut-1-yl |
| 326 | CH₃ | CH₃ | 4-(4'-Chlorophenyl)but-1-yl |
| 327 | CH₃ | CH₃ | 6-(4'-Chlorophenyl)hex-1-yl |
| 328 | CH₃ | CH₃ | 2-Pyridylmethyl |
| 329 | CH₃ | CH₃ | 3-Pyridylmethyl |
| 330 | CH₃ | CH₃ | 4-Pyridylmethyl |
| 331 | CH₃ | CH₃ | 4-Chloropyrid-2-ylmethyl |
| 332 | CH₃ | CH₃ | 5-Chloropyrid-2-ylmethyl |
| 333 | CH₃ | CH₃ | 6-Chloropyrid-2-ylmethyl |
| 334 | CH₃ | CH₃ | 5-Chloropyrid-3-ylmethyl |
| 335 | CH₃ | CH₃ | 6-Chloropyrid-3-ylmethyl |
| 336 | CH₃ | CH₃ | 2-Chloropyrid-4-ylmethyl |
| 337 | CH₃ | CH₃ | 2-Pyrimidinylmethyl |
| 338 | CH₃ | CH₃ | 4-Chloropyrimidin-2-ylmethyl |
| 339 | CH₃ | CH₃ | 5-Chloropyrimidin-2-ylmethyl |
| 340 | CH₃ | CH₃ | 2-Chloropyrimidin-4-ylmethyl |

TABLE A-continued

| No. | R² | R³ | R⁴ |
|---|---|---|---|
| 341 | CH₃ | CH₃ | 6-Chloropyrimidin-4-ylmethyl |
| 342 | CH₃ | CH₃ | 2-Chloropyrimidin-5-ylmethyl |
| 343 | CH₃ | CH₃ | 4-Pyridazinylmethyl |
| 344 | CH₃ | CH₃ | 2-Pyrazinylmethyl |
| 345 | CH₃ | CH₃ | 5-Chloropyrazin-2-ylmethyl |
| 346 | CH₃ | CH₃ | 6-Chloropyrazin-2-ylmethyl |
| 347 | CH₃ | CH₃ | 3-Pyridazinylmethyl |
| 348 | CH₃ | CH₃ | 6-Chloropyridazin-3-ylmethyl |
| 349 | CH₃ | CH₃ | 1,3,5-Triazinylmethyl |
| 350 | CH₃ | CH₃ | 2-Furylmethyl |
| 351 | CH₃ | CH₃ | 3-Furylmethyl |
| 352 | CH₃ | CH₃ | 4-Bromofur-2-ylmethyl |
| 353 | CH₃ | CH₃ | 5-Chlorofur-2-ylmethyl |
| 354 | CH₃ | CH₃ | 2-Thienylmethyl |
| 355 | CH₃ | CH₃ | 3-Thienylmethyl |
| 356 | CH₃ | CH₃ | 5-Methylthien-3-ylmethyl |
| 357 | CH₃ | CH₃ | 5-Chlorothien-2-ylmethyl |
| 358 | CH₃ | CH₃ | 2-Chlorothien-4-ylmethyl |
| 359 | CH₃ | CH₃ | 2-Pyrrolylmethyl |
| 360 | CH₃ | CH₃ | 3-Pyrrolylmethyl |
| 361 | CH₃ | CH₃ | 2-Oxazolylmethyl |
| 362 | CH₃ | CH₃ | 4-Methyloxazol-2-ylmethyl |
| 363 | CH₃ | CH₃ | 5-Methyloxazol-2-ylmethyl |
| 364 | CH₃ | CH₃ | 4-Chlorooxazol-2-ylmethyl |
| 365 | CH₃ | CH₃ | 5-Chlorooxazol-2-ylmethyl |
| 366 | CH₃ | CH₃ | 4-Oxazolylmethyl |
| 367 | CH₃ | CH₃ | 2-Methyloxazol-4-ylmethyl |
| 368 | CH₃ | CH₃ | 5-Methyloxazol-4-ylmethyl |
| 369 | CH₃ | CH₃ | 2-Chlorooxazol-4-ylmethyl |
| 370 | CH₃ | CH₃ | 5-Chlorooxazol-4-ylmethyl |
| 371 | CH₃ | CH₃ | 5-Oxazolylmethyl |
| 372 | CH₃ | CH₃ | 2-Methyloxazol-5-ylmethyl |
| 373 | CH₃ | CH₃ | 4-Methyloxazol-5-ylmethyl |
| 374 | CH₃ | CH₃ | 2-Chlorooxazol-5-ylmethyl |
| 375 | CH₃ | CH₃ | 4-Chlorooxazol-5-ylmethyl |
| 376 | CH₃ | CH₃ | 2-Thiazolylmethyl |
| 377 | CH₃ | CH₃ | 4-Methylthiazol-2-ylmethyl |
| 378 | CH₃ | CH₃ | 5-Methylthiazol-2-ylmethyl |
| 379 | CH₃ | CH₃ | 4-Chlorothiazol-2-ylmethyl |
| 380 | CH₃ | CH₃ | 5-Chlorothiazol-2-ylmethyl |
| 381 | CH₃ | CH₃ | 4-Thiazolylmethyl |
| 382 | CH₃ | CH₃ | 2-Methylthiazol-4-ylmethyl |
| 383 | CH₃ | CH₃ | 5-Methylthiazol-4-ylmethyl |
| 384 | CH₃ | CH₃ | 2-Chlorothiazol-4-ylmethyl |
| 385 | CH₃ | CH₃ | 5-Chlorothiazol-4-ylmethyl |
| 386 | CH₃ | CH₃ | 5-Thiazolylmethyl |
| 387 | CH₃ | CH₃ | 2-Methylthiazol-5-ylmethyl |
| 388 | CH₃ | CH₃ | 4-Methylthiazol-5-ylmethyl |
| 389 | CH₃ | CH₃ | 2-Chlorothiazol-5-ylmethyl |
| 390 | CH₃ | CH₃ | 4-Chlorothiazol-5-ylmethyl |
| 391 | CH₃ | CH₃ | 3-Isoxazolylmethyl |
| 392 | CH₃ | CH₃ | 4-Methylisoxazol-3-ylmethyl |
| 393 | CH₃ | CH₃ | 5-Methylisoxazol-3-ylmethyl |
| 394 | CH₃ | CH₃ | 4-Chloroisoxazol-3-ylmethyl |
| 395 | CH₃ | CH₃ | 5-Chloroisoxazol-3-ylmethyl |
| 396 | CH₃ | CH₃ | 4-Isoxazolylmethyl |
| 397 | CH₃ | CH₃ | 3-Methylisoxazol-4-ylmethyl |
| 398 | CH₃ | CH₃ | 5-Methylisoxazol-4-ylmethyl |
| 399 | CH₃ | CH₃ | 3-Chloroisoxazol-4-ylmethyl |
| 400 | CH₃ | CH₃ | 5-Chloroisoxazol-4-ylmethyl |
| 401 | CH₃ | CH₃ | 5-Isoxazolylmethyl |
| 402 | CH₃ | CH₃ | 3-Methylisoxazol-5-ylmethyl |
| 403 | CH₃ | CH₃ | 4-Methylisoxazol-5-ylmethyl |
| 404 | CH₃ | CH₃ | 3-Chloroisoxazol-5-ylmethyl |
| 405 | CH₃ | CH₃ | 4-Chloroisoxazol-5-ylmethyl |
| 406 | CH₃ | CH₃ | 3-Isothiazolylmethyl |
| 407 | CH₃ | CH₃ | 4-Methylisothiazol-3-ylmethyl |
| 408 | CH₃ | CH₃ | 5-Methylisothiazol-3-ylmethyl |
| 409 | CH₃ | CH₃ | 4-Chloroisothiazol-3-ylmethyl |
| 410 | CH₃ | CH₃ | 5-Chloroisothiazol-3-ylmethyl |
| 411 | CH₃ | CH₃ | 4-Isothiazolylmethyl |
| 412 | CH₃ | CH₃ | 3-Methylisothiazol-4-ylmethyl |
| 413 | CH₃ | CH₃ | 5-Methylisothiazol-4-ylmethyl |
| 414 | CH₃ | CH₃ | 3-Chloroisothiazol-4-ylmethyl |
| 415 | CH₃ | CH₃ | 5-Chloroisothiazol-4-ylmethyl |
| 416 | CH₃ | CH₃ | 5-Isothiazolylmethyl |
| 417 | CH₃ | CH₃ | 3-Methylisothiazol-5-ylmethyl |

TABLE A-continued

| No. | R² | R³ | R⁴ |
|---|---|---|---|
| 418 | CH₃ | CH₃ | 4-Methylisothiazol-5-ylmethyl |
| 419 | CH₃ | CH₃ | 3-Chloroisothiazol-5-ylmethyl |
| 420 | CH₃ | CH₃ | 4-Chloroisothiazol-5-ylmethyl |
| 421 | CH₃ | CH₃ | 4-Imidazolylmethyl |
| 422 | CH₃ | CH₃ | 1-Phenylpyrazol-3-ylmethyl |
| 423 | CH₃ | CH₃ | 1-Methylimidazol-4-ylmethyl |
| 424 | CH₃ | CH₃ | 1-Phenyl-1,2,4-triazol-3-ylmethyl |
| 425 | CH₃ | CH₃ | 1,2,4-Oxadiazol-3-ylmethyl |
| 426 | CH₃ | CH₃ | 5-Chloro-1,2,4-oxadiazol-3-ylmethyl |
| 427 | CH₃ | CH₃ | 5-Methyl-1,2,4-oxadiazol-3-ylmethyl |
| 428 | CH₃ | CH₃ | S-Trifluromethyl-1,2,4-oxadiazol-3-yl-methyl |
| 429 | CH₃ | CH₃ | 1,3,4-Oxadiazol-2-ylmethyl |
| 430 | CH₃ | CH₃ | 5-Chloro-1,3,4-oxadiazol-2-ylmethyl |
| 431 | CH₃ | CH₃ | 5-Methyl-1,3,4-oxadiazol-2-ylmethyl |
| 432 | CH₃ | CH₃ | 5-Methoxy1,3,4-oxadiazol-2-ylmethyl |
| 433 | CH₃ | CH₃ | 1,2,4-Thiadiazol-3-ylmethyl |
| 434 | CH₃ | CH₃ | 5-Chloro-1,2,4-thiadiazol-3-ylmethyl |
| 435 | CH₃ | CH₃ | 5-Methyl-1,2,4-thiadiazol-3-ylmethyl |
| 436 | CH₃ | CH₃ | 1,3,4-Thiadiazol-2-ylmethyl |
| 437 | CH₃ | CH₃ | 5-Chloro-1,3,4-thiadiazol-2-ylmethyl |
| 438 | CH₃ | CH₃ | 5-Methyl-1,3,4-thiadiazol-2-ylmethyl |
| 439 | CH₃ | CH₃ | 5-Cyano-1,3,4-thiadiazol-2-ylmethyl |
| 440 | CH₃ | CH₃ | 2-(2'-Pyridyloxy)eth-1-yl |
| 441 | CH₃ | CH₃ | 2-(3'-Pyridyloxy)eth-1-yl |
| 442 | CH₃ | CH₃ | 2-(4'-Pyridyloxy)eth-1-yl |
| 443 | CH₃ | CH₃ | 2-(2'-Pyrimidinyloxy)eth-1-yl |
| 444 | CH₃ | CH₃ | 2-(4'-Pyrimidinyloxy)eth-1-yl |
| 445 | CH₃ | CH₃ | 2-(5'-Pyrimidinyloxy)eth-1-yl |
| 446 | CH₃ | CH₃ | 2-(2'-Pyrazinyloxy)eth-1-yl |
| 447 | CH₃ | CH₃ | 2-(2'-Pyridazinyloxy)eth-1-yl |
| 448 | CH₃ | CH₃ | 2-(3'-Pyridazinyloxy)eth-1-yl |
| 449 | CH₃ | CH₃ | 2-(1',3',5'-Triazinyloxy)eth-1-yl |
| 450 | CH₃ | CH₃ | 2-(5'-Methylisoxazol-3'-yloxy)eth-1-yl |
| 451 | CH₃ | CH₃ | 2-(5'-Chloroisoxazol-3'-yloxy)eth-1-yl |
| 452 | CH₃ | CH₃ | 2-(2'-Methoxythiazol-4'-yloxy)eth-1-yl |
| 453 | CH₃ | CH₃ | 2-(4'-Chlorooxazol-2'-yloxy)eth-1-yl |
| 454 | CH₃ | CH₃ | 2-(1'-Phenyl-1'H-1',2',4'-triazol-3'-yl-oxy)eth-1-yl |
| 455 | CH₃ | CH₃ | 2-(1'-Phenylpyrazol-3'-yloxy)eth-1-yl |
| 456 | CH₃ | CH₃ | C₆H₅ |
| 457 | CH₃ | CH₃ | 2-Cl-C₆H₄ |
| 458 | CH₃ | CH₃ | 3-Cl-C₆H₄ |
| 459 | CH₃ | CH₃ | 4-Cl-C₆H₄ |
| 460 | CH₃ | CH₃ | 2,3-Cl₂-C₆H₃ |
| 461 | CH₃ | CH₃ | 2,4-Cl₂-C₆H₃ |
| 462 | CH₃ | CH₃ | 2,5-Cl₂-C₆H₃ |
| 463 | CH₃ | CH₃ | 3,4-Cl₂-C₆H₃ |
| 464 | CH₃ | CH₃ | 3,5-Cl₂-C₆H₃ |
| 465 | CH₃ | CH₃ | 4-CN-C₆H₄ |
| 466 | CH₃ | CH₃ | 2-NO₂-C₆H₄ |
| 467 | CH₃ | CH₃ | 3-NO₂-C₆H₄ |
| 468 | CH₃ | CH₃ | 4-NO₂-C₆H₄ |
| 469 | CH₃ | CH₃ | 2,4-(NO₂)₂-C₆H₃ |
| 470 | CH₃ | CH₃ | 2-CH₃-C₆H₄ |
| 471 | CH₃ | CH₃ | 3-CH₃-C₆H₄ |
| 472 | CH₃ | CH₃ | 4-CH₃-C₆H₄ |
| 473 | CH₃ | CH₃ | 2,3-(CH₃)₂-C₆H₃ |
| 474 | CH₃ | CH₃ | 2,4-(CH₃)₂-C₆H₃ |
| 475 | CH₃ | CH₃ | 2,5-(CH₃)₂-C₆H₃ |
| 476 | CH₃ | CH₃ | 2,6-(CH₃)₂-C₆H₃ |
| 477 | CH₃ | CH₃ | 2-C₆H₅-C₆H₄ |
| 478 | CH₃ | CH₃ | 3-C₆H₅-C₆H₄ |
| 479 | CH₃ | CH₃ | 4-C₆H₅-C₆H₄ |
| 480 | CH₃ | CH₃ | 3-OCH₃-C₆H₄ |
| 481 | CH₃ | CH₃ | 4-OCH₃-C₆H₄ |
| 482 | CH₃ | CH₃ | 3-Acetyl-C₆H₄ |
| 483 | CH₃ | CH₃ | 4-Acetyl-C₆H₄ |
| 484 | CH₃ | CH₃ | 3-Methoxycarbonyl-C₆H₄ |
| 485 | CH₃ | CH₃ | 4-Methoxycarbonyl-C₆H₄ |
| 486 | CH₃ | CH₃ | 3-CF₃-C₆H₄ |
| 487 | CH₃ | CH₃ | 4-CF₃-C₆H₄ |
| 488 | CH₃ | CH₃ | 2-Naphthyl |
| 489 | CH₃ | CH₃ | 6-Chloropyridazin-3-yl |
| 490 | CH₃ | CH₃ | 5-Chloropyrazin-2-yl |
| 491 | CH₃ | CH₃ | Quinolin-2-yl |
| 492 | CH₃ | CH₃ | 2,5-Dimethylpyrazin-3-yl |

TABLE A-continued

| No. | R² | R³ | R⁴ |
| --- | --- | --- | --- |
| 493 | CH₃ | CH₃ | Pyrazin-2-yl |
| 494 | CH₃ | CH₃ | 3-Chloropyrid-2-yl |
| 495 | CH₃ | CH₃ | 6-Chloropyrid-2-yl |
| 496 | CH₃ | CH₃ | 4-Trifluoromethyl,6-Chloropyrid-2-yl |
| 497 | CH₃ | CH₃ | 4-Trifluoromethylpyrid-2-yl |
| 498 | CH₃ | CH₃ | 6-Trifluoromethylpyrid-2-yl |
| 499 | CH₃ | CH₃ | 6-Methoxypyrid-2-yl |
| 500 | CH₃ | CH₃ | 5-Chloropyrid-2-yl |
| 501 | CH₃ | CH₃ | Pyrid-2-yl |
| 502 | CH₃ | CH₃ | Benzothiazol-2-yl |
| 503 | CH₃ | CH₃ | 7-Chloroquinolin-4-yl |
| 504 | CH₃ | CH₃ | 3-Nitropyrid-2-yl |
| 505 | CH₃ | CH₃ | Pyrrol-3-yl |
| 506 | CH₃ | CH₃ | Pyrrol-2-yl |
| 507 | CH₃ | CH₃ | 2,6-Dioctylpyrid-4-yl |
| 508 | CH₃ | CH₃ | 5-Nitropyrid-2-yl |
| 509 | CH₃ | CH₃ | Pyrid-4-yl |
| 510 | CH₃ | CH₃ | Pyrid-3-yl |
| 511 | CH₃ | CH₃ | Pyrimidin-2-yl |
| 512 | CH₃ | CH₃ | Pyrimidin-4-yl |
| 513 | CH₃ | CH₃ | Quinazolin-4-yl |
| 514 | CH₃ | CH₃ | 6-Chloropyrimidin-4-yl |
| 515 | CH₃ | CH₃ | 6-Methoxypyrimidin-4-yl |
| 516 | CH₃ | CH₃ | 2,5,6-Trichloropyrimidin-4-yl |
| 517 | CH₃ | CH₃ | 2,6-Dimethylpyrimidin-4-yl |
| 518 | CH₃ | CH₃ | 2-Methyl,6-Chloropyrimidin-4-yl |
| 519 | CH₃ | CH₃ | 2-Methyl,6-Ethoxypyrimidin-4-yl |
| 520 | CH₃ | CH₃ | 4,5,6-Trichloropyrimidin-2-yl |
| 521 | CH₃ | CH₃ | 4,6-Dimethoxypyrimidin-2-yl |
| 522 | CH₃ | CH₃ | 4,6-Dimethylpyrimidin-2-yl |
| 523 | CH₃ | CH₃ | 4,6-Dichloropyrimidin-2-yl |
| 524 | CH₃ | CH₃ | 4-Methyl,6-methoxypyrimidin-2-yl |
| 525 | CH₃ | CH₃ | 4-Chloro,6-methoxypyrimidin-2-yl |
| 526 | CH₃ | CH₃ | 6-Chloroquinoxalin-2-yl |
| 527 | CH₃ | CH₃ | 3,6-Dichloro-1,2,4-triazin-5-yl |
| 528 | CH₃ | CH₃ | 4-Methoxy-1,3,5-triazin-2-yl |
| 529 | CH₃ | CH₃ | 4-Ethoxy-1,3,5-triazin-2-yl |
| 530 | CH₃ | CH₃ | 4,6-Dichloro-1,3,5-triazin-2-yl |
| 531 | CH₃ | CH₃ | 4-Ethoxy,6-Chloro-1,3,5-triazin-2-yl |
| 532 | CH₃ | CH₃ | Isoxazol-3-yl |
| 533 | CH₃ | CH₃ | Thien-2-yl |
| 534 | CH₃ | CH₃ | Fur-2-yl |
| 535 | CH₃ | CH₃ | Thiatriazol-5-yl |
| 536 | CH₃ | CH₃ | (E)-1-Chloropropen-3-yl |
| 537 | CH₃ | CH₃ | (E)-4-(4'-Chlorophenyl)but-2-en-1-yl |
| 538 | CH₃ | CH₃ | Propyn-3-yl |
| 539 | CH₃ | CH₃ | Methylcarbonyl |
| 540 | CH₃ | CH₃ | Ethylcarbonyl |
| 541 | CH₃ | CH₃ | n-Propylcarbonyl |
| 542 | CH₃ | CH₃ | i-Propylcarbonyl |
| 543 | CH₃ | CH₃ | n-Butylcarbonyl |
| 544 | CH₃ | CH₃ | s-Butylcarbonyl |
| 545 | CH₃ | CH₃ | i-Butylcarbonyl |
| 546 | CH₃ | CH₃ | t-Butylcarbonyl |
| 547 | CH₃ | CH₃ | n-Pentylcarbonyl |
| 548 | CH₃ | CH₃ | i-Pentylcarbonyl |
| 549 | CH₃ | CH₃ | neo-Pentylcarbonyl |
| 550 | CH₃ | CH₃ | n-Hexylcarbonyl |
| 551 | CH₃ | CH₃ | n-Octylcarbonyl |
| 552 | CH₃ | CH₃ | 1-Propenylcarbonyl |
| 553 | CH₃ | CH₃ | 2-Penten-1-ylcarbonyl |
| 554 | CH₃ | CH₃ | 2,5-Heptadien-1-ylcarbonyl |
| 555 | CH₃ | CH₃ | Benzoyl |
| 556 | CH₃ | CH₃ | 2-Chlorobenzoyl |
| 557 | CH₃ | CH₃ | 3-Chlorobenzoyl |
| 558 | CH₃ | CH₃ | 4-Chlorobenzoyl |
| 559 | CH₃ | CH₃ | 2-Cyanobenzoyl |
| 560 | CH₃ | CH₃ | 3-Cyanobenzoyl |
| 561 | CH₃ | CH₃ | 4-Cyanobenzoyl |
| 562 | CH₃ | CH₃ | 4-Methoxybenzoyl |
| 563 | CH₃ | CH₃ | 2-Pyridylcarbonyl |
| 564 | CH₃ | CH₃ | 3-Pyridylcarbonyl |
| 565 | CH₃ | CH₃ | 4-Pyridylcarbonyl |
| 566 | CH₃ | CH₃ | 2-Pyrimidinylcarbonyl |
| 567 | CH₃ | CH₃ | 2-Oxazolylcarbonyl |
| 568 | CH₃ | CH₃ | 4-Methylisoxazol-5-ylcarbonyl |
| 569 | CH₃ | CH₃ | Methylsulfonyl |

TABLE A-continued

| No. | R² | R³ | R⁴ |
|---|---|---|---|
| 570 | CH₃ | CH₃ | Ethylsulfonyl |
| 571 | CH₃ | CH₃ | n-Propylsulfonyl |
| 572 | CH₃ | CH₃ | i-Propylsulfonyl |
| 573 | CH₃ | CH₃ | n-Butylsulfonyl |
| 574 | CH₃ | CH₃ | t-Butylsulfonyl |
| 575 | CH₃ | CH₃ | n-Pentylsulfonyl |
| 576 | CH₃ | CH₃ | neo-Pentylsulfonyl |
| 577 | CH₃ | CH₃ | n-Hexylsulfonyl |
| 578 | CH₃ | CH₃ | n-Octylsulfonyl |
| 579 | CH₃ | CH₃ | Phenylsulfonyl |
| 580 | CH₃ | CH₃ | 2-Chlorophenylsulfonyl |
| 581 | CH₃ | CH₃ | 3-Chlorophenylsulfonyl |
| 582 | CH₃ | CH₃ | 4-Chlorophenylsulfonyl |
| 583 | CH₃ | CH₃ | 2-Cyanophenylsulfonyl |
| 584 | CH₃ | CH₃ | 3-Cyanophenylsulfonyl |
| 585 | CH₃ | CH₃ | 4-Cyanophenylsulfonyl |
| 586 | CH₃ | CH₃ | 2-Pyridylsulfonyl |
| 587 | CH₃ | CH₃ | 3-Pyridylsulfonyl |
| 588 | CH₃ | CH₃ | 4-Pyridylsulfonyl |
| 589 | CH₃ | CH₃ | 2-Pyrimidinylsulfonyl |
| 590 | CH₃ | CH₃ | 4-Oxazolylsulfonyl |
| 591 | CH₃ | CH₃ | 5-Chlorothiazol-2ylsulfonyl |
| 592 | CH₃ | CH₃ | 2-t-C₄H₉-C₆H₄-CH₂ |
| 593 | CH₃ | CH₃ | 3-t-C₄H₉-C₆H₄-CH₂ |
| 594 | CH₃ | CH₃ | 4-t-C₄H₉-C₆H₄-CH₂ |
| 595 | CH₃ | CH₃ | 2-(4'-Chlorothiazol-2'-yloxy)eth-1-yl |
| 596 | CH₃ | CH₃ | 2-(1'-Methylpyrazol-4'-yloxy)eth-1-yl |
| 597 | CH₃ | CH₃ | 4-Br-C₆H₄ |
| 598 | CH₃ | CH₃ | 3,5-(CH₃)₂-C₆H₃ |
| 599 | CH₃ | CH₃ | 4-C₂H₅-C₆H₄ |
| 600 | CH₃ | CH₃ | 3-Dimethylaminocarbonyl-C₆H₄ |
| 601 | CH₃ | CH₃ | 4-Dimethylaminocarbonyl-C₆H₄ |
| 602 | CH₃ | CH₃ | 2-Hydroxyprop-1-yl |
| 603 | CH₃ | CH₃ | 6-Hydroxy-2-methylpyrimidin-4-ylmethyl |
| 604 | CH₃ | CH₃ | [6-OH,2-CH(CH₃)₂-pyrimidin-4-yl]-CH₂ |
| 605 | CH₃ | CH₃ | [6-OH,2-CH(CH₂)₂-pyrimidin-4-yl]-CH₂ |
| 606 | CH₃ | CH₃ | 5-(2'-Furan)pent-1-yl |
| 607 | CH₃ | CH₃ | 5-(2'-N-Methylpyrrol)-pent-1-yl |
| 608 | CH₃ | CH₃ | [2-(4-Cl-C₆H₄)-oxazol-4-yl]-CH₂ |
| 609 | CH₃ | CH₃ | 3-CF₃-pyridin-2-yl |
| 610 | CH₃ | CH₃ | 5-CF₃-pyridin-2-yl |
| 611 | CH₃ | CH₃ | 6-(2'-Thienyl)hex-1-yl |
| 612 | CH₃ | t-C₄H₉ | H |
| 613 | CH₃ | t-C₄H₉ | CH₃ |
| 614 | CH₃ | t-C₄H₉ | C₂H₅ |
| 615 | CH₃ | t-C₄H₉ | n-C₃H₇ |
| 616 | CH₃ | t-C₄H₉ | i-C₃H₇ |
| 617 | CH₃ | t-C₄H₉ | Cyclopropyl |
| 618 | CH₃ | t-C₄H₉ | n-C₄H₉ |
| 619 | CH₃ | t-C₄H₉ | t-C₄H₉ |
| 620 | CH₃ | t-C₄H₉ | n-C₆H₁₃ |
| 621 | CH₃ | t-C₄H₉ | (E)-1-Chloropropen-3-yl |
| 622 | CH₃ | t-C₄H₉ | Propyn-3-yl |
| 623 | CH₃ | t-C₄H₉ | 3-Methylbut-2-en-1-yl |
| 624 | CH₃ | t-C₄H₉ | 2-Naphthyl-CH₂ |
| 625 | CH₃ | t-C₄H₉ | 4-Cl-C₆H₄-CH₂ |
| 626 | CH₃ | t-C₄H₉ | (E)-4-(4'-Chlorophenyl)but-2-en-1-yl |
| 627 | CH₃ | t-C₄H₉ | 6-(4'-Chlorophenyl)hex-1-yl |
| 628 | CH₃ | t-C₄H₉ | 3-CF₃-C₆H₄ |
| 629 | CH₃ | C₆H₅ | H |
| 630 | CH₃ | C₆H₅ | CH₃ |
| 631 | CH₃ | C₆H₅ | C₂H₅ |
| 632 | CH₃ | C₆H₅ | n-C₃H₇ |
| 633 | CH₃ | C₆H₅ | i-C₃H₇ |
| 634 | CH₃ | C₆H₅ | Cyclopropyl |
| 635 | CH₃ | C₆H₅ | n-C₄H₉ |
| 636 | CH₃ | C₆H₅ | t-C₄H₉ |
| 637 | CH₃ | C₆H₅ | n-C₆H₁₃ |
| 638 | CH₃ | C₆H₅ | 4-Cl-C₆H₄-CH₂ |
| 639 | CH₃ | C₆H₅ | 3-CF₃-C₆H₄ |
| 640 | CH₃ | C₆H₅ | 6-(4'-Chlorophenyl)hex-1-yl |
| 641 | CH₃ | C₆H₅ | (E)-4-(4'-Chlorophenyl)but-2-en-1-yl |
| 642 | CH₃ | H | H |
| 643 | CH₃ | H | CH₃ |
| 644 | CH₃ | H | C₂H₅ |
| 645 | CH₃ | H | n-C₃H₇ |
| 646 | CH₃ | H | i-C₃H₇ |

TABLE A-continued

| No. | R² | R³ | R⁴ |
|---|---|---|---|
| 647 | CH₃ | OH | H |
| 648 | CH₃ | OH | CH₃ |
| 649 | CH₃ | OH | C₂H₅ |
| 650 | CH₃ | OH | n-C₃H₇ |
| 651 | CH₃ | OH | i-C₃H₇ |
| 652 | CH₃ | Cl | CH₃ |
| 653 | CH₃ | Cl | C₂H₅ |
| 654 | CH | Cl | n-C₃H₇ |
| 655 | CH₃ | Cl | i-C₃H₇ |
| 656 | CH₃ | OCH₃ | H |
| 657 | CH₃ | OCH₃ | CH₃ |
| 658 | CH₃ | OCH₃ | C₂H₅ |
| 659 | CH₃ | OCH₃ | n-C₃H₇ |
| 660 | CH₃ | OCH₃ | i-C₃H₇ |
| 661 | CH₃ | SCH₃ | H |
| 662 | CH₃ | SCH₃ | CH₃ |
| 663 | CH₃ | SCH₃ | C₂H₅ |
| 664 | CH₃ | SCH₃ | n-C₃H₇ |
| 665 | CH₃ | SCH₃ | i-C₃H₇ |
| 666 | CH₃ | Cyclopropyl | H |
| 667 | CH₃ | Cyclopropyl | CH₃ |
| 668 | CH₃ | Cyclopropyl | C₂H₅ |
| 669 | CH₃ | Cyclopropyl | n-C₃H₇ |
| 670 | CH₃ | Cyclopropyl | i-C₃H₇ |
| 671 | CH₃ | 2-Pyridyl | H |
| 672 | CH₃ | 2-Pyridyl | CH₃ |
| 673 | CH₃ | 2-Pyridyl | C₂H₅ |
| 674 | CH₃ | 2-Pyridyl | n-C₃H₇ |
| 675 | CH₃ | 2-Pyridyl | i-C₃H₇ |
| 676 | CH₃ | 3-Pyridyl | H |
| 677 | CH₃ | 3-Pyridyl | CH₃ |
| 678 | CH₃ | 3-Pyridyl | C₂H₅ |
| 679 | CH₃ | 3-Pyridyl | n-C₃H₇ |
| 680 | CH₃ | 3-Pyridyl | i-C₃H₇ |
| 681 | CH₃ | 4-Pyridyl | H |
| 682 | CH₃ | 4-Pyridyl | CH₃ |
| 683 | CH₃ | 4-Pyridyl | C₂H₅ |
| 684 | CH₃ | 4-Pyridyl | n-C₃H₇ |
| 685 | CH₃ | 4-Pyridyl | i-C₃H₇ |
| 686 | CH₃ | 2-Pyridimidyl | H |
| 687 | CH₃ | 2-Pyridimidyl | CH₃ |
| 688 | CH₃ | 2-Pyridimidyl | C₂H₅ |
| 689 | CH₃ | 2-Pyridimidyl | n-C₃H₇ |
| 690 | CH₃ | 2-Pyridimidyl | i-C₃H₇ |
| 691 | CH₃ | 4-Pyridimidy | H |
| 692 | CH₃ | 4-Pyridimidyl | CH₃ |
| 693 | CH₃ | 4-Pyridimidyl | C₂H₅ |
| 694 | CH₃ | 4-Pyridimidyl | n-C₃H₇ |
| 695 | CH₃ | 4-Pyridimidyl | i-C₃H₇ |
| 696 | CH₃ | 5-Pyridimidyl | H |
| 697 | CH₃ | 5-Pyridimidyl | CH₃ |
| 698 | CH₃ | 5-Pyridimidyl | C₂H₅ |
| 699 | CH₃ | 5-Pyridimidyl | n-C₃H₇ |
| 700 | CH₃ | 5-Pyridimidyl | i-C₃H₇ |
| 701 | CH₃ | 1,3,5-Triazinyl | H |
| 702 | CH₃ | 1,3,5-Triazinyl | CH₃ |
| 703 | CH₃ | 1,3,5-Triazinyl | C₂H₅ |
| 704 | CH₃ | 1,3,5-Triazinyl | n-C₃H₇ |
| 705 | CH₃ | 1,3,5-Triazinyl | i-C₃H₇ |
| 706 | CH₃ | 2-Furyl | H |
| 707 | CH₃ | 2-Furyl | CH₃ |
| 708 | CH₃ | 2-Furyl | C₂H₅ |
| 709 | CH₃ | 2-Furyl | n-C₃H₇ |
| 710 | CH₃ | 2-Furyl | i-C₃H₇ |
| 711 | CH₃ | 3-Furyl | H |
| 712 | CH₃ | 3-Furyl | CH₃ |
| 713 | CH₃ | 3-Furyl | C₂H₅ |
| 714 | CH₃ | 3-Furyl | n-C₃H₇ |
| 715 | CH₃ | 3-Furyl | i-C₃H₇ |
| 716 | CH₃ | 2-Thienyl | H |
| 717 | CH₃ | 2-Thienyl | CH₃ |
| 718 | CH₃ | 2-Thienyl | C₂H₅ |
| 719 | CH₃ | 2-Thienyl | n-C₃H₇ |
| 720 | CH₃ | 2-Thienyl | i-C₃H₇ |
| 721 | CH₃ | 3-Thienyl | H |
| 722 | CH₃ | 3-Thienyl | CH₃ |
| 723 | CH₃ | 3-Thienyl | C₂H₅ |

TABLE A-continued

| No. | R² | R³ | R⁴ |
|---|---|---|---|
| 724 | CH₃ | 3-Thienyl | n-C₃H₇ |
| 725 | CH₃ | 3-Thienyl | i-C₃H₇ |
| 726 | CH₃ | 2-Oxazolyl | H |
| 727 | CH₃ | 2-Oxazolyl | CH₃ |
| 728 | CH₃ | 2-Oxazolyl | C₂H₅ |
| 729 | CH₃ | 2-Oxazolyl | n-C₃H₇ |
| 730 | CH₃ | 2-Oxazolyl | i-C₃H₇ |
| 731 | CH₃ | 4-Oxazolyl | H |
| 732 | CH₃ | 4-Oxazolyl | CH₃ |
| 733 | CH₃ | 4-Oxazolyl | C₂H₅ |
| 734 | CH₃ | 4-Oxazolyl | n-C₃H₇ |
| 735 | CH₃ | 4-Oxazolyl | i-C₃H₇ |
| 736 | CH₃ | 2-Thiazolyl | H |
| 737 | CH₃ | 2-Thiazolyl | CH₃ |
| 738 | CH₃ | 2-Thiazolyl | C₂H₅ |
| 739 | CH₃ | 2-Thiazolyl | n-C₃H₇ |
| 740 | CH₃ | 2-Thiazolyl | i-C₃H₇ |
| 741 | CH₃ | 4-Thiazolyl | H |
| 742 | CH₃ | 4-Thiazolyl | CH₃ |
| 743 | CH₃ | 4-Thiazolyl | C₂H₅ |
| 744 | CH₃ | 4-Thiazolyl | n-C₃H₇ |
| 745 | CH₃ | 4-Thiazolyl | i-C₃H₇ |
| 746 | CH₃ | 3-Isoxazolyl | H |
| 747 | CH₃ | 3-Isoxazolyl | CH₃ |
| 748 | CH₃ | 3-Isoxazolyl | C₂H₅ |
| 749 | CH₃ | 3-Isoxazolyl | n-C₃H₇ |
| 750 | CH₃ | 3-Isoxazolyl | i-C₃H₇ |
| 751 | CH₃ | 5-Isoxazolyl | H |
| 752 | CH₃ | 5-Isoxazolyl | CH₃ |
| 753 | CH₃ | 5-Isoxazolyl | C₂H₅ |
| 754 | CH₃ | 5-Isoxazolyl | n-C₃H₇ |
| 755 | CH₃ | 5-Isoxazolyl | i-C₃H₇ |
| 756 | CH₃ | 2-Imidazolyl | H |
| 757 | CH₃ | 2-Imidazolyl | CH₃ |
| 758 | CH₃ | 2-Imidazolyl | C₂H₅ |
| 759 | CH₃ | 2-Imidazolyl | n-C₃H₇ |
| 760 | CH₃ | 2-Imidazolyl | i-C₃H₇ |
| 761 | CH₃ | 3-Pyrazolyl | H |
| 762 | CH₃ | 3-Pyrazolyl | CH₃ |
| 763 | CH₃ | 3-Pyrazolyl | C₂H₅ |
| 764 | CH₃ | 3-Pyrazolyl | n-C₃H₇ |
| 765 | CH₃ | 3-Pyrazolyl | i-C₃H₇ |
| 766 | CH₃ | 4-Pyrazolyl | H |
| 767 | CH₃ | 4-Pyrazolyl | CH₃ |
| 768 | CH₃ | 4-Pyrazolyl | C₂H₅ |
| 769 | CH₃ | 4-Pyrazolyl | n-C₃H₇ |
| 770 | CH₃ | 4-Pyrazolyl | i-C₃H₇ |
| 771 | OCH₃ | H | H |
| 772 | OCH₃ | H | CH₃ |
| 773 | OCH₃ | H | C₂H₅ |
| 774 | OCH₃ | H | n-C₃H₇ |
| 775 | OCH₃ | H | i-C₃H₇ |
| 776 | OCH₃ | OH | H |
| 777 | OCH₃ | OH | CH₃ |
| 778 | OCH₃ | OH | C₂H₅ |
| 779 | OCH₃ | OH | n-C₃H₇ |
| 780 | OCH₃ | OH | i-C₃H₇ |
| 781 | OCH₃ | Cl | n-C₄H₉ |
| 782 | OCH₃ | Cl | CH₃ |
| 783 | OCH₃ | Cl | C₂H₅ |
| 784 | OCH₃ | Cl | n-C₃H₇ |
| 785 | OCH₃ | Cl | i-C₃H₇ |
| 786 | OCH₃ | OCH₃ | H |
| 787 | OCH₃ | OCH₃ | CH₃ |
| 788 | OCH₃ | OCH₃ | C₂H₅ |
| 789 | OCH₃ | OCH₃ | n-C₃H₇ |
| 790 | OCH₃ | OCH₃ | i-C₃H₇ |
| 791 | OCH₃ | SCH₃ | H |
| 792 | OCH₃ | SCH₃ | CH₃ |
| 793 | OCH₃ | SCH₃ | C₂H₅ |
| 794 | OCH₃ | SCH₃ | n-C₃H₇ |
| 795 | OCH₃ | SCH₃ | i-C₃H₇ |
| 796 | OCH₃ | CH₃ | H |
| 797 | OCH₃ | CH₃ | CH₃ |
| 798 | OCH₃ | CH₃ | C₂H₅ |
| 799 | OCH₃ | CH₃ | n-C₃H₇ |
| 800 | OCH₃ | CH₃ | i-C₃H₇ |

TABLE A-continued

| No. | R² | R³ | R⁴ |
|---|---|---|---|
| 801 | OCH₃ | Cyclopropyl | H |
| 802 | OCH₃ | Cyclopropyl | CH₃ |
| 803 | OCH₃ | Cyclopropyl | C₂H₅ |
| 804 | OCH₃ | Cyclopropyl | n-C₃H₇ |
| 805 | OCH₃ | Cyclopropyl | i-C₃H₇ |
| 806 | OCH₃ | 2-Pyridyl | H |
| 807 | OCH₃ | 2-Pyridyl | CH₃ |
| 808 | OCH₃ | 2-Pyridyl | C₂H₅ |
| 809 | OCH₃ | 2-Pyridyl | n-C₃H₇ |
| 810 | OCH₃ | 2-Pyridyl | i-C₃H₇ |
| 811 | OCH₃ | 3-Pyridyl | H |
| 812 | OCH₃ | 3-Pyridyl | CH₃ |
| 813 | OCH₃ | 3-Pyridyl | C₂H₅ |
| 814 | OCH₃ | 3-Pyridyl | n-C₃H₇ |
| 815 | OCH₃ | 3-Pyridyl | i-C₃H₇ |
| 816 | OCH₃ | 4-Pyridyl | H |
| 817 | OCH₃ | 4-Pyridyl | CH₃ |
| 818 | OCH₃ | 4-Pyridyl | C₂H₅ |
| 819 | OCH₃ | 4-Pyridyl | n-C₃H₇ |
| 820 | OCH₃ | 4-Pyrimidyl | i-C₃H₇ |
| 821 | OCH₃ | 2-Pyrimidyl | H |
| 822 | OCH₃ | 2-Pyrimidyl | CH₃ |
| 823 | OCH₃ | 2-Pyrimidyl | C₂H₅ |
| 824 | OCH₃ | 2-Pyrimidyl | n-C₃H₇ |
| 825 | OCH₃ | 2-Pyrimidyl | i-C₃H₇ |
| 826 | OCH₃ | 4-Pyrimidyl | H |
| 827 | OCH₃ | 4-Pyrimidyl | CH₃ |
| 828 | OCH₃ | 4-Pyrimidyl | C₂H₅ |
| 829 | OCH₃ | 4-Pyrimidyl | n-C₃H₇ |
| 830 | OCH₃ | 4-Pyrimidyl | i-C₃H₇ |
| 831 | OCH₃ | 5-Pyrimidyl | H |
| 832 | OCH₃ | 5-Pyrimidyl | CH₃ |
| 833 | OCH₃ | 5-Pyrimidyl | C₂H₅ |
| 834 | OCH₃ | 5-Pyrimidyl | n-C₃H₇ |
| 835 | OCH₃ | 5-Pyrimidyl | i-C₃H₇ |
| 836 | OCH₃ | 1,3,5-Triazinyl | H |
| 837 | OCH₃ | 1,3,5-Triazinyl | CH₃ |
| 838 | OCH₃ | 1,3,5-Triazinyl | C₂H₅ |
| 839 | OCH₃ | 1,3,5-Triazinyl | n-C₃H₇ |
| 840 | OCH₃ | 1,3,5-Triazinyl | i-C₃H₇ |
| 841 | OCH₃ | 2-Furyl | H |
| 842 | OCH₃ | 2-Furyl | CH₃ |
| 843 | OCH₃ | 2-Furyl | C₂H₅ |
| 844 | OCH₃ | 2-Furyl | n-C₃H₇ |
| 845 | OCH₃ | 2-Furyl | i-C₃H₇ |
| 846 | OCH₃ | 3-Furyl | H |
| 847 | OCH₃ | 3-Furyl | CH₃ |
| 848 | OCH₃ | 3-Furyl | C₂H₅ |
| 849 | OCH₃ | 3-Furyl | n-C₃H₇ |
| 850 | OCH₃ | 3-Furyl | i-C₃H₇ |
| 851 | OCH₃ | 2-Thienyl | H |
| 852 | OCH₃ | 2-Thienyl | CH₃ |
| 853 | OCH₃ | 2-Thienyl | C₂H₅ |
| 854 | OCH₃ | 2-Thienyl | n-C₃H₇ |
| 855 | OCH₃ | 2-Thienyl | i-C₃H₇ |
| 856 | OCH₃ | 3-Thienyl | H |
| 857 | OCH₃ | 3-Thienyl | CH₃ |
| 858 | OCH₃ | 3-Thienyl | C₂H₅ |
| 859 | OCH₃ | 3-Thienyl | n-C₃H₇ |
| 860 | OCH₃ | 3-Thienyl | i-C₃H₇ |
| 861 | OCH₃ | 2-Oxazolyl | H |
| 862 | OCH₃ | 2-Oxazolyl | CH₃ |
| 863 | OCH₃ | 2-Oxazolyl | C₂H₅ |
| 864 | OCH₃ | 2-Oxazolyl | n-C₃H₇ |
| 865 | OCH₃ | 2-Oxazolyl | i-C₃H₇ |
| 866 | OCH₃ | 4-Oxazolyl | H |
| 867 | OCH₃ | 4-Oxazolyl | CH₃ |
| 868 | OCH₃ | 4-Oxazolyl | C₂H₅ |
| 869 | OCH₃ | 4-Oxazolyl | n-C₃H₇ |
| 870 | OCH₃ | 4-Oxazolyl | i-C₃H₇ |
| 871 | OCH₃ | 2-Thiazolyl | H |
| 872 | OCH₃ | 2-Thiazolyl | CH₃ |
| 873 | OCH₃ | 2-Thiazolyl | C₂H₅ |
| 874 | OCH₃ | 2-Thiazolyl | n-C₃H₇ |
| 875 | OCH₃ | 2-Thiazolyl | i-C₃H₇ |
| 876 | OCH₃ | 4-Thiazolyl | H |
| 877 | OCH₃ | 4-Thiazolyl | CH₃ |

TABLE A-continued

| No. | R² | R³ | R⁴ |
|---|---|---|---|
| 878 | OCH₃ | 4-Thiazolyl | C₂H₅ |
| 879 | OCH₃ | 4-Thiazolyl | n-C₃H₇ |
| 880 | OCH₃ | 4-Thiazolyl | i-C₃H₇ |
| 881 | OCH₃ | 3-Isoxazolyl | H |
| 882 | OCH₃ | 3-Isoxazolyl | CH₃ |
| 883 | OCH₃ | 3-Isoxazolyl | C₂H₅ |
| 884 | OCH₃ | 3-Isoxazolyl | n-C₃H₇ |
| 885 | OCH₃ | 3-Isoxazolyl | i-C₃H₇ |
| 886 | OCH₃ | 5-Isoxazolyl | H |
| 887 | OCH₃ | 5-Isoxazolyl | CH₃ |
| 888 | OCH₃ | 5-Isoxazolyl | C₂H₅ |
| 889 | OCH₃ | 5-Isoxazolyl | n-C₃H₇ |
| 890 | OCH₃ | 5-Isoxazolyl | i-C₃H₇ |
| 891 | OCH₃ | 2-Imidazolyl | H |
| 892 | OCH₃ | 2-Imidazolyl | CH₃ |
| 893 | OCH₃ | 2-Imidazolyl | C₂H₅ |
| 894 | OCH₃ | 2-Imidazolyl | n-C₃H₇ |
| 895 | OCH₃ | 2-Imidazolyl | i-C₃H₇ |
| 896 | OCH₃ | 3-Pyrazolyl | H |
| 897 | OCH₃ | 3-Pyrazolyl | CH₃ |
| 898 | OCH₃ | 3-Pyrazolyl | C₂H₅ |
| 899 | OCH₃ | 3-Pyrazolyl | n-C₃H₇ |
| 900 | OCH₃ | 3-Pyrazolyl | i-C₃H₇ |
| 901 | OCH₃ | 4-Pyrazolyl | H |
| 902 | OCH₃ | 4-Pyrazolyl | CH₃ |
| 903 | OCH₃ | 4-Pyrazolyl | C₂H₅ |
| 904 | OCH₃ | 4-Pyrazolyl | n-C₃H₇ |
| 905 | OCH₃ | 4-Pyrazolyl | i-C₃H₇ |
| 906 | OH | H | H |
| 907 | OH | H | CH₃ |
| 908 | OH | H | C₂H₅ |
| 909 | OH | H | n-C₃H₇ |
| 910 | OH | H | i-C₃H₇ |
| 911 | OH | OH | H |
| 912 | OH | OH | CH₃ |
| 913 | OH | OH | C₂H₅ |
| 914 | OH | OH | n-C₃H₇ |
| 915 | OH | OH | i-C₃H₇ |
| 916 | OH | Cl | n-C₄H₉ |
| 917 | OH | Cl | CH₃ |
| 918 | OH | Cl | C₂H₅ |
| 919 | OH | Cl | n-C₃H₇ |
| 920 | OH | Cl | i-C₃H₇ |
| 921 | OH | OCH₃ | H |
| 922 | OH | OCH₃ | CH₃ |
| 923 | OH | OCH₃ | C₂H₅ |
| 924 | OH | OCH₃ | n-C₃H₇ |
| 925 | OH | OCH₃ | i-C₃H₇ |
| 926 | OH | SCH₃ | H |
| 927 | OH | SCH₃ | CH₃ |
| 928 | OH | SCH₃ | C₂H₅ |
| 929 | OH | SCH₃ | n-C₃H₇ |
| 930 | OH | SCH₃ | i-C₃H₇ |
| 931 | OH | CH₃ | H |
| 932 | OH | CH₃ | CH₃ |
| 933 | OH | CH₃ | C₂H₅ |
| 934 | OH | CH₃ | n-C₃H₇ |
| 935 | OH | CH₃ | i-C₃H₇ |
| 936 | OH | Cyclopropyl | H |
| 937 | OH | Cyclopropyl | CH₃ |
| 938 | OH | Cyclopropyl | C₂H₅ |
| 939 | OH | Cyclopropyl | n-C₃H₇ |
| 940 | OH | Cyclopropyl | i-C₃H₇ |
| 941 | OH | 2-Pyridyl | H |
| 942 | OH | 2-Pyridyl | CH₃ |
| 943 | OH | 2-Pyridyl | C₂H₅ |
| 944 | OH | 2-Pyridyl | n-C₃H₇ |
| 945 | OH | 2-Pyridyl | i-C₃H₇ |
| 946 | OH | 3-Pyridyl | H |
| 947 | OH | 3-Pyridyl | CH₃ |
| 948 | OH | 3-Pyridyl | C₂H₅ |
| 949 | OH | 3-Pyridyl | n-C₃H₇ |
| 950 | OH | 3-Pyridyl | i-C₃H₇ |
| 951 | OH | 4-Pyridyl | H |
| 952 | OH | 4-Pyridyl | CH₃ |
| 953 | OH | 4-Pyridyl | C₂H₅ |
| 954 | OH | 4-Pyridyl | n-C₃H₇ |

TABLE A-continued

| No. | R² | R³ | R⁴ |
|---|---|---|---|
| 955 | OH | 4-Pyridyl | i-C₃H₇ |
| 956 | OH | 2-Pyrimidyl | H |
| 957 | OH | 2-Pyrimidyl | CH₃ |
| 958 | OH | 2-Pyrimidyl | C₂H₅ |
| 959 | OH | 2-Pyrimidyl | n-C₃H₇ |
| 960 | OH | 2-Pyrimidyl | i-C₃H₇ |
| 961 | OH | 4-Pyrimidyl | H |
| 962 | OH | 4-Pyrimidyl | CH₃ |
| 963 | OH | 4-Pyrimidyl | C₂H₅ |
| 964 | OH | 4-Pyrimidyl | n-C₃H₇ |
| 965 | OH | 4-Pyrimidyl | i-C₃H₇ |
| 966 | OH | 5-Pyrimidyl | H |
| 967 | OH | 5-Pyrimidyl | CH₃ |
| 968 | OH | 5-Pyrimidyl | C₂H₅ |
| 969 | OH | 5-Pyrimidyl | n-C₃H₇ |
| 970 | OH | 5-Pyrimidyl | i-C₃H₇ |
| 971 | OH | 1,3,5-Triazinyl | H |
| 972 | OH | 1,3,5-Triazinyl | CH₃ |
| 973 | OH | 1,3,5-Triazinyl | C₂H₅ |
| 974 | OH | 1,3,5-Triazinyl | n-C₃H₇ |
| 975 | OH | 1,3,5-Triazinyl | i-C₃H₇ |
| 976 | OH | 2-Furyl | H |
| 977 | OH | 2-Furyl | CH₃ |
| 978 | OH | 2-Furyl | C₂H₅ |
| 979 | OH | 2-Furyl | n-C₃H₇ |
| 980 | OH | 2-Furyl | i-C₃H₇ |
| 981 | OH | 3-Furyl | H |
| 982 | OH | 3-Furyl | CH₃ |
| 983 | OH | 3-Furyl | C₂H₅ |
| 984 | OH | 3-Furyl | n-C₃H₇ |
| 985 | OH | 3-Furyl | i-C₃H₇ |
| 986 | OH | 2-Thienyl | H |
| 987 | OH | 2-Thenyl | CH₃ |
| 988 | OH | 2-Thienyl | C₂H₅ |
| 989 | OH | 2-Thienyl | n-C₃H₇ |
| 990 | OH | 2-Thienyl | i-C₃H₇ |
| 991 | OH | 3-Thienyl | H |
| 992 | OH | 3-Thenyl | CH₃ |
| 993 | OH | 3-Thienyl | C₂H₅ |
| 994 | OH | 3-Thienyl | n-C₃H₇ |
| 995 | OH | 3-Thienyl | i-C₃H₇ |
| 996 | OH | 2-Oxazolyl | H |
| 997 | OH | 2-Qxazolyl | CH₃ |
| 998 | OH | 2-Oxazolyl | C₂H₅ |
| 999 | OH | 2-Oxazolyl | n-C₃H₇ |
| 1000 | OH | 2-Oxazolyl | i-C₃H₇ |
| 1001 | OH | 4-Oxazolyl | H |
| 1002 | OH | 4-Oxazolyl | CH₃ |
| 1003 | OH | 4-Oxazolyl | C₂H₅ |
| 1004 | OH | 4-Oxazolyl | n-C₃H₇ |
| 1005 | OH | 2-Thiazolyl | i-C₃H₇ |
| 1006 | OH | 2-Thiazolyl | H |
| 1007 | OH | 2-Thiazolyl | CH₃ |
| 1008 | OH | 2-Thiazolyl | C₂H₅ |
| 1009 | OH | 2-Thiazolyl | n-C₃H₇ |
| 1010 | OH | 2-Thiazolyl | i-C₃H₇ |
| 1011 | OH | 4-Thiazolyl | H |
| 1012 | OH | 4-Thiazolyl | CH₃ |
| 1013 | OH | 4-Thiazolyl | C₂H₅ |
| 1014 | OH | 4-Isoxazolyl | n-C₃H₇ |
| 1015 | OH | 4-Isoxazolyl | i-C₃H₇ |
| 1016 | OH | 3-Isoxazolyl | H |
| 1017 | OH | 3-Isoxazolyl | CH₃ |
| 1018 | OH | 3-Isoxazolyl | C₂H₅ |
| 1019 | OH | 3-Isoxazolyl | n-C₃H₇ |
| 1020 | OH | 3-Isoxazolyl | i-C₃H₇ |
| 1021 | OH | 5-Isoxazolyl | H |
| 1022 | OH | 5-Isoxazolyl | CH₃ |
| 1023 | OH | 5-Isoxazolyl | C₂H₅ |
| 1024 | OH | 5-Isoxazolyl | n-C₃H₇ |
| 1025 | OH | 5-Isoxazolyl | i-C₃H₇ |
| 1026 | OH | 2-Imidazolyl | H |
| 1027 | OH | 2-Imidazolyl | CH₃ |
| 1028 | OH | 2-Imidazolyl | C₂H₅ |
| 1029 | OH | 2-Imidazolyl | n-C₃H₇ |
| 1030 | OH | 2-Imidazolyl | i-C₃H₇ |
| 1031 | OH | 3-Pyrazolyl | H |

TABLE A-continued

| No. | R² | R³ | R⁴ |
|---|---|---|---|
| 1032 | OH | 3-Pyrazolyl | CH₃ |
| 1033 | OH | 3-Pyrazolyl | C₂H₅ |
| 1034 | OH | 3-Pyrazolyl | n-C₃H₇ |
| 1035 | OH | 3-Pyrazolyl | i-C₃H₇ |
| 1036 | OH | 4-Pyrazolyl | H |
| 1037 | OH | 4-Pyrazolyl | CH₃ |
| 1038 | OH | 4-Pyrazolyl | C₂H₅ |
| 1039 | OH | 4-Pyrazolyl | n-C₃H₇ |
| 1040 | OH | 4-Pyrazolyl | i-C₃H₇ |
| 1041 | H | H | H |
| 1042 | H | H | CH₃ |
| 1043 | H | H | C₂H₅ |
| 1044 | H | H | n-C₃H₇ |
| 1045 | H | H | i-C₃H₇ |
| 1046 | H | OH | H |
| 1047 | H | OH | CH₃ |
| 1048 | H | OH | C₂H₅ |
| 1049 | H | OH | n-C₃H₇ |
| 1050 | H | OH | i-C₃H₇ |
| 1051 | H | Cl | n-C₄H₉ |
| 1052 | H | Cl | CH₃ |
| 1053 | H | Cl | C₂H₅ |
| 1054 | H | Cl | n-C₃H₇ |
| 1055 | H | Cl | i-C₃H₇ |
| 1056 | H | OCH₃ | H |
| 1057 | H | OCH₃ | CH₃ |
| 1058 | H | OCH₃ | C₂H₅ |
| 1059 | H | OCH₃ | n-C₃H₇ |
| 1060 | H | OCH₃ | i-C₃H₇ |
| 1061 | H | CH₃ | H |
| 1062 | H | CH₃ | CH₃ |
| 1063 | H | CH₃ | C₂H₅ |
| 1064 | H | CH₃ | n-C₃H₇ |
| 1065 | H | CH₃ | i-C₃H₇ |
| 1066 | H | Cyclopropyl | H |
| 1067 | H | Cyclopropyl | CH₃ |
| 1068 | H | Cyclopropyl | C₂H₅ |
| 1069 | H | Cyclopropyl | n-C₃H₇ |
| 1070 | H | Cyclopropyl | i-C₃H₇ |
| 1071 | Cl | H | H |
| 1072 | Cl | H | CH₃ |
| 1073 | Cl | H | C₂H₅ |
| 1074 | Cl | H | n-C₃H₇ |
| 1075 | Cl | H | i-C₃H₇ |
| 1076 | Cl | OH | H |
| 1077 | Cl | OH | CH₃ |
| 1078 | Cl | OH | C₂H₅ |
| 1079 | Cl | OH | n-C₃H₇ |
| 1080 | Cl | OH | i-C₃H₇ |
| 1081 | Cl | Cl | n-C₄H₉ |
| 1082 | Cl | Cl | CH₃ |
| 1083 | C1 | Cl | C₂H₅ |
| 1084 | Cl | Cl | n-C₃H₇ |
| 1085 | Cl | Cl | i-C₃H₇ |
| 1086 | Cl | OCH₃ | H |
| 1087 | Cl | OCH₃ | CH₃ |
| 1088 | Cl | OCH₃ | C₂H₅ |
| 1089 | Cl | OCH₃ | n-C₃H₇ |
| 1090 | Cl | OCH₃ | i-C₃H₇ |
| 1091 | Cl | CH₃ | H |
| 1092 | Cl | CH₃ | CH₃ |
| 1093 | Cl | CH₃ | C₂H₅ |
| 1094 | Cl | CH₃ | n-C₃H₇ |
| 1095 | Cl | CH₃ | i-C₃H₇ |
| 1096 | Cl | Cyclopropyl | H |
| 1097 | Cl | Cyclopropyl | CH₃ |
| 1098 | Cl | Cyclopropyl | C₂H₅ |
| 1099 | Cl | Cyclopropyl | n-C₃H₇ |
| 1100 | Cl | Cyclopropyl | i-C₃H₇ |
| 1101 | SCH₃ | H | H |
| 1102 | SCH₃ | H | CH₃ |
| 1103 | SCH₃ | H | C₂H₅ |
| 1104 | SCH₃ | H | n-C₃H₇ |
| 1105 | SCH₃ | H | i-C₃H₇ |
| 1106 | SCH₃ | OH | H |
| 1107 | SCH₃ | OH | CH₃ |
| 1108 | SCH₃ | OH | C₂H₅ |

TABLE A-continued

| No. | R² | R³ | R⁴ |
|---|---|---|---|
| 1109 | SCH₃ | OH | n-C₃H₇ |
| 1110 | SCH₃ | OH | i-C₃H₇ |
| 1111 | SCH₃ | CH₃ | H |
| 1112 | SCH₃ | CH₃ | CH₃ |
| 1113 | SCH₃ | CH₃ | C₂H₅ |
| 1114 | SCH₃ | CH₃ | n-C₃H₇ |
| 1115 | SCH₃ | CH₃ | i-C₃H₇ |
| 1116 | SCH₃ | SCH₃ | H |
| 1117 | SCH₃ | SCH₃ | CH₃ |
| 1118 | SCH₃ | SCH₃ | C₂H₅ |
| 1119 | SCH₃ | SCH₃ | n-C₃H₇ |
| 1120 | SCH₃ | SCH₃ | i-C₃H₇ |
| 1121 | SCH₃ | Cyclopropyl | H |
| 1122 | SCH₃ | Cyclopropyl | CH₃ |
| 1123 | SCH₃ | Cyclopropyl | C₂H₅ |
| 1124 | SCH₃ | Cyclopropyl | n-C₃H₇ |
| 1125 | SCH₃ | Cyclopropyl | i-C₃H₇ |
| 1126 | Cyclopropyl | H | H |
| 1127 | Cyclopropyl | H | CH₃ |
| 1128 | Cyclopropyl | H | C₂H₅ |
| 1129 | Cyclopropyl | H | n-C₃H₇ |
| 1130 | Cyclopropyl | H | i-C₃H₇ |
| 1131 | Cyclopropyl | OH | H |
| 1132 | Cyclopropyl | OH | CH₃ |
| 1133 | Cyclopropyl | OH | C₂H₅ |
| 1134 | Cyclopropyl | OH | n-C₃H₇ |
| 1135 | Cyclopropyl | OH | i-C₃H₇ |
| 1136 | Cyclopropyl | Cl | n-C₄H₉ |
| 1137 | Cyclopropyl | Cl | CH₃ |
| 1138 | Cyclopropyl | Cl | C₂H₅ |
| 1139 | Cyclopropyl | Cl | n-C₃H₇ |
| 1140 | Cyclopropyl | Cl | i-C₃H₇ |
| 1141 | Cyclopropyl | OCH₃ | H |
| 1142 | Cyclopropyl | OCH₃ | CH₃ |
| 1143 | Cyclopropyl | OCH₃ | C₂H₅ |
| 1144 | Cyclopropyl | OCH₃ | n-C₃H₇ |
| 1145 | Cyclopropyl | OCH₃ | i-C₃H₇ |
| 1146 | Cyclopropyl | SCH₃ | H |
| 1147 | Cyclopropyl | SCH₃ | CH₃ |
| 1148 | Cyclopropyl | SCH₃ | C₂H₅ |
| 1149 | Cyclopropyl | SCH₃ | n-C₃H₇ |
| 1150 | Cyclopropyl | SCH₃ | i-C₃H₇ |
| 1151 | Cyclopropyl | CH₃ | H |
| 1152 | Cyclopropyl | CH₃ | CH₃ |
| 1153 | Cyclopropyl | CH₃ | C₂H₅ |
| 1154 | Cyclopropyl | CH₃ | n-C₃H₇ |
| 1155 | Cyclopropyl | CH₃ | i-C₃H₇ |
| 1156 | CH₃ | 2-F-C₆H₄ | H |
| 1157 | CH₃ | 2-F-C₆H₄ | CH₃ |
| 1158 | CH₃ | 2-F-C₆H₄ | C₂H₅ |
| 1159 | CH₃ | 2-F-C₆H₄ | n-C₃H₇ |
| 1160 | CH₃ | 2-F-C₆H₄ | i-C₃H₇ |
| 1161 | CH₃ | 2-F-C₆H₄ | n-C₄H₉ |
| 1162 | CH₃ | 2-F-C₆H₄ | t-C₄H₉ |
| 1163 | CH₃ | 2-F-C₆H₄ | n-C₆H₁₃ |
| 1164 | CH₃ | 2-F-C₆H₄ | Prop-1-en-3-yl |
| 1165 | CH₃ | 2-F-C₆H₄ | (E)-1-Chloroprop-1-en-3-yl |
| 1166 | CH₃ | 2-F-C₆H₄ | Propyn-3-yl |
| 1167 | CH₃ | 2-F-C₆H₄ | 3-Methylbut-2-en-1-yl |
| 1168 | CH₃ | 3-F-C₆H₄ | H |
| 1169 | CH₃ | 3-F-C₆H₄ | CH₃ |
| 1170 | CH₃ | 3-F-C₆H₄ | C₂H₅ |
| 1171 | CH₃ | 3-F-C₆H₄ | n-C₃H₇ |
| 1172 | CH₃ | 3-F-C₆H₄ | i-C₃H₇ |
| 1173 | CH₃ | 3-F-C₆H₄ | n-C₄H₉ |
| 1174 | CH₃ | 3-F-C₆H₄ | t-C₄H₉ |
| 1175 | CH₃ | 3-F-C₆H₄ | n-C₆H₁₃ |
| 1176 | CH₃ | 3-F-C₆H₄ | Prop-1-en-3-yl |
| 1177 | CH₃ | 3-F-C₆H₄ | (E)-1-Chloroprop-1-en-3-yl |
| 1178 | CH₃ | 3-F-C₆H₄ | Propyn-3-yl |
| 1179 | CH₃ | 3-F-C₆H₄ | 3-Methylbut-2-en-1-yl |
| 1180 | CH₃ | 4-F-C₆H₄ | H |
| 1181 | CH₃ | 4-F-C₆H₄ | CH₃ |
| 1182 | CH₃ | 4-F-C₆H₄ | C₂H₅ |
| 1183 | CH₃ | 4-F-C₆H₄ | n-C₃H₇ |
| 1184 | CH₃ | 4-F-C₆H₄ | i-C₃H₇ |
| 1185 | CH₃ | 4-F-C₆H₄ | n-C₄H₉ |

TABLE A-continued

| No. | R² | R³ | R⁴ |
|---|---|---|---|
| 1186 | CH₃ | 4-F-C₆H₄ | t-C₄H₉ |
| 1187 | CH₃ | 4-F-C₆H₄ | n-C₆H₁₃ |
| 1188 | CH₃ | 4-F-C₆H₄ | Prop-1-en-3-yl |
| 1189 | CH₃ | 4-F-C₆H₄ | (E)-1-Chloroprop-1-en-3-yl |
| 1190 | CH₃ | 4-F-C₆H₄ | Propyn-3-yl |
| 1191 | CH₃ | 4-F-C₆H₄ | 3-Methylbut-2-en-1-yl |
| 1192 | CH₃ | 2-Cl-C₆H₄ | H |
| 1193 | CH₃ | 2-Cl-C₆H₄ | CH₃ |
| 1194 | CH₃ | 2-Cl-C₆H₄ | C₂H₅ |
| 1195 | CH₃ | 2-Cl-C₆H₄ | n-C₃H₇ |
| 1196 | CH₃ | 2-Cl-C₆H₄ | i-C₃H₇ |
| 1197 | CH₃ | 2-Cl-C₆H₄ | n-C₄H₉ |
| 1198 | CH₃ | 2-Cl-C₆H₄ | t-C₄H₉ |
| 1199 | CH₃ | 2-Cl-C₆H₄ | n-C₄H₉ |
| 1200 | CH₃ | 2-Cl-C₆H₄ | Prop-1-en-3-yl |
| 1201 | CH₃ | 2-Cl-C₆H₄ | (E)-1-Chloroprop-1-en-3-yl |
| 1202 | CH₃ | 2-Cl-C₆H₄ | Propyn-3-yl |
| 1203 | CH₃ | 2-Cl-C₆H₄ | 3-Methylbut-2-en-1-yl |
| 1204 | CH₃ | 3-Cl-C₆H₄ | H |
| 1205 | CH₃ | 3-Cl-C₆H₄ | CH₃ |
| 1206 | CH₃ | 3-Cl-C₆H₄ | C₂H₅ |
| 1207 | CH₃ | 3-Cl-C₆H₄ | n-C₃H₇ |
| 1208 | CH₃ | 3-Cl-C₆H₄ | i-C₃H₇ |
| 1209 | CH₃ | 3-Cl-C₆H₄ | n-C₄H₉ |
| 1210 | CH₃ | 3-Cl-C₆H₄ | t-C₄H₉ |
| 1211 | CH₃ | 3-Cl-C₆H₄ | n-C₆H₁₃ |
| 1212 | CH₃ | 3-Cl-C₆H₄ | Prop-1-en-3-yl |
| 1213 | CH₃ | 3-Cl-C₆H₄ | (E)-1-Chloroprop-1-en-3-yl |
| 1214 | CH₃ | 3-Cl-C₆H₄ | Propyn-3-yl |
| 1215 | CH₃ | 3-Cl-C₆H₄ | 3-Methylbut-2-en-1-yl |
| 1216 | CH₃ | 4-Cl-C₆H₄ | H |
| 1217 | CH₃ | 4-Cl-C₆H₄ | CH₃ |
| 1218 | CH₃ | 4-Cl-C₆H₄ | C₂H₅ |
| 1219 | CH₃ | 4-Cl-C₆H₄ | n-C₃H₇ |
| 1220 | CH₃ | 4-Cl-C₆H₄ | i-C₃H₇ |
| 1221 | CH₃ | 4-Cl-C₆H₄ | n-C₄H₉ |
| 1222 | CH₃ | 4-Cl-C₆H₄ | t-C₄H₉ |
| 1223 | CH₃ | 4-Cl-C₆H₄ | n-C₆H₁₃ |
| 1224 | CH₃ | 4-Cl-C₆H₄ | Prop-1-en-3-yl |
| 1225 | CH₃ | 4-Cl-C₆H₄ | (E)-1-Chloroprop-1-en-3-yl |
| 1226 | CH₃ | 4-Cl-C₆H₄ | Propyn-3-yl |
| 1227 | CH₃ | 4-Cl-C₆H₄ | 3-Methylbut-2-en-1-yl |
| 1228 | CH₃ | 2,3-Cl₂-C₆H₃ | H |
| 1229 | CH₃ | 2,3-Cl₂-C₆H₃ | CH₃ |
| 1230 | CH₃ | 2,3-Cl₂-C₆H₃ | C₂H₅ |
| 1231 | CH₃ | 2,3-Cl₂-C₆H₃ | n-C₃H₇ |
| 1232 | CH₃ | 2,3-Cl₂-C₆H₃ | i-C₃H₇ |
| 1233 | CH₃ | 2,3-Cl₂-C₆H₃ | n-C₄H₉ |
| 1234 | CH₃ | 2,3-Cl₂-C₆H₃ | t-C₄H₉ |
| 1235 | CH₃ | 2,3-Cl₂-C₆H₃ | n-C₆H₁₃ |
| 1236 | CH₃ | 2,3-Cl₂-C₆H₃ | Prop-1-en-3-yl |
| 1237 | CH₃ | 2,3-Cl₂-C₆H₃ | (E)-1-Chloroprop-1-en-3-yl |
| 1238 | CH₃ | 2,3-Cl₂-C₆H₃ | Propyn-3-yl |
| 1239 | CH₃ | 2,3-Cl₂-C₆H₃ | 3-Methylbut-2-en-1-yl |
| 1240 | CH₃ | 2,4-Cl₂-C₆H₃ | H |
| 1241 | CH₃ | 2,4-Cl₂-C₆H₃ | CH₃ |
| 1242 | CH₃ | 2,4-Cl₂-C₆H₃ | C₂H₅ |
| 1243 | CH₃ | 2,4-Cl₂-C₆H₃ | n-C₃H₇ |
| 1244 | CH₃ | 2,4-Cl₂-C₆H₃ | i-C₃H₇ |
| 1245 | CH₃ | 2,4-Cl₂-C₆H₃ | n-C₄H₉ |
| 1246 | CH₃ | 2,4-Cl₂-C₆H₃ | t-C₄H₉ |
| 1247 | CH₃ | 2,4-Cl₂-C₆H₃ | n-C₆H₁₃ |
| 1248 | CH₃ | 2,4-Cl₂-C₆H₃ | Prop-1-en-3-yl |
| 1249 | CH₃ | 2,4-Cl₂-C₆H₃ | (E)-1-Chloroprop-1-en-3-yl |
| 1250 | CH₃ | 2,4-Cl₂-C₆H₃ | Propyn-3-yl |
| 1251 | CH₃ | 2,4-Cl₂-C₆H₃ | 3-Methylbut-2-en-1-yl |
| 1252 | CH₃ | 2,5-Cl₂-C₆H₃ | H |
| 1253 | CH₃ | 2,5-Cl₂-C₆H₃ | CH₃ |
| 1254 | CH₃ | 2,5-Cl₂-C₆H₃ | C₂H₅ |
| 1255 | CH₃ | 2,5-Cl₂-C₆H₃ | n-C₃H₇ |
| 1256 | CH₃ | 2,5-Cl₂-C₆H₃ | i-C₃H₇ |
| 1257 | CH₃ | 2,5-Cl₂-C₆H₃ | n-C₄H₉ |
| 1258 | CH₃ | 2,5-Cl₂-C₆H₃ | t-C₄H₉ |
| 1259 | CH₃ | 2,5-Cl₂-C₆H₃ | n-C₆H₁₃ |
| 1260 | CH₃ | 2,5-Cl₂-C₆H₃ | Prop-1-en-3-yl |
| 1261 | CH₃ | 2,5-Cl₂-C₆H₃ | (E)-1-Chloroprop-1-en-3-yl |
| 1262 | CH₃ | 2,5-Cl₂-C₆H₃ | Propyn-3-yl |

TABLE A-continued

| No. | R² | R³ | R⁴ |
|---|---|---|---|
| 1263 | CH₃ | 2,5-Cl₂-C₆H₃ | 3-Methylbut-2-en-1-yl |
| 1264 | CH₃ | 2,6-Cl₂-C₆H₃ | H |
| 1265 | CH₃ | 2,6-Cl₂-C₆H₃ | CH₃ |
| 1266 | CH₃ | 2,6-Cl₂-C₆H₃ | C₂H₅ |
| 1267 | CH₃ | 2,6-Cl₂-C₆H₃ | n-C₃H₇ |
| 1268 | CH₃ | 2,6-Cl₂-C₆H₃ | i-C₃H₇ |
| 1269 | CH₃ | 2,6-Cl₂-C₆H₃ | n-C₄H₉ |
| 1270 | CH₃ | 2,6-Cl₂-C₆H₃ | t-C₄H₉ |
| 1271 | CH₃ | 2,6-Cl₂-C₆H₃ | n-C₆H₁₃ |
| 1272 | CH₃ | 2,6-Cl₂-C₆H₃ | Prop-1-en-3-yl |
| 1273 | CH₃ | 2,6-Cl₂-C₆H₃ | (E)-1-Chloroprop-1-en-3-yl |
| 1274 | CH₃ | 2,6-Cl₂-C₆H₃ | Propyn-3-yl |
| 1275 | CH₃ | 2,6-Cl₂-C₆H₃ | 3-Methylbut-2-en-1-yl |
| 1276 | CH₃ | 3,4-Cl₂-C₆H₃ | H |
| 1277 | CH₃ | 3,4-Cl₂-C₆H₃ | CH₃ |
| 1278 | CH₃ | 3,4-Cl₂-C₆H₃ | C₂H₅ |
| 1279 | CH₃ | 3,4-Cl₂-C₆H₃ | n-C₃H₇ |
| 1280 | CH₃ | 3,4-Cl₂-C₆H₃ | i-C₃H₇ |
| 1281 | CH₃ | 3,4-Cl₂-C₆H₃ | n-C₄H₉ |
| 1282 | CH₃ | 3,4-Cl₂-C₆H₃ | t-C₄H₉ |
| 1283 | CH₃ | 3,4-Cl₂-C₆H₃ | n-C₆H₁₃ |
| 1284 | CH₃ | 3,4-Cl₂-C₆H₃ | Prop-1-en-3-yl |
| 1285 | CH₃ | 3,4-Cl₂-C₆H₃ | (E)-1-Chloroprop-1-en-3-yl |
| 1286 | CH₃ | 3,4-Cl₂-C₆H₃ | Propyn-3-yl |
| 1287 | CH₃ | 3,4-Cl₂-C₆H₃ | 3-Methylbut-2-en-1-yl |
| 1288 | CH₃ | 3,5-Cl₂-C₆H₃ | H |
| 1289 | CH₃ | 3,5-Cl₂-C₆H₃ | CH₃ |
| 1290 | CH₃ | 3,5-Cl₂-C₆H₃ | C₂H₅ |
| 1291 | CH₃ | 3,5-Cl₂-C₆H₃ | n-C₃H₇ |
| 1292 | CH₃ | 3,5-Cl₂-C₆H₃ | i-C₃H₇ |
| 1293 | CH₃ | 3,5-Cl₂-C₆H₃ | n-C₄H₉ |
| 1294 | CH₃ | 3,5-Cl₂-C₆H₃ | t-C₄H₉ |
| 1295 | CH₃ | 3,5-Cl₂-C₆H₃ | n-C₆H₁₃ |
| 1296 | CH₃ | 3,5-Cl₂-C₆H₃ | Prop-1-en-3-yl |
| 1297 | CH₃ | 3,5-Cl₂-C₆H₃ | (E)-1-Chloroprop-1-en-3-yl |
| 1298 | CH₃ | 3,5-Cl₂-C₆H₃ | Propyn-3-yl |
| 1299 | CH₃ | 3,5-Cl₂-C₆H₃ | 3-Methylbut-2-en-1-yl |
| 1300 | CH₃ | 2-Br-C₆H₄ | H |
| 1301 | CH₃ | 2-Br-C₆H₄ | CH₃ |
| 1302 | CH₃ | 2-Br-C₆H₄ | C₂H₅ |
| 1303 | CH₃ | 2-Br-C₆H₄ | n-C₃H₇ |
| 1304 | CH₃ | 2-Br-C₆H₄ | i-C₃H₇ |
| 1305 | CH₃ | 2-Br-C₆H₄ | n-C₄H₉ |
| 1306 | CH₃ | 2-Br-C₆H₄ | t-C₄H₉ |
| 1307 | CH₃ | 2-Br-C₆H₄ | n-C₆H₁₃ |
| 1308 | CH₃ | 2-Br-C₆H₄ | Prop-1-en-3-yl |
| 1309 | CH₃ | 2-Br-C₆H₄ | (E)-1-Chloroprop-1-en-3-yl |
| 1310 | CH₃ | 2-Br-C₆H₄ | Propyn-3-yl |
| 1311 | CH₃ | 2-Br-C₆H₄ | 3-Methylbut-2-en-1-yl |
| 1312 | CH₃ | 3-Br-C₆H₄ | H |
| 1313 | CH₃ | 3-Br-C₆H₄ | CH₃ |
| 1314 | CH₃ | 3-Br-C₆H₄ | C₂H₅ |
| 1315 | CH₃ | 3-Br-C₆H₄ | n-C₃H₇ |
| 1316 | CH₃ | 3-Br-C₆H₄ | i-C₃H₇ |
| 1317 | CH₃ | 3-Br-C₆H₄ | n-C₄H₉ |
| 1318 | CH₃ | 3-Br-C₆H₄ | t-C₄H₉ |
| 1319 | CH₃ | 3-Br-C₆H₄ | n-C₆H₁₃ |
| 1320 | CH₃ | 3-Br-C₆H₄ | Prop-1-en-3-yl |
| 1321 | CH₃ | 3-Br-C₆H₄ | (E)-1-Chloroprop-1-en-3-yl |
| 1322 | CH₃ | 3-Br-C₆H₄ | Propyn-3-yl |
| 1323 | CH₃ | 3-Br-C₆H₄ | 3-Methylbut-2-en-1-yl |
| 1324 | CH₃ | 4-Br-C₆H₄ | H |
| 1325 | CH₃ | 4-Br-C₆H₄ | CH₃ |
| 1326 | CH₃ | 4-Br-C₆H₄ | C₂H₅ |
| 1317 | CH₃ | 4-Br-C₆H₄ | n-C₃H₇ |
| 1328 | CH₃ | 4-Br-C₆H₄ | i-C₃H₇ |
| 1329 | CH₃ | 4-Br-C₆H₄ | n-C₄H₉ |
| 1330 | CH₃ | 4-Br-C₆H₄ | t-C₄H₉ |
| 1331 | CH₃ | 4-Br-C₆H₄ | n-C₆H₁₃ |
| 1332 | CH₃ | 4-Br-C₆H₄ | Prop-1-en-3-yl |
| 1333 | CH₃ | 4-Br-C₆H₄ | (E)-l-Chloroprop-1-en-3-yl |
| 1334 | CH₃ | 4-Br-C₆H₄ | Propyn-3-yl |
| 1335 | CH₃ | 4-Br-C₆H₄ | 3-Methylbut-2-en-1-yl |
| 1336 | CH₃ | 2-I-C₆H₄ | H |
| 1337 | CH₃ | 2-I-C₆H₄ | CH₃ |
| 1338 | CH₃ | 2-I-C₆H₄ | C₂H₅ |
| 1339 | CH₃ | 2-I-C₆H₄ | n-C₃H₇ |

TABLE A-continued

| No. | R² | R³ | R⁴ |
|---|---|---|---|
| 1340 | CH₃ | 2-I-C₆H₄ | i-C₃H₇ |
| 1341 | CH₃ | 2-I-C₆H₄ | n-C₄H₉ |
| 1342 | CH₃ | 2-I-C₆H₄ | t-C₄H₉ |
| 1343 | CH₃ | 2-I-C₆H₄ | n-C₆H₁₃ |
| 1344 | CH₃ | 2-I-C₆H₄ | Prop-1-en-3-yl |
| 1345 | CH₃ | 2-I-C₆H₄ | (E)-1-Chloroprop-1-en-3 yl |
| 1346 | CH₃ | 2-I-C₆H₄ | Propyn-3-yl |
| 1347 | CH₃ | 2-I-C₆H₄ | 3-Methylbut-2-en-1-yl |
| 1348 | CH₃ | 3-I-C₆H₄ | H |
| 1349 | CH₃ | 3-I-C₆H₄ | CH₃ |
| 1350 | CH₃ | 3-I-C₆H₄ | C₂H₅ |
| 1351 | CH₃ | 3-I-C₆H₄ | n-C₃H₇ |
| 1352 | CH₃ | 3-I-C₆H₄ | i-C₃H₇ |
| 1353 | CH₃ | 3-I-C₆H₄ | n-C₄H₉ |
| 1354 | CH₃ | 3-I-C₆H₄ | t-C₄H₉ |
| 1355 | CH₃ | 3-I-C₆H₄ | n-C₆H₁₃ |
| 1356 | CH₃ | 3-I-C₆H₄ | Prop-1-en-3-yl |
| 1357 | CH₃ | 3-I-C₆H₄ | (E)-1-Chloroprop-1-en-3-yl |
| 1358 | CH₃ | 3-I-C₆H₄ | Propyn-3-yl |
| 1359 | CH₃ | 3-I-C₆H₄ | 3-Methylbut-2-en-1-yl |
| 1360 | CH₃ | 4-I-C₆H₄ | H |
| 1361 | CH₃ | 4-I-C₆H₄ | CH₃ |
| 1362 | CH₃ | 4-I-C₆H₄ | C₂H₅ |
| 1363 | CH₃ | 4-I-C₆H₄ | n-C₃H₇ |
| 1364 | CH₃ | 4-I-C₆H₄ | i-C₃H₇ |
| 1365 | CH₃ | 4-I-C₆H₄ | n-C₄H₉ |
| 1366 | CH₃ | 4-I-C₆H₄ | t-C₄H₉ |
| 1367 | CH₃ | 4-I-C₆H₄ | n-C₆H₁₃ |
| 1368 | CH₃ | 4-I-C₆H₄ | Prop-1-en-3-yl |
| 1369 | CH₃ | 4-I-C₆H₄ | (E)-1-Chloroprop-1-en-3-yl |
| 1370 | CH₃ | 4-I-C₆H₄ | Propyn-3-yl |
| 1371 | CH₃ | 4-I-C₆H₄ | 3-Methylbut-2-en-1-yl |
| 1372 | CH₃ | 2-CN-C₆H₄ | H |
| 1373 | CH₃ | 2-CN-C₆H₄ | CH₃ |
| 1374 | CH₃ | 2-CN-C₆H₄ | C₂H₅ |
| 1375 | CH₃ | 2-CN-C₆H₄ | n-C₃H₇ |
| 1376 | CH₃ | 2-CN-C₆H₄ | i-C₃H₇ |
| 1377 | CH₃ | 2-CN-C₆H₄ | n-C₄H₉ |
| 1378 | CH₃ | 2-CN-C₆H₄ | t-C₄H₉ |
| 1379 | CH₃ | 2-CN-C₆H₄ | n-C₄H₉ |
| 1380 | CH₃ | 2-CN-C₆H₄ | Prop-1-en-3-yl |
| 1381 | CH₃ | 2-CN-C₆H₄ | (E)-1-Chloroprop-1-en-3-yl |
| 1382 | CH₃ | 2-CN-C₆H₄ | Propyn-3-yl |
| 1383 | CH₃ | 2-CN-C₆H₄ | 3-Methylbut-2-en-1-yl |
| 1384 | CH₃ | 3-CN-C₆H₄ | H |
| 1385 | CH₃ | 3-CN-C₆H₄ | CH₃ |
| 1386 | CH₃ | 3-CN-C₆H₄ | C₂H₅ |
| 1387 | CH₃ | 3-CN-C₆H₄ | n-C₃H₇ |
| 1388 | CH₃ | 3-CN-C₆H₄ | i-C₃H₇ |
| 1389 | CH₃ | 3-CN-C₆H₄ | n-C₄H₉ |
| 1390 | CH₃ | 3-CN-C₆H₄ | t-C₄H₉ |
| 1391 | CH₃ | 3-CN-C₆H₄ | n-C₆H₁₃ |
| 1392 | CH₃ | 3-CN-C₆H₄ | Prop-1-en-3-yl |
| 1393 | CH₃ | 3-CN-C₆H₄ | (E)-1-Chloroprop-1-en-3-yl |
| 1394 | CH₃ | 3-CN-C₆H₄ | Propyn-3-yl |
| 1395 | CH₃ | 3-CN-C₆H₄ | 3-Methylbut-2-en-1-yl |
| 1396 | CH₃ | 4-CN-C₆H₄ | H |
| 1397 | CH₃ | 4-CN-C₆H₄ | CH₃ |
| 1398 | CH₃ | 4-CN-C₆H₄ | C₂H₅ |
| 1399 | CH₃ | 4-CN-C₆H₄ | n-C₃H₇ |
| 1400 | CH₃ | 4-CN-C₆H₄ | i-C₃H₇ |
| 1401 | CH₃ | 4-CN-C₆H₄ | n-C₄H₉ |
| 1402 | CH₃ | 4-CN-C₆H₄ | t-C₄H₉ |
| 1403 | CH₃ | 4-CN-C₆H₄ | n-C₆H₁₃ |
| 1404 | CH₃ | 4-CN-C₆H₄ | Prop-1-en-3-yl |
| 1405 | CH₃ | 4-CN-C₆H₄ | (E)-1-Chloroprop-1-en-3-yl |
| 1406 | CH₃ | 4-CN-C₆H₄ | Propyn-3-yl |
| 1407 | CH₃ | 4-CN-C₆H₄ | 3-Methylbut-2-en-1-yl |
| 1408 | CH₃ | 2-NO₂-C₆H₄ | H |
| 1409 | CH₃ | 2-NO₂-C₆H₄ | CH₃ |
| 1410 | CH₃ | 2-NO₂-C₆H₄ | C₂H₅ |
| 1411 | CH₃ | 2-NO₂-C₆H₄ | n-C₃H₇ |
| 1412 | CH₃ | 2-NO₂-C₆H₄ | i-C₃H₇ |
| 1413 | CH₃ | 2-NO₂-C₆H₄ | n-C₄H₉ |
| 1414 | CH₃ | 2-NO₂-C₆H₄ | t-C₄H₉ |
| 1415 | CH₃ | 2-NO₂-C₆H₄ | n-C₆H₁₃ |
| 1416 | CH₃ | 2-NO₂-C₆H₄ | Prop-1-en-3-yl |

TABLE A-continued

| No. | R² | R³ | R⁴ |
|---|---|---|---|
| 1417 | CH₃ | 2-NO₂-C₆H₄ | (E)-1-Chloroprop-1-en-3-yl |
| 1418 | CH₃ | 2-NO₂-C₆H₄ | Propyn-3-yl |
| 1419 | CH₃ | 2-NO₂-C₆H₄ | 3-Methylbut-2-en-1-yl |
| 1420 | CH₃ | 3-NO₂-C₆H₄ | H |
| 1421 | CH₃ | 3-NO₂-C₆H₄ | CH₃ |
| 1422 | CH₃ | 3-NO₂-C₆H₄ | C₂H₅ |
| 1423 | CH₃ | 3-NO₂-C₆H₄ | n-C₃H₇ |
| 1424 | CH₃ | 3-NO₂-C₆H₄ | i-C₃H₇ |
| 1425 | CH₃ | 3-NO₂-C₆H₄ | n-C₄H₉ |
| 1426 | CH₃ | 3-NO₂-C₆H₄ | t-C₄H₉ |
| 1427 | CH₃ | 3-NO₂-C₆H₄ | n-C₆H₁₃ |
| 1428 | CH₃ | 3-NO₂-C₆H₄ | Prop-1-en-3-yl |
| 1429 | CH₃ | 3-NO₂-C₆H₄ | (E)-1-Chloroprop-1-en-3-yl |
| 1430 | CH₃ | 3-NO₂-C₆H₄ | Propyn-3-yl |
| 1431 | CH₃ | 3-NO₂-C₆H₄ | 3-Methylbut-2-en-1-yl |
| 1432 | CH₃ | 4-NO₂-C₆H₄ | H |
| 1433 | CH₃ | 4-NO₂-C₆H₄ | CH₃ |
| 1434 | CH₃ | 4-NO₂-C₆H₄ | C₂H₅ |
| 1435 | CH₃ | 4-NO₂-C₆H₄ | n-C₃H₇ |
| 1436 | CH₃ | 4-NO₂-C₆H₄ | i-C₃H₇ |
| 1437 | CH₃ | 4-NO₂-C₆H₄ | n-C₄H₉ |
| 1438 | CH₃ | 4-NO₂-C₆H₄ | t-C₄H₉ |
| 1439 | CH₃ | 4-NO₂-C₆H₄ | n-C₆H₁₃ |
| 1440 | CH₃ | 4-NO₂-C₆H₄ | Prop-1-en-3-yl |
| 1441 | CH₃ | 4-NO₂-C₆H₄ | (E)-1-Chloroprop-1-en-3-yl |
| 1442 | CH₃ | 4-NO₂-C₆H₄ | Propyn-3-yl |
| 1443 | CH₃ | 4-NO₂-C₆H₄ | 3-Methylbut-2-en-1-yl |
| 1444 | CH₃ | 2-CH₃-C₆H₄ | H |
| 1445 | CH₃ | 2-CH₃-C₆H₄ | CH₃ |
| 1456 | CH₃ | 2-CH₃-C₆H₄ | C₂H₅ |
| 1447 | CH₃ | 2-CH₃-C₆H₄ | n-C₃H₇ |
| 1448 | CH₃ | 2-CH₃-C₆H₄ | i-C₃H₇ |
| 1449 | CH₃ | 2-CH₃-C₆H₄ | n-C₄H₉ |
| 1450 | CH₃ | 2-CH₃-C₆H₄ | t-C₄H₉ |
| 1451 | CH₃ | 2-CH₃-C₆H₄ | n-C₆H₁₃ |
| 1452 | CH₃ | 2-CH₃-C₆H₄ | Prop-1-en-3-yl |
| 1453 | CH₃ | 2-CH₃-C₆H₄ | (E)-1-Chloroprop-1-en-3-yl |
| 1454 | CH₃ | 2-CH₃-C₆H₄ | Propyn-3-yl |
| 1455 | CH₃ | 2-CH₃-C₆H₄ | 3-Methylbut-2 en-1-yl |
| 1456 | CH₃ | 3-CH₃-C₆H₄ | H |
| 1457 | CH₃ | 3-CH₃-C₆H₄ | CH₃ |
| 1458 | CH₃ | 3-CH₃-C₆H₄ | C₂H₅ |
| 1459 | CH₃ | 3-CH₃-C₆H₄ | n-C₃H₇ |
| 1460 | CH₃ | 3-CH₃-C₆H₄ | i-C₃H₇ |
| 1461 | CH₃ | 3-CH₃-C₆H₄ | n-C₄H₉ |
| 1462 | CH₃ | 3-CH₃-C₆H₄ | t-C₄H₉ |
| 1463 | CH₃ | 3-CH₃-C₆H₄ | n-C₆H₁₃ |
| 1464 | CH₃ | 3-CH₃-C₆H₄ | Prop-1-en-3-yl |
| 1465 | CH₃ | 3-CH₃-C₆H₄ | (E)-1-Chloroprop-1-en-3-yl |
| 1466 | CH₃ | 3-CH₃-C₆H₄ | Propyn-3-yl |
| 1467 | CH₃ | 3-CH₃-C₆H₄ | 3-Methylbut-2-en-1-yl |
| 1468 | CH₃ | 4-CH₃-C₆H₄ | H |
| 1469 | CH₃ | 4-CH₃-C₆H₄ | CH₃ |
| 1470 | CH₃ | 4-CH₃-C₆H₄ | C₂H₅ |
| 1471 | CH₃ | 4-CH₃-C₆H₄ | n-C₃H₇ |
| 1472 | CH₃ | 4-CH₃-C₆H₄ | i-C₃H₇ |
| 1473 | CH₃ | 4-CH₃-C₆H₄ | n-C₄H₉ |
| 1474 | CH₃ | 4-CH₃-C₆H₄ | t-C₄H₉ |
| 1475 | CH₃ | 4-CH₃-C₆H₄ | n-C₆H₁₃ |
| 1476 | CH₃ | 4-CH₃-C₆H₄ | Prop-1-en-3-yl |
| 1477 | CH₃ | 4-CH₃-C₆H₄ | (E)-1-Chloroprop-1-en-3-yl |
| 1478 | CH₃ | 4-CH₃-C₆H₄ | Propyn-3-yl |
| 1479 | CH₃ | 4-CH₃-C₆H₄ | 3-Methylbut-2-en-1-yl |
| 1480 | CH₃ | 2,3-(CH₃)₂-C₆H₃ | H |
| 1481 | CH₃ | 2,3-(CH₃)₂-C₆H₃ | CH₃ |
| 1482 | CH₃ | 2,3-(CH₃)₂-C₆H₃ | C₂H₅ |
| 1483 | CH₃ | 2,3-(CH₃)₂-C₆H₃ | n-C₃H₇ |
| 1484 | CH₃ | 2,3-(CH₃)₂-C₆H₃ | i-C₃H₇ |
| 1485 | CH₃ | 2,3-(CH₃)₂-C₆H₃ | n-C₄H₉ |
| 1486 | CH₃ | 2,3-(CH₃)₂-C₆H₃ | t-C₄H₉ |
| 1487 | CH₃ | 2,3-(CH₃)₂-C₆H₃ | n-C₆H₁₃ |
| 1488 | CH₃ | 2,3-(CH₃)₂-C₆H₃ | Prop-1-en-3-yl |
| 1489 | CH₃ | 2,3-(CH₃)₂-C₆H₃ | (E)-1-Chloroprop-1-en-3-yl |
| 1490 | CH₃ | 2,3-(CH₃)₂-C₆H₃ | Propyn-3-yl |
| 1491 | CH₃ | 2,3-(CH₃)₂-C₆H₃ | 3-Methylbut-2-en-1-yl |
| 1492 | CH₃ | 2,4-(CH₃)₂-C₆H₃ | H |
| 1493 | CH₃ | 2,4-(CH₃)₂-C₆H₃ | CH₃ |

TABLE A-continued

| No. | R² | R³ | R⁴ |
|---|---|---|---|
| 1494 | $CH_3$ | 2,4-$(CH_3)_2$-$C_6H_3$ | $C_2H_5$ |
| 1495 | $CH_3$ | 2,4-$(CH_3)_2$-$C_6H_3$ | n-$C_3H_7$ |
| 1496 | $CH_3$ | 2,4-$(CH_3)_2$-$C_6H_3$ | i-$C_3H_7$ |
| 1497 | $CH_3$ | 2,4-$(CH_3)_2$-$C_6H_3$ | n-$C_4H_9$ |
| 1498 | $CH_3$ | 2,4-$(CH_3)_2$-$C_6H_3$ | t-$C_4H_9$ |
| 1499 | $CH_3$ | 2,4-$(CH_3)_2$-$C_6H_3$ | n-$C_6H_{13}$ |
| 1500 | $CH_3$ | 2,4-$(CH_3)_2$-$C_6H_3$ | Prop-1-en-3-yl |
| 1501 | $CH_3$ | 2,4-$(CH_3)_2$-$C_6H_3$ | (E)-1-Chloroprop-1-en-3-yl |
| 1502 | $CH_3$ | 2,4-$(CH_3)_2$-$C_6H_3$ | Propyn-3-yl |
| 1503 | $CH_3$ | 2,4-$(CH_3)_2$-$C_6H_3$ | 3-Methylbut-2-en-1-yl |
| 1504 | $CH_3$ | 2,5-$(CH_3)_2$-$C_6H_3$ | H |
| 1505 | $CH_3$ | 2,5-$(CH_3)_2$-$C_6H_3$ | $CH_3$ |
| 1506 | $CH_3$ | 2,5-$(CH_3)_2$-$C_6H_3$ | $C_2H_5$ |
| 1507 | $CH_3$ | 2,5-$(CH_3)_2$-$C_6H_3$ | n-$C_3H_7$ |
| 1508 | $CH_3$ | 2,5-$(CH_3)_2$-$C_6H_3$ | i-$C_3H_7$ |
| 1509 | $CH_3$ | 2,5-$(CH_3)_2$-$C_6H_3$ | n-$C_4H_9$ |
| 1510 | $CH_3$ | 2,5-$(CH_3)_2$-$C_6H_3$ | t-$C_4H_9$ |
| 1511 | $CH_3$ | 2,5-$(CH_3)_2$-$C_6H_3$ | n-$C_6H_{13}$ |
| 1512 | $CH_3$ | 2,5-$(CH_3)_2$-$C_6H_3$ | Prop-1-en-3-yl |
| 1513 | $CH_3$ | 2,5-$(CH_3)_2$-$C_6H_3$ | (E)-1-Chloroprop-1-en-3-yl |
| 1514 | $CH_3$ | 2,5-$(CH_3)_2$-$C_6H_3$ | Propyn-3-yl |
| 1515 | $CH_3$ | 2,5-$(CH_3)_2$-$C_6H_3$ | 3-Methylbut-2-en-1-yl |
| 1516 | $CH_3$ | 2,6-$(CH_3)_2$-$C_6H_3$ | H |
| 1517 | $CH_3$ | 2,6-$(CH_3)_2$-$C_6H_3$ | $CH_3$ |
| 1518 | $CH_3$ | 2,6-$(CH_3)_2$-$C_6H_3$ | $C_2H_5$ |
| 1519 | $CH_3$ | 2,6-$(CH_3)_2$-$C_6H_3$ | n-$C_3H_7$ |
| 1520 | $CH_3$ | 2,6-$(CH_3)_2$-$C_6H_3$ | i-$C_3H_7$ |
| 1521 | $CH_3$ | 2,6-$(CH_3)_2$-$C_6H_3$ | n-$C_4H_9$ |
| 1522 | $CH_3$ | 2,6-$(CH_3)_2$-$C_6H_3$ | t-$C_4H_9$ |
| 1523 | $CH_3$ | 2,6-$(CH_3)_2$-$C_6H_3$ | n-$C_6H_{13}$ |
| 1524 | $CH_3$ | 2,6-$(CH_3)_2$-$C_6H_3$ | Prop-1-en-3-yl |
| 1525 | $CH_3$ | 2,6-$(CH_3)_2$-$C_6H_3$ | (E)-1-Chloroprop-1-en-3-yl |
| 1526 | $CH_3$ | 2,6-$(CH_3)_2$-$C_6H_3$ | Propyn-3-yl |
| 1527 | $CH_3$ | 2,6-$(CH_3)_2$-$C_6H_3$ | 3-Methylbut-2-en-1-yl |
| 1528 | $CH_3$ | 3,4-$(CH_3)_2$-$C_6H_3$ | H |
| 1529 | $CH_3$ | 3,4-$(CH_3)_2$-$C_6H_3$ | $CH_3$ |
| 1530 | $CH_3$ | 3,4-$(CH_3)_2$-$C_6H_3$ | $C_2H_5$ |
| 1531 | $CH_3$ | 3,4-$(CH_3)_2$-$C_6H_3$ | n-$C_3H_7$ |
| 1532 | $CH_3$ | 3,4-$(CH_3)_2$-$C_6H_3$ | i-$C_3H_7$ |
| 1533 | $CH_3$ | 3,4-$(CH_3)_2$-$C_6H_3$ | n-$C_4H_9$ |
| 1534 | $CH_3$ | 3,4-$(CH_3)_2$-$C_6H_3$ | t-$C_4H_9$ |
| 1535 | $CH_3$ | 3,4-$(CH_3)_2$-$C_6H_3$ | n-$C_6H_{13}$ |
| 1536 | $CH_3$ | 3,4-$(CH_3)_2$-$C_6H_3$ | Prop-1-en-3-yl |
| 1537 | $CH_3$ | 3,4-$(CH_3)_2$-$C_6H_3$ | (E)-1-Chloroprop-1-en-3-yl |
| 1538 | $CH_3$ | 3,4-$(CH_3)_2$-$C_6H_3$ | Propyn-3-yl |
| 1539 | $CH_3$ | 3,4-$(CH_3)_2$-$C_6H_3$ | 3-Methylbut-2-en-1-yl |
| 1540 | $CH_3$ | 3,5-$(CH_3)_2$-$C_6H_3$ | H |
| 1541 | $CH_3$ | 3,5-$(CH_3)_2$-$C_6H_3$ | $CH_3$ |
| 1542 | $CH_3$ | 3,5-$(CH_3)_2$-$C_6H_3$ | $C_2H_5$ |
| 1543 | $CH_3$ | 3,5-$(CH_3)_2$-$C_6H_3$ | n-$C_3H_7$ |
| 1544 | $CH_3$ | 3,5-$(CH_3)_2$-$C_6H_3$ | i-$C_3H_7$ |
| 1545 | $CH_3$ | 3,5-$(CH_3)_2$-$C_6H_3$ | n-$C_4H_9$ |
| 1546 | $CH_3$ | 3,5-$(CH_3)_2$-$C_6H_3$ | t-$C_4H_9$ |
| 1547 | $CH_3$ | 3,5-$(CH_3)_2$-$C_6H_3$ | n-$C_6H_{13}$ |
| 1548 | $CH_3$ | 3,5-$(CH_3)_2$-$C_6H_3$ | Prop-1-en-3-yl |
| 1549 | $CH_3$ | 3,5-$(CH_3)_2$-$C_6H_3$ | (E)-1-Chloroprop-1-en-3-yl |
| 1550 | $CH_3$ | 3,5-$(CH_3)_2$-$C_6H_3$ | Propyn-3-yl |
| 1551 | $CH_3$ | 3,5-$(CH_3)_2$-$C_6H_3$ | 3-Methylbut-2-en-1-yl |
| 1552 | $CH_3$ | 2-$C_2H_5$-$C_6H_4$ | H |
| 1553 | $CH_3$ | 2-$C_2H_5$-$C_6H_4$ | $CH_3$ |
| 1554 | $CH_3$ | 2-$C_2H_5$-$C_6H_4$ | $C_2H_5$ |
| 1555 | $CH_3$ | 2-$C_2H_5$-$C_6H_4$ | n-$C_3H_7$ |
| 1556 | $CH_3$ | 2-$C_2H_5$-$C_6H_4$ | i-$C_3H_7$ |
| 1557 | $CH_3$ | 2-$C_2H_5$-$C_6H_4$ | n-$C_4H_9$ |
| 1558 | $CH_3$ | 2-$C_2H_5$-$C_6H_4$ | t-$C_4H_9$ |
| 1559 | $CH_3$ | 2-$C_2H_5$-$C_6H_4$ | n-$C_6H_{13}$ |
| 1560 | $CH_3$ | 2-$C_2H_5$-$C_6H_4$ | Prop-1-en-3-yl |
| 1561 | $CH_3$ | 2-$C_2H_5$-$C_6H_4$ | (E)-1-Chloroprop-1-en-3-yl |
| 1562 | $CH_3$ | 2-$C_2H_5$-$C_6H_4$ | Propyn-3-yl |
| 1563 | $CH_3$ | 2-$C_2H_5$-$C_6H_4$ | 3-Methylbut-2-en-1-yl |
| 1564 | $CH_3$ | 3-$C_2H_5$-$C_6H_4$ | H |
| 1565 | $CH_3$ | 3-$C_2H_5$-$C_6H_4$ | $CH_3$ |
| 1566 | $CH_3$ | 3-$C_2H_5$-$C_6H_4$ | $C_2H_5$ |
| 1567 | $CH_3$ | 3-$C_2H_5$-$C_6H_4$ | n-$C_3H_7$ |
| 1568 | $CH_3$ | 3-$C_2H_5$-$C_6H_4$ | i-$C_3H_7$ |
| 1569 | $CH_3$ | 3-$C_2H_5$-$C_6H_4$ | n-$C_4H_9$ |
| 1570 | $CH_3$ | 3-$C_2H_5$-$C_6H_4$ | t-$C_4H_9$ |

TABLE A-continued

| No. | R² | R³ | R⁴ |
|---|---|---|---|
| 1571 | CH₃ | 3-C₂H₅-C₆H₄ | n-C₆H₁₃ |
| 1572 | CH₃ | 3-C₂H₅-C₆H₄ | Prop-1-en-3-yl |
| 1573 | CH₃ | 3-C₂H₅-C₆H₄ | (E)-1-Chloroprop-1-en-3-yl |
| 1574 | CH₃ | 3-C₂H₅-C₆H₄ | Propyn-3-yl |
| 1575 | CH₃ | 3-C₂H₅-C₆H₄ | 3-Methylbut-2-en-1-yl |
| 1576 | CH₃ | 4-C₂H₅-C₆H₄ | H |
| 1577 | CH₃ | 4-C₂H₅-C₆H₄ | CH₃ |
| 1578 | CH₃ | 4-C₂H₅-C₆H₄ | C₂H₅ |
| 1579 | CH₃ | 4-C₂H₅-C₆H₄ | n-C₃H₇ |
| 1580 | CH₃ | 4-C₂H₅-C₆H₄ | i-C₃H₇ |
| 1581 | CH₃ | 4-C₂H₅-C₆H₄ | n-C₄H₉ |
| 1582 | CH₃ | 4-C₂H₅-C₆H₄ | t-C₄H₉ |
| 1583 | CH₃ | 4-C₂H₅-C₆H₄ | n-C₆H₁₃ |
| 1584 | CH₃ | 4-C₂H₅-C₆H₄ | Prop-1-en-3-yl |
| 1585 | CH₃ | 4-C₂H₅-C₆H₄ | (E)-1-Chloroprop1-en-3-yl |
| 1586 | CH₃ | 4-C₂H₅-C₆H₄ | Propyn-3-yl |
| 1587 | CH₃ | 4-C₂H₅-C₆H₄ | 3-Methylbut-2-en-1-yl |
| 1588 | CH₃ | 2-i-C₃H₇-C₆H₄ | H |
| 1589 | CH₃ | 2-i-C₃H₇-C₆H₄ | CH₃ |
| 1590 | CH₃ | 2-i-C₃H₇-C₆H₄ | C₂H₅ |
| 1591 | CH₃ | 2-i-C₃H₇-C₆H₄ | n-C₃H₇ |
| 1592 | CH₃ | 2-i-C₃H₇-C₆H₄ | i-C₃H₇ |
| 1593 | CH₃ | 2-i-C₃H₇-C₆H₄ | n-C₄H₉ |
| 1594 | CH₃ | 2-i-C₃H₇-C₆H₄ | t-C₄H₉ |
| 1595 | CH₃ | 2-i-C₃H₇-C₆H₄ | n-C₆H₁₃ |
| 1596 | CH₃ | 2-i-C₃H₇-C₆H₄ | Prop-1-en-3-yl |
| 1597 | CH₃ | 2-i-C₃H₇-C₆H₄ | (E)-1-Chloroprop-1-en-3-yl |
| 1598 | CH₃ | 2-i-C₃H₇-C₆H₄ | Propyn-3-yl |
| 1599 | CH₃ | 2-i-C₃H₇-C₆H₄ | 3-Methylbut-2-en-1-yl |
| 1600 | CH₃ | 3-i-C₃H₇-C₆H₄ | H |
| 1601 | CH₃ | 3-i-C₃H₇-C₆H₄ | CH₃ |
| 1602 | CH₃ | 3-i-C₃H₇-C₆H₄ | C₂H₅ |
| 1603 | CH₃ | 3-i-C₃H₇-C₆H₄ | n-C₃H₇ |
| 1604 | CH₃ | 3-i-C₃H₇-C₆H₄ | i-C₃H₇ |
| 1605 | CH₃ | 3-i-C₃H₇-C₆H₄ | n-C₄H₉ |
| 1606 | CH₃ | 3-i-C₃H₇-C₆H₄ | t-C₄H₉ |
| 1607 | CH₃ | 3-i-C₃H₇-C₆H₄ | n-C₆H₁₃ |
| 1608 | CH₃ | 3-i-C₃H₇-C₆H₄ | Prop-1-en-3-yl |
| 1609 | CH₃ | 3-i-C₃H₇-C₆H₄ | (E)-1-Chloroprop-1-en-3-yl |
| 1610 | CH₃ | 3-i-C₃H₇-C₆H₄ | Propyn-3-yl |
| 1611 | CH₃ | 3-i-C₃H₇-C₆H₄ | 3-Methylbut-2-en-1-yl |
| 1612 | CH₃ | 4-i-C₃H₇-C₆H₄ | H |
| 1613 | CH₃ | 4-i-C₃H₇-C₆H₄ | CH₃ |
| 1614 | CH₃ | 4-i-C₃H₇-C₆H₄ | C₂H₅ |
| 1615 | CH₃ | 4-i-C₃H₇-C₆H₄ | n-C₃H₇ |
| 1616 | CH₃ | 4-i-C₃H₇-C₆H₄ | i-C₃H₇ |
| 1617 | CH₃ | 4-i-C₃H₇-C₆H₄ | n-C₄H₉ |
| 1618 | Cf 3 | 4-i-C₃H₇-C₆H₄ | t-C₄H₉ |
| 1619 | CH₃ | 4-i-C₃H₇-C₆H₄ | n-C₆H₁₃ |
| 1620 | CH₃ | 4-i-C₃H₇-C₆H₄ | Prop-1-en-3-yl |
| 1621 | CH₃ | 4-i-C₃H₇-C₆H₄ | (E)-1-Chloroprop-1-en-3-yl |
| 1622 | CH₃ | 4-i-C₃H₇-C₆H₄ | Propyn-3-yl |
| 1623 | CH₃ | 4-i-C₃H₇-C₆H₄ | 3-Methylbut-2-en-1-yl |
| 1624 | CH₃ | 2-OH-C₆H₄ | H |
| 1625 | CH₃ | 2-OH-C₆H₄ | CH₃ |
| 1626 | CH₃ | 2-OH-C₆H₄ | C₂H₅ |
| 1627 | CH₃ | 2-OH-C₆H₄ | n-C₃H₇ |
| 1628 | CH₃ | 2-OH-C₆H₄ | i-C₃H₇ |
| 1629 | CH₃ | 2-OH-C₆H₄ | n-C₄H₉ |
| 1630 | CH₃ | 2-OH-C₆H₄ | t-C₄H₉ |
| 1631 | CH₃ | 2-OH-C₆H₄ | n-C₆H₁₃ |
| 1632 | CH₃ | 2-OH-C₆H₄ | Prop-1-en-3-yl |
| 1633 | CH₃ | 2-OH-C₆H₄ | (E)-1-Chloroprop-1-en-3-yl |
| 1634 | CH₃ | 2-OH-C₆H₄ | Propyn-3-yl |
| 1635 | CH₃ | 2-OH-C₆H₄ | 3-Methylbut-2-en-1-yl |
| 1636 | CH₃ | 3-OH-C₆H₄ | H |
| 1637 | CH₃ | 3-OH-C₆H₄ | CH₃ |
| 1638 | CH₃ | 3-OH-C₆H₄ | C₂H₅ |
| 1639 | CH₃ | 3-OH-C₆H₄ | n-C₃H₇ |
| 1640 | CH₃ | 3-OH-C₆H₄ | i-C₃H₇ |
| 1641 | CH₃ | 3-OH-C₆H₄ | n-C₄H₉ |
| 1642 | CH₃ | 3-OH-C₆H₄ | t-C₄H₉ |
| 1643 | CH₃ | 3-OH-C₆H₄ | n-C₆H₁₃ |
| 1644 | CH₃ | 3-OH-C₆H₄ | Prop-1-en-3-yl |
| 1645 | CH₃ | 3-OH-C₆H₄ | (E)-1-Chloroprop-1-en-3-yl |
| 1646 | CH₃ | 3-OH-C₆H₄ | Propyn-3-yl |
| 1647 | CH₃ | 3-OH-C₆H₄ | 3-Methylbut-2-en-1-yl |

TABLE A-continued

| No. | R² | R³ | R⁴ |
|---|---|---|---|
| 1648 | $CH_3$ | 4-OH-$C_6H_4$ | H |
| 1649 | $CH_3$ | 4-OH-$C_6H_4$ | $CH_3$ |
| 1650 | $CH_3$ | 4-OH-$C_6H_4$ | $C_2H_5$ |
| 1651 | $CH_3$ | 4-OH-$C_6H_4$ | n-$C_3H_7$ |
| 1652 | $CH_3$ | 4-OH-$C_6H_4$ | i-$C_3H_7$ |
| 1653 | $CH_3$ | 4-OH-$C_6H_4$ | n-$C_4H_9$ |
| 1654 | $CH_3$ | 4-OH-$C_6H_4$ | t-$C_4H_9$ |
| 1655 | $CH_3$ | 4-OH-$C_6H_4$ | n-$C_6H_{13}$ |
| 1656 | $CH_3$ | 4-OH-$C_6H_4$ | Prop-1-en-3-yl |
| 1657 | $CH_3$ | 4-OH-$C_6H_4$ | (E)-1-Chloroprop-1-en-3-yl |
| 1658 | $CH_3$ | 4-OH-$C_6H_4$ | Propyn-3-yl |
| 1659 | $CH_3$ | 4-OH-$C_6H_4$ | 3-Methylbut-2-en-1-yl |
| 1660 | $CH_3$ | 2-$OCH_3$-$C_6H_4$ | H |
| 1661 | $CH_3$ | 2-$OCH_3$-$C_6H_4$ | $CH_3$ |
| 1662 | $CH_3$ | 2-$OCH_3$-$C_6H_4$ | $C_2H_5$ |
| 1663 | $CH_3$ | 2-$OCH_3$-$C_6H_4$ | n-$C_3H_7$ |
| 1664 | $CH_3$ | 2-$OCH_3$-$C_6H_4$ | i-$C_3H_7$ |
| 1665 | $CH_3$ | 2-$OCH_3$-$C_6H_4$ | n-$C_4H_9$ |
| 1666 | $CH_3$ | 2-$OCH_3$-$C_6H_4$ | t-$C_4H_9$ |
| 1667 | $CH_3$ | 2-$OCH_3$-$C_6H_4$ | n-$C_6H_{13}$ |
| 1668 | $CH_3$ | 2-$OCH_3$-$C_6H_4$ | Prop-1-en-3-yl |
| 1669 | $CH_3$ | 2-$OCH_3$-$C_6H_4$ | (E)-1-Chloroprop-1-en-3-yl |
| 1670 | $CH_3$ | 2-$OCH_3$-$C_6H_4$ | Propyn-3-yl |
| 1671 | $CH_3$ | 2-$OCH_3$-$C_6H_4$ | 3-Methylbut-2-en-1-yl |
| 1672 | $CH_3$ | 3-$OCH_3$-$C_6H_4$ | H |
| 1673 | $CH_3$ | 3-$OCH_3$-$C_6H_4$ | $CH_3$ |
| 1674 | $CH_3$ | 3-$OCH_3$-$C_6H_4$ | $C_2H_5$ |
| 1675 | $CH_3$ | 3-$OCH_3$-$C_6H_4$ | n-$C_3H_7$ |
| 1676 | $CH_3$ | 3-$OCH_3$-$C_6H_4$ | i-$C_3H_7$ |
| 1677 | $CH_3$ | 3-$OCH_3$-$C_6H_4$ | n-$C_4H_9$ |
| 1678 | $CH_3$ | 3-$OCH_3$-$C_6H_4$ | t-$C_4H_9$ |
| 1679 | $CH_3$ | 3-$OCH_3$-$C_6H_4$ | n-$C_6H_{13}$ |
| 1680 | $CH_3$ | 3-$OCH_3$-$C_6H_4$ | Prop-1-en-3-yl |
| 1681 | $CH_3$ | 3-$OCH_3$-$C_6H_4$ | (E)-1-Chloroprop-1-en-3-yl |
| 1682 | $CH_3$ | 3-$OCH_3$-$C_6H_4$ | Propyn-3-yl |
| 1683 | $CH_3$ | 3-$OCH_3$-$C_6H_4$ | 3-Methylbut-2-n-1-yl |
| 1684 | $CH_3$ | 4-$OCH_3$-$C_6H_4$ | H |
| 1685 | $CH_3$ | 4-$OCH_3$-$C_6H_4$ | $CH_3$ |
| 1686 | $CH_3$ | 4-$OCH_3$-$C_6H_4$ | $C_2H_5$ |
| 1687 | $CH_3$ | 4-$OCH_3$-$C_6H_4$ | n-$C_3H_7$ |
| 1688 | $CH_3$ | 4-$OCH_3$-$C_6H_4$ | i-$C_3H_7$ |
| 1689 | $CH_3$ | 4-$OCH_3$-$C_6H_4$ | n-$C_4H_9$ |
| 1690 | $CH_3$ | 4-$OCH_3$-$C_6H_4$ | t-$C_4H_9$ |
| 1691 | $CH_3$ | 4-$OCH_3$-$C_6H_4$ | n-$C_6H_{13}$ |
| 1692 | $CH_3$ | 4-$OCH_3$-$C_6H_4$ | Prop-1-en-3-yl |
| 1693 | $CH_3$ | 4-$OCH_3$-$C_6H_4$ | (E)-1-Chloroprop-1-en-3-yl |
| 1694 | $CH_3$ | 4-$OCH_3$-$C_6H_4$ | Propyn-3-yl |
| 1695 | $CH_3$ | 4-$OCH_3$-$C_6H_4$ | 3-Methylbut-2-en-1-yl |
| 1696 | $CH_3$ | 2-$OC_2H_5$-$C_6H_4$ | H |
| 1697 | $CH_3$ | 2-$OC_2H_5$-$C_6H_4$ | $CH_3$ |
| 1698 | $CH_3$ | 2-$OC_2H_5$-$C_6H_4$ | $C_2H_5$ |
| 1699 | $CH_3$ | 2-$OC_2H_5$-$C_6H_4$ | n-$C_3H_7$ |
| 1700 | $CH_3$ | 2-$OC_2H_5$-$C_6H_4$ | i-$C_3H_7$ |
| 1701 | $CH_3$ | 2-$OC_2H_5$-$C_6H_4$ | n-$C_4H_9$ |
| 1702 | $CH_3$ | 2-$OC_2H_5$-$C_6H_4$ | t-$C_4H_9$ |
| 1703 | $CH_3$ | 2-$OC_2H_5$-$C_6H_4$ | n-$C_6H_{13}$ |
| 1704 | $CH_3$ | 2-$OC_2H_5$-$C_6H_4$ | Prop-1-en-3-yl |
| 1705 | $CH_3$ | 2-$OC_2H_5$-$C_6H_4$ | (E)-1-Chloroprop-1-en-3-yl |
| 1706 | $CH_3$ | 2-$OC_2H_5$-$C_6H_4$ | Propyn-3-yl |
| 1707 | $CH_3$ | 2-$OC_2H_5$-$C_6H_4$ | 3-Methylbut-2-en-1-yl |
| 1708 | $CH_3$ | 3-$OC_2H_5$-$C_6H_4$ | H |
| 1709 | $CH_3$ | 3-$OC_2H_5$-$C_6H_4$ | $CH_3$ |
| 1710 | $CH_3$ | 3-$OC_2H_5$-$C_6H_4$ | $C_2H_5$ |
| 1711 | $CH_3$ | 3-$OC_2H_5$-$C_6H_4$ | n-$C_3H_7$ |
| 1712 | $CH_3$ | 3-$OC_2H_5$-$C_6H_4$ | i-$C_3H_7$ |
| 1713 | $CH_3$ | 3-$OC_2H_5$-$C_6H_4$ | n-$C_4H_9$ |
| 1714 | $CH_3$ | 3-$OC_2H_5$-$C_6H_4$ | t-$C_4H_9$ |
| 1715 | $CH_3$ | 3-$OC_2H_5$-$C_6H_4$ | n-$C_6H_{13}$ |
| 1716 | $CH_3$ | 3-$OC_2H_5$-$C_6H_4$ | Prop-1-en-3-yl |
| 1717 | $CH_3$ | 3-$OC_2H_5$-$C_6H_4$ | (E)-1-Chloroprop-1-en-3-yl |
| 1718 | $CH_3$ | 3-$OC_2H_5$-$C_6H_4$ | Propyn-3-yl |
| 1719 | $CH_3$ | 3-$OC_2H_5$-$C_6H_4$ | 3-Methylbut-2-en-1-yl |
| 1720 | $CH_3$ | 4-$OC_2H_5$-$C_6H_4$ | H |
| 1721 | $CH_3$ | 4-$OC_2H_5$-$C_6H_4$ | $CH_3$ |
| 1722 | $CH_3$ | 4-$OC_2H_5$-$C_6H_4$ | $C_2H_5$ |
| 1723 | $CH_3$ | 4-$OC_2H_5$-$C_6H_4$ | n-$C_3H_7$ |
| 1724 | $CH_3$ | 4-$OC_2H_5$-$C_6H_4$ | i-$C_3H_7$ |

TABLE A-continued

| No. | R² | R³ | R⁴ |
|---|---|---|---|
| 1725 | CH₃ | 4-OC₂H₅-C₆H₄ | n-C₄H₉ |
| 1726 | CH₃ | 4-OC₂H₅-C₆H₄ | t-C₄H₉ |
| 1727 | CH₃ | 4-OC₂H₅-C₆H₄ | n-C₆H₁₃ |
| 1728 | CH₃ | 4-OC₂H₅-C₆H₄ | Prop-1-en-3-yl |
| 1729 | CH₃ | 4-OC₂H₅-C₆H₄ | (E)-1-Chloropro-1-en-3-yl |
| 1730 | CH₃ | 4-OC₂H₅-C₆H₄ | Propyn-3-yl |
| 1731 | CH₃ | 4-OC₂H₅-C₆H₄ | 3-Methylbut-2-en-1-yl |
| 1732 | CH₃ | 2-O-(i-C₃H₇)-C₆H₄ | H |
| 1733 | CH₃ | 2-O-(i-C₃H₇)-C₆H₄ | CH₃ |
| 1734 | CH₃ | 2-O-(i-C₃H₇)-C₆H₄ | C₂H₅ |
| 1735 | CH₃ | 2-O-(i-C₃H₇)-C₆H₄ | n-C₃H₇ |
| 1736 | CH₃ | 2-O-(i-C₃H₇)-C₆H₄ | i-C₃H₇ |
| 1737 | CH₃ | 2-O-(i-C₃H₇)-C₆H₄ | n-C₄H₉ |
| 1738 | CH₃ | 2-O-(i-C₃H₇)-C₆H₄ | t-C₄H₉ |
| 1739 | CH₃ | 2-O-(i-C₃H₇)-C₆H₄ | n-C₆H₁₃ |
| 1740 | CH₃ | 2-O-(i-C₃H₇)-C₆H₄ | Prop-1-en-3-yl |
| 1741 | CH₃ | 2-O-(i-C₃H₇)-C₆H₄ | (E)-1-Chloroprop-1-en-3-yl |
| 1742 | CH₃ | 2-O-(i-C₃H₇)-C₆H₄ | Propyn-3-yl |
| 1743 | CH₃ | 2-O-(i-C₃H₇)-C₆H₄ | 3-Methylbut-2-en-1-yl |
| 1744 | CH₃ | 3-O-(i-C₃H₇)-C₆H₄ | H |
| 1745 | CH₃ | 3-O-(i-C₃H₇)-C₆H₄ | CH₃ |
| 1746 | CH₃ | 3-O-(i-C₃H₇)-C₆H₄ | C₂H₅ |
| 1747 | CH₃ | 3-O-(i-C₃H₇)-C₆H₄ | n-C₃H₇ |
| 1748 | CH₃ | 3-O-(i-C₃H₇)-C₆H₄ | i-C₃H₇ |
| 1749 | CH₃ | 3-O-(i-C₃H₇)-C₆H₄ | n-C₄H₉ |
| 1750 | CH₃ | 3-O-(i-C₃H₇)-C₆H₄ | t-C₄H₉ |
| 1751 | CH₃ | 3-O-(i-C₃H₇)-C₆H₄ | n-C₆H₁₃ |
| 1752 | CH₃ | 3-O-(i-C₃H₇)-C₆H₄ | Prop-1-en-3-yl |
| 1753 | CH₃ | 3-O-(i-C₃H₇)-C₆H₄ | (E)-1-Chloroprop-1-en-3-yl |
| 1754 | CH₃ | 3-O-(i-C₃H₇)-C₆H₄ | Propyn-3-yl |
| 1755 | CH₃ | 3-O-(i-C₃H₇)-C₆H₄ | 3-Methylbut-2-en-1-yl |
| 1756 | CH₃ | 4-O-(i-C₃H₇)-C₆H₄ | H |
| 1757 | CH₃ | 4-O-(i-C₃H₇)-C₆H₄ | CH₃ |
| 1758 | CH₃ | 4-O-(i-C₃H₇)-C₆H₄ | C₂H₅ |
| 1759 | CH₃ | 4-O-(i-C₃H₇)-C₆H₄ | n-C₃H₇ |
| 1760 | CH₃ | 4-O-(i-C₃H₇)-C₆H₄ | i-C₃H₇ |
| 1761 | CH₃ | 4-O-(i-C₃H₇)-C₆H₄ | n-C₄H₉ |
| 1762 | CH₃ | 4-O-(i-C₃H₇)-C₆H₄ | t-C₄H₉ |
| 1763 | CH₃ | 4-O-(i-C₃H₇)-C₆H₄ | n-C₆H₁₃ |
| 1764 | CH₃ | 4-O-(i-C₃H₇)-C₆H₄ | Prop-1-en-3-yl |
| 1765 | CH₃ | 4-O-(i-C₃H₇)-C₆H₄ | (E)-1-Chloroprop-1-en-3-yl |
| 1766 | CH₃ | 4-O-(i-C₃H₇)-C₆H₄ | Propyn-3-yl |
| 1767 | CH₃ | 4-O-(i-C₃H₇)-C₆H₄ | 3-Methylbut-2-en-1-yl |
| 1768 | CH₃ | 2-O-(t-C₄H₉)-C₆H₄ | H |
| 1769 | CH₃ | 2-O-(t-C₄H₉)-C₆H₄ | CH₃ |
| 1770 | CH₃ | 2-O-(t-C₄H₉)-C₆H₄ | C₂H₅ |
| 1771 | CH₃ | 2-O-(t-C₄H₉)-C₆H₄ | n-C₃H₇ |
| 1772 | CH₃ | 2-O-(t-C₄H₉)-C₆H₄ | i-C₃H₇ |
| 1773 | CH₃ | 2-O-(t-C₄H₉)-C₆H₄ | n-C₄H₉ |
| 1774 | CH₃ | 2-O-(t-C₄H₉)-C₆H₄ | t-C₄H₉ |
| 1775 | CH₃ | 2-O-(t-C₄H₉)-C₆H₄ | n-C₆H₁₃ |
| 1776 | CH₃ | 2-O-(t-C₄H₉)-C₆H₄ | Prop-1-en-3-yl |
| 1777 | CH₃ | 2-O-(t-C₄H₉)-C₆H₄ | (E)-1-Chloroprop-1-en-3-yl |
| 1778 | CH₃ | 2-O-(t-C₄H₉)-C₆H₄ | Propyn-3-yl |
| 1779 | CH₃ | 2-O-(t-C₄H₉)-C₆H₄ | 3-Methylbut-2-en-1-yl |
| 1780 | CH₃ | 3-O-(t-C₄H₉)-C₆H₄ | H |
| 1781 | CH₃ | 3-O-(t-C₄H₉)-C₆H₄ | CH₃ |
| 1782 | CH₃ | 3-O-(t-C₄H₉)-C₆H₄ | C₂H₅ |
| 1783 | CH₃ | 3-O-(t-C₄H₉)-C₆H₄ | n-C₃H₇ |
| 1784 | CH₃ | 3-O-(t-C₄H₉)-C₆H₄ | i-C₃H₇ |
| 1785 | CH₃ | 3-O-(t-C₄H₉)-C₆H₄ | n-C₄H₉ |
| 1786 | CH₃ | 3-O-(t-C₄H₉)-C₆H₄ | t-C₄H₉ |
| 1787 | CH₃ | 3-O-(t-C₄H₉)-C₆H₄ | n-C₆H₁₃ |
| 1788 | CH₃ | 3-O-(t-C₄H₉)-C₆H₄ | Prop-1-en-3-yl |
| 1789 | CH₃ | 3-O-(t-C₄H₉)-C₆H₄ | (E)-1-Chloroprop-1-en-3-yl |
| 1790 | CH₃ | 3-O-(t-C₄H₉)-C₆H₄ | Propyn-3-yl |
| 1791 | CH₃ | 3-O-(t-C₄H₉)-C₆H₄ | 3-Methylbut-2-en-1-yl |
| 1792 | CH₃ | 4-O-(t-C₄H₉)-C₆H₄ | H |
| 1793 | CH₃ | 4-O-(t-C₄H₉)-C₆H₄ | CH₃ |
| 1794 | CH₃ | 4-O-(t-C₄H₉)-C₆H₄ | C₂H₅ |
| 1795 | CH₃ | 4-O-(t-C₄H₉)-C₆H₄ | n-C₃H₇ |
| 1796 | CH₃ | 4-O-(t-C₄H₉)-C₆H₄ | i-C₃H₇ |
| 1797 | CH₃ | 4-O-(t-C₄H₉)-C₆H₄ | n-C₄H₉ |
| 1798 | CH₃ | 4-O-(t-C₄H₉)-C₆H₄ | t-C₄H₉ |
| 1799 | CH₃ | 4-O-(t-C₄H₉)-C₆H₄ | n-C₆H₁₃ |
| 1800 | CH₃ | 4-O-(t-C₄H₉)-C₆H₄ | Prop-1-en-3-yl |
| 1801 | CH₃ | 4-O-(t-C₄H₉)-C₆H₄ | (E)-1-Chloroprop-1-en-3-yl |

TABLE A-continued

| No. | R² | R³ | R⁴ |
|---|---|---|---|
| 1802 | CH₃ | 4-O-(t-C₄H₉)-C₆H₄ | Propyn-3-yl |
| 1803 | CH₃ | 4-O-(t-C₄H₉)-C₆H₄ | 3-Methylbut-2-en-1-yl |
| 1804 | CH₃ | 2-CF₃-C₆H₄ | H |
| 1805 | CH₃ | 2-CF₃-C₆H₄ | CH₃ |
| 1806 | CH₃ | 2-CF₃-C₆H₄ | C₂H₅ |
| 1807 | CH₃ | 2-CF₃-C₆H₄ | n-C₃H₇ |
| 1808 | CH₃ | 2-CF₃-C₆H₄ | i-C₃H₇ |
| 1809 | CH₃ | 2-CF₃-C₆H₄ | n-C₄H₉ |
| 1810 | CH₃ | 2-CF₃-C₆H₄ | t-C₄H₉ |
| 1811 | CH₃ | 2-CF₃-C₆H₄ | n-C₆H₁₃ |
| 1812 | CH₃ | 2-CF₃-C₆H₄ | Prop-1-en-3-yl |
| 1813 | CH₃ | 2-CF₃-C₆H₄ | (E)-1-Chloroprop-1-en-3-yl |
| 1814 | CH₃ | 2-CF₃-C₆H₄ | Propyn-3-yl |
| 1815 | CH₃ | 2-CF₃-C₆H₄ | 3-Methylbut-2-en-1-yl |
| 1816 | CH₃ | 3-CF₃-C₆H₄ | H |
| 1817 | CH₃ | 3-CF₃-C₆H₄ | CH₃ |
| 1818 | CH₃ | 3-CF₃-C₆H₄ | C₂H₅ |
| 1819 | CH₃ | 3-CF₃-C₆H₄ | n-C₃H₇ |
| 1820 | CH₃ | 3-CF₃-C₆H₄ | i-C₃H₇ |
| 1821 | CH₃ | 3-CF₃-C₆H₄ | n-C₄H₉ |
| 1822 | CH₃ | 3-CF₃-C₆H₄ | t-C₄H₉ |
| 1823 | CH₃ | 3-CF₃-C₆H₄ | n-C₆H₁₃ |
| 1824 | CH₃ | 3-CF₃-C₆H₄ | Prop-1-en-3-yl |
| 1825 | CH₃ | 3-CF₃-C₆H₄ | (E)-1-Chloroprop-1-en-3-yl |
| 1826 | CH₃ | 3-CF₃-C₆H₄ | Propyn-3-yl |
| 1827 | CH₃ | 3-CF₃-C₆H₄ | 3-Methylbut-2-en-1-yl |
| 1828 | CH₃ | 4-CF₃-C₆H₄ | H |
| 1829 | CH₃ | 4-CF₃-C₆H₄ | CH₃ |
| 1830 | CH₃ | 4-CF₃-C₆H₄ | C₂H₅ |
| 1831 | CH₃ | 4-CF₃-C₆H₄ | n-C₃H₇ |
| 1832 | CH₃ | 4-CF₃-C₆H₄ | i-C₃H₇ |
| 1833 | CH₃ | 4-CF₃-C₆H₄ | n-C₄H₉ |
| 1834 | CH₃ | 4-CF₃-C₆H₄ | t-C₄H₉ |
| 1835 | CH₃ | 4-CF₃-C₆H₄ | n-C₆H₁₃ |
| 1836 | CH₃ | 4-CF₃-C₆H₄ | Prop-1-en-3-yl |
| 1837 | CH₃ | 4-CF₃-C₆H₄ | (E)-1-Chloroprop-1-en-3-yl |
| 1838 | CH₃ | 4-CF₃-C₆H₄ | Propyn-3-yl |
| 1839 | CH₃ | 4-CF₃-C₆H₄ | 3-Methylbut-2-en-1-yl |
| 1840 | CH₃ | 2-NH₂-C₆H₄ | H |
| 1841 | CH₃ | 2-NH₂-C₆H₄ | CH₃ |
| 1842 | CH₃ | 2-NH₂-C₆H₄ | C₂H₅ |
| 1843 | CH₃ | 2-NH₂-C₆H₄ | n-C₃H₇ |
| 1844 | CH₃ | 2-NH₂-C₆H₄ | i-C₃H₇ |
| 1845 | CH₃ | 2-NH₂-C₆H₄ | n-C₄H₉ |
| 1846 | CH₃ | 2-NH₂-C₆H₄ | t-C₄H₉ |
| 1847 | CH₃ | 2-NH₂-C₆H₄ | n-C₆H₁₃ |
| 1848 | CH₃ | 2-NH₂-C₆H₄ | Prop-1-en-3-yl |
| 1849 | CH₃ | 2-NH₂-C₆H₄ | (E)-1-Chloroprop-1-en-3-yl |
| 1850 | CH₃ | 2-NH₂-C₆H₄ | Propyn-3-yl |
| 1851 | CH₃ | 2-NH₂-C₆H₄ | 3-Methylbut-2-en-1-yl |
| 1852 | CH₃ | 3-NH₂-C₆H₄ | H |
| 1853 | CH₃ | 3-NH₂-C₆H₄ | CH₃ |
| 1854 | CH₃ | 3-NH₂-C₆H₄ | C₂H₅ |
| 1855 | CH₃ | 3-NH₂-C₆H₄ | n-C₃H₇ |
| 1856 | CH₃ | 3-NH₂-C₆H₄ | i-C₃H₇ |
| 1857 | CH₃ | 3-NH₂-C₆H₄ | n-C₄H₉ |
| 1858 | CH₃ | 3-NH₂-C₆H₄ | t-C₄H₉ |
| 1859 | CH₃ | 3-NH₂-C₆H₄ | n-C₆H₁₃ |
| 1860 | CH₃ | 3-NH₂-C₆H₄ | Prop-1-en-3-yl |
| 1861 | CH₃ | 3-NH₂-C₆H₄ | (E)-1-Chloroprop-1-en-3-yl |
| 1862 | CH₃ | 3-NH₂-C₆H₄ | Propyn-3-yl |
| 1863 | CH₃ | 3-NH₂-C₆H₄ | 3-Methylbut-2-en-1-yl |
| 1864 | CH₃ | 4-NH₂-C₆H₄ | H |
| 1865 | CH₃ | 4-NH₂-C₆H₄ | CH₃ |
| 1866 | CH₃ | 4-NH₂-C₆H₄ | C₂H₅ |
| 1867 | CH₃ | 4-NH₂-C₆H₄ | n-C₃H₇ |
| 1868 | CH₃ | 4-NH₂-C₆H₄ | i-C₃H₇ |
| 1869 | CH₃ | 4-NH₂-C₆H₄ | n-C₄H₉ |
| 1870 | CH₃ | 4-NH₂-C₆H₄ | t-C₄H₉ |
| 1871 | CH₃ | 4-NH₂-C₆H₄ | n-C₆H₁₃ |
| 1872 | CH₃ | 4-NH₂-C₆H₄ | Prop-1-en-3-yl |
| 1873 | CH₃ | 4-NH₂-C₆H₄ | (E)-1-Chloroprop-1-en-3-yl |
| 1874 | CH₃ | 4-NH₂-C₆H₄ | Propyn-3-yl |
| 1875 | CH₃ | 4-NH₂-C₆H₄ | 3-Methylbut-2-en-1-yl |
| 1876 | CH₃ | 2-NMe₂-C₆H₄ | H |
| 1877 | CH₃ | 2-NMe₂-C₆H₄ | CH₃ |
| 1878 | CH₃ | 2-NMe₂-C₆H₄ | C₂H₅ |

TABLE A-continued

| No. | R² | R³ | R⁴ |
|---|---|---|---|
| 1879 | CH₃ | 2-NMe₂-C₆H₄ | n-C₃H₇ |
| 1880 | CH₃ | 2-NMe₂-C₆H₄ | i-C₃H₇ |
| 1881 | CH₃ | 2-NMe₂-C₆H₄ | n-C₄H₉ |
| 1882 | CH₃ | 2-NMe₂-C₆H₄ | t-C₄H₉ |
| 1883 | CH₃ | 2-NMe₂-C₆H₄ | n-C₆H₁₃ |
| 1884 | CH₃ | 2-NMe₂-C₆H₄ | Prop-1-en-3-yl |
| 1885 | CH₃ | 2-NMe₂-C₆H₄ | (E)-1-Chloroprop-1-en-3-yl |
| 1886 | CH₃ | 2-NMe₂-C₆H₄ | Propyn-3-yl |
| 1887 | CH₃ | 2-NMe₂-C₆H₄ | 3-Methylbut-2-en-1-yl |
| 1888 | CH₃ | 3-NMe₂-C₆H₄ | H |
| 1889 | CH₃ | 3-NMe₂-C₆H₄ | CH₃ |
| 1890 | CH₃ | 3-NMe₂-C₆H₄ | C₂H₅ |
| 1891 | CH₃ | 3-NMe₂-C₆H₄ | n-C₃H₇ |
| 1892 | CH₃ | 3-NMe₂-C₆H₄ | i-C₃H₇ |
| 1893 | CH₃ | 3-NMe₂-C₆H₄ | n-C₄H₉ |
| 1894 | CH₃ | 3-NMe₂-C₆H₄ | t-C₄H₉ |
| 1895 | CH₃ | 3-NMe₂-C₆H₄ | n-C₆H₁₃ |
| 1896 | CH₃ | 3-NMe₂-C₆H₄ | Prop-1-en-3-yl |
| 1897 | CH₃ | 3-NMe₂-C₆H₄ | (E)-1-Chloroprop-1-en-3-yl |
| 1898 | CH₃ | 3-NMe₂-C₆H₄ | Propyn-3-yl |
| 1899 | CH₃ | 3-NMe₂-C₆H₄ | 3-Methylbut-2-en-1-yl |
| 1900 | CH₃ | 4-NMe₂-C₆H₄ | H |
| 1901 | CH₃ | 4-NMe₂-C₆H₄ | CH₃ |
| 1902 | CH₃ | 4-NMe₂-C₆H₄ | C₂H₅ |
| 1903 | CH₃ | 4-NMe₂-C₆H₄ | n-C₃H₇ |
| 1904 | CH₃ | 4-NMe₂-C₆H₄ | i-C₃H₇ |
| 1905 | CH₃ | 4-NMe₂-C₆H₄ | n-C₄H₉ |
| 1906 | CH₃ | 4-NMe₂-C₆H₄ | t-C₄H₉ |
| 1907 | CH₃ | 4-NMe₂-C₆H₄ | n-C₆H₁₃ |
| 1908 | CH₃ | 4-NMe₂-C₆H₄ | Prop-1-en-3-yl |
| 1909 | CH₃ | 4-NMe₂-C₆H₄ | (E)-1-Chloroprop-1-en-3-yl |
| 1910 | CH₃ | 4-NMe₂-C₆H₄ | Propyn-3-yl |
| 1911 | CH₃ | 4-NMe₂-C₆H₄ | 3-Methylbut-2-en-1-yl |
| 1912 | CH₃ | 2-Aminothiocarbonyl-C₆H₄ | H |
| 1913 | CH₃ | 2-Aminothiocarbonyl-C₆H₄ | CH₃ |
| 1914 | CH₃ | 2-Aminothiocarbonyl-C₆H₄ | C₂H₅ |
| 1915 | CH₃ | 2-Aminothiocarbonyl-C₆H₄ | n-C₃H₇ |
| 1916 | CH₃ | 2-Aminothiocarbonyl-C₆H₄ | i-C₃H₇ |
| 1917 | CH₃ | 2-Aminothiocarbonyl-C₆H₄ | n-C₄H₉ |
| 1918 | CH₃ | 2-Aminothiocarbonyl-C₆H₄ | t-C₄H₉ |
| 1919 | CH₃ | 2-Aminothiocarbonyl-C₆H₄ | n-C₆H₁₃ |
| 1920 | CH₃ | 2-Aminothiocarbonyl-C₆H₄ | Prop-1-en-3-yl |
| 1921 | CH₃ | 2-Aminothiocarbonyl-C₆H₄ | (E)-1-Chloroprop-1-en-3-yl |
| 1922 | CH₃ | 2-Aminothiocarbonyl-C₆H₄ | Propyn-3-yl |
| 1923 | CH₃ | 2-Aminothiocarbonyl-C₆H₄ | 3-Methylbut-2-en-1-yl |
| 1924 | CH₃ | 2-Aminothiocarbonyl-C₆H₄ | H |
| 1925 | CH₃ | 3-Aminothiocarbonyl-C₆H₄ | CH₃ |
| 1926 | CH₃ | 3-Aminothiocarbonyl-C₆H₄ | C₂H₅ |
| 1927 | CH₃ | 3-Aminothiocarbonyl-C₆H₄ | n-C₃H₇ |
| 1928 | CH₃ | 3-Aminothiocarbonyl-C₆H₄ | i-C₃H₇ |
| 1929 | CH₃ | 3-Aminothiocarbonyl-C₆H₄ | n-C₄H₉ |
| 1930 | CH₃ | 3-Aminothiocarbonyl-C₆H₄ | t-C₄H₉ |
| 1931 | CH₃ | 3-Aminothiocarbonyl-C₆H₄ | n-C₆H₁₃ |
| 1932 | CH₃ | 3-Aminothiocarbonyl-C₆H₄ | Prop-1-en-3-yl |
| 1933 | CH₃ | 3-Aminothiocarbonyl-C₆H₄ | (E)-1-Chloropro-1-en-3-yl |
| 1934 | CH₃ | 3-Aminothiocarbonyl-C₆H₄ | Propyn-3-yl |
| 1935 | CH₃ | 3-Aminothiocarbonyl-C₆H₄ | 3-Methylbut-2-en-1-yl |
| 1936 | CH₃ | 4-Aminothiocarbonyl-C₆H₄ | H |
| 1937 | CH₃ | 4-Aminothiocarbonyl-C₆H₄ | CH₃ |
| 1938 | CH₃ | 4-Aminothiocarbonyl-C₆H₄ | C₂H₅ |
| 1939 | CH₃ | 4-Aminothiocarbonyl-C₆H₄ | n-C₃H₇ |
| 1940 | CH₃ | 4-Aminothiocarbonyl-C₆H₄ | i-C₃H₇ |
| 1941 | CH₃ | 4-Aminothiocarbonyl-C₆H₄ | n-C₄H₉ |
| 1942 | CH₃ | 4-Aminothiocarbonyl-C₆H₄ | t-C₄H₉ |
| 1943 | CH₃ | 4-Aminothiocarbonyl-C₆H₄ | n-C₆H₁₃ |
| 1944 | CH₃ | 4-Aminothiocarbonyl-C₆H₄ | Prop-1-en-3-yl |
| 1945 | CH₃ | 4-Aminothiocarbonyl-C₆H₄ | (E)-1-Chloroprop-1-en-3-yl |
| 1946 | CH₃ | 4-Aminothiocarbonyl-C₆H₄ | Propyn-3-yl |
| 1947 | CH₃ | 4-Aminothiocarbonyl-C₆H₄ | 3-Methylbut-2-en-1-yl |
| 1948 | CH₃ | 2-OCF₃-C₆H₄ | H |
| 1949 | CH₃ | 2-OCF₃-C₆H₄ | CH₃ |
| 1950 | CH₃ | 2-OCF₃-C₆H₄ | C₂H₅ |
| 1951 | CH₃ | 2-OCF₃-C₆H₄ | n-C₃H₇ |
| 1952 | CH₃ | 2-OCF₃-C₆H₄ | i-C₃H₇ |
| 1953 | CH₃ | 2-OCF₃-C₆H₄ | n-C₄H₉ |
| 1954 | CH₃ | 2-OCF₃-C₆H₄ | t-C₄H₉ |
| 1955 | CH₃ | 2-OCF₃-C₆H₄ | n-C₆H₁₃ |

TABLE A-continued

| No. | R² | R³ | R⁴ |
|---|---|---|---|
| 1956 | $CH_3$ | 2-$OCF_3$-$C_6H_4$ | Prop-1-en-3-yl |
| 1957 | $CH_3$ | 2-$OCF_3$-$C_6H_4$ | (E)-1-Chloroprop-1-en-3-yl |
| 1958 | $CH_3$ | 2-$OCF_3$-$C_6H_4$ | Propyn-3-yl |
| 1959 | $CH_3$ | 2-$OCF_3$-$C_6H_4$ | 3-Methylbut-2-en-1-yl |
| 1960 | $CH_3$ | 3-$OCF_3$-$C_6H_4$ | H |
| 1961 | $CH_3$ | 3-$OCF_3$-$C_6H_4$ | $CH_3$ |
| 1962 | $CH_3$ | 3-$OCF_3$-$C_6H_4$ | $C_2H_5$ |
| 1963 | $CH_3$ | 3-$OCF_3$-$C_6H_4$ | n-$C_3H_7$ |
| 1964 | $CH_3$ | 3-$OCF_3$-$C_6H_4$ | i-$C_3H_7$ |
| 1965 | $CH_3$ | 3-$OCF_3$-$C_6H_4$ | n-$C_4H_9$ |
| 1966 | $CH_3$ | 3-$OCF_3$-$C_6H_4$ | t-$C_4H_9$ |
| 1967 | $CH_3$ | 3-$OCF_3$-$C_6H_4$ | n-$C_6H_{13}$ |
| 1968 | $CH_3$ | 3-$OCF_3$-$C_6H_4$ | Prop-1-en-3-yl |
| 1969 | $CH_3$ | 3-$OCF_3$-$C_6H_4$ | (E)-1-Chloroprop-1-en-3-yl |
| 1970 | $CH_3$ | 3-$OCF_3$-$C_6H_4$ | Propyn-3-yl |
| 1971 | $CH_3$ | 3-$OCF_3$-$C_6H_4$ | 3-Methylbut-2-en-1-yl |
| 1972 | $CH_3$ | 4-$OCF_3$-$C_6H_4$ | H |
| 1973 | $CH_3$ | 4-$OCF_3$-$C_6H_4$ | $CH_3$ |
| 1974 | $CH_3$ | 4-$OCF_3$-$C_6H_4$ | $C_2H_5$ |
| 1975 | $CH_3$ | 4-$OCF_3$-$C_6H_4$ | n-$C_3H_7$ |
| 1976 | $CH_3$ | 4-$OCF_3$-$C_6H_4$ | i-$C_3H_7$ |
| 1977 | $CH_3$ | 4-$OCF_3$-$C_6H_4$ | n-$C_4H_9$ |
| 1978 | $CH_3$ | 4-$OCF_3$-$C_6H_4$ | t-$C_4H_9$ |
| 1979 | $CH_3$ | 4-$OCF_3$-$C_6H_4$ | n-$C_6H_{13}$ |
| 1980 | $CH_3$ | 4-$OCF_3$-$C_6H_4$ | Prop-1-en-3-yl |
| 1981 | $CH_3$ | 4-$OCF_3$-$C_6H_4$ | (E)-1-Chloroprop-1-en-3-yl |
| 1982 | $CH_3$ | 4-$OCF_3$-$C_6H_4$ | Propyn-3-yl |
| 1983 | $CH_3$ | 4-$OCF_3$-$C_6H_4$ | 3-Methylbut-2-en-1-yl |
| 1984 | $CH_3$ | 2-$SCH_3$-$C_6H_4$ | H |
| 1985 | $CH_3$ | 2-$SCH_3$-$C_6H_4$ | $CH_3$ |
| 1986 | $CH_3$ | 2-$SCH_3$-$C_6H_4$ | $C_2H_5$ |
| 1987 | $CH_3$ | 2-$SCH_3$-$C_6H_4$ | n-$C_3H_7$ |
| 1988 | $CH_3$ | 2-$SCH_3$-$C_6H_4$ | i-$C_3H_7$ |
| 1989 | $CH_3$ | 2-$SCH_3$-$C_6H_4$ | n-$C_4H_9$ |
| 1990 | $CH_3$ | 2-$SCH_3$-$C_6H_4$ | t-$C_4H_9$ |
| 1991 | $CH_3$ | 2-$SCH_3$-$C_6H_4$ | n-$C_6H_{13}$ |
| 1992 | $CH_3$ | 2-$SCH_3$-$C_6H_4$ | Prop-1-en-3-yl |
| 1993 | $CH_3$ | 2-$SCH_3$-$C_6H_4$ | (E)-1-Chloroprop-1-en-3-yl |
| 1994 | $CH_3$ | 2-$SCH_3$-$C_6H_4$ | Propyn-3-yl |
| 1995 | $CH_3$ | 2-$SCH_3$-$C_6H_4$ | 3-Methylbut-2-en-1-yl |
| 1996 | $CH_3$ | 3-$SCH_3$-$C_6H_4$ | H |
| 1997 | $CH_3$ | 3-$SCH_3$-$C_6H_4$ | $CH_3$ |
| 1998 | $CH_3$ | 3-$SCH_3$-$C_6H_4$ | $C_2H_5$ |
| 1999 | $CH_3$ | 3-$SCH_3$-$C_6H_4$ | n-$C_3H_7$ |
| 2000 | $CH_3$ | 3-$SCH_3$-$C_6H_4$ | i-$C_3H_7$ |
| 2001 | $CH_3$ | 3-$SCH_3$-$C_6H_4$ | n-$C_4H_9$ |
| 2002 | $CH_3$ | 3-$SCH_3$-$C_6H_4$ | t-$C_4H_9$ |
| 2003 | $CH_3$ | 3-$SCH_3$-$C_6H_4$ | n-$C_6H_{13}$ |
| 2004 | $CH_3$ | 3-$SCH_3$-$C_6H_4$ | Prop-1-en-3-yl |
| 2005 | $CH_3$ | 3-$SCH_3$-$C_6H_4$ | (E)-1-Chloroprop-1-en-3-yl |
| 2006 | $CH_3$ | 3-$SCH_3$-$C_6H_4$ | Propyn-3-yl |
| 2007 | $CH_3$ | 3-$SCH_3$-$C_6H_4$ | 3-Methylbut-2-en-1-yl |
| 2008 | $CH_3$ | 4-$SCH_3$-$C_6H_4$ | H |
| 2009 | $CH_3$ | 4-$SCH_3$-$C_6H_4$ | $CH_3$ |
| 2010 | $CH_3$ | 4-$SCH_3$-$C_6H_4$ | $C_2H_5$ |
| 2011 | $CH_3$ | 4-$SCH_3$-$C_6H_4$ | n-$C_3H_7$ |
| 2012 | $CH_3$ | 4-$SCH_3$-$C_6H_4$ | i-$C_3H_7$ |
| 2013 | $CH_3$ | 4-$SCH_3$-$C_6H_4$ | n-$C_4H_9$ |
| 2014 | $CH_3$ | 4-$SCH_3$-$C_6H_4$ | t-$C_4H_9$ |
| 2015 | $CH_3$ | 4-$SCH_3$-$C_6H_4$ | n-$C_6H_{13}$ |
| 2016 | $CH_3$ | 4-$SCH_3$-$C_6H_4$ | Prop-1-en-3-yl |
| 2017 | $CH_3$ | 4-$SCH_3$-$C_6H_4$ | (E)-1-Chloroprop-1-en-3-yl |
| 2018 | $CH_3$ | 4-$SCH_3$-$C_6H_4$ | Propyn-3-yl |
| 2019 | $CH_3$ | 4-$SCH_3$-$C_6H_4$ | 3-Methylbut-2-en-1-yl |
| 2020 | $CH_3$ | 2-Methylsulfonyl-$C_6H_4$ | H |
| 2021 | $CH_3$ | 2-Methylsulfonyl-$C_6H_4$ | $CH_3$ |
| 2022 | $CH_3$ | 2-Methylsulfonyl-$C_6H_4$ | $C_2H_5$ |
| 2023 | $CH_3$ | 2-Methylsulfonyl-$C_6H_4$ | n-$C_3H_7$ |
| 2024 | $CH_3$ | 2-Methylsulfonyl-$C_6H_4$ | i-$C_3H_7$ |
| 2025 | $CH_3$ | 2-Methylsulfonyl-$C_6H_4$ | n-$C_4H_9$ |
| 2026 | $CH_3$ | 2-Methylsulfonyl-$C_6H_4$ | t-$C_4H_9$ |
| 2027 | $CH_3$ | 2-Methylsulfonyl-$C_6H_4$ | n-$C_6H_{13}$ |
| 2028 | $CH_3$ | 2-Methylsulfonyl-$C_6H_4$ | Prop-1-en-3-yl |
| 2029 | $CH_3$ | 2-Methylsulfonyl-$C_6H_4$ | (E)-1-Chloroprop-1-en-3-yl |
| 2030 | $CH_3$ | 2-Methylsulfonyl-$C_6H_4$ | Propyn-3-yl |
| 2031 | $CH_3$ | 2-Methylsulfonyl-$C_6H_4$ | 3-Methylbut-2-en-1-yl |
| 2032 | $CH_3$ | 3-Methylsulfonyl-$C_6H_4$ | H |

TABLE A-continued

| No. | R² | R³ | R⁴ |
|---|---|---|---|
| 2033 | CH₃ | 3-Methylsulfonyl-C₆H₄ | CH₃ |
| 2034 | CH₃ | 3-Methylsulfonyl-C₆H₄ | C₂H₅ |
| 2035 | CH₃ | 3-Methylsulfonyl-C₆H₄ | n-C₃H₇ |
| 2036 | CH₃ | 3-Methylsulfonyl-C₆H₄ | i-C₃H₇ |
| 2037 | CH₃ | 3-Methylsulfonyl-C₆H₄ | n-C₄H₉ |
| 2038 | CH₃ | 3-Methylsulfonyl-C₆H₄ | t-C₄H₉ |
| 2039 | CH₃ | 3-Methylsulfonyl-C₆H₄ | n-C₆H₁₃ |
| 2040 | CH₃ | 3-Methylsulfonyl-C₆H₄ | Prop-1-en-3-yl |
| 2041 | CH₃ | 3-Methylsulfonyl-C₆H₄ | (E)-1-Chloroprop-1-en-3-yl |
| 2042 | CH₃ | 3-Methylsulfonyl-C₆H₄ | Propyn-3-yl |
| 2043 | CH₃ | 3-Methylsulfonyl-C₆H₄ | 3-Methylbut-2-en-1-yl |
| 2044 | CH₃ | 4-Methylsulfonyl-C₆H₄ | H |
| 2045 | CH₃ | 4-Methylsulfonyl-C₆H₄ | CH₃ |
| 2046 | CH₃ | 4-Methylsulfonyl-C₆H₄ | C₂H₅ |
| 2047 | CH₃ | 4-Methylsulfonyl-C₆H₄ | n-C₃H₇ |
| 2048 | CH₃ | 4-Methylsulfonyl-C₆H₄ | i-C₃H₇ |
| 2049 | CH₃ | 4-Methylsulfonyl-C₆H₄ | n-C₄H₉ |
| 2050 | CH₃ | 4-Methylsulfonyl-C₆H₄ | t-C₄H₉ |
| 2051 | CH₃ | 4-Methylsulfonyl-C₆H₄ | n-C₆H₁₃ |
| 2052 | CH₃ | 4-Methylsulfonyl-C₆H₄ | Prop-1-en-3-yl |
| 2053 | CH₃ | 4-Methylsulfonyl-C₆H₄ | (E)-1-Chloroprop-1-en-3-yl |
| 2054 | CH₃ | 4-Methylsulfonyl-C₆H₄ | Propyn-3-yl |
| 2055 | CH₃ | 4-Methylsulfonyl-C₆H₄ | 3-Methylbut-2-en-1-yl |
| 2056 | CH₃ | 2-Methoxycarbonyl-C₆H₄ | H |
| 2057 | CH₃ | 2-Methoxycarbonyl-C₆H₄ | CH₃ |
| 2058 | CH₃ | 2-Methoxycarbonyl-C₆H₄ | C₂H₅ |
| 2059 | CH₃ | 2-Methoxycarbonyl-C₆H₄ | n-C₃H₇ |
| 2060 | CH₃ | 2-Methoxycarbonyl-C₆H₄ | i-C₃H₇ |
| 2061 | CH₃ | 2-Methoxycarbonyl-C₆H₄ | n-C₄H₉ |
| 2062 | CH₃ | 2-Methoxycarbonyl-C₆H₄ | t-C₄H₉ |
| 2063 | CH₃ | 2-Methoxycarbonyl-C₆H₄ | n-C₆H₁₃ |
| 2064 | CH₃ | 2-Methoxycarbonyl-C₆H₄ | Prop-1-en-3-yl |
| 2065 | CH₃ | 2-Methoxycarbonyl-C₆H₄ | (E)-1-Chloroprop-1-en-3-yl |
| 2066 | CH₃ | 2-Methoxycarbonyl-C₆H₄ | Propyn-3-yl |
| 2067 | CH₃ | 2-Methoxycarbonyl-C₆H₄ | 3-Methylbut-2-en-1-yl |
| 2068 | CH₃ | 3-Methoxycarbonyl-C₆H₄ | H |
| 2069 | CH₃ | 3-Methoxycarbonyl-C₆H₄ | CH₃ |
| 2070 | CH₃ | 3-Methoxycarbonyl-C₆H₄ | C₂H₅ |
| 2071 | CH₃ | 3-Methoxycarbonyl-C₆H₄ | n-C₃H₇ |
| 2072 | CH₃ | 3-Methoxycarbonyl-C₆H₄ | i-C₃H₇ |
| 2073 | CH₃ | 3-Methoxycarbonyl-C₆H₄ | n-C₄H₉ |
| 2074 | CH₃ | 3-Methoxycarbonyl-C₆H₄ | t-C₄H₉ |
| 2075 | CH₃ | 3-Methoxycarbonyl-C₆H₄ | n-C₆H₁₃ |
| 2076 | CH₃ | 3-Methoxycarbonyl-C₆H₄ | Prop-1-en-3-yl |
| 2077 | CH₃ | 3-Methoxycarbonyl-C₆H₄ | (E)-1-Chloroprop-1-en-3-yl |
| 2078 | CH₃ | 3-Methoxycarbonyl-C₆H₄ | Propyn-3-yl |
| 2079 | CH₃ | 3-Methoxycarbonyl-C₆H₄ | 3-Methylbut-2-en-1-yl |
| 2080 | CH₃ | 4-Methoxycarbonyl-C₆H₄ | H |
| 2081 | CH₃ | 4-Methoxycarbonyl-C₆H₄ | CH₃ |
| 2082 | CH₃ | 4-Methoxycarbonyl-C₆H₄ | C₂H₅ |
| 2083 | CH₃ | 4-Methoxycarbonyl-C₆H₄ | n-C₃H₇ |
| 2084 | CH₃ | 4-Methoxycarbonyl-C₆H₄ | i-C₃H₇ |
| 2085 | CH₃ | 4-Methoxycarbonyl-C₆H₄ | n-C₄H₉ |
| 2086 | CH₃ | 4-Methoxycarbonyl-C₆H₄ | t-C₄H₉ |
| 2087 | CH₃ | 4-Methoxycarbonyl-C₆H₄ | n-C₆H₁₃ |
| 2088 | CH₃ | 4-Methoxycarbonyl-C₆H₄ | Prop-1-en-3-yl |
| 2089 | CH₃ | 4-Methoxycarbonyl-C₆H₄ | (E)-1-Chloroprop-1-en-3-yl |
| 2090 | CH₃ | 4-Methoxycarbonyl-C₆H₄ | Propyn-3-yl |
| 2091 | CH₃ | 4-Methoxycarbonyl-C₆H₄ | 3-Methylbut-2-en-1-yl |
| 2092 | CH₃ | 2-Ethoxycarbonyl-C₆H₄ | H |
| 2093 | CH₃ | 2-Ethoxycarbonyl-C₆H₄ | CH₃ |
| 2094 | CH₃ | 2-Ethoxycarbonyl-C₆H₄ | C₂H₅ |
| 2095 | CH₃ | 2-Ethoxycarbonyl-C₆H₄ | n-C₃H₇ |
| 2096 | CH₃ | 2-Ethoxycarbonyl-C₆H₄ | i-C₃H₇ |
| 2097 | CH₃ | 2-Ethoxycarbonyl-C₆H₄ | n-C₄H₉ |
| 2098 | CH₃ | 2-Ethoxycarbonyl-C₆H₄ | t-C₄H₉ |
| 2099 | CH₃ | 2-Ethoxycarbonyl-C₆H₄ | n-C₆H₁₃ |
| 2100 | CH₃ | 2-Ethoxycarbonyl-C₆H₄ | Prop-1-en-3-yl |
| 2101 | CH₃ | 2-Ethoxycarbonyl-C₆H₄ | (E)-1-Chloroprop-1-en-3-yl |
| 2102 | CH₃ | 2-Ethoxycarbonyl-C₆H₄ | Propyn-3-yl |
| 2103 | CH₃ | 2-Ethoxycarbonyl-C₆H₄ | 3-Methylbut-2-en-1-yl |
| 2104 | CH₃ | 3-Ethoxycarbonyl-C₆H₄ | H |
| 2105 | CH₃ | 3-Ethoxycarbonyl-C₆H₄ | CH₃ |
| 2106 | CH₃ | 3-Ethoxycarbonyl-C₆H₄ | C₂H₅ |
| 2107 | CH₃ | 3-Ethoxycarbonyl-C₆H₄ | n-C₃H₇ |
| 2108 | CH₃ | 3-Ethoxycarbonyl-C₆H₄ | i-C₃H₇ |
| 2109 | CH₃ | 3-Ethoxycarbonyl-C₆H₄ | n-C₄H₉ |

TABLE A-continued

| No. | R² | R³ | R⁴ |
|---|---|---|---|
| 2110 | CH₃ | 3-Ethoxycarbonyl-C₆H₄ | t-C₄H₉ |
| 2111 | CH₃ | 3-Ethoxycarbonyl-C₆H₄ | n-C₆H₁₃ |
| 2112 | CH₃ | 3-Ethoxycarbonyl-C₆H₄ | Prop-1-en-3-yl |
| 2113 | CH₃ | 3-Ethoxycarbonyl-C₆H₄ | (E)-1-Chloroprop-1-en-3-yl |
| 2114 | CH₃ | 3-Ethoxycarbonyl-C₆H₄ | Propyn-3-yl |
| 2115 | CH₃ | 3-Ethoxycarbonyl-C₆H₄ | 3-Methylbut-2-en-1-yl |
| 2116 | CH₃ | 4-Ethoxycarbonyl-C₆H₄ | H |
| 2117 | CH₃ | 4-Ethoxycarbonyl-C₆H₄ | CH₃ |
| 2118 | CH₃ | 4-Ethoxycarbonyl-C₆H₄ | C₂H₅ |
| 2119 | CH₃ | 4-Ethoxycarbonyl-C₆H₄ | n-C₃H₇ |
| 2120 | CH₃ | 4-Ethoxycarbonyl-C₆H₄ | i-C₃H₇ |
| 2121 | CH₃ | 4-Ethoxycarbonyl-C₆H₄ | n-C₄H₉ |
| 2122 | CH₃ | 4-Ethoxycarbonyl-C₆H₄ | t-C₄H₉ |
| 2123 | CH₃ | 4-Ethoxycarbonyl-C₆H₄ | n-C₆H₁₃ |
| 2124 | CH₃ | 4-Ethoxycarbonyl-C₆H₄ | Prop-1-en-3-yl |
| 2125 | CH₃ | 4-Ethoxycarbonyl-C₆H₄ | (E)-1-Chloroprop-1-en-3-yl |
| 2126 | CH₃ | 4-Ethoxycarbonyl-C₆H₄ | Propyn-3-yl |
| 2127 | CH₃ | 4-Ethoxycarbonyl-C₆H₄ | 3-Methylbut-2-en-1-yl |
| 2128 | CH₃ | 2-Aminocarbonyl-C₆H₄ | H |
| 2129 | CH₃ | 2-Aminocarbonyl-C₆H₄ | CH₃ |
| 2130 | CH₃ | 2-Aminocarbonyl-C₆H₄ | C₂H₅ |
| 2131 | CH₃ | 2-Aminocarbonyl-C₆H₄ | n-C₃H₇ |
| 2132 | CH₃ | 2-Aminocarbonyl-C₆H₄ | i-C₃H₇ |
| 2133 | CH₃ | 2-Aminocarbonyl-C₆H₄ | n-C₄H₉ |
| 2134 | CH₃ | 2-Aminocarbonyl-C₆H₄ | t-C₄H₉ |
| 2135 | CH₃ | 2-Aminocarbonyl-C₆H₄ | n-C₆H₁₃ |
| 2136 | CH₃ | 2-Aminocarbonyl-C₆H₄ | Prop-1-en-3-yl |
| 2137 | CH₃ | 2-Aminocarbonyl-C₆H₄ | (E)-1-Chloroprop-1-en-3-yl |
| 2138 | CH₃ | 2-Aminocarbonyl-C₆H₄ | Propyn-3-yl |
| 2139 | CH₃ | 2-Aminocarbonyl-C₆H₄ | 3-Methylbut-2-en-1-yl |
| 2140 | CH₃ | 3-Aminocarbonyl-C₆H₄ | H |
| 2141 | CH₃ | 3-Aminocarbonyl-C₆H₄ | CH₃ |
| 2142 | CH₃ | 3-Aminocarbonyl-C₆H₄ | C₂H₅ |
| 2143 | CH₃ | 3-Aminocarbonyl-C₆H₄ | n-C₃H₇ |
| 2144 | CH₃ | 3-Aminocarbonyl-C₆H₄ | i-C₃H₇ |
| 2145 | CH₃ | 3-Aminocarbonyl-C₆H₄ | n-C₄H₉ |
| 2146 | CH₃ | 3-Aminocarbonyl-C₆H₄ | t-C₄H₉ |
| 2147 | CH₃ | 3-Aminccarbonyl-C₆H₄ | n-C₆H₁₃ |
| 2148 | CH₃ | 3-Aminocarbonyl-C₆H₄ | Prop-1-en-3-yl |
| 2149 | CH₃ | 3-Aminocarbonyl-C₆H₄ | (E)-1-Chloroprop-1-en-3-yl |
| 2150 | CH₃ | 3-Aminocarbonyl-C₆H₄ | Propyn-3-yl |
| 2151 | CH₃ | 3-Aminocarbonyl-C₆H₄ | 3-Methylbut-2-en-1-yl |
| 2152 | CH₃ | 4-Aminocarbonyl-C₆H₄ | H |
| 2153 | CH₃ | 4-Aminocarbonyl-C₆H₄ | CH₃ |
| 2154 | CH₃ | 4-Aminocarbonyl-C₆H₄ | C₂H₅ |
| 2155 | CH₃ | 4-Aminocarbonyl-C₆H₄ | n-C₃H₇ |
| 2156 | CH₃ | 4-Aminocarbonyl-C₆H₄ | i-C₃H₇ |
| 2157 | CH₃ | 4-Aminocarbonyl-C₆H₄ | n-C₄H₉ |
| 2158 | CH₃ | 4-Aminocarbonyl-C₆H₄ | t-C₄H₉ |
| 2159 | CH₃ | 4-Aminocarbonyl-C₆H₄ | n-C₆H₁₃ |
| 2160 | CH₃ | 4-Aminocarbonyl-C₆H₄ | Prop-1-en-3-yl |
| 2161 | CH₃ | 4-Aminocarbonyl-C₆H₄ | (E)-1-Chloropro-1-en-3-yl |
| 2162 | CH₃ | 4-Aminocarbonyl-C₆H₄ | Propyn-3-yl |
| 2163 | CH₃ | 4-Aminocarbonyl-C₆H₄ | 3-Methylbut-2-en-1-yl |
| 2164 | CH₃ | 2-(N-Methylaminocarbonyl)-C₆H₄ | H |
| 2165 | CH₃ | 2-(N-Methylaminocarbonyl)-C₆H₄ | CH₃ |
| 2166 | CH₃ | 2-(N-Methylaminocarbonyl)-C₆H₄ | C₂H₅ |
| 2167 | CH₃ | 2-(N-Methylaminocarbonyl)-C₆H₄ | n-C₃H₇ |
| 2168 | CH₃ | 2-(N-Methylaminocarbonyl)-C₆H₄ | i-C₃H₇ |
| 2169 | CH₃ | 2-(N-Methylaminocarbonyl)-C₆H₄ | n-C₄H₉ |
| 2170 | CH₃ | 2-(N-Methylaminocarbonyl)-C₆H₄ | t-C₄H9 |
| 2171 | CH₃ | 2-(N-Methylaminocarbonyl)-C₆H₄ | n-C₆H₁₃ |
| 2172 | CH₃ | 2-(N-Methylaminocarbonyl)-C₆H₄ | Prop-1-en-3-yl |
| 2173 | CH₃ | 2-(N-Methylaminocarbonyl)-C₆H₄ | (E)-1-Chloroprop-1-en-3-yl |
| 2174 | CH₃ | 2-(N-Methylaminocarbonyl)-C₆H₄ | Propyn-3-yl |
| 2175 | CH₃ | 2-(N-Methylaminocarbonyl)-C₆H₄ | 3-Methylbut-2-en-1-yl |

TABLE A-continued

| No. | R² | R³ | R⁴ |
|---|---|---|---|
| 2176 | CH₃ | 3-(N-Methylaminocarbonyl)-C₆H₄ | H |
| 2177 | CH₃ | 3-(N-Methylaminocarbonyl)-C₆H₄ | CH₃ |
| 2178 | CH₃ | 3-(N-Methylaminocarbonyl)-C₆H₄ | C₂H₅ |
| 2179 | CH₃ | 3-(N-Methylaminocarbonyl)-C₆H₄ | n-C₃H₇ |
| 2180 | CH₃ | 3-(N-Methylaminocarbonyl)-C₆H₄ | C₃H₇ |
| 2181 | CH₃ | 3-(N-Methylaminocarbonyl)-C₆H₄ | n-C₄H₉ |
| 2182 | CH₃ | 3-(N-Methylaminocarbonyl)-C₆H₄ | t-C₄H₉ |
| 2183 | CH₃ | 3-(N-Methylaminocarbonyl)-C₆H₄ | n-C₆H₁₃ |
| 2184 | CH₃ | 3-(N-Methylaminocarbonyl)-C₆H₄ | Prop-1-en-3-yl |
| 2185 | CH₃ | 3-(N-Methylaminocarbonyl)-C₆H₄ | (E)-1-Chloroprop-1-en-3-yl |
| 2186 | CH₃ | 3-(N-Methylaminocarbonyl)-C₆H₄ | Propyn-3-yl |
| 2187 | CH₃ | 3-(N-Methylaininocarbonyl)-C₆H₄ | 3-Methylbut-2-en-1-yl |
| 2188 | CH₃ | 4-(N-Methylaminocarbonyl)-C₆H₄ | H |
| 2189 | CH₃ | 4-(N-Methylaminocarbonyl)-C₆h | CH₃ |
| 2190 | CH₃ | 4-(N-Methylaminocarbonyl)-C₆H₄ | C₂H₅ |
| 2191 | CH₃ | 4-(N-Methylaminocarbonyl)-C₆H₄ | n-C₃H₇ |
| 2192 | CH₃ | 4-(N-Methylaminocarbonyl)-C₆H₄ | i-C₃H₇ |
| 2193 | CH₃ | 4-(N-Methylaminocarhonyl)-C₆H₄ | n-C₄H₉ |
| 2194 | CH₃ | 4-(N-Methylaminocarbonyl)-C₆H₄ | t-C₄H₉ |
| 2195 | CH₃ | 4-(N-Methylaminocarbonyl)-C₆H₄ | n-C₆H₁₃ |
| 2196 | CH₃ | 4-(N-Methylaminocarbonyl)-C₆H₄ | Prop-1-en-3-yl |
| 2197 | CH₃ | 4-(N-Methylaminocarbonyl)-C₆H₄ | (E)-1-Chloroprop-1-en-3-yl |
| 2198 | CH₃ | 4-(N-Methylaminocarbonyl)-C₆H₄ | Propyn-3-yl |
| 2199 | CH₃ | (N-Methylaminocarbonyl)-C₆H₄ | 3-Methylbut-2-en-1-yl |
| 2200 | CH₃ | 2-Dimethylaminocarbonyl-C₆H₄ | H |
| 2201 | CH₃ | 2-Dimethylaminocarbonyl-C₆H₄ | CH₃ |
| 2202 | CH₃ | 2-Dimethylaminocarbonyl-C₆H₄ | C₂H₅ |
| 2203 | CH₃ | 2-Dimethylaminocarbonyl-C₆H₄ | n-C₃H₇ |
| 2204 | CH₃ | 2-Dimethylaminocarbonyl-C₆H₄ | i-C₃H₇ |
| 2205 | CH₃ | 2-Diinethylaminocarbonyl-C₆H₄ | n-C₄H₉ |
| 2206 | CH₃ | 2-Dimethylaminocarbonyl-C₆H₄ | t-C₄H₉ |
| 2207 | CH₃ | 2-Dimethylaminocarbonyl-C₆H₄ | n-C₆H₁₃ |
| 2208 | CH₃ | 2-Dimethylaminocarbonyl-C₆H₄ | Prop-1-en-3-yl |
| 2209 | CH₃ | 2-Dimethylaminocarbonyl-C₆H₄ | (E)-1-Chloroprop-1-en-3-yl |
| 2210 | CH₃ | 2-Dimethylaminocarbonyl-C₆H₄ | Propyn-3-yl |
| 2211 | CH₃ | 2-Dimethylaminocarbonyl-C₆H₄ | 3-Methylbut-2-en-1-yl |
| 2212 | CH₃ | 3-Dimethylaminocarbonyl-C₆H₄ | H |
| 2213 | CH₃ | 3-Dimethylaminocarbonyl-C₆H₄ | CH₃ |

TABLE A-continued

| No. | R² | R³ | R⁴ |
|---|---|---|---|
| 2214 | CH₃ | 3-Dimethylaminocarbonyl-C₆H₄ | C₂H₅ |
| 2215 | CH₃ | 3-Dimethylaminocarbonyl-C₆H₄ | n-C₃H₇ |
| 2216 | CH₃ | 3-Dimethylaminocarbonyl-C₆H₄ | i-C₃H₇ |
| 2217 | CH₃ | 3-Dimethylaminocarbonyl-C₆H₄ | n-C₄H₉ |
| 2218 | CH₃ | 3-Dimethylaminocarbonyl-C₆H₄ | t-C₄H₉ |
| 2219 | CH₃ | 3-Dimethylaminocarbonyl-C₆H₄ | n-C₆H₁₃ |
| 2220 | CH₃ | 3-Dimethylaminocarbonyl-C₆H₄ | Prop-1-en-3-yl |
| 2221 | CH₃ | 3-Dimethylaminocarbonyl-C₆H₄ | (E)-1-Chloroprop-1-en-3-yl |
| 2222 | CH₃ | 3-Dimethylaminocarbonyl-C₆H₄ | Propyn-3-yl |
| 2223 | CH₃ | 3-Dimethylaminocarbonyl-C₆H₄ | 3-Methylbut-2-en-1-yl |
| 2224 | CH₃ | 4-Dimethylaminocarbonyl-C₆H₄ | H |
| 2225 | CH₃ | 4-Dimethylaminocarbonyl-C₆H₄ | CH₃ |
| 2226 | CH₃ | 4-Dimethylaminocarbonyl-C₆H₄ | C₂H₅ |
| 2227 | CH₃ | 4-Dimethylaminocarbonyl-C₆H₄ | n-C₃H₇ |
| 2228 | C₆H₃ | 4-Dimethylaminocarbonyl-C₆H₄ | i-C₃H₇ |
| 2229 | CH₃ | 4-Dimethylaminocarbonyl-C₆H₄ | n-C₄H₉ |
| 2230 | CH₃ | 4-Dimethylaminocarbonyl-C₆H₄ | t-C₄H₉ |
| 2231 | CH₃ | 4-Dimethylaminocarbonyl-C₆H₄ | n-C₃H₇ |
| 2232 | CH₃ | 4-Dimethylaininocarbonyl-C₆H₄ | Prop-1-en-3-yl |
| 2233 | CH₃ | 4-Dimethylaminocarbonyl-C₆H₄ | (E)-1-Chloroprop-1-en-3-yl |
| 2234 | CH₃ | 4-Dimethylaminocarbonyl-C₆H₄ | Propyn-3-yl |
| 2235 | CH₃ | 4-Dimethylaminocarbonyl-C₆H₄ | 3-Methylbut-2-en-1-yl |
| 2236 | C₂H₅ | 2-F-C₆H₄ | H |
| 2237 | C₂H₅ | 2-F-C₆H₄ | CH₃ |
| 2238 | C₂H₅ | 2-F-C₆H₄ | C₂H₅ |
| 2239 | C₂H₅ | 2-F-C₆H₄ | n-C₃H₇ |
| 2240 | C₂H₅ | 2-F-C₆H₄ | i-C₃H₇ |
| 2241 | C₂H₅ | 2-F-C₆H₄ | n-C₄H₉ |
| 2242 | C₂H₅ | 2-F-C₆H₄ | t-C₄H₉ |
| 2243 | C₂H₅ | 2-F-C₆H₄ | n-C₆H₁₃ |
| 2244 | C₂H₅ | 2-F-C₆H₄ | Prop-1-en-3-yl |
| 2245 | C₂H₅ | 2-F-C₆H₄ | (E)-1-Chloroprop-1-en-3-yl |
| 2246 | C₂H₅ | 2-F-C₆H₄ | Propyn-3-yl |
| 2247 | C₂H₅ | 2-F-C₆H₄ | 3-Methylbut-2-en-1-yl |
| 2248 | C₂H₅ | 3-F-C₆H₄ | H |
| 2249 | C₂H₅ | 3-F-C₆H₄ | CH₃ |
| 2250 | C₂H₅ | 3-F-C₆H₄ | C₂H₅ |
| 2251 | C₂H₅ | 3-F-C₆H₄ | n-C₃H₇ |
| 2252 | C₂H₅ | 3-F-C₆H₄ | i-C₃H₇ |
| 2253 | C₂H₅ | 3-F-C₆H₄ | n-C₄H₉ |
| 2254 | C₂H₅ | 3-F-C₆H₄ | t-C₄H₉ |
| 2255 | C₂H₅ | 3-F-C₆H₄ | n-C₆H₁₃ |
| 2256 | C₂H₅ | 3-F-C₆H₄ | Prop-1-en-3-yl |
| 2257 | C₂H₅ | 3-F-C₆H₄ | (E)-1-Chloroprop-1-en-3-yl |
| 2258 | C₂H₅ | 3-F-C₆H₄ | Propyn-3-yl |
| 2259 | C₂H₅ | 3-F-C₆H₄ | 3-Methylbut-2-en-1-yl |
| 2260 | C₂H₅ | 4-F-C₆H₄ | H |
| 2261 | C₂H₅ | 4-F-C₆H₄ | CH₃ |
| 2262 | C₂H₅ | 4-C-C₆H₄ | C₂H₅ |
| 2263 | C₂H₅ | 4-F-C₆H₄ | n-C₃H₇ |
| 2264 | C₂H₅ | 4-F-C₆H₄ | i-C₃H₇ |
| 2265 | C₂H₅ | 4-F-C₆H₄ | n-C₄H₉ |
| 2266 | C₂H₅ | 4-F-C₆H₄ | t-C₄H₉ |
| 2267 | C₂H₅ | 4-F-C₆H₄ | n-C₆H₁₃ |
| 2268 | C₂H₅ | 4-F-C₆H₄ | Prop-1-en-3-yl |

TABLE A-continued

| No. | R² | R³ | R⁴ |
|---|---|---|---|
| 2269 | C₂H₅ | 4-F-C₆H₄ | (E)-1-Chloroprop-1-en-3-yl |
| 2270 | C₂H₅ | 4-F-C₆H₄ | Propyn-3-yl |
| 2271 | C₂H₅ | 4-F-C₆H₄ | 3-Methylbut-2-en-1-yl |
| 2272 | C₂H₅ | 2-Cl-C₆H₄ | H |
| 2273 | C₂H₅ | 2-Cl-C₆H₄ | CH₃ |
| 2274 | C₂H₅ | 2-Cl-C₆H₄ | C₂H₅ |
| 2275 | C₂H₅ | 2-Cl-C₆H₄ | n-C₃H₇ |
| 2276 | C₂H₅ | 2-Cl-C₆H₄ | i-C₃H₇ |
| 2277 | C₂H₅ | 2-Cl-C₆H₄ | n-C₄H₉ |
| 2278 | C₂H₅ | 2-Cl-C₆H₄ | t-C₄H₉ |
| 2279 | C₂H₅ | 2-Cl-C₆H₄ | n-C₆H₁₃ |
| 2280 | C₂H₅ | 2-Cl-C₆H₄ | Prop-1-en-3-yl |
| 2281 | C₂H₅ | 2-Cl-C₆H₄ | (E)-1-Chloroprop-1-en-3-yl |
| 2282 | C₂H₅ | 2-Cl-C₆H₄ | Propyn-3-yl |
| 2283 | C₂H₅ | 2-Cl-C₆H₄ | 3-Methylbut-2-en-1-yl |
| 2284 | C₂H₅ | 3-Cl-C₆H₄ | H |
| 2285 | C₂H₅ | 3-Cl-C₆H₄ | CH₃ |
| 2286 | C₂H₅ | 3-Cl-C₆H₄ | C₂H₅ |
| 2287 | C₂H₅ | 3-Cl-C₆H₄ | n-C₃H₇ |
| 2288 | C₂H₅ | 3-Cl-C₆H₄ | i-C₃H₇ |
| 2289 | C₂H₅ | 3-Cl-C₆H₄ | n-C₄H₉ |
| 2290 | C₂H₅ | 3-Cl-C₆H₄ | t-C₄H₉ |
| 2291 | C₂H₅ | 3-Cl-C₆H₄ | n-C₆H₁₃ |
| 2292 | C₂H₅ | 3-Cl-C₆H₄ | Prop-1-en-3-yl |
| 2293 | C₂H₅ | 3-Cl-C₆H₄ | (E)-1-Chloroprop-1-en-3-yl |
| 2294 | C₂H₅ | 3-Cl-C₆H₄ | Propyn-3-yl |
| 2295 | C₂H₅ | 3-Cl-C₆H₄ | 3-Methylbut-2-en-1-yl |
| 2296 | C₂H₅ | 4-Cl-C₆H₄ | H |
| 2297 | C₂H₅ | 4-Cl-C₆H₄ | CH₃ |
| 2298 | C₂H₅ | 4-Cl-C₆H₄ | C₂H₅ |
| 2299 | C₂H₅ | 4-Cl-C₆H₄ | n-C₃H₇ |
| 2300 | C₂H₅ | 4-Cl-C₆H₄ | i-C₃H₇ |
| 2301 | C₂H₅ | 4-Cl-C₆H₄ | n-C₄H₉ |
| 2302 | C₂H₅ | 4-Cl-C₆H₄ | t-C₄H₉ |
| 2303 | C₂H₅ | 4-Cl-C₆H₄ | n-C₆H₁₃ |
| 2304 | C₂H₅ | 4-Cl-C₆H₄ | Prop-1-en-3-yl |
| 2305 | C₂H₅ | 4-Cl-C₆H₄ | (E)-1-Chloroprop-1-en-3-yl |
| 2306 | C₂H₅ | 4-Cl-C₆H₄ | Propyn-3-yl |
| 2307 | C₂H₅ | 4-Cl-C₆H₄ | 3-Methylbut-2-en-1-yl |
| 2308 | C₂H₅ | 2,3-Cl₂-C₆H₃ | H |
| 2309 | C₂H₅ | 2,3-Cl₂-C₆H₃ | CH₃ |
| 2310 | C₂H₅ | 2,3-Cl₂-C₆H₃ | C₂H₅ |
| 2311 | C₂H₅ | 2,3-Cl₂-C₆H₃ | n-C₃H₇ |
| 2312 | C₂H₅ | 2,3-Cl₂-C₆H₃ | i-C₃H₇ |
| 2313 | C₂H₅ | 2,3-Cl₂-C₆H₃ | n-C₄H₉ |
| 2314 | C₂H₅ | 2,3-Cl₂-C₆H₃ | t-C₄H₉ |
| 2315 | C₂H₅ | 2,3-Cl₂-C₆H₃ | n-C₆H₁₃ |
| 2316 | C₂H₅ | 2,3-Cl₂-C₆H₃ | Prop-1-en-3-yl |
| 2317 | C₂H₅ | 2,3-Cl₂-C₆H₃ | (E)-1-Chloroprop-1-en-3-yl |
| 2318 | C₂H₅ | 2,3-Cl₂-C₆H₃ | Propyn-3-yl |
| 2319 | C₂H₅ | 2,3-Cl₂-C₆H₃ | 3-Methylbut-2-en-1-yl |
| 2320 | C₂H₅ | 2,4-Cl₂-C₆H₃ | H |
| 2321 | C₂H₅ | 2,4-Cl₂-C₆H₃ | CH₃ |
| 2322 | C₂H₅ | 2,4-Cl₂-C₆H₃ | C₂H₅ |
| 2323 | C₂H₅ | 2,4-Cl₂-C₆H₃ | n-C₃H₇ |
| 2324 | C₂H₅ | 2,4-Cl₂-C₆H₃ | i-C₃H₇ |
| 2325 | C₂H₅ | 2,4-Cl₂-C₆H₃ | n-C₄H₉ |
| 2326 | C₂H₅ | 2,4-Cl₂-C₆H₃ | t-C₄H₉ |
| 2327 | C₂H₅ | 2,4-Cl₂-C₆H₃ | n-C₆H₁₃ |
| 2328 | C₂H₅ | 2,4-Cl₂-C₆H₃ | Prop-1-en-3-yl |
| 2329 | C₂H₅ | 2,4-Cl₂-C₆H₃ | (E)-1-Chloroprop-1-en-3-yl |
| 2330 | C₂H₅ | 2,4-Cl₂-C₆H₃ | Propyn-3-yl |
| 2331 | C₂H₅ | 2,4-Cl₂-C₆H₃ | 3-Methylbut-2-en-1-yl |
| 2332 | C₂H₅ | 2,5-Cl₂-C₆H₃ | H |
| 2333 | C₂H₅ | 2,5-Cl₂-C₆H₃ | CH₃ |
| 2334 | C₂H₅ | 2,5-Cl₂-C₆H₃ | C₂H₅ |
| 2335 | C₂H₅ | 2,5-Cl₂-C₆H₃ | n-C₃H₇ |
| 2336 | C₂H₅ | 2,5-Cl₂-C₆H₃ | i-C₃H₇ |
| 2337 | C₂H₅ | 2,5-Cl₂-C₆H₃ | n-C₄H₉ |
| 2338 | C₂H₅ | 2,5-Cl₂-C₆H₃ | t-C₄H₉ |
| 2339 | C₂H₅ | 2,5-Cl₂-C₆H₃ | n-C₆H₁₃ |
| 2340 | C₂H₅ | 2,5-Cl₂-C₆H₃ | Prop-1-en-3-yl |
| 2341 | C₂H₅ | 2,5-Cl₂-C₆H₃ | (E)-1-Chloroprop-1-en-3-yl |
| 2342 | C₂H₅ | 2,5-Cl₂-C₆H₃ | Propyn-3-yl |
| 2343 | C₂H₅ | 2,5-Cl₂-C₆H₃ | 3-Methylbut-2-en-1-yl |
| 2344 | C₂H₅ | 2,6-Cl₂-C₆H₃ | H |
| 2345 | C₂H₅ | 2,6-Cl₂-C₆H₃ | CH₃ |

TABLE A-continued

| No. | R² | R³ | R⁴ |
|---|---|---|---|
| 2346 | $C_2H_5$ | 2,6-$Cl_2$-$C_6H_3$ | $C_2H_5$ |
| 2347 | $C_2H_5$ | 2,6-$Cl_2$-$C_6H_3$ | n-$C_3H_7$ |
| 2348 | $C_2H_5$ | 2,6-$Cl_2$-$C_6H_3$ | i-$C_3H_7$ |
| 2349 | $C_2H_5$ | 2,6-$Cl_2$-$C_6H_3$ | n-$C_4H_9$ |
| 2350 | $C_2H_5$ | 2,6-$Cl_2$-$C_6H_3$ | t-$C_4H_9$ |
| 2351 | $C_2H_5$ | 2,6-$Cl_2$-$C_6H_3$ | n-$C_6H_{15}$ |
| 2352 | $C_2H_5$ | 2,6-$Cl_2$-$C_6H_3$ | Prop-1-en-3-yl |
| 2353 | $C_2H_5$ | 2,6-$Cl_2$-$C_6H_3$ | (E)-1-Chloroprop-1-en-3-yl |
| 2354 | $C_2H_5$ | 2,6-$Cl_2$-$C_6H_3$ | Propyn-3-yl |
| 2355 | $C_2H_5$ | 2,6-$Cl_2$-$C_6H_3$ | 3-Methylbut-2-en-1-yl |
| 2356 | $C_2H_5$ | 3,4-$Cl_2$-$C_6H_3$ | H |
| 2357 | $C_2H_5$ | 3,4-$Cl_2$-$C_6H_3$ | $CH_3$ |
| 2358 | $C_2H_5$ | 3,4-$Cl_2$-$C_6H_3$ | $C_2H_5$ |
| 2359 | $C_2H_5$ | 3,4-$Cl_2$-$C_6H_3$ | n-$C_3H_7$ |
| 2360 | $C_2H_5$ | 3,4-$Cl_2$-$C_6H_3$ | i-$C_3H_7$ |
| 2361 | $C_2H_5$ | 3,4-$Cl_2$-$C_6H_3$ | n-$C_4H_9$ |
| 2362 | $C_2H_5$ | 3,4-$Cl_2$-$C_6H_3$ | t-$C_4H_9$ |
| 2363 | $C_2H_5$ | 3,4-$Cl_2$-$C_6H_3$ | n-$C_6H_{13}$ |
| 2364 | $C_2H_5$ | 3,4-$Cl_2$-$C_6H_3$ | Prop-1-en-3-yl |
| 2365 | $C_2H_5$ | 3,4-$Cl_2$-$C_6H_3$ | (E)-1-Chloroprop-1-en-3-yl |
| 2366 | $C_2H_5$ | 3,4-$Cl_2$-$C_6H_3$ | Propyn-3-yl |
| 2367 | $C_2H_5$ | 3,4-$Cl_2$-$C_6H_3$ | 3-Methylbut-2-en-I-yl |
| 2368 | $C_2H_5$ | 3,5-$Cl_2$-$C_6H_3$ | H |
| 2369 | $C_2H_5$ | 3,5-$Cl_2$-$C_6H_3$ | $CH_3$ |
| 2370 | $C_2H_5$ | 3,5-$Cl_2$-$C_6H_3$ | $C_2H_5$ |
| 2371 | $C_2H_5$ | 3,5-$Cl_2$-$C_6H_3$ | n-$C_3H_7$ |
| 2372 | $C_2H_5$ | 3,5-$Cl_2$-$C_6H_3$ | i-$C_3H_7$ |
| 2373 | $C_2H_5$ | 3,5-$Cl_2$-$C_6H_3$ | n-$C_4H_9$ |
| 2374 | $C_2H_5$ | 3,5-$Cl_2$-$C_6H_3$ | t-$C_4H_9$ |
| 2375 | $C_2H_5$ | 3,5-$Cl_2$-$C_6H_3$ | n-$C_3H_7$ |
| 2376 | $C_2H_5$ | 3,5-$Cl_2$-$C_6H_3$ | Prop-1-en-3-yl |
| 2377 | $C_2H_5$ | 3,5-$Cl_2$-$C_6H_3$ | (E)-1-Chloroprop-1-en-3-yl |
| 2378 | $C_2H_5$ | 3,5-$Cl_2$-$C_6H_3$ | Propyn-3-yl |
| 2379 | $C_2H_5$ | 3,5-$Cl_2$-$C_6H_3$ | 3-Methylbut-2-en-1-yl |
| 2380 | $C_2H_5$ | 2-Br-$C_6H_4$ | H |
| 2381 | $C_2H_5$ | 2-Br-$C_6H_4$ | $CH_3$ |
| 2382 | $C_2H_5$ | 2-Br-$C_6H_4$ | $C_2H_5$ |
| 2383 | $C_2H_5$ | 2-Br-$C_6H_4$ | n-$C_3H_7$ |
| 2384 | $C_2H_5$ | 2-Br-$C_6H_4$ | i-$C_3H_7$ |
| 2385 | $C_2H_5$ | 2-Br-$C_6H_4$ | n-$C_4H_9$ |
| 2386 | $C_2H_5$ | 2-Br-$C_6H_4$ | t-$C_4H_9$ |
| 2387 | $C_2H_5$ | 2-Br-$C_6H_4$ | n-$C_6H_{13}$ |
| 2388 | $C_2H_5$ | 2-Br-$C_6H_4$ | Prop-1-en-3-yl |
| 2389 | $C_2H_5$ | 2-Br-$C_6H_4$ | (E)-1-Chloroprop-1-en-3-yl |
| 2390 | $C_2H_5$ | 2-Br-$C_6H_4$ | Propyn-3-yl |
| 2391 | $C_2H_5$ | 2-Br-$C_6H_4$ | 3-Methylbut-2-en-1-yl |
| 2392 | $C_2H_5$ | 3-Br-$C_6H_4$ | H |
| 2393 | $C_2H_5$ | 3-Br-$C_6H_4$ | $CH_3$ |
| 2394 | $C_2H_5$ | 3-Br-$C_6H_4$ | $C_2H_5$ |
| 2395 | $C_2H_5$ | 3-Br-$C_6H_4$ | n-$C_3H_7$ |
| 2396 | $C_2H_5$ | 3-Br-$C_6H_4$ | i-$C_3H_7$ |
| 2397 | $C_2H_5$ | 3-Br-$C_6H_4$ | n-$C_4H_9$ |
| 2398 | $C_2H_5$ | 3-Br-$C_6H_4$ | t-$C_4H_9$ |
| 2399 | $C_2H_5$ | 3-Br-$C_6H_4$ | n-$C_6H_{13}$ |
| 2400 | $C_2H_5$ | 3-Br-$C_6H_4$ | Prop-1-en-3-yl |
| 2401 | $C_2H_5$ | 3-Br-$C_6H_4$ | (E)-1-Chloroprop-1-en-3-yl |
| 2402 | $C_2H_5$ | 3-Br-$C_6H_4$ | Propyn-3-yl |
| 2403 | $C_2H_5$ | 3-Br-$C_6H_4$ | 3-Methylbut-2-en-1-yl |
| 2404 | $C_2H_5$ | 4-Br-$C_6H_4$ | H |
| 2405 | $C_2H_5$ | 4-Br-$C_6H_4$ | $CH_3$ |
| 2406 | $C_2H_5$ | 4-Br-$C_6H_4$ | $C_2H_5$ |
| 2407 | $C_2H_5$ | 4-Br-$C_6H_4$ | n-$C_3H_7$ |
| 2408 | $C_2H_5$ | 4-Br-$C_6H_4$ | i-$C_3H_7$ |
| 2409 | $C_2H_5$ | 4-Br-$C_6H_4$ | n-$C_4H_9$ |
| 2410 | $C_2H_5$ | 4-Br-$C_6H_4$ | t-$C_4H_9$ |
| 2411 | $C_2H_5$ | 4-Br-$C_6H_4$ | n-$C_6H_{13}$ |
| 2412 | $C_2H_5$ | 4-Br-$C_6H_4$ | Prop-1-en-3-yl |
| 2413 | $C_2H_5$ | 4-Br-$C_6H_4$ | (E)-1-Chloroprop-1-en-3-yl |
| 2414 | $C_2H_5$ | 4-Br-$C_6H_4$ | Propyn-3-yl |
| 2415 | $C_2H_5$ | 4-Br-$C_6H_4$ | 3-Methylbut-2-en-1-yl |
| 2416 | $C_2H_5$ | 2-I-$C_6H_4$ | H |
| 2417 | $C_2H_5$ | 2-I-$C_6H_4$ | $CH_3$ |
| 2418 | $C_2H_5$ | 2-I-$C_6H_4$ | $C_2H_5$ |
| 2419 | $C_2H_5$ | 2-I-$C_6H_4$ | n-$C_3H_7$ |
| 2420 | $C_2H_5$ | 2-I-$C_6H_4$ | i-$C_3H_7$ |
| 2421 | $C_2H_5$ | 2-I-$C_6H_4$ | n-$C_4H_9$ |
| 2422 | $C_2H_5$ | 2-I-$C_6H_4$ | t-$C_4H_9$ |

TABLE A-continued

| No. | R² | R³ | R⁴ |
|---|---|---|---|
| 2423 | C₂H₅ | 2-I-C₆H₄ | n-C₆H₁₃ |
| 2424 | C₂H₅ | 2-I-C₆H₄ | Prop-1-en-3-yl |
| 2425 | C₂H₅ | 2-I-C₆H₄ | (E)-1-Chloroprop-1-en-3-yl |
| 2426 | C₂H₅ | 2-I-C₆H₄ | Propyn-3-yl |
| 2427 | C₂H₅ | 2-I-C₆H₄ | 3-Methylbut-2-en-1-yl |
| 2428 | C₂H₅ | 3-I-C₆H₄ | H |
| 2429 | C₂H₅ | 3-I-C₆H₄ | CH₃ |
| 2430 | C₂H₅ | 3-I-C₆H₄ | C₂H₅ |
| 2431 | C₂H₅ | 3-I-C₆H₄ | n-C₃H₇ |
| 2432 | C₂H₅ | 3-I-C₆H₄ | i-C₃H₇ |
| 2433 | C₂H₅ | 3-I-C₆H₄ | n-C₄H₉ |
| 2434 | C₂H₅ | 3-I-C₆H₄ | t-C₄H₉ |
| 2435 | C₂H₅ | 3-I-C₆H₄ | n-C₆H₁₃ |
| 2436 | C₂H₅ | 3-I-C₆H₄ | Prop-1-en-3-yl |
| 2437 | C₂H₅ | 3-I-C₆H₄ | (E)-1-Chloroprop-1-en-3-yl |
| 2438 | C₂H₅ | 3-I-C₆H₄ | Propyn-3-yl |
| 2439 | C₂H₅ | 3-I-C₆H₄ | 3-Methylbut-2-en-1-yl |
| 2440 | C₂H₅ | 4-I-C₆H₄ | H |
| 2441 | C₂H₅ | 4-I-C₆H₄ | CH₃ |
| 2442 | C₂H₅ | 4-I-C₆H₄ | C₂H₅ |
| 2443 | C₂H₅ | 4-I-C₆H₄ | n-C₃H₇ |
| 2444 | C₂H₅ | 4-I-C₆H₄ | i-C₃H₇ |
| 2445 | C₂H₅ | 4-I-C₆H₄ | n-C₄H₉ |
| 2446 | C₂H₅ | 4-I-C₆H₄ | t-C₄H₉ |
| 2447 | C₂H₅ | 4-I-C₆H₄ | n-C₆H₁₃ |
| 2448 | C₂H₅ | 4-I-C₆H₄ | Prop-1-en-3-yl |
| 2449 | C₂H₅ | 4-I-C₆H₄ | (E)-1-Chloroprop-1-en-3-yl |
| 2450 | C₂H₅ | 4-I-C₆H₄ | Propyn-3-yl |
| 2451 | C₂H₅ | 4-I-C₆H₄ | 3-Methylbut-2-en-1-yl |
| 2452 | C₂H₅ | 2-CN-C₆H₄ | H |
| 2453 | C₂H₅ | 2-CN-C₆H₄ | CH₃ |
| 2454 | C₂H₅ | 2-CN-C₆H₄ | C₂H₅ |
| 2455 | C₂H₅ | 2-CN-C₆H₄ | n-C₃H₇ |
| 2456 | C₂H₅ | 2-CN-C₆H₄ | i-C₃H₇ |
| 2457 | C₂H₅ | 2-CN-C₆H₄ | n-C₄H₉ |
| 2458 | C₂H₅ | 2-CN-C₆H₄ | t-C₄H₉ |
| 2459 | C₂H₅ | 2-CN-C₆H₄ | n-C₆H₁₃ |
| 2460 | C₂H₅ | 2-CN-C₆H₄ | Prop-1-en-3-yl |
| 2461 | C₂H₅ | 2-CN-C₆H₄ | (E)-1-Chloroprop-1-en-3-yl |
| 2462 | C₂H₅ | 2-CN-C₆H₄ | Propyn-3-yl |
| 2463 | C₂H₅ | 2-CN-C₆H₄ | 3-Methylbut-2-en-1-yl |
| 2464 | C₂H₅ | 3-CN-C₆H₄ | H |
| 2465 | C₂H₅ | 3-CN-C₆H₄ | CH₃ |
| 2466 | C₂H₅ | 3-CN-C₆H₄ | C₂H₅ |
| 2467 | C₂H₅ | 3-CN-C₆H₄ | n-C₃H₇ |
| 2468 | C₂H₅ | 3-CN-C₆H₄ | i-C₃H₇ |
| 2469 | C₂H₅ | 3-CN-C₆H₄ | n-C₄H₉ |
| 2470 | C₂H₅ | 3-CN-C₆H₄ | t-C₄H₉ |
| 2471 | C₂H₅ | 3-CN-C₆H₄ | n-C₆H₁₃ |
| 2472 | C₂H₅ | 3-CN-C₆H₄ | Prop-1-en-3-yl |
| 2473 | C₂H₅ | 3-CN-C₆H₄ | (E)-1-Chloroprop-1-en-3-yl |
| 2474 | C₂H₅ | 3-CN-C₆H₄ | Propyn-3-yl |
| 2475 | C₂H₅ | 3-CN-C₆H₄ | 3-Methylbut-2-en-1-yl |
| 2476 | C₂H₅ | 4-CN-C₆H₄ | H |
| 2477 | C₂H₅ | 4-CN-C₆H₄ | CH₃ |
| 2478 | C₂H₅ | 4-CN-C₆H₄ | C₂H₅ |
| 2479 | C₂H₅ | 4-CN-C₆H₄ | n-C₃H₇ |
| 2480 | C₂H₅ | 4-CN-C₆H₄ | i-C₃H₇ |
| 2481 | C₂H₅ | 4-CN-C₆H₄ | n-C₄H₉ |
| 2482 | C₂H₅ | 4-CN-C₆H₄ | t-C₄H₉ |
| 2483 | C₂H₅ | 4-CN-C₆H₄ | n-C₆H₁₃ |
| 2484 | C₂H₅ | 4-CN-C₆H₄ | Prop-1-en-3-yl |
| 2485 | C₂H₅ | 4-CN-C₆H₄ | (E)-1-Chloroprop-1-en-3-yl |
| 2486 | C₂H₅ | 4-CN-C₆H₄ | Propyn-3-yl |
| 2487 | C₂H₅ | 4-CN-C₆H₄ | 3-Methylbut-2-en-1-yl |
| 2488 | C₂H₅ | 2-NO₂-C₆H₄ | H |
| 2489 | C₂H₅ | 2-NO₂-C₆H₄ | CH₃ |
| 2490 | C₂H₅ | 2-NO₂-C₆H₄ | C₂H₅ |
| 2491 | C₂H₅ | 2-NO₂-C₆H₄ | n-C₃H₇ |
| 2492 | C₂H₅ | 2-NO₂-C₆H₄ | i-C₃H₇ |
| 2493 | C₂H₅ | 2-NO₂-C₆H₄ | n-C₄H₉ |
| 2494 | C₂H₅ | 2-NO₂-C₆H₄ | t-C₄H₉ |
| 2495 | C₂H₅ | 2-NO₂-C₆H₄ | n-C₆H₁₃ |
| 2496 | C₂H₅ | 2-NO₂-C₆H₄ | Prop-1-en-3-yl |
| 2497 | C₂H₅ | 2-NO₂-C₆H₄ | (E)-1-Chloroprop-1-en-3-yl |
| 2498 | C₂H₅ | 2-NO₂-C₆H₄ | Propyn-3-yl |
| 2499 | C₂H₅ | 2-NO₂-C₆H₄ | 3-Methylbut-2-en-1-yl |

TABLE A-continued

| No. | R² | R³ | R⁴ |
|---|---|---|---|
| 2500 | C₂H₅ | 3-NO₂-C₆H₄ | H |
| 2501 | C₂H₅ | 3-NO₂-C₆H₄ | CH₃ |
| 2502 | C₂H₅ | 3-NO₂-C₆H₄ | C₂H₅ |
| 2503 | C₂H₅ | 3-NO₂-C₆H₄ | n-C₃H₇ |
| 2504 | C₂H₅ | 3-NO₂-C₆H₄ | i-C₃H₇ |
| 2505 | C₂H₅ | 3-NO₂-C₆H₄ | n-C₄H₉ |
| 2506 | C₂H₅ | 3-NO₂-C₆H₄ | t-C₄H₉ |
| 2507 | C₂H₅ | 3-NO₂-C₆H₄ | n-C₆H₁₃ |
| 2508 | C₂H₅ | 3-NO₂-C₆H₄ | Prop-1-en-3-yl |
| 2509 | C₂H₅ | 3-NO₂-C₆H₄ | (E)-1-Chloroprop-1-en-3-yl |
| 2510 | C₂H₅ | 3-NO₂-C₆H₂ | Propyn-3-yl |
| 2511 | C₂H₅ | 3-NO₂-C₆H₄ | 3-Methylbut-2-en-1-yl |
| 2512 | C₂H₅ | 4-NO₂-C₆H₄ | H |
| 2513 | C₂H₅ | 4-NO₂-C₆H₄ | CH₃ |
| 2514 | C₂H₅ | 4-NO₂-C₆H₄ | C₂H₅ |
| 2515 | C₂H₅ | 4-NO₂-C₆H₄ | n-C₃H₇ |
| 2516 | C₂H₅ | 4-NO₂-C₆H₄ | i-C₃H₇ |
| 2517 | C₂H₅ | 4-NO₂-C₆H₄ | n-C₄H₉ |
| 2518 | C₂H₅ | 4-NO₂-C₆H₄ | t-C₄H₉ |
| 2519 | C₂H₅ | 4-NO₂-C₆H₄ | n-C₆H₁₃ |
| 2520 | C₂H₅ | 4-NO₂-C₆H₄ | Prop-1-en-3-yl |
| 2521 | C₂H₅ | 4-NO₂-C₆H₄ | (E)-1-Chloroprop-1-en-3-yl |
| 2522 | C₂H₅ | 4-NO₂-C₆H₄ | Propyn-3-yl |
| 2523 | C₂H₅ | 4-NO₂-C₆H₄ | 3-Methylbut-2-en-1-yl |
| 2524 | C₂H₅ | 2-CH₃-C₆H₄ | H |
| 2525 | C₂H₅ | 2-CH₃-C₆H₄ | CH₃ |
| 2526 | C₂H₅ | 2-CH₃-C₆H₄ | C₂H₅ |
| 2527 | C₂H₅ | 2-CH₃-C₆H₄ | n-C₃H₇ |
| 2528 | C₂H₅ | 2-CH₃-C₆H₄ | i-C₃H₇ |
| 2529 | C₂H₅ | 2-CH₃-C₆H₄ | n-C₄H₉ |
| 2530 | C₂H₅ | 2-CH₃-C₆H₄ | t-C₄H₉ |
| 2531 | C₂H₅ | 2-CH₃-C₆H₄ | n-C₆H₁₃ |
| 2532 | C₂H₅ | 2-CH₃-C₆H₄ | Prop-1-en-3-yl |
| 2533 | C₂H₅ | 2-CH₃-C₆H₄ | (E)-1-Chloroprop-1-en-3-yl |
| 2534 | C₂H₅ | 2-CH₃-C₆H₄ | Propyn-3-yl |
| 2535 | C₂H₅ | 2-CH₃-C₆H₄ | 3-Methylbut-2-en-1-yl |
| 2536 | C₂H₅ | 3-CH₃-C₆H₄ | H |
| 2537 | C₂H₅ | 3-CH₃-C₆H₄ | CH₃ |
| 2538 | C₂H₅ | 3-CH₃-C₆H₄ | C₂H₅ |
| 2539 | C₂H₅ | 3-CH₃-C₆H₄ | n-C₃H₇ |
| 2540 | C₂H₅ | 3-CH₃-C₆H₄ | i-C₃H₇ |
| 2541 | C₂H₅ | 3-CH₃-C₆H₄ | n-C₄H₉ |
| 2542 | C₂H₅ | 3-CH₃-C₆H₄ | t-C₄H₉ |
| 2543 | C₂H₅ | 3-CH₃-C₆H₄ | n-C₆H₁₃ |
| 2544 | C₂H₅ | 3-CH₃-C₆H₄ | Prop-1-en-3-yl |
| 2545 | C₂H₅ | 3-CH₃-C₆H₄ | (E)-1-Chloroprop-1-en-3-yl |
| 2546 | C₂H₅ | 3-CH₃-C₆H₄ | Propyn-3-yl |
| 2547 | C₂H₅ | 3-CH₃-C₆H₄ | 3-Methylbut-2-en-1-yl |
| 2548 | C₂H₅ | 4-CH₃-C₆H₄ | H |
| 2549 | C₂H₅ | 4-CH₃-C₆H₄ | CH₃ |
| 2550 | C₂H₅ | 4-CH₃-C₆H₄ | C₂H₅ |
| 2551 | C₂H₅ | 4-CH₃-C₆H₄ | n-C₃H₇ |
| 2552 | C₂H₅ | 4-CH₃-C₆H₄ | i-C₃H₇ |
| 2553 | C₂H₅ | 4-CH₃-C₆H₄ | n-C₄H₉ |
| 2554 | C₂H₅ | 4-CH₃-C₆H₄ | t-C₄H₉ |
| 2555 | C₂H₅ | 4-CH₃-C₆H₄ | n-C₆H₁₃ |
| 2556 | C₂H₅ | 4-CH₃-C₆H₄ | Prop-1-en-3-yl |
| 2557 | C₂H₅ | 4-CH₃-C₆H₄ | (E)-1-Chloroprop-1-en-3-yl |
| 2558 | C₂H₅ | 4-CH₃-C₆H₄ | Propyn-3-yl |
| 2559 | C₂H₅ | 4-CH₃-C₆H₄ | 3-Methylbut-2-en-1-yl |
| 2560 | C₂H₅ | 2,3-(CH₃)₂-C₆H₃ | H |
| 2561 | C₂H₅ | 2,3-(CH₃)₂-C₆H₃ | CH₃ |
| 2562 | C₂H₅ | 2,3-(CH₃)₂-C₆H₃ | C₂H₅ |
| 2563 | C₂H₅ | 2,3-(CH₃)₂-C₆H₃ | n-C₃H₇ |
| 2564 | C₂H₅ | 2,3-(CH₃)₂-C₆H₃ | i-C₃H₇ |
| 2565 | C₂H₅ | 2,3-(CH₃)₂-C₆H₃ | n-C₄H₉ |
| 2566 | C₂H₅ | 2,3-(CH₃)₂-C₆H₃ | t-C₄H₉ |
| 2567 | C₂H₅ | 2,3-(CH₃)₂-C₆H₃ | n-C₆H₁₃ |
| 2568 | C₂H₅ | 2,3-(CH₃)₂-C₆H₃ | Prop-1-en-3-yl |
| 2569 | C₂H₅ | 2,3-(CH₃)₂-C₆H₃ | (E)-1-Chloroprop-1-en-3-yl |
| 2570 | C₂H₅ | 2,3-(CH₃)₂-C₆H₃ | Propyn-3-yl |
| 2571 | C₂H₅ | 2,3-(CH₃)₂-C₆H₃ | 3-Methylbut-2-en-1-yl |
| 2572 | C₂H₅ | 2,4-(CH₃)₂-C₆H₃ | H |
| 2573 | C₂H₅ | 2,4-(CH₃)₂-C₆H₃ | CH₃ |
| 2574 | C₂H₅ | 2,4-(CH₃)₂-C₆H₃ | C₂H₅ |
| 2575 | C₂H₅ | 2,4-(CH₃)₂-C₆H₃ | n-C₃H₇ |
| 2576 | C₂H₅ | 2,4-(CH₃)₂-C₆H₃ | i-C₃H₇ |

TABLE A-continued

| No. | R² | R³ | R⁴ |
|---|---|---|---|
| 2577 | $C_2H_5$ | 2,4-$(CH_3)_2$-$C_6H_3$ | n-$C_4H_9$ |
| 2578 | $C_2H_5$ | 2,4-$(CH_3)_2$-$C_6H_3$ | t-$C_4H_9$ |
| 2579 | $C_2H_5$ | 2,4-$(CH_3)_2$-$C_6H_3$ | n-$C_6H_{13}$ |
| 2580 | $C_2H_5$ | 2,4-$(CH_3)_2$-$C_6H_3$ | Prop-1-en-3-yl |
| 2581 | $C_2H_5$ | 2,4-$(CH_3)_2$-$C_6H_3$ | (E)-1-Chloroprop-1-en-3-yl |
| 2582 | $C_2H_5$ | 2,4-$(CH_3)_2$-$C_6H_3$ | Propyn-3-yl |
| 2583 | $C_2H_5$ | 2,4-$(CH_3)_2$-$C_6H_3$ | 3-Methylbut-2-en-1-yl |
| 2584 | $C_2H_5$ | 2,5-$(CH_3)_2$-$C_6H_3$ | H |
| 2585 | $C_2H_5$ | 2,5-$(CH_3)_2$-$C_6H_3$ | $CH_3$ |
| 2586 | $C_2H_5$ | 2,5-$(CH_3)_2$-$C_6H_3$ | $C_2H_5$ |
| 2587 | $C_2H_5$ | 2,5-$(CH_3)_2$-$C_6H_3$ | n-$C_3H_7$ |
| 2588 | $C_2H_5$ | 2,5-$(CH_3)_2$-$C_6H_3$ | i-$C_3H_7$ |
| 2589 | $C_2H_5$ | 2,5-$(CH_3)_2$-$C_6H_3$ | n-$C_4H_9$ |
| 2590 | $C_2H_5$ | 2,5-$(CH_3)_2$-$C_6H_3$ | t-$C_4H_9$ |
| 2591 | $C_2H_5$ | 2,5-$(CH_3)_2$-$C_6H_3$ | n-$C_6H_{13}$ |
| 2592 | $C_2H_5$ | 2,5-$(CH_3)_2$-$C_6H_3$ | Prop-1-en-3-yl |
| 2593 | $C_2H_5$ | 2,5-$(CH_3)_2$-$C_6H_3$ | (E)-1-Chloroprop-1-en-3-yl |
| 2594 | $C_2H_5$ | 2,5-$(CH_3)_2$-$C_6H_3$ | Propyn-3-yl |
| 2595 | $C_2H_5$ | 2,5-$(CH_3)_2$-$C_6H_3$ | 3-Methylbut-2-en-1-yl |
| 2596 | $C_2H_5$ | 2,6-$(CH_3)_2$-$C_6H_3$ | H |
| 2597 | $C_2H_5$ | 2,6-$(CH_3)_2$-$C_6H_3$ | $CH_3$ |
| 2598 | $C_2H_5$ | 2,6-$(CH_3)_2$-$C_6H_3$ | $C_2H_5$ |
| 2599 | $C_2H_5$ | 2,6-$(CH_3)_2$-$C_6H_3$ | n-$C_3H_7$ |
| 2600 | $C_2H_5$ | 2,6-$(CH_3)_2$-$C_6H_3$ | i-$C_3H_7$ |
| 2601 | $C_2H_5$ | 2,6-$(CH_3)_2$-$C_6H_3$ | n-$C_4H_9$ |
| 2602 | $C_2H_5$ | 2,6-$(CH_3)_2$-$C_6H_3$ | t-$C_4H_9$ |
| 2603 | $C_2H_5$ | 2,6-$(CH_3)_2$-$C_6H_3$ | n-$C_6H_{13}$ |
| 2604 | $C_2H_5$ | 2,6-$(CH_3)_2$-$C_6H_3$ | Prop-1-en-3-yl |
| 2605 | $C_2H_5$ | 2,6-$(CH_3)_2$-$C_6H_3$ | (E)-1-Chloroprop-1-en-3-yl |
| 2606 | $C_2H_5$ | 2,6-$(CH_3)_2$-$C_6H_3$ | Propyn-3-yl |
| 2607 | $C_2H_5$ | 2,6-$(CH_3)_2$-$C_6H_3$ | 3-Methylbut-2-en-1-yl |
| 2608 | $C_2H_5$ | 3,4-$(CH_3)_2$-$C_6H_3$ | H |
| 2609 | $C_2H_5$ | 3,4-$(CH_3)_2$-$C_6H_3$ | $CH_3$ |
| 2610 | $C_2H_5$ | 3,4-$(CH_3)_2$-$C_6H_3$ | $C_2H_5$ |
| 2611 | $C_2H_5$ | 3,4-$(CH_3)_2$-$C_6H_3$ | n-$C_3H_7$ |
| 2612 | $C_2H_5$ | 3,4-$(CH_3)_2$-$C_6H_3$ | i-$C_3H_7$ |
| 2613 | $C_2H_5$ | 3,4-$(CH_3)_2$-$C_6H_3$ | n-$C_4H_9$ |
| 2614 | $C_2H_5$ | 3,4-$(CH_3)_2$-$C_6H_3$ | t-$C_4H_9$ |
| 2615 | $C_2H_5$ | 3,4-$(CH_3)_2$-$C_6H_3$ | n-$C_6H_{13}$ |
| 2616 | $C_2H_5$ | 3,4-$(CH_3)_2$-$C_6H_3$ | Prop-1-en-3-yl |
| 2617 | $C_2H_5$ | 3,4-$(CH_3)_2$-$C_6H_3$ | (E)-1-Chloroprop-1-en-3-yl |
| 2618 | $C_2H_5$ | 3,4-$(CH_3)_2$-$C_6H_3$ | Propyn-3-yl |
| 2619 | $C_2H_5$ | 3,4-$(CH_3)_2$-$C_6H_3$ | 3-Methylbut-2-en-1-yl |
| 2620 | $C_2H_5$ | 3,5-$(CH_3)_2$-$C_6H_3$ | H |
| 2621 | $C_2H_5$ | 3,5-$(CH_3)_2$-$C_6H_3$ | $CH_3$ |
| 2622 | $C_2H_5$ | 3,5-$(CH_3)_2$-$C_6H_3$ | $C_2H_5$ |
| 2623 | $C_2H_5$ | 3,5-$(CH_3)_2$-$C_6H_3$ | n-$C_3H_7$ |
| 2624 | $C_2H_5$ | 3,5-$(CH_3)_2$-$C_6H_3$ | i-$C_3H_7$ |
| 2625 | $C_2H_5$ | 3,5-$(CH_3)_2$-$C_6H_3$ | n-$C_4H_9$ |
| 2626 | $C_2H_5$ | 3,5-$(CH_3)_2$-$C_6H_3$ | t-$C_4H_9$ |
| 2627 | $C_2H_5$ | 3,5-$(CH_3)_2$-$C_6H_3$ | n-$C_6H_{13}$ |
| 2628 | $C_2H_5$ | 3,5-$(CH_3)_2$-$C_6H_3$ | Prop-1-en-3-yl |
| 2629 | $C_2H_5$ | 3,5-$(CH_3)_2$-$C_6H_3$ | (E)-1-Chloroprop-1-en-3-yl |
| 2630 | $C_2H_5$ | 3,5-$(CH_3)_2$-$C_6H_3$ | Propyn-3-yl |
| 2631 | $C_2H_5$ | 3,5-$(CH_3)_2$-$C_6H_3$ | 3-Methylbut-2-en-1-yl |
| 2632 | $C_2H_5$ | 2-$C_2H_5$-$C_6H_4$ | H |
| 2633 | $C_2H_5$ | 2-$C_2H_5$-$C_6H_4$ | $CH_3$ |
| 2634 | $C_2H_5$ | 2-$C_2H_5$-$C_6H_4$ | $C_2H_5$ |
| 2635 | $C_2H_5$ | 2-$C_2H_5$-$C_6H_4$ | n-$C_3H_7$ |
| 2636 | $C_2H_5$ | 2-$C_2H_5$-$C_6H_4$ | i-$C_3H_7$ |
| 2637 | $C_2H_5$ | 2-$C_2H_5$-$C_6H_4$ | n-$C_4H_9$ |
| 2638 | $C_2H_5$ | 2-$C_2H_5$-$C_6H_4$ | t-$C_4H_9$ |
| 2639 | $C_2H_5$ | 2-$C_2H_5$-$C_6H_4$ | n-$C_6H_{13}$ |
| 2640 | $C_2H_5$ | 2-$C_2H_5$-$C_6H_4$ | Prop-1-en-3-yl |
| 2641 | $C_2H_5$ | 2-$C_2H_5$-$C_6H_4$ | (E)-1-Chloroprop-1-en-3-yl |
| 2642 | $C_2H_5$ | 2-$C_2H_5$-$C_6H_4$ | Propyn-3-yl |
| 2643 | $C_2H_5$ | 2-$C_2H_5$-$C_6H_4$ | 3-Methylbut-2-en-1-yl |
| 2644 | $C_2H_5$ | 3-$C_2H_5$-$C_6H_4$ | H |
| 2645 | $C_2H_5$ | 3-$C_2H_5$-$C_6H_4$ | $CH_3$ |
| 2646 | $C_2H_5$ | 3-$C_2H_5$-$C_6H_4$ | $C_2H_5$ |
| 2647 | $C_2H_5$ | 3-$C_2H_5$-$C_6H_4$ | n-$C_3H_7$ |
| 2648 | $C_2H_5$ | 3-$C_2H_5$-$C_6H_4$ | i-$C_3H_7$ |
| 2649 | $C_2H_5$ | 3-$C_2H_5$-$C_6H_4$ | n-$C_4H_9$ |
| 2650 | $C_2H_5$ | 3-$C_2H_5$-$C_6H_4$ | t-$C_4H_9$ |
| 2651 | $C_2H_5$ | 3-$C_2H_5$-$C_6H_4$ | n-$C_6H_{13}$ |
| 2652 | $C_2H_5$ | 3-$C_2H_5$-$C_6H_4$ | Prop-1-en-3-yl |
| 2653 | $C_2H_5$ | 3-$C_2H_5$-$C_6H_4$ | (E)-1-Chloroprop-1-en-3-yl |

TABLE A-continued

| No. | R² | R³ | R⁴ |
|---|---|---|---|
| 2654 | $C_2H_5$ | 3-$C_2H_5$-$C_6H_4$ | Propyn-3-yl |
| 2655 | $C_2H_5$ | 3-$C_2H_5$-$C_6H_4$ | 3-Methylbut-2-en-1-yl |
| 2656 | $C_2H_5$ | 4-$C_2H_5$-$C_6H_4$ | H |
| 2657 | $C_2H_5$ | 4-$C_2H_5$-$C_6H_4$ | $CH_3$ |
| 2658 | $C_2H_5$ | 4-$C_2H_5$-$C_6H_4$ | $C_2H_5$ |
| 2659 | $C_2H_5$ | 4-$C_2H_5$-$C_6H_4$ | n-$C_3H_7$ |
| 2660 | $C_2H_5$ | 4-$C_2H_5$-$C_6H_4$ | i-$C_3H_7$ |
| 2661 | $C_2H_5$ | 4-$C_2H_5$-$C_6H_4$ | n-$C_4H_9$ |
| 2662 | $C_2H_5$ | 4-$C_2H_5$-$C_6H_4$ | t-$C_4H_9$ |
| 2663 | $C_2H_5$ | 4-$C_2H_5$-$C_6H_4$ | n-$C_6H_{13}$ |
| 2664 | $C_2H_5$ | 4-$C_2H_5$-$C_6H_4$ | Prop-1-en-3-yl |
| 2665 | $C_2H_5$ | 4-$C_2H_5$-$C_6H_4$ | (E)-1-Chloroprop-1-en-3-yl |
| 2666 | $C_2H_5$ | 4-$C_2H_5$-$C_6H_4$ | Propyn-3-yl |
| 2667 | $C_2H_5$ | 4-$C_2H_5$-$C_6H_4$ | 3-Methylbut-2-en-1-yl |
| 2668 | $C_2H_5$ | 2-i-$C_3H_7$-$C_6H_4$ | H |
| 2669 | $C_2H_5$ | 2-i-$C_3H_7$-$C_6H_4$ | $CH_3$ |
| 2670 | $C_2H_5$ | 2-i-$C_3H_7$-$C_6H_4$ | $C_2H_5$ |
| 2671 | $C_2H_5$ | 2-i-$C_3H_7$-$C_6H_4$ | n-$C_3H_7$ |
| 2672 | $C_2H_5$ | 2-i-$C_3H_7$-$C_6H_4$ | i-$C_3H_7$ |
| 2673 | $C_2H_5$ | 2-i-$C_3H_7$-$C_6H_4$ | n-$C_4H_9$ |
| 2674 | $C_2H_5$ | 2-i-$C_3H_7$-$C_6H_4$ | t-$C_4H_9$ |
| 2675 | $C_2H_5$ | 2-i-$C_3H_7$-$C_6H_4$ | n-$C_6H_{13}$ |
| 2676 | $C_2H_5$ | 2-i-$C_3H_7$-$C_6H_4$ | Prop-1-en-3-yl |
| 2677 | $C_2H_5$ | 2-i-$C_3H_7$-$C_6H_4$ | (E)-1-Chloroprop-1-en-3-yl |
| 2678 | $C_2H_5$ | 2-i-$C_3H_7$-$C_6H_4$ | Propyn-3-yl |
| 2679 | $C_2H_5$ | 2-i-$C_3H_7$-$C_6H_4$ | 3-Methylbut-2-en-1-yl |
| 2680 | $C_2H_5$ | 3-i-$C_3H_7$-$C_6H_4$ | H |
| 2681 | $C_2H_5$ | 3-i-$C_3H_7$-$C_6H_4$ | $CH_3$ |
| 2682 | $C_2H_5$ | 3-i-$C_3H_7$-$C_6H_4$ | $C_2H_5$ |
| 2683 | $C_2H_5$ | 3-i-$C_3H_7$-$C_6H_4$ | n-$C_3H_7$ |
| 2684 | $C_2H_5$ | 3-i-$C_3H_7$-$C_6H_4$ | i-$C_3H_7$ |
| 2685 | $C_2H_5$ | 3-i-$C_3H_7$-$C_6H_4$ | n-$C_4H_9$ |
| 2686 | $C_2H_5$ | 3-i-$C_3H_7$-$C_6H_4$ | t-$C_4H_9$ |
| 2687 | $C_2H_5$ | 3-i-$C_3H_7$-$C_6H_4$ | n-$C_6H_{13}$ |
| 2688 | $C_2H_5$ | 3-i-$C_3H_7$-$C_6H_4$ | Prop-1-en-3-yl |
| 2689 | $C_2H_5$ | 3-i-$C_3H_7$-$C_6H_4$ | (E)-1-Chloroprop-1-en-3-yl |
| 2690 | $C_2H_5$ | 3-i-$C_3H_7$-$C_6H_4$ | Propyn-3-yl |
| 2691 | $C_2H_5$ | 3-i-$C_3H_7$-$C_6H_4$ | 3-Methylbut-2-en-1-yl |
| 2692 | $C_2H_5$ | 4-i-$C_3H_7$-$C_6H_4$ | H |
| 2693 | $C_2H_5$ | 4-i-$C_3H_7$-$C_6H_4$ | $CH_3$ |
| 2694 | $C_2H_5$ | 4-i-$C_3H_7$-$C_6H_4$ | $C_2H_5$ |
| 2695 | $C_2H_5$ | 4-i-$C_3H_7$-$C_6H_4$ | n-$C_3H_7$ |
| 2696 | $C_2H_5$ | 4-i-$C_3H_7$-$C_6H_4$ | i-$C_3H_7$ |
| 2697 | $C_2H_5$ | 4-i-$C_3H_7$-$C_6H_4$ | n-$C_4H_9$ |
| 2698 | $C_2H_5$ | 4-i-$C_3H_7$-$C_6H_4$ | t-$C_4H_9$ |
| 2699 | $C_2H_5$ | 4-i-$C_3H_7$-$C_6H_4$ | n-$C_6H_{13}$ |
| 2700 | $C_2H_5$ | 4-i-$C_3H_7$-$C_6H_4$ | Prop-1-en-3-yl |
| 2701 | $C_2H_5$ | 4-i-$C_3H_7$-$C_6H_4$ | (E)-1-Chloroprop-1-en-3-yl |
| 2702 | $C_2H_5$ | 4-i-$C_3H_7$-$C_6H_4$ | Propyn-3-yl |
| 2703 | $C_2H_5$ | 4-i-$C_3H_7$-$C_6H_4$ | 3-Methylbut-2-en-1-yl |
| 2704 | $C_2H_5$ | 2-OH-$C_6H_4$ | H |
| 2705 | $C_2H_5$ | 2-OH-$C_6H_4$ | $CH_3$ |
| 2706 | $C_2H_5$ | 2-OH-$C_6H_4$ | $C_2H_5$ |
| 2707 | $C_2H_5$ | 2-OH-$C_6H_4$ | n-$C_3H_7$ |
| 2708 | $C_2H_5$ | 2-OH-$C_6H_4$ | i-$C_3H_7$ |
| 2709 | $C_2H_5$ | 2-OH-$C_6H_4$ | n-$C_4H_9$ |
| 2710 | $C_2H_5$ | 2-OH-$C_6H_4$ | t-$C_4H_9$ |
| 2711 | $C_2H_5$ | 2-OH-$C_6H_4$ | n-$C_6H_{13}$ |
| 2712 | $C_2H_5$ | 2-OH-$C_6H_4$ | Prop-1-en-3-yl |
| 2713 | $C_2H_5$ | 2-OH-$C_6H_4$ | (E)-1-Chloroprop-1-en-3-yl |
| 2714 | $C_2H_5$ | 2-OH-$C_6H_4$ | Propyn-3-yl |
| 2715 | $C_2H_5$ | 2-OH-$C_6H_4$ | 3-Methylbut-2-en-1-yl |
| 2716 | $C_2H_5$ | 3-OH-$C_6H_4$ | H |
| 2717 | $C_2H_5$ | 3-OH-$C_6H_4$ | $CH_3$ |
| 2718 | $C_2H_5$ | 3-OH-$C_6H_4$ | $C_2H_5$ |
| 2719 | $C_2H_5$ | 3-OH-$C_6H_4$ | n-$C_3H_7$ |
| 2720 | $C_2H_5$ | 3-OH-$C_6H_4$ | i-$C_3H_7$ |
| 2721 | $C_2H_5$ | 3-OH-$C_6H_4$ | n-$C_4H_9$ |
| 2722 | $C_2H_5$ | 3-OH-$C_6H_4$ | t-$C_4H_9$ |
| 2723 | $C_2H_5$ | 3-OH-$C_6H_4$ | n-$C_6H_{13}$ |
| 2724 | $C_2H_5$ | 3-OH-$C_6H_4$ | Prop-1-en-3-yl |
| 2725 | $C_2H_5$ | 3-OH-$C_6H_4$ | (E)-1-Chloroprop-1-en-3-yl |
| 2726 | $C_2H_5$ | 3-OH-$C_6H_4$ | Propyn-3-yl |
| 2727 | $C_2H_5$ | 3-OH-$C_6H_4$ | 3-Methylbut-2-en-1-yl |
| 2728 | $C_2H_5$ | 4-OH-$C_6H_4$ | H |
| 2729 | $C_2H_5$ | 4-OH-$C_6H_4$ | $CH_3$ |
| 2730 | $C_2H_5$ | 4-OH-$C_6H_4$ | $C_2H_5$ |

TABLE A-continued

| No. | R² | R³ | R⁴ |
|---|---|---|---|
| 2731 | C₂H₅ | 4-OH-C₆H₄ | n-C₃H₇ |
| 2732 | C₂H₅ | 4-OH-C₆H₄ | i-C₃H₇ |
| 2733 | C₂H₅ | 4-OH-C₆H₄ | n-C₄H₉ |
| 2734 | C₂H₅ | 4-OH-C₆H₄ | t-C₄H₉ |
| 2735 | C₂H₅ | 4-OH-C₆H₄ | n-C₆H₁₃ |
| 2736 | C₂H₅ | 4-OH-C₆H₄ | Prop-1-en-3-yl |
| 2737 | C₂H₅ | 4-OH-C₆H₄ | (E)-1-Chloroprop-1-en-3-yl |
| 2738 | C₂H₅ | 4-OH-C₆H₄ | Propyn-3-yl |
| 2739 | C₂H₅ | 4-OH-C₆H₄ | 3-Methylbut-2-en-1-yl |
| 2740 | C₂H₅ | 2-OCH₃-C₆H₄ | H |
| 2741 | C₂H₅ | 2-OCH₃-C₆H₄ | CH₃ |
| 2742 | C₂H₅ | 2-OCH₃-C₆H₄ | C₂H₅ |
| 2743 | C₂H₅ | 2-OCH₃-C₆H₄ | n-C₃H₇ |
| 2744 | C₂H₅ | 2-OCH₃-C₆H₄ | i-C₃H₇ |
| 2745 | C₂H₅ | 2-OCH₃-C₆H₄ | n-C₄H₉ |
| 2746 | C₂H₅ | 2-OCH₃-C₆H₄ | t-C₄H₉ |
| 2747 | C₂H₅ | 2-OCH₃-C₆H₄ | n-C₆H₁₃ |
| 2748 | C₂H₅ | 2-OCH₃-C₆H₄ | Prop-1-en-3-yl |
| 2749 | C₂H₅ | 2-OCH₃-C₆H₄ | (E)-1-Chloroprop-1-en-3-yl |
| 2750 | C₂H₅ | 2-OCH₃-C₆H₄ | Propyn-3-yl |
| 2751 | C₂H₅ | 2-OCH₃-C₆H₄ | 3-Methylbut-2-en-1-yl |
| 2752 | C₂H₅ | 3-OCH₃-C₆H₄ | H |
| 2753 | C₂H₅ | 3-OCH₃-C₆H₄ | CH₃ |
| 2754 | C₂H₅ | 3-OCH₃-C₆H₄ | C₂H₅ |
| 2755 | C₂H₅ | 3-OCH₃-C₆H₄ | n-C₃H₇ |
| 2756 | C₂H₅ | 3-OCH₃-C₆H₄ | i-C₃H₇ |
| 2757 | C₂H₅ | 3-OCH₃-C₆H₄ | n-C₄H₉ |
| 2758 | C₂H₅ | 3-OCH₃-C₆H₄ | t-C₄H₉ |
| 2759 | C₂H₅ | 3-OCH₃-C₆H₄ | n-C₆H₁₃ |
| 2760 | C₂H₅ | 3-OCH₃-C₆H₄ | Prop-1-en-3-yl |
| 2761 | C₂H₅ | 3-OCH₃-C₆H₄ | (E)-1-Chloroprop-1-en-3-yl |
| 2762 | C₂H₅ | 3-OCH₃-C₆H₄ | Propyn-3-yl |
| 2763 | C₂H₅ | 3-OCH₃-C₆H₄ | 3-Methylbut-2-en-1-yl |
| 2764 | C₂H₅ | 4-OCH₃-C₆H₄ | H |
| 2765 | C₂H₅ | 4-OCH₃-C₆H₄ | CH₃ |
| 2766 | C₂H₅ | 4-OCH₃-C₆H₄ | C₂H₅ |
| 2767 | C₂H₅ | 4-OCH₃-C₆H₄ | n-C₃H₇ |
| 2768 | C₂H₅ | 4-OCH₃-C₆H₄ | i-C₃H₇ |
| 2769 | C₂H₅ | 4-OCH₃-C₆H₄ | n-C₄H₉ |
| 2770 | C₂H₅ | 4-OCH₃-C₆H₄ | t-C₄H₉ |
| 2771 | C₂H₅C₂H₅ | 4-OCH₃-C₆H₄ | n-C₆H₁₃ |
| 2772 | C₂H₅ | 4-OCH₃-C₆H₄ | Prop-1-en-3-yl |
| 2773 | C₂H₅ | 4-OCH₃-C₆H₄ | (E)-1-Chloroprop-1-en-3-yl |
| 2774 | C₂H₅ | 4-OCH₃-C₆H₄ | Propyn-3-yl |
| 2775 | C₂H₅ | 4-OCH₃-C₆H₄ | 3-Methylbut-2-en-1-yl |
| 2776 | C₂H₅ | 2-OC₂H₅-C₆H₄ | H |
| 2777 | C₂H₅ | 2-OC₂H₅-C₆H₄ | CH₃ |
| 2778 | C₂H₅ | 2-OC₂H₅-C₆H₄ | C₂H₅ |
| 2779 | C₂H₅ | 2-OC₂H₅-C₆H₄ | n-C₃H₇ |
| 2780 | C₂H₅ | 2-OC₂H₅-C₆H₄ | i-C₃H₇ |
| 2781 | C₂H₅ | 2-OC₂H₅-C₆H₄ | n-C₄H₉ |
| 2782 | C₂H₅ | 2-OC₂H₅-C₆H₄ | t-C₄H₉ |
| 2783 | C₂H₅ | 2-OC₂H₅-C₆H₄ | n-C₆H₁₃ |
| 2784 | C₂H₅ | 2-OC₂H₅-C₆H₄ | Prop-1-en-3-yl |
| 2785 | C₂H₅ | 2-OC₂H₅-C₆H₄ | (E)-1-Chloroprop-1-en-3-yl |
| 2786 | C₂H₅ | 2-OC₂H₅-C₆H₄ | Propyn-3-yl |
| 2787 | C₂H₅ | 2-OC₂H₅-C₆H₄ | 3-Methylbut-2-en-1-yl |
| 2788 | C₂H₅ | 3-OC₂H₅-C₆H₄ | H |
| 2789 | C₂H₅ | 3-OC₂H₅-C₆H₄ | CH₃ |
| 2790 | C₂H₅ | 3-OC₂H₅-C₆H₄ | C₂H₅ |
| 2791 | C₂H₅ | 3-OC₂H₅-C₆H₄ | n-C₃H₇ |
| 2792 | C₂H₅ | 3-OC₂H₅-C₆H₄ | i-C₃H₇ |
| 2793 | C₂H₅ | 3-OC₂H₅-C₆H₄ | n-C₄H₉ |
| 2794 | C₂H₅ | 3-OC₂H₅-C₆H₄ | t-C₄H₉ |
| 2795 | C₂H₅ | 3-OC₂H₅-C₆H₄ | n-C₆H₁₃ |
| 2796 | C₂H₅ | 3-OC₂H₅-C₆H₄ | Prop-1-en-3-yl |
| 2797 | C₂H₅ | 3-OC₂H₅-C₆H₄ | (E)-1-Chloroprop 1-en-3-yl |
| 2798 | C₂H₅ | 3-OC₂H₅-C₆H₄ | Propyn-3-yl |
| 2799 | C₂H₅ | 3-OC₂H₅-C₆H₄ | 3-Methylbut-2-en-1-yl |
| 2800 | C₂H₅ | 4-OC₂H₅-C₆H₄ | H |
| 2801 | C₂H₅ | 4-OC₂H₅-C₆H₄ | CH₃ |
| 2802 | C₂H₅ | 4-OC₂H₅-C₆H₄ | C₂H₅ |
| 2803 | C₂H₅ | 4-OC₂H₅-C₆H₄ | n-C₃H₇ |
| 2804 | C₂H₅ | 4-OC₂H₅-C₆H₄ | i-C₃H₇ |
| 2805 | C₂H₅ | 4-OC₂H₅-C₆H₄ | n-C₄H₉ |
| 2806 | C₂H₅ | 4-OC₂H₅-C₆H₄ | t-C₄H₉ |
| 2807 | C₂H₅ | 4-OC₂H₅-C₆H₄ | n-C₆H₁₃ |

TABLE A-continued

| No. | R² | R³ | R⁴ |
|---|---|---|---|
| 2808 | $C_2H_5$ | 4-$OC_2H_5$-$C_6H_4$ | Prop-1-en-3-yl |
| 2809 | $C_2H_5$ | 4-$OC_2H_5$-$C_6H_4$ | (E)-1-Chloroprop-1-en-3-yl |
| 2810 | $C_2H_5$ | 4-$OC_2H_5$-$C_6H_4$ | Propyn-3-yl |
| 2811 | $C_2H_5$ | 4-$OC_2H_5$-$C_6H_4$ | 3-Methylbut-2-en-1-yl |
| 2812 | $C_2H_5$ | 2-O-(i-$C_3H_7$)-$C_6H_4$ | H |
| 2813 | $C_2H_5$ | 2-O-(i-$C_3H_7$)-$C_6H_4$ | $CH_3$ |
| 2814 | $C_2H_5$ | 2-O-(i-$C_3H_7$)-$C_6H_4$ | $C_2H_5$ |
| 2815 | $C_2H_5$ | 2-O-(i-$C_3H_7$)-$C_6H_4$ | n-$C_3H_7$ |
| 2816 | $C_2H_5$ | 2-O-(i-$C_3H_7$)-$C_6H_4$ | i-$C_3H_7$ |
| 2817 | $C_2H_5$ | 2-O-(i-$C_3H_7$)-$C_6H_4$ | n-$C_4H_9$ |
| 2818 | $C_2H_5$ | 2-O-(i-$C_3H_7$)-$C_6H_4$ | t-$C_4H_9$ |
| 2819 | $C_2H_5$ | 2-O-(i-$C_3H_7$)-$C_6H_4$ | n-$C_6H_{13}$ |
| 2820 | $C_2H_5$ | 2-O-(i-$C_3H_7$)-$C_6H_4$ | Prop-1-en-3-yl |
| 2821 | $C_2H_5$ | 2-O-(i-$C_3H_7$)-$C_6H_4$ | (E)-1-Chloroprop-1-en-3-yl |
| 2822 | $C_2H_5$ | 2-O-(i-$C_3H_7$)-$C_6H_4$ | Propyn-3-yl |
| 2823 | $C_2H_5$ | 2-O-(i-$C_3H_7$)-$C_6H_4$ | 3-Methylbut-2-en-1-yl |
| 2824 | $C_2H_5$ | 3-O-(i-$C_3H_7$)-$C_6H_4$ | H |
| 2825 | $C_2H_5$ | 3-O-(i-$C_3H_7$)-$C_6H_4$ | $CH_3$ |
| 2826 | $C_2H_5$ | 3-O-(i-$C_3H_7$)-$C_6H_4$ | $C_2H_5$ |
| 2827 | $C_2H_5$ | 3-O-(i-$C_3H_7$)-$C_6H_4$ | n-$C_3H_7$ |
| 2828 | $C_2H_5$ | 3-O-(i-$C_3H_7$)-$C_6H_4$ | i-$C_3H_7$ |
| 2829 | $C_2H_5$ | 3-O-(i-$C_3H_7$)-$C_6H_4$ | n-$C_4H_9$ |
| 2830 | $C_2H_5$ | 3-O-(i-$C_3H_7$)-$C_6H_4$ | t-$C_4H_9$ |
| 2831 | $C_2H_5$ | 3-O-(i-$C_3H_7$)-$C_6H_4$ | n-$C_6H_{13}$ |
| 2832 | $C_2H_5$ | 3-O-(i-$C_3H_7$)-$C_6H_4$ | Prop-1-en-3-yl |
| 2833 | $C_2H_5$ | 3-O-(i-$C_3H_7$)-$C_6H_4$ | (E)-1-Chloroprop-1-en-3-yl |
| 2834 | $C_2H_5$ | 3-O-(i-$C_3H_7$)-$C_6H_4$ | Propyn-3-yl |
| 2835 | $C_2H_5$ | 3-O-(i-$C_3H_7$)-$C_6H_4$ | 3-Methylbut-2-en-1-yl |
| 2836 | $C_2H_5$ | 4-O-(i-$C_3H_7$)-$C_6H_4$ | H |
| 2837 | $C_2H_5$ | 4-O-(i-$C_3H_7$)-$C_6H_4$ | $CH_3$ |
| 2838 | $C_2H_5$ | 4-O-(i-$C_3H_7$)-$C_6H_4$ | $C_2H_5$ |
| 2839 | $C_2H_5$ | 4-O-(i-$C_3H_7$)-$C_6H_4$ | n-$C_3H_7$ |
| 2840 | $C_2H_5$ | 4-O-(i-$C_3H_7$)-$C_6H_4$ | i-$C_3H_7$ |
| 2841 | $C_2H_5$ | 4-O-(i-$C_3H_7$)-$C_6H_4$ | n-$C_4H_9$ |
| 2842 | $C_2H_5$ | 4-O-(i-$C_3H_7$)-$C_6H_4$ | t-$C_4H_9$ |
| 2843 | $C_2H_5$ | 4-O-(i-$C_3H_7$)-$C_6H_4$ | n-$C_6H_{13}$ |
| 2844 | $C_2H_5$ | 4-O-(i-$C_3H_7$)-$C_6H_4$ | Prop-1-en-3-yl |
| 2845 | $C_2H_5$ | 4-O-(i-$C_3H_7$)-$C_6H_4$ | (E)-1-Chloroprop-1-en-3-yl |
| 2846 | $C_2H_5$ | 4-O-(i-$C_3H_7$)-$C_6H_4$ | Propyn-3-yl |
| 2847 | $C_2H_5$ | 4-O-(i-$C_3H_7$)-$C_6H_4$ | 3-Methylbut-2-en-1-yl |
| 2848 | $C_2H_5$ | 2-O-(t-$C_4H_9$)-$C_6H_4$ | H |
| 2849 | $C_2H_5$ | 2-O-(t-$C_4H_9$)-$C_6H_4$ | $CH_3$ |
| 2850 | $C_2H_5$ | 2-O-(t-$C_4H_9$)-$C_6H_4$ | $C_2H_5$ |
| 2851 | $C_2H_5$ | 2-O-(t-$C_4H_9$)-$C_6H_4$ | n-$C_3H_7$ |
| 2852 | $C_2H_5$ | 2-O-(t-$C_4H_9$)-$C_6H_4$ | i-$C_3H_7$ |
| 2853 | $C_2H_5$ | 2-O-(t-$C_4H_9$)-$C_6H_4$ | n-$C_4H_9$ |
| 2854 | $C_2H_5$ | 2-O-(t-$C_4H_9$)-$C_6H_4$ | t-$C_4H_9$ |
| 2855 | $C_2H_5$ | 2-O-(t-$C_4H_9$)-$C_6H_4$ | n-$C_6H_{13}$ |
| 2856 | $C_2H_5$ | 2-O-(t-$C_4H_9$)-$C_6H_4$ | Prop-1-en-3-yl |
| 2857 | $C_2H_5$ | 2-O-(t-$C_4H_9$)-$C_6H_4$ | (E)-1-Chloroprop-1-en-3-yl |
| 2858 | $C_2H_5$ | 2-O-(t-$C_4H_9$)-$C_6H_4$ | Propyn-3-yl |
| 2859 | $C_2H_5$ | 2-O-(t-$C_4H_9$)-$C_6H_4$ | 3-Methylbut-2-en-1-yl |
| 2860 | $C_2H_5$ | 3-O-(t-$C_4H_9$)-$C_6H_4$ | H |
| 2861 | $C_2H_5$ | 3-O-(t-$C_4H_9$)-$C_6H_4$ | $CH_3$ |
| 2862 | $C_2H_5$ | 3-O-(t-$C_4H_9$)-$C_6H_4$ | $C_2H_5$ |
| 2863 | $C_2H_5$ | 3-O-(t-$C_4H_9$)-$C_6H_4$ | n-$C_3H_7$ |
| 2864 | $C_2H_5$ | 3-(5-(t-$C_4H_9$)-$C_6H_4$ | i-$C_3H_7$ |
| 2865 | $C_2H_5$ | 3-O-(t-$C_4H_9$)-$C_6H_4$ | n-$C_4H_9$ |
| 2866 | $C_2H_5$ | 3-O-(t-$C_4H_9$)-$C_6H_4$ | t-$C_4H_9$ |
| 2867 | $C_2H_5$ | 3-O-(t-$C_4H_9$)-$C_6H_4$ | n-$C_6H_{13}$ |
| 2868 | $C_2H_5$ | 3-O-(t-$C_4H_9$)-$C_6H_4$ | Prop-1-en-3-yl |
| 2869 | $C_2H_5$ | 3-O-(t-$C_4H_9$)-$C_6H_4$ | (E)-1-Chloroprop-1-en-3-yl |
| 2870 | $C_2H_5$ | 3-O-(t-$C_4H_9$)-$C_6H_4$ | Propyn-3-yl |
| 2871 | $C_2H_5$ | 3-O-(t-$C_4H_9$)-$C_6H_4$ | 3-Methylbut-2-en-1-yl |
| 2872 | $C_2H_5$ | 4-O-(t-$C_4H_9$)-$C_6H_4$ | H |
| 2873 | $C_2H_5$ | 4-O-(t-$C_4H_9$)-$C_6H_4$ | $CH_3$ |
| 2874 | $C_2H_5$ | 4-O-(t-$C_4H_9$)-$C_6H_4$ | $C_2H_5$ |
| 2875 | $C_2H_5$ | 4-O-(t-$C_4H_9$)-$C_6H_4$ | n-$C_3H_7$ |
| 2876 | $C_2H_5$ | 4-O-(t-$C_4H_9$)-$C_6H_4$ | i-$C_3H_7$ |
| 2877 | $C_2H_5$ | 4-O-(t-$C_4H_9$)-$C_6H_4$ | n-$C_4H_9$ |
| 2878 | $C_2H_5$ | 4-O-(t-$C_4H_9$)-$C_6H_4$ | t-$C_4H_9$ |
| 2879 | $C_2H_5$ | 4-O-(t-$C_4H_9$)-$C_6H_4$ | n-$C_6H_{13}$ |
| 2880 | $C_2H_5$ | 4-O-(t-$C_4H_9$)-$C_6H_4$ | Prop-1-en-3-yl |
| 2881 | $C_2H_5$ | 4-O-(t-$C_4H_9$)-$C_6H_4$ | (E)-1-Chloroprop-1-en-3-yl |
| 2882 | $C_2H_5$ | 4-O-(t-$C_4H_9$)-$C_6H_4$ | Propyn-3-yl |
| 2883 | $C_2H_5$ | 4-O-(t-$C_4H_9$)-$C_6H_4$ | 3-Methylbut-2-en-1-yl |
| 2884 | $C_2H_5$ | 2-$CF_3$-$C_6H_4$ | H |

TABLE A-continued

| No. | R² | R³ | R⁴ |
|---|---|---|---|
| 2885 | $C_2H_5$ | 2-$CF_3$-$C_6H_4$ | $CH_3$ |
| 2886 | $C_2H_5$ | 2-$CF_3$-$C_6H_4$ | $C_2H_5$ |
| 2887 | $C_2H_5$ | 2-$CF_3$-$C_6H_4$ | n-$C_3H_7$ |
| 2888 | $C_2H_5$ | 2-$CF_3$-$C_6H_4$ | i-$C_3H_7$ |
| 2889 | $C_2H_5$ | 2-$CF_3$-$C_6H_4$ | n-$C_4H_9$ |
| 2890 | $C_2H_5$ | 2-$CF_3$-$C_6H_4$ | t-$C_4H_9$ |
| 2891 | $C_2H_5$ | 2-$CF_3$-$C_6H_4$ | n-$C_6H_{13}$ |
| 2892 | $C_2H_5$ | 2-$CF_3$-$C_6H_4$ | Prop-1-en-3-yl |
| 2893 | $C_2H_5$ | 2-$CF_3$-$C_6H_4$ | (E)-1-Chloroprop-1-en-3-yl |
| 2894 | $C_2H_5$ | 2-$CF_3$-$C_6H_4$ | Propyn-3-yl |
| 2895 | $C_2H_5$ | 2-$CF_3$-$C_6H_4$ | 3-Methylbut-2-en-1-yl |
| 2896 | $C_2H_5$ | 3-$CF_3$-$C_6H_4$ | H |
| 2897 | $C_2H_5$ | 3-$CF_3$-$C_6H_4$ | $CH_3$ |
| 2898 | $C_2H_5$ | 3-$CF_3$-$C_6H_4$ | $C_2H_5$ |
| 2899 | $C_2H_5$ | 3-$CF_3$-$C_6H_4$ | n-$C_3H_7$ |
| 2900 | $C_2H_5$ | 3-$CF_3$-$C_6H_4$ | i-$C_3H_7$ |
| 2901 | $C_2H_5$ | 3-$CF_3$-$C_6H_4$ | n-$C_4H_9$ |
| 2902 | $C_2H_5$ | 3-$CF_3$-$C_6H_4$ | t-$C_4H_9$ |
| 2903 | $C_2H_5$ | 3-$CF_3$-$C_6H_4$ | n-$C_6H_{13}$ |
| 2904 | $C_2H_5$ | 3-$CF_3$-$C_6H_4$ | Prop-1-en-3-yl |
| 2905 | $C_2H_5$ | 3-$CF_3$-$C_6H_4$ | (E)-1-Chloroprop-1-en-3-yl |
| 2906 | $C_2H_5$ | 3-$CF_3$-$C_6H_4$ | Propyn-3-yl |
| 2907 | $C_2H_5$ | 3-$CF_3$-$C_6H_4$ | 3-Methylbut-2-en-1-yl |
| 2908 | $C_2H_5$ | 4-$CF_3$-$C_6H_4$ | H |
| 2909 | $C_2H_5$ | 4-$CF_3$-$C_6H_4$ | $CH_3$ |
| 2910 | $C_2H_5$ | 4-$CF_3$-$C_6H_4$ | $C_2H_5$ |
| 2911 | $C_2H_5$ | 4-$CF_3$-$C_6H_4$ | n-$C_3H_7$ |
| 2912 | $C_2H_5$ | 4-$CF_3$-$C_6H_4$ | i-$C_3H_7$ |
| 2913 | $C_2H_5$ | 4-$CF_3$-$C_6H_4$ | n-$C_4H_9$ |
| 2914 | $C_2H_5$ | 4-$CF_3$-$C_6H_4$ | t-$C_4H_9$ |
| 2915 | $C_2H_5$ | 4-$CF_3$-$C_6H_4$ | n-$C_6H_{13}$ |
| 2916 | $C_2H_5$ | 4-$CF_3$-$C_6H_4$ | Prop-1-en-3-yl |
| 2917 | $C_2H_5$ | 4-$CF_3$-$C_6H_4$ | (E)-1-Chloroprop-1-en-3-yl |
| 2918 | $C_2H_5$ | 4-$CF_3$-$C_6H_4$ | Propyn-3-yl |
| 2919 | $C_2H_5$ | 4-$CF_3$-$C_6H_4$ | 3-Methylbut-2-en-1-yl |
| 2920 | $C_2H_5$ | 2-$NH_2$-$C_6H_4$ | H |
| 2921 | $C_2H_5$ | 2-$NH_2$-$C_6H_4$ | $CH_3$ |
| 2922 | $C_2H_5$ | 2-$NH_2$-$C_6H_4$ | $C_2H_5$ |
| 2923 | $C_2H_5$ | 2-$NH_2$-$C_6H_4$ | n-$C_3H_7$ |
| 2924 | $C_2H_5$ | 2-$NH_2$-$C_6H_4$ | i-$C_3H_7$ |
| 2925 | $C_2H_5$ | 2-$NH_2$-$C_6H_4$ | n-$C_4H_9$ |
| 2926 | $C_2H_5$ | 2-$NH_2$-$C_6H_4$ | t-$C_4H_9$ |
| 2927 | $C_2H_5$ | 2-$NH_2$-$C_6H_4$ | n-$C_6H_{13}$ |
| 2928 | $C_2H_5$ | 2-$NH_2$-$C_6H_4$ | Prop-1-en-3-yl |
| 2929 | $C_2H_5$ | 2-$NH_2$-$C_6H_4$ | (E)-1-Chloroprop-1-en-3-yl |
| 2930 | $C_2H_5$ | 2-$NH_2$-$C_6H_4$ | Propyn-3-yl |
| 2931 | $C_2H_5$ | 2-$NH_2$-$C_6H_4$ | 3-Methylbut-2-en-1-yl |
| 2932 | $C_2H_5$ | 3-$NH_2$-$C_6H_4$ | H |
| 2933 | $C_2H_5$ | 3-$NH_2$-$C_6H_4$ | $CH_3$ |
| 2934 | $C_2H_5$ | 3-$NH_2$-$C_6H_4$ | $C_2H_5$ |
| 2935 | $C_2H_5$ | 3-$NH_2$-$C_6H_4$ | n-$C_3H_7$ |
| 2936 | $C_2H_5$ | 3-$NH_2$-$C_6H_4$ | i-$C_3H_7$ |
| 2937 | $C_2H_5$ | 3-$NH_2$-$C_6H_4$ | n-$C_4H_9$ |
| 2938 | $C_2H_5$ | 3-$NH_2$-$C_6H_4$ | t-$C_4H_9$ |
| 2939 | $C_2H_5$ | 3-$NH_2$-$C_6H_4$ | n-$C_6H_{13}$ |
| 2940 | $C_2H_5$ | 3-$NH_2$-$C_6H_4$ | Prop-1-en-3-yl |
| 2941 | $C_2H_5$ | 3-$NH_2$-$C_6H_4$ | (E)-1-Chloroprop-1-en-3-yl |
| 2942 | $C_2H_5$ | 3-$NH_2$-$C_6H_4$ | Propyn-3-yl |
| 2943 | $C_2H_5$ | 3-$NH_2$-$C_6H_4$ | 3-Methylbut-2-en-1-yl |
| 2944 | $C_2H_5$ | 4-$NH_2$-$C_6H_4$ | H |
| 2945 | $C_2H_5$ | 4-$NH_2$-$C_6H_4$ | $CH_3$ |
| 2946 | $C_2H_5$ | 4-$NH_2$-$C_6H_4$ | $C_2H_5$ |
| 2947 | $C_2H_5$ | 4-$NH_2$-$C_6H_4$ | n-$C_3H_7$ |
| 2948 | $C_2H_5$ | 4-$NH_2$-$C_6H_4$ | i-$C_3H_7$ |
| 2949 | $C_2H_5$ | 4-$NH_2$-$C_6H_4$ | n-$C_4H_9$ |
| 2950 | $C_2H_5$ | 4-$NH_2$-$C_6H_4$ | t-$C_4H_9$ |
| 2951 | $C_2H_5$ | 4-$NH_2$-$C_6H_4$ | n-$C_6H_{13}$ |
| 2952 | $C_2H_5$ | 4-$NH_2$-$C_6H_4$ | Prop-1-en-3-yl |
| 2953 | $C_2H_5$ | 4-$NH_2$-$C_6H_4$ | (E)-1-Chloroprop-1-en-3-yl |
| 2954 | $C_2H_5$ | 4-$NH_2$-$C_6H_4$ | Propyn-3-yl |
| 2955 | $C_2H_5$ | 4-$NH_2$-$C_6H_4$ | 3-Methylbut-2-en-1-yl |
| 2956 | $C_2H_5$ | 2-$NMe_2$-$C_6H_4$ | H |
| 2957 | $C_2H_5$ | 2-$NMe_2$-$C_6H_4$ | $CH_3$ |
| 2958 | $C_2H_5$ | 2-$NMe_2$-$C_6H_4$ | $C_2H_5$ |
| 2959 | $C_2H_5$ | 2-$NMe_2$-$C_6H_4$ | n-$C_3H_7$ |
| 2960 | $C_2H_5$ | 2-$NMe_2$-$C_6H_4$ | i-$C_3H_7$ |
| 2961 | $C_2H_5$ | 2-$NMe_2$-$C_6H_4$ | n-$C_4H_9$ |

TABLE A-continued

| No. | R² | R³ | R⁴ |
|---|---|---|---|
| 2962 | C₂H₅ | 2-NMe₂-C₆H₄ | t-C₄H₉ |
| 2963 | C₂H₅ | 2-NMe₂-C₆H₄ | n-C₆H₁₃ |
| 2964 | C₂H₅ | 2-NMe₂-C₆H₄ | Prop-1-en-3-yl |
| 2965 | C₂H₅ | 2-NMe₂-C₆H₄ | (E)-1-Chloroprop-1-en-3-yl |
| 2966 | C₂H₅ | 2-NMe₂-C₆H₄ | Propyn-3-yl |
| 2967 | C₂H₅ | 2-NMe₂-C₆H₄ | 3-Methylbut-2-en-1-yl |
| 2968 | C₂H₅ | 3-NMe₂-C₆H₄ | H |
| 2969 | C₂H₅ | 3-NMe₂-C₆H₄ | CH₃ |
| 2970 | C₂H₅ | 3-NMe₂-C₆H₄ | C₂H₅ |
| 2971 | C₂H₅ | 3-NMe₂-C₆H₄ | n-C₃H₇ |
| 2972 | C₂H₅ | 3-NMe₂-C₆H₄ | i-C₃H₇ |
| 2973 | C₂H₅ | 3-NMe₂-C₆H₄ | n-C₄H₉ |
| 2974 | C₂H₅ | 3-NMe₂-C₆H₄ | t-C₄H₉ |
| 2975 | C₂H₅ | 3-NMe₂-C₆H₄ | n-C₆H₁₃ |
| 2976 | C₂H₅ | 3-NMe₂-C₆H₄ | Prop-1-en-3-yl |
| 2977 | C₂H₅ | 3-NMe₂-C₆H₄ | (E)-1-Chloroprop-1-en-3-yl |
| 2978 | C₂H₅ | 3-NMe₂-C₆H₄ | Propyn-3-yl |
| 2979 | C₂H₅ | 3-NMe₂-C₆H₄ | 3-Methylbut-2-en-1-yl |
| 2980 | C₂H₅ | 4-NMe₂-C₆H₄ | H |
| 2981 | C₂H₅ | 4-NMe₂-C₆H₄ | CH₃ |
| 2982 | C₂H₅ | 4-NMe₂-C₆H₄ | C₂H₅ |
| 2983 | C₂H₅ | 4-NMe₂-C₆H₄ | n-C₃H₇ |
| 2984 | C₂H₅ | 4-NMe₂-C₆H₄ | i-C₃H₇ |
| 2985 | C₂H₅ | 4-NMe₂-C₆H₄ | n-C₄H₉ |
| 2986 | C₂H₅ | 4-NMe₂-C₆H₄ | t-C₄H₉ |
| 2987 | C₂H₅ | 4-NMe₂-C₆H₄ | n-C₆H₁₃ |
| 2988 | C₂H₅ | 4-NMe₂-C₆H₄ | Prop-1-en-3-yl |
| 2989 | C₂H₅ | 4-NMe₂-C₆H₄ | (E)-1-Chloroprop-1-en-3-yl |
| 2990 | C₂H₅ | 4-NMe₂-C₆H₄ | Propyn-3-yl |
| 2991 | C₂H₅ | 4-NMe₂-C₆H₄ | 3-Methylbut-2-en-1-yl |
| 2992 | C₂H₅ | 2-Aminothiocarbonyl-C₆H₄ | H |
| 2993 | C₂H₅ | 2-Aminothiocarbonyl-C₆H₄ | CH₃ |
| 2994 | C₂H₅ | 2-Aminothiocarbonyl-C₆H₄ | C₂H₅ |
| 2995 | C₂H₅ | 2-Aminothiocarbonyl-C₆H₄ | n-C₃H₇ |
| 2996 | C₂H₅ | 2-Aminothiocarbonyl-C₆H₄ | i-C₃H₇ |
| 2997 | C₂H₅ | 2-Aminothiocarbonyl-C₆H₄ | n-C₄H₉ |
| 2998 | C₂H₅ | 2-Aminothiocarbonyl-C₆H₄ | t-C₄H₉ |
| 2999 | C₂H₅ | 2-Aminothiocarbonyl-C₆H₄ | n-C₆H₁₃ |
| 3000 | C₂H₅ | 2-Aminothiocarbonyl-C₆H₄ | Prop-1-en-3-yl |
| 3001 | C₂H₅ | 2-Aminothiocarbonyl-C₆H₄ | (E)-1-Chloroprop-1-en-3-yl |
| 3002 | C₂H₅ | 2-Aminothiocarbonyl-C₆H₄ | Propyn-3-yl |
| 3003 | C₂H₅ | 2-Aminothiocarbonyl-C₆H₄ | 3-Methylbut-2-en-1-yl |
| 3004 | C₂H₅ | 3-Aminothiocarbonyl-C₆H₄ | H |
| 3005 | C₂H₅ | 3-Aminothiocarbonyl-C₆H₄ | CH₃ |
| 3006 | C₂H₅ | 3-Aminothiocarbonyl-C₆H₄ | C₂H₅ |
| 3007 | C₂H₅ | 3-Aminothiocarbonyl-C₆H₄ | n-C₃H₇ |
| 3008 | C₂H₅ | 3-Aminothiocarbonyl-C₆H₄ | i-C₃H₇ |
| 3009 | C₂H₅ | 3-Aminothiocarbonyl-C₆H₄ | n-C₄H₉ |
| 3010 | C₂H₅ | 3-Aminothiocarbonyl-C₆H₄ | t-C₄H₉ |
| 3011 | C₂H₅ | 3-Aminothiocarbonyl-C₆H₄ | n-C₆H₁₃ |
| 3012 | C₂H₅ | 3-Aminothiocarbonyl-C₆H₄ | Prop-1-en-3-yl |
| 3013 | C₂H₅ | 3-Aminothiocarbonyl-C₆H₄ | (E)-1-Chloroprop-1-en-3-yl |
| 3014 | C₂H₅ | 3-Aminothiocarbonyl-C₆H₄ | Propyn-3-yl |
| 3015 | C₂H₅ | 3-Aminothiocarbonyl-C₆H₄ | 3-Methylbut-2-en-1-yl |
| 3016 | C₂H₅ | 4-Aminothiocarbonyl-C₆H₄ | H |
| 3017 | C₂H₅ | 4-Aminothiocarbonyl-C₆H₄ | CH₃ |
| 3018 | C₂H₅ | 4-Aminothiocarbonyl-C₆H₄ | C₂H₅ |
| 3019 | C₂H₅ | 4-Aminothiocarbonyl-C₆H₄ | n-C₃H₇ |
| 3020 | C₂H₅ | 4-Aminothiocarbonyl-C₆H₄ | i-C₃H₇ |
| 3021 | C₂H₅ | 4-Aminothiocarbonyl-C₆H₄ | n-C₄H₉ |
| 3022 | C₂H₅ | 4-Aminothiocarbonyl-C₆H₄ | t-C₄H₉ |
| 3023 | C₂H₅ | 4-Aminothiocarbonyl-C₆H₄ | n-C₆H₁₃ |
| 3024 | C₂H₅ | 4-Aminothiocarbonyl-C₆H₄ | Prop-1-en-3-yl |
| 3025 | C₂H₅ | 4-Aminothiocarbonyl-C₆H₄ | (E)-1-Cloroprop-1-en-3-yl |
| 3026 | C₂H₅ | 4-Aminothiocarbonyl-C₆H₄ | Propyn-3-yl |
| 3027 | C₂H₅ | 4-Aminothiocarbonyl-C₆H₄ | 3-Methylbut-2-en-1-yl |
| 3028 | C₂H₅ | 2-OCF₃-C₆H₄ | H |
| 3029 | C₂H₅ | 2-OCF₃-C₆H₄ | CH₃ |
| 3030 | C₂H₅ | 2-OCF₃-C₆H₄ | C₂H₅ |
| 3031 | C₂H₅ | 2-OCF₃-C₆H₄ | n-C₃H₇ |
| 3032 | C₂H₅ | 2-OCF₃-C₆H₄ | i-C₃H₇ |
| 3033 | C₂H₅ | 2-OCF₃-C₆H₄ | n-C₄H₉ |
| 3034 | C₂H₅ | 2-OCF₃-C₆H₄ | t-C₄H₉ |
| 3035 | C₂H₅ | 2-OCF₃-C₆H₄ | n-C₆H₁₃ |
| 3036 | C₂H₅ | 2-OCF₃-C₆H₄ | Prop-1-en-3-yl |
| 3037 | C₂H₅ | 2-OCF₃-C₆H₄ | (E)-1-Chloroprop-1-en-3-yl |
| 3038 | C₂H₅ | 2-OCF₃-C₆H₄ | Propyn-3-yl |

TABLE A-continued

| No. | R² | R³ | R⁴ |
|---|---|---|---|
| 3039 | $C_2H_5$ | 2-$OCF_3$-$C_6H_4$ | 3-Methylbut-2-en-1-yl |
| 3040 | $C_2H_5$ | 3-$OCF_3$-$C_6H_4$ | H |
| 3041 | $C_2H_5$ | 3-$OCF_3$-$C_6H_4$ | $CH_3$ |
| 3042 | $C_2H_5$ | 3-$OCF_3$-$C_6H_4$ | $C_2H_5$ |
| 3043 | $C_2H_5$ | 3-$OCF_3$-$C_6H_4$ | n-$C_3H_7$ |
| 3044 | $C_2H_5$ | 3-$OCF_3$-$C_6H_4$ | i-$C_3H_7$ |
| 3045 | $C_2H_5$ | 3-$OCF_3$-$C_6H_4$ | n-$C_4H_9$ |
| 3046 | $C_2H_5$ | 3-$OCF_3$-$C_6H_4$ | t-$C_4H_9$ |
| 3047 | $C_2H_5$ | 3-$OCF_3$-$C_6H_4$ | n-$C_6H_{13}$ |
| 3048 | $C_2H_5$ | 3-$OCF_3$-$C_6H_4$ | Prop-1-en-3-yl |
| 3049 | $C_2H_5$ | 3-$OCF_3$-$C_6H_4$ | (E)-1-Chloroprop-1-en-3-yl |
| 3050 | $C_2H_5$ | 3-$OCF_3$-$C_6H_4$ | Propyn-3-yl |
| 3051 | $C_2H_5$ | 3-$OCF_3$-$C_6H_4$ | 3-Methylbut-2-en-1-yl |
| 3052 | $C_2H_5$ | 4-$OCF_3$-$C_6H_4$ | H |
| 3053 | $C_2H_5$ | 4-$OCF_3$-$C_6H_4$ | $CH_3$ |
| 3054 | $C_2H_5$ | 4-$OCF_3$-$C_6H_4$ | $C_2H_5$ |
| 3055 | $C_2H_5$ | 4-$OCF_3$-$C_6H_4$ | n-$C_3H_7$ |
| 3056 | $C_2H_5$ | 4-$OCF_3$-$C_6H_4$ | i-$C_3H_7$ |
| 3057 | $C_2H_5$ | 4-$OCF_3$-$C_6H_4$ | n-$C_4H_9$ |
| 3058 | $C_2H_5$ | 4-$OCF_3$-$C_6H_4$ | t-$C_4H_9$ |
| 3059 | $C_2H_5$ | 4-$OCF_3$-$C_6H_4$ | n-$C_6H_{13}$ |
| 3060 | $C_2H_5$ | 4-$OCF_3$-$C_6H_4$ | Prop-1-en-3-yl |
| 3061 | $C_2H_5$ | 4-$OCF_3$-$C_6H_4$ | (E)-1-Chlororoprop-1-en-3-yl |
| 3062 | $C_2H_5$ | 4-$OCF_3$-$C_6H_4$ | Propyn-3-yl |
| 3063 | $C_2H_5$ | 4-$OCF_3$-$C_6H_4$ | 3-Methylbut-2-en-1-yl |
| 3064 | $C_2H_5$ | 2-$SCH_3$-$C_6H_4$ | H |
| 3065 | $C_2H_5$ | 2-$SCH_3$-$C_6H_4$ | $CH_3$ |
| 3066 | $C_2H_5$ | 2-$SCH_3$-$C_6H_4$ | $C_2H_5$ |
| 3067 | $C_2H_5$ | 2-$SCH_3$-$C_6H_4$ | n-$C_3H_7$ |
| 3068 | $C_2H_5$ | 2-$SCH_3$-$C_6H_4$ | i-$C_3H_7$ |
| 3069 | $C_2H_5$ | 2-$SCH_3$-$C_6H_4$ | n-$C_4H_9$ |
| 3070 | $C_2H_5$ | 2-$SCH_3$-$C_6H_4$ | t-$C_4H_9$ |
| 3071 | $C_2H_5$ | 2-$SCH_3$-$C_6H_4$ | n-$C_6H_{13}$ |
| 3072 | $C_2H_5$ | 2-$SCH_3$-$C_6H_4$ | Prop-1-en-3-yl |
| 3073 | $C_2H_5$ | 2-$SCH_3$-$C_6H_4$ | (E)-1-Chloroprop-1-en-3-yl |
| 3074 | $C_2H_5$ | 2-$SCH_3$-$C_6H_4$ | Propyn-3-yl |
| 3075 | $C_2H_5$ | 2-$SCH_3$-$C_6H_4$ | 3-Methylbut-2-en-1-yl |
| 3076 | $C_2H_5$ | 3-$SCH_3$-$C_6H_4$ | H |
| 3077 | $C_2H_5$ | 3-$SCH_3$-$C_6H_4$ | $CH_3$ |
| 3078 | $C_2H_5$ | 3-$SCH_3$-$C_6H_4$ | $C_2H_5$ |
| 3079 | $C_2H_5$ | 3-$SCH_3$-$C_6H_4$ | n-$C_3H_7$ |
| 3080 | $C_2H_5$ | 3-$SCH_3$-$C_6H_4$ | i-$C_3H_7$ |
| 3081 | $C_2H_5$ | 3-$SCH_3$-$C_6H_4$ | n-$C_4H_9$ |
| 3082 | $C_2H_5$ | 3-$SCH_3$-$C_6H_4$ | t-$C_4H_9$ |
| 3083 | $C_2H_5$ | 3-$SCH_3$-$C_6H_4$ | n-$C_6H_{13}$ |
| 3084 | $C_2H_5$ | 3-$SCH_3$-$C_6H_4$ | Prop-1-en-3-yl |
| 3085 | $C_2H_5$ | 3-$SCH_3$-$C_6H_4$ | (E)-1-Chloroprop-1-en-3-yl |
| 3086 | $C_2H_5$ | 3-$SCH_3$-$C_6H_4$ | Propyn-3-yl |
| 3087 | $C_2H_5$ | 3-$SCH_3$-$C_6H_4$ | 3-Methylbut-2-en-1-yl |
| 3088 | $C_2H_5$ | 4-$SCH_3$-$C_6H_4$ | H |
| 3089 | $C_2H_5$ | 4-$SCH_3$-$C_6H_4$ | $CH_3$ |
| 3090 | $C_2H_5$ | 4-$SCH_3$-$C_6H_4$ | $C_2H_5$ |
| 3091 | $C_2H_5$ | 4-$SCH_3$-$C_6H_4$ | n-$C_3H_7$ |
| 3092 | $C_2H_5$ | 4-$SCH_3$-$C_6H_4$ | i-$C_3H_7$ |
| 3093 | $C_2H_5$ | 4-$SCH_3$-$C_6H_4$ | n-$C_4H_9$ |
| 3094 | $C_2H_5$ | 4-$SCH_3$-$C_6H_4$ | t-$C_4H_9$ |
| 3095 | $C_2H_5$ | 4-$SCH_3$-$C_6H_4$ | n-$C_6H_{13}$ |
| 3096 | $C_2H_5$ | 4-$SCH_3$-$C_6H_4$ | Prop-1-en-3-yl |
| 3097 | $C_2H_5$ | $SCH_3$-$C_6H_4$ | (E)-1-Chloroprop-1-en-3-yl |
| 3098 | $C_2H_5$ | 4-$SCH_3$-$C_6H_4$ | Propyn-3-yl |
| 3099 | $C_2H_5$ | 4-$SCH_3$-$C_6H_4$ | 3-Methylbut-2-en-1-yl |
| 3100 | $C_2H_5$ | 2-Methylsulfonyl-$C_6H_4$ | H |
| 3101 | $C_2H_5$ | 2-Methylsulfonyl-$C_6H_4$ | $CH_3$ |
| 3102 | $C_2H_5$ | 2-Methylsulfonyl-$C_6H_4$ | $C_2H_5$ |
| 3103 | $C_2H_5$ | 2-Methylsulfonyl-$C_6H_4$ | n-$C_3H_7$ |
| 3104 | $C_2H_5$ | 2-Methylsulfonyl-$C_6H_4$ | i-$C_3H_7$ |
| 3105 | $C_2H_5$ | 2-Methylsulfonyl-$C_6H_4$ | n-$C_4H_9$ |
| 3106 | $C_2H_5$ | 2-Methylsulfonyl-$C_6H_4$ | t-$C_4H_9$ |
| 3107 | $C_2H_5$ | 2-Methylsulfonyl-$C_6H_4$ | n-$C_6H_{13}$ |
| 3108 | $C_2H_5$ | 2-Methylsulfonyl-$C_6H_4$ | Prop-1-en-3-yl |
| 3109 | $C_2H_5$ | 2-Methylsulfonyl-$C_6H_4$ | (E)-1-chloroprop-1-en-3-yl |
| 3110 | $C_2H_5$ | 2-Methylsulfonyl-$C_6H_4$ | Propyn-3-yl |
| 3111 | $C_2H_5$ | 2-Methylsulfonyl-$C_6H_4$ | 3-Methylbut-2-en-1-yl |
| 3112 | $C_2H_5$ | 3-Methylsulfonyl-$C_6H_4$ | H |
| 3113 | $C_2H_5$ | 3-Methylsulfonyl-$C_6H_4$ | $CH_3$ |
| 3114 | $C_2H_5$ | 3-Methylsulfonyl-$C_6H_4$ | $C_2H_5$ |
| 3115 | $C_2H_5$ | 3-Methylsulfonyl-$C_6H_4$ | n-$C_3H_7$ |

TABLE A-continued

| No. | R² | R³ | R⁴ |
|---|---|---|---|
| 3116 | C₂H₅ | 3-Methylsulfonyl-C₆H₄ | i-C₃H₇ |
| 3117 | C₂H₅ | 3-Methylsulfonyl-C₆H₄ | n-C₄H₉ |
| 3118 | C₂H₅ | 3-Methylsulfonyl-C₆H₄ | t-C₄H₉ |
| 3119 | C₂H₅ | 3-Methylsulfonyl-C₆H₄ | n-C₆H₁₃ |
| 3120 | C₂H₅ | 3-Methylsulfonyl-C₆H₄ | Prop-1-en-3-yl |
| 3121 | C₂H₅ | 3-Methylsulfonyl-C₆H₄ | (E)-1-Chloroprop-1-en-3-yl |
| 3122 | C₂H₅ | 3-Methylsulfonyl-C₆H₄ | Propyn-3-yl |
| 3123 | C₂H₅ | 3-Methylsulfonyl-C₆H₄ | 3-Methylbut-2-en-1-yl |
| 3124 | C₂H₅ | 4-Methylsulfonyl-C₆H₄ | H |
| 3125 | C₂H₅ | 4-Methylsulfonyl-C₆H₄ | CH₃ |
| 3126 | C₂H₅ | 4-Methylsulfonyl-C₆H₄ | C₂H₅ |
| 3127 | C₂H₅ | 4-Methylsulfonyl-C₆H₄ | n-C₃H₇ |
| 3128 | C₂H₅ | 4-Methylsulfonyl-C₆H₄ | i-C₃H₇ |
| 3129 | C₂H₅ | 4-Methylsulfonyl-C₆H₄ | n-C₄H₉ |
| 3130 | C₂H₅ | 4-Methylsulfonyl-C₆H₄ | t-C₄H₉ |
| 3131 | C₂H₅ | 4-Methylsulfonyl-C₆H₄ | n-C₆H₁₃ |
| 3132 | C₂H₅ | 4-Methylsulfonyl-C₆H₄ | Prop-1-en-3-yl |
| 3133 | C₂H₅ | 4-Methylsulfonyl-C₆H₄ | (E)-1-Chloroprop-1-en-3-yl |
| 3134 | C₂H₅ | 4-Methylsulfonyl-C₆H₄ | Propyn-3-yl |
| 3135 | C₂H₅ | 4-Methylsulfonyl-C₆H₄ | 3-Methylbut-2-en-1-yl |
| 3136 | C₂H₅ | 2-Methoxycarbonyl-C₆H₄ | H |
| 3137 | C₂H₅ | 2-Methoxycarbonyl-C₆H₄ | CH₃ |
| 3138 | C₂H₅ | 2-Methoxycarbonyl-C₆H₄ | C₂H₅ |
| 3139 | C₂H₅ | 2-Methoxycarbonyl-C₆H₄ | n-C₃H₇ |
| 3140 | C₂H₅ | 2-Methoxycarbonyl-C₆H₄ | i-C₃H₇ |
| 3141 | C₂H₅ | 2-Methoxycarbbnyl-C₆H₄ | n-C₄H₉ |
| 3142 | C₂H₅ | 2-Methoxycarbonyl-C₆H₄ | t-C₄H₉ |
| 3143 | C₂H₅ | 2-Methoxycarbonyl-C₆H₄ | n-C₆H₁₃ |
| 3144 | C₂H₅ | 2-Methoxycarbonyl-C₆H₄ | Prop-1-en-3-yl |
| 3145 | C₂H₅ | 2-Methoxycarbonyl-C₆H₄ | (E)-1-Chloropro-1-en-3-yl |
| 3146 | C₂H₅ | 2-Methoxycarbonyl-C₆H₄ | Propyn-3-yl |
| 3147 | C₂H₅ | 2-Methoxycarbonyl-C₆H₄ | 3-Methylbut-2-en-1-yl |
| 3148 | C₂H₅ | 3-Methoxycarbonyl-C₆H₄ | H |
| 3149 | C₂H₅ | 3-Methoxycarbonyl-C₆H₄ | CH₃ |
| 3150 | C₂H₅ | 3-Methoxycarbonyl-C₆H₄ | C₂H₅ |
| 3151 | C₂H₅ | 3-Methoxycarbonyl-C₆H₄ | n-C₃H₇ |
| 3152 | C₂H₅ | 3-Methoxycarbonyl-C₆H₄ | i-C₃H₇ |
| 3153 | C₂H₅ | 3-Methoxycarbonyl-C₆H₄ | n-C₄H₉ |
| 3154 | C₂H₅ | 3-Methoxycarbonyl-C₆H₄ | t-C₄H₉ |
| 3155 | C₂H₅ | 3-Methoxycarbonyl-C₆H₄ | n-C₆H₁₃ |
| 3156 | C₂H₅ | 3-Methoxycarbonyl-C₆H₄ | Prop-1-en-3-yl |
| 3157 | C₂H₅ | 3-Methoxycarbonyl-C₆H₄ | (E)-1-Chloropro-1-en-3-yl |
| 3158 | C₂H₅ | 3-Methoxycarbonyl-C₆H₄ | Propyn-3-yl |
| 3159 | C₂H₅ | 3-Methoxycarbonyl-C₆H₄ | 3-Methylbut-2-en-1-yl |
| 3160 | C₂H₅ | 4-Methoxycarbonyl-C₆H₄ | H |
| 3161 | C₂H₅ | 4-Methoxycarbonyl-C₆H₄ | CH₃ |
| 3162 | C₂H₅ | 4-Methoxycarbonyl-C₆H₄ | C₂H₅ |
| 3163 | C₂H₅ | 4-Methoxycarbonyl-C₆H₄ | n-C₃H₇ |
| 3164 | C₂H₅ | 4-Methoxycarbonyl-C₆H₄ | i-C₃H₇ |
| 3165 | C₂H₅ | 4-Methoxycarbonyl-C₆H₄ | n-C₄H₉ |
| 3166 | C₂H₅ | 4-Methoxycarbonyl-C₆H₄ | t-C₄H₉ |
| 3167 | C₂H₅ | 4-Methoxycarbonyl-C₆H₄ | n-C₆H₁₃ |
| 3168 | C₂H₅ | 4-Methoxycarbonyl-C₆H₄ | Prop-1-en-3-yl |
| 3169 | C₂H₅ | 4-Methoxycarbonyl-C₆H₄ | (E)-1-Chloroprop-1-en-3-yl |
| 3170 | C₂H₅ | 4-Methoxycarbonyl-C₆H₄ | Propyn-3-yl |
| 3171 | C₂H₅ | 4-Methoxycarbonyl-C₆H₄ | 3-Methylbut-2-en-1-yl |
| 3172 | C₂H₅ | 2-Ethoxycarbonyl-C₆H₄ | H |
| 3173 | C₂H₅ | 2-Ethoxycarbonyl-C₆H₄ | CH₃ |
| 3174 | C₂H₅ | 2-Ethoxycarbonyl-C₆H₄ | C₂H₅ |
| 3175 | C₂H₅ | 2-Ethoxycarbonyl-C₆H₄ | n-C₃H₇ |
| 3176 | C₂H₅ | 2-Ethoxycarbonyl-C₆H₄ | i-C₃H₇ |
| 3177 | C₂H₅ | 2-Ethoxycarbonyl-C₆H₄ | n-C₄H₉ |
| 3178 | C₂H₅ | 2-Ethoxycarbonyl-C₆H₄ | t-C₄H₉ |
| 3179 | C₂H₅ | 2-Ethoxycarbonyl-C₆H₄ | n-C₆H₁₃ |
| 3180 | C₂H₅ | 2-Ethoxycarbonyl-C₆H₄ | Prop-1-en-3-yl |
| 3181 | C₂H₅ | 2-Ethoxycarbonyl-C₆H₄ | (E)-1-Chloroprop-1-en-3-yl |
| 3182 | C₂H₅ | 2-Ethoxycarbonyl-C₆H₄ | Propyn-3-yl |
| 3183 | C₂H₅ | 2-Ethoxycarbonyl-C₆H₄ | 3-Methylbut-2-en-1-yl |
| 3184 | C₂H₅ | 3-Ethoxycarbonyl-C₆H₄ | H |
| 3185 | C₂H₅ | 3-Ethoxycarbonyl-C₆H₄ | CH₃ |
| 3186 | C₂H₅ | 3-Ethoxycarbonyl-C₆H₄ | C₂H₅ |
| 3187 | C₂H₅ | 3-Ethoxycarbonyl-C₆H₄ | n-C₃H₇ |
| 3188 | C₂H₅ | 3-Ethoxycarbonyl-C₆H₄ | i-C₃H₇ |
| 3189 | C₂H₅ | 3-Ethoxycarbonyl-C₆H₄ | n-C₄H₉ |
| 3190 | C₂H₅ | 3-Ethoxycarbonyl-C₆H₄ | t-C₄H₉ |
| 3191 | C₂H₅ | 3-Ethoxycarbonyl-C₆H₄ | n-C₆H₁₃ |
| 3192 | C₂H₅ | 3-Ethoxycarbonyl-C₆H₄ | Prop-1-en-3-yl |

TABLE A-continued

| No. | R² | R³ | R⁴ |
|---|---|---|---|
| 3193 | $C_2H_5$ | 3-Ethoxycarbonyl-$C_6H_4$ | (E)-1-Chloroprop-1-en-3-yl |
| 3194 | $C_2H_5$ | 3-Ethoxycarbonyl-$C_6H_4$ | Propyn-3-yl |
| 3195 | $C_2H_5$ | 3-Ethoxycarbonyl-$C_6H_4$ | 3-Methylbut-2-en-1-yl |
| 3196 | $C_2H_5$ | 4-Ethoxycarbonyl-$C_6H_4$ | H |
| 3197 | $C_2H_5$ | 4-Ethoxycarbonyl-$C_6H_4$ | $CH_3$ |
| 3198 | $C_2H_5$ | 4-Ethoxycarbonyl-$C_6H_4$ | $C_2H_5$ |
| 3199 | $C_2H_5$ | 4-Ethoxycarbonyl-$C_6H_4$ | n-$C_3H_7$ |
| 3200 | $C_2H_5$ | 4-Ethoxycarbonyl-$C_6H_4$ | i-$C_3H_7$ |
| 3201 | $C_2H_5$ | 4-Ethoxycarbonyl-$C_6H_4$ | n-$C_4H_9$ |
| 3202 | $C_2H_5$ | 4-Ethoxycarbonyl-$C_6H_4$ | t-$C_4H_9$ |
| 3203 | $C_2H_5$ | 4-Ethoxycarbonyl-$C_6H_4$ | n-$C_6H_{13}$ |
| 3204 | $C_2H_5$ | 4-Ethoxycarbonyl-$C_6H_4$ | Prop-1-en-3-yl |
| 3205 | $C_2H_5$ | 4-Ethoxycarbonyl-$C_6H_4$ | (E)-1-Chloropro-1-en-3-yl |
| 3206 | $C_2H_5$ | 4-Ethoxycarbonyl-$C_6H_4$ | Propyn-3-yl |
| 3207 | $C_2H_5$ | 4-Ethoxycarbonyl-$C_6H_4$ | 3-Methylbut-2-en-1-yl |
| 3208 | $C_2H_5$ | 2-Aminocarbonyl-$C_6H_4$ | H |
| 3209 | $C_2H_5$ | 2-Aminocarbonyl-$C_6H_4$ | $CH_3$ |
| 3210 | $C_2H_5$ | 2-Aminocarbonyl-$C_6H_4$ | $C_2H_5$ |
| 3211 | $C_2H_5$ | 2-Aminocarbonyl-$C_6H_4$ | n-$C_3H_7$ |
| 3212 | $C_2H_5$ | 2-Aminocarbonyl-$C_6H_4$ | i-$C_3H_7$ |
| 3213 | $C_2H_5$ | 2-Aminocarbonyl-$C_6H_4$ | n-$C_4H_9$ |
| 3214 | $C_2H_5$ | 2-Aminocarbonyl-$C_6H_4$ | t-$C_4H_9$ |
| 3215 | $C_2H_5$ | 2-Aminocarbonyl-$C_6H_4$ | n-$C_6H_{13}$ |
| 3216 | $C_2H_5$ | 2-Aminocarbonyl-$C_6H_4$ | Prop-1-en-3-yl |
| 3217 | $C_2H_5$ | 2-Aminocarbonyl-$C_6H_4$ | (E)-1-Chloroprop-1-en-3-yl |
| 3218 | $C_2H_5$ | 2-Aminocarbonyl-$C_6H_4$ | Propyn-3-yl |
| 3219 | $C_2H_5$ | 2-Aminocarbonyl-$C_6H_4$ | 3-Methylbut-2-en-1-yl |
| 3220 | $C_2H_5$ | 3-Aminocarbonyl-$C_6H_4$ | H |
| 3221 | $C_2H_5$ | 3-Aminocarbonyl-$C_6H_4$ | $CH_3$ |
| 3222 | $C_2H_5$ | 3-Aminocarbonyl-$C_6H_4$ | $C_2H_5$ |
| 3223 | $C_2H_5$ | 3-Aminocarbonyl-$C_6H_4$ | n-$C_3H_7$ |
| 3224 | $C_2H_5$ | 3-Aminocarbonyl-$C_6H_4$ | i-$C_3H_7$ |
| 3225 | $C_2H_5$ | 3-Aminocarbonyl-$C_6H_4$ | n-$C_4H_9$ |
| 3226 | $C_2H_5$ | 3-Aminocarbonyl-$C_6H_4$ | t-$C_4H_9$ |
| 3227 | $C_2H_5$ | 3-Aminocarbonyl-$C_6H_4$ | n-$C_6H_{13}$ |
| 3228 | $C_2H_5$ | 3-Aminocarbonyl-$C_6H_4$ | Prop-1-en-3-yl |
| 3229 | $C_2H_5$ | 3-Aminocarbonyl-$C_6H_4$ | (E)-1-Chloroprop-1-en-3-yl |
| 3230 | $C_2H_5$ | 3-Aminocarbonyl-$C_6H_4$ | Propyn-3-yl |
| 3231 | $C_2H_5$ | 3-Aminocarbonyl-$C_6H_4$ | 3-Methylbut-2-en-1-yl |
| 3232 | $C_2H_5$ | 4-Aminocarbonyl-$C_6H_4$ | H |
| 3233 | $C_2H_5$ | 4-Aminocarbonyl-$C_6H_4$ | $CH_3$ |
| 3234 | $C_2H_5$ | 4-Aminocarbonyl-$C_6H_4$ | $C_2H_5$ |
| 3235 | $C_2H_5$ | 4-Aminocarbonyl-$C_6H_4$ | n-$C_3H_7$ |
| 3236 | $C_2H_5$ | 4-Aminocarbonyl-$C_6H_4$ | i-$C_3H_7$ |
| 3237 | $C_2H_5$ | 4-Aminocarbonyl-$C_6H_4$ | n-$C_4H_9$ |
| 3238 | $C_2H_5$ | 4-Aminocarbonyl-$C_6H_4$ | t-$C_4H_9$ |
| 3239 | $C_2H_5$ | 4-Aminocarbonyl-$C_6H_4$ | n-$C_6H_{13}$ |
| 3240 | $C_2H_5$ | 4-Aminocarbonyl-$C_6H_4$ | Prop-1-en-3-yl |
| 3241 | $C_2H_5$ | 4-Aminocarbonyl-$C_6H_4$ | (E)-1-Chloroprop-1-en-3-yl |
| 3242 | $C_2H_5$ | 4-Aminocarbonyl-$C_6H_4$ | Propyn-3-yl |
| 3243 | $C_2H_5$ | 4-Aminocarbonyl-$C_6H_4$ | 3-Methylbut-2-en-1-yl |
| 3244 | $C_2H_5$ | 2-(N-Methylaminocarbonyl)-$C_6H_4$ | H |
| 3245 | $C_2H_5$ | 2-(N-Methylaminocarbonyl)-$C_6H_4$ | $CH_3$ |
| 3246 | $C_2H_5$ | 2-(N-Methylaminocarbonyl)-$C_6H_4$ | $C_2H_5$ |
| 3247 | $C_2H_5$ | 2-(N-Methylaminocarbonyl)-$C_6H_4$ | n-$C_3H_7$ |
| 3248 | $C_2H_5$ | 2-(N-Methylaminocarbonyl)-$C_6H_4$ | i-$C_3H_7$ |
| 3249 | $C_2H_5$ | 2-(N-Methylaminocarbonyl)-$C_6H_4$ | n-$C_4H_9$ |
| 3250 | $C_2H_5$ | 2-(N-Methylaminocarbonyl)-$C_6H_4$ | t-$C_4H_9$ |
| 3251 | $C_2H_5$ | 2-(N-Methylaminocarbonyl)-$C_6H_4$ | n-$C_6H_{13}$ |
| 3252 | $C_2H_5$ | 2-(N-Methylaminocarbonyl)-$C_6H_4$ | Prop-1-en-3-yl |
| 3253 | $C_2H_5$ | 2-(N-Methylaminocarbonyl)-$C_6H_4$ | (E)-1-Chloroprop-1-en-3-yl |
| 3254 | $C_2H_5$ | 2-(N-Methylaminocarbonyl)-$C_6H_4$ | Propyn-3-yl |
| 3255 | $C_2H_5$ | 2-(N-Methylaminocarbonyl)-$C_6H_4$ | 3-Methylbut-2-en-1-yl |
| 3256 | $C_2H_5$ | 3-(N-Methylaminocarbonyl)-$C_6H_4$ | H |

TABLE A-continued

| No. | R² | R³ | R⁴ |
|---|---|---|---|
| 3257 | C₂H₅ | 3-(N-Methylaminocarbonyl)-C₆H₄ | CH₃ |
| 3258 | C₂H₅ | 3-(N-Methylaminocarbonyl)-C₆H₄ | C₂H₅ |
| 3259 | C₂H₅ | 3-(N-Methylaminocarbonyl-C₆H₄ | n-C₃H₇ |
| 3260 | C₂H₅ | 3-(N-Methylaminocarbonyl)-C₆H₄ | i-C₃H₇ |
| 3261 | C₂H₅ | 3-(N-Methylaminocarbonyl)-C₆H₄ | n-C₄H₉ |
| 3262 | C₂H₅ | 3-(N-Methylaminocarbonyl)-C₆H₄ | t-C₄H₉ |
| 3263 | C₂H₅ | 3-(N-Methylaminocarbonyl)-C₆H₄ | n-C₆H₁₃ |
| 3264 | C₂H₅ | 3-(N-Methylaminocarbonyl)-C₆H₄ | Prop-1-en-3-yl |
| 3265 | C₂H₅ | 3-(N-Methylaminocarbonyl)-C₆H₄ | (E)-1-Chloroprop-1-en-3-yl |
| 3266 | C₂H₅ | 3-(N-Methylaminocarbonyl)-C₆H₄ | Propyn-3-yl |
| 3267 | C₂H₅ | 3-(N-Methylaminocarbonyl)-C₆H₄ | 3-Methylbut-2-en-1-yl |
| 3268 | C₂H₅ | 4-(N-Methylaminocarbonyl)-C₆H₄ | H |
| 3269 | C₂H₅ | 4-(N-Methylaminocarbonyl)-C₆H₄ | CH₃ |
| 3270 | C₂H₅ | 4-(N-Methylaminocarbonyl)-C₆H₄ | C₂H₅ |
| 3271 | C₂H₅ | 4-(N-Methylaminocarbonyl)-C₆H₄ | n-C₃H₇ |
| 3272 | C₂H₅ | 4-(N-Methylaminocarbonyl)-C₆H₄ | i-C₃H₇ |
| 3273 | C₂H₅ | 4-(N-Methylaminocarbonyl)-C₆H₄ | n-C₄H₉ |
| 3274 | C₂H₅ | 4-(N-Methylaminocarbonyl)-C₆H₄ | t-C₄H₉ |
| 3275 | C₂H₅ | 4-(N-Methylaminocarbonyl)-C₆H₄ | n-C₆H₁₃ |
| 3276 | C₂H₅ | 4-(N-Methylaminocarbonyl)-C₆H₄ | Prop-1-en-3-yl |
| 3277 | C₂H₅ | 4-(N-Methylaminocarbonyl)-C₆H₄ | (E)-1-Chloroprop-1-en-3-yl |
| 3278 | C₂H₅ | 4-(N-Methylaminocarbonyl)-C₆H₄ | Propyn-3-yl |
| 3279 | C₂H₅ | 4-(N-Methylaminocarbonyl)-C₆H₄ | 3-Methylbut-2-en-1-yl |
| 3280 | C₂H₅ | 2-Dimethylaminocarbonyl-C₆H₄ | H |
| 3281 | C₂H₅ | 2-Dimethylaminocarbonyl-C₆H₄ | CH₃ |
| 3282 | C₂H₅ | 2-Dimethylaminocarbonyl-C₆H₄ | C₂H₅ |
| 3283 | C₂H₅ | 2-Dimethylaminocarbonyl-C₆H₄ | n-C₃H₇ |
| 3284 | C₂H₅ | 2-Dimethylaminocarbonyl-C₆H₄ | i-C₃H₇ |
| 3285 | C₂H₅ | 2-Dimethylaminocarbonyl-C₆H₄ | n-C₄H₉ |
| 3286 | C₂H₅ | 2-Dimethylaminocarbonyl-C₆H₄ | t-C₄H₉ |
| 3287 | C₂H₅ | 2-Dimethylaminocarbonyl-C₆H₄ | n-C₆H₁₃ |
| 3288 | C₂H₅ | 2-Dimethylaminocarbonyl-C₆H₄ | Prop-1-en-3-yl |
| 3289 | C₂H₅ | 2-Dimethylaminocarbonyl-C₆H₄ | (E)-1-Chloroprop-1-en-3-yl |
| 3290 | C₂H₅ | 2-Dimethylaminocarbonyl-C₆H₄ | Propyn-3-yl |
| 3291 | C₂H₅ | 2-Dimethylaminocarbonyl-C₆H₄ | 3-Methylbut-2-en-1-yl |
| 3292 | C₂H₅ | 3-Dimethylaminocarbonyl-C₆H₄ | H |
| 3293 | C₂H₅ | 3-Dimethylaminocarbonyl-C₆H₄ | CH₃ |
| 3294 | C₂H₅ | 3-Dimethylaminocarbonyl-C₆H₄ | C₂H₅ |
| 3295 | C₂H₅ | 3-Dimethylaminocarbonyl- | n-C₃H₇ |

TABLE A-continued

| No. | $R^2$ | $R^3$ | $R^4$ |
|---|---|---|---|
| 3296 | $C_2H_5$ | 3-Dimethylaminocarbonyl-$C_6H_4$ | i-$C_3H_7$ |
| 3297 | $C_2H_5$ | 3-Dimethylaminocarbonyl-$C_6H_4$ | n-$C_4H_9$ |
| 3298 | $C_2H_5$ | 3-Dimethylaminocarbonyl-$C_6H_4$ | t-$C_4H_9$ |
| 3299 | $C_2H_5$ | 3-Dimethylaminocarbonyl-$C_6H_4$ | n-$C_6H_{13}$ |
| 3300 | $C_2H_5$ | 3-Dimethylaminocarbonyl-$C_6H_4$ | Prop-1-en-3-yl |
| 3301 | $C_2H_5$ | 3-Dimethylaminocarbonyl-$C_6H_4$ | (E)-1-Chloroprop-1-en-3-yl |
| 3302 | $C_2H_5$ | 3-Dimethylaminocarbonyl-$C_6H_4$ | Propyn-3-yl |
| 3303 | $C_2H_5$ | 3-Dimethylaminocarbonyl-$C_6H_4$ | 3-Methylbut-2-en-1-yl |
| 3304 | $C_2H_5$ | 4-Dimethylaminocarbonyl-$C_6H_4$ | H |
| 3305 | $C_2H_5$ | 4-Dimethylaminocarbonyl-$C_6H_4$ | $CH_3$ |
| 3306 | $C_2H_5$ | 4-Dimethylaminocarbonyl-$C_6H_4$ | $C_2H_5$ |
| 3307 | $C_2H_5$ | 4-Dimethylaminocarbonyl-$C_6H_4$ | n-$C_3H_7$ |
| 3308 | $C_2H_5$ | 4-Dimethylaminocarbonyl-$C_6H_4$ | i-$C_3H_7$ |
| 3309 | $C_2H_5$ | 4-Dimethylaminocarbonyl-$C_6H_4$ | n-$C_4H_9$ |
| 3310 | $C_2H_5$ | 4-Dimethylaminocarbonyl-$C_6H_4$ | t-$C_4H_9$ |
| 3311 | $C_2H_5$ | 4-Dimethylaminocarbonyl-$C_6H_4$ | n-$C_6H_{13}$ |
| 3312 | $C_2H_5$ | 4-Dimethylaminocarbonyl-$C_6H_4$ | Prop-1-en-3-yl |
| 3313 | $C_2H_5$ | 4-Dimethylaminocarbonyl-$C_6H_4$ | (E)-1-Chloroprop-1-en-3-yl |
| 3314 | $C_2H_5$ | 4-Dimethylaminocarbonyl-$C_6H_4$ | Propyn-3-yl |
| 3315 | $C_2H_5$ | 4-Dimethylaminocarbonyl-$C_6H_4$ | 3-Methylbut-2-en-1-yl |

TABLE 5

Compounds of the formula I.C

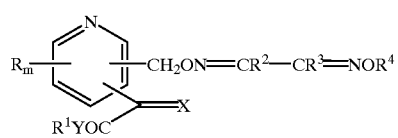

I.C

| No. | Position of group $R^1YOC\diagup^X$ | X | Y | $R^1$ | Position of group $CH_2ON{=}CR^2{-}CR^3{=}NOR^4$ | $R^2$ | $R^3$ | $R^4$ |
|---|---|---|---|---|---|---|---|---|
| 1 | 2 | $NOCH_3$ | O | $CH_3$ | 3 | $CH_3$ | Phenyl | $CH_3$ |
| 2 | 2 | $CHCH_3$ | O | $CH_3$ | 3 | $CH_3$ | Phenyl | $CH_3$ |
| 3 | 2 | $CHOCH_3$ | O | $CH_3$ | 3 | $CH_3$ | Phenyl | $CH_3$ |
| 4 | 2 | $NOCH_3$ | NH | $CH_3$ | 3 | $CH_3$ | Phenyl | $CH_3$ |
| 5 | 3 | $NOCH_3$ | O | $CH_3$ | 4 | $CH_3$ | Phenyl | $CH_3$ |
| 6 | 3 | $CHCH_3$ | O | $CH_3$ | 4 | $CH_3$ | Phenyl | $CH_3$ |
| 7 | 3 | $CHOCH_3$ | O | $CH_3$ | 4 | $CH_3$ | Phenyl | $CH_3$ |
| 8 | 3 | $NOCH_3$ | NH | $CH_3$ | 4 | $CH_3$ | Phenyl | $CH_3$ |
| 9 | 4 | $NOCH_3$ | O | $CH_3$ | 3 | $CH_3$ | Phenyl | $CH_3$ |
| 10 | 4 | $CHCH_3$ | O | $CH_3$ | 3 | $CH_3$ | Phenyl | $CH_3$ |
| 11 | 4 | $CHOCH_3$ | O | $CH_3$ | 3 | $CH_3$ | Phenyl | $CH_3$ |
| 12 | 4 | $NOCH_3$ | NH | $CH_3$ | 3 | $CH_3$ | Phenyl | $CH_3$ |

TABLE I

Selected physical data of some compounds

| No. | Formula | R² | R³ | R⁴ | Physical data |
|---|---|---|---|---|---|
| I.1 | IA.1 | CH₃ | 2,4-Cl₂—C₆H₃ | CH₃ | 111–112 |
| I.2 | IA.1 | CH₃ | C₆H₅ | CH₃ | 133–135 |
| I.3 | IA.1 | CH₃ | 4-F—C₆H₄ | CH₃ | 102–103 |
| I.4 | IA.1 | CH₃ | 4-Cl—C₆H₄ | CH₃ | 141–142 |
| I.5 | IA.1 | CH₃ | 4-i-C₃H₇—C₆H₄ | CH₃ | 121–122 |
| I.6 | IB.1 | CH₃ | 4-F—C₆H₄ | CH₃ | 120–122 |
| I.7 | IB.1 | CH₃ | 4-Cl—C₆H₄ | CH₃ | 133–135 |
| I.8 | IB.1 | CH₃ | 2,4-Cl₂—C₆H₃ | CH₃ | 160–162 |
| I.9 | IB.1 | CH₃ | 4-i-C₃H₇—C₆H₄ | CH₃ | 114–117 |

Physical data:
Mp. [° C.]
IR [cm$^{-1}$] or
$^1$H-NMR [ppm]

The compounds I are suitable as fungicides.

The compounds I have excellent activity against a broad spectrum of phytopathogenic fungi, in particular from the class consisting of the Ascomycetes and Basidiomycetes. Some of them have systemic activity and can be used as foliar and soil fungicides.

They are particularly important for controlling a large number of fungi on various crops, such as wheat, rye, barley, oats, rice, corn, grass, cotton, soybean, coffee, sugar cane, grapevines, fruit and ornamental plants and vegetable plants, such as cucumbers, beans and cucurbitaceae, and on the seeds of these plants.

They are particularly suitable for controlling the following plant diseases: Erysiphe graminis (powdery mildew) in cereals, Erysiphe cichoracearum and Sphaerotheca fuliginea on cucurbitaceae, Podosphaera leucotricha on apples, Uncinula necator on grapevines, Puccinia species on cereals, Rhizoctonia species on cotton and lawns, Ustilago species on cereals and sugar cane, Venturia inaequalis (scab) on apples, Helminthosporium species on cereals, Septoria nodorum on wheat, Botrytis cinerea (gray mold) on strawberries and grapevines, Cercospora arachidicola on peanuts, Pseudocercosporella herpotrichoides on wheat and barley, Pyricularia oryzae on rice, Phytophthora infestans on potatoes and tomatoes, Fusarium and verticillium species on various plants, Plasmopara viticola on grapevines and Alternaria species on vegetables and fruit.

The compounds I are used by treating the fungi or the plants, seeds or materials to be protected from fungal attack or the soil with a fungicidal amount of the active ingredients. The application is effected before or after the infection of the materials, plants or seeds by the fungi.

They can be converted into conventional formulations, such as solutions, emulsions, suspensions, dusts, powders, pastes and granules. The application form depends on the particular intended use; they should in any case ensure a fine and uniform distribution of the novel compounds. The formulations are prepared in a known manner, for example by extending the active ingredient with solvents and/or carriers, if desired with the use of emulsifiers and dispersants, it also being possible to use organic solvents as auxiliary solvents when water is used as a diluent. Suitable assistants for this purpose are essentially solvents, such as aromatics (eg. xylene), chlorinated aromatics (eg. chlorobenzenes), paraffins (eg. mineral oil fractions), alcohols (eg. methanol and butanol), ketones (eg. cyclohexanone), amines (eg. ethanolamine and dimethylformamide) and water; carriers, such as crushed natural minerals (eg. kaolins, aluminas, talc, chalk) and crushed synthetic minerals (eg. finely divided silica and silicates); emulsifiers, such as nonionic and anionic emulsifiers (eg. polyoxyethylene fatty alcohol ethers, alkylsulfonates and arylsulfonates) and dispersants, such as lignin sulfite waste liquors and methylcellulose.

The fungicides contain in general from 0.1 to 95, preferably from 0.5 to 90, % by weight of active ingredient.

The application rates are from 0.01 to 2.0 kg of active ingredient per ha, depending on the type of effect desired.

In seed treatment, from 0.001 to 0.1, preferably from 0.01 to 0.05, g of active ingredient per kilogram of seed are generally required.

In the application form as fungicides, the novel agents may also be present together with other active ingredients, for example with herbicides, insecticides, growth regulators or fungicides and also with fertilizers.

When mixed with fungicides, the fungicidal action spectrum is increased in many cases.

The following list of fungicides together with which the novel compounds may be used is intended to describe possible combinations but not to impose restrictions:

sulfur, dithiocarbamates and derivatives thereof, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc (N,N'-ethylenebisdithiocarbamate), ammonia complex of zinc (N,N'-propylenebisdithiocarbamate), zinc (N,N'-propylenebisdithiocarbamate) and N,N'-polypropylennitro diocarbamoyl disulfide);

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino) -phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1,2,2-tetrachloroethylthio)tetrahydrophthalimide, N-trichloromethylthiotetrahydrophthalimide and N-trichloromethylthiophthalimide, the diamide of N-dichlorofluoromethylthio-N',N'-dimethyl-N-phenylsulfuric acid, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodbenzanilide, N-formyl-N-morpholine-2,2,2-trichloroethyl acetal, piperazin-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6- dimethylmorpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido)benzene and 1,2-bis-(3-methoxycarbonyl-2-thioureido)benzene, and various fungicides, such as dodecylguanidine acetate, 3-[3-(3,5-dimethyl-2-oxycyclohexyl)-2-hydroxyethyl] glutarimide, hexachlorobenzene, methyl DL-N-(2,6-dimethylphenyl)-N-2-furoylalaninate, methyl ester of DL-N-(2,6-dimethylphenyl)-N-(2'-methoxyacetyl)alanine, N-(2,6-dimethylphenyl)-N-chloroacetyl-D,L-2-aminobutyrolactone, methyl ester of DL-N-(2,6-dimethylphenyl)-N-(phenylacetyl)alanine, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine and 1-((bis(4-fluorophenyl)methylsilyl)methyl)-1H-1,2,4-triazole.

The compounds of the formula I are also suitable for effectively controlling pests from the class consisting of the insects, arachnids and nematodes. In crop protection, they can be used both in the hygiene, material protection and veterinary sectors and in pest control.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

From the order of the beetles (Coleoptera), for example *Agrilus sinuatus, Agriotes lineatus, Agriotes obscurus, Amphimallus sostitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis,* Diabrotica 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria.*

From the order of the Diptera, for example *Aedes aegypti, Aedes vexans, Anastrepha ludens, Anopheles maculipennis, Ceratitis capitata, Chrysomya bezziana, chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

From the order of the Thysanoptera, for example *Frankliniella fusca, Frankliniella occidentalis, Frankliniella tritici, Scirtothrips citri, Thrips oryzae, Thrips palmi* and *Thrips tabaci.*

From the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

From the order of the Heteroptera, for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor.*

From the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

From the order of the Isoptera, for example *Calotermes flavicollis, Leucotermes flavipes, Reticulitermes lucifugus* and *Termes natalensis.*

From the order of the Orthoptera, for example *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

From the order of the Arachnoidea, for example Acarina, such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae.*

From the class of the Nematodes, for example root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, nebulizing, dusting, broadcasting or pouring. The application forms depend entirely on the intended uses; they should in any case ensure a very fine distribution of the novel active ingredients.

The active ingredient concentrations in the ready-to-use formulations can be varied within relatively wide ranges.

In general, they are from 0.0001 to 10%, preferably from 0.01 to 1%.

The active ingredients can also be successfully used by the ultralow volume (ULV) method, it being possible to apply formulations containing more than 95% by weight of active ingredient or even the active ingredient without additives.

The application rate of active ingredient for controlling pests is from 0.1 to 2.0, preferably from 0.2 to 1.0, kg/ha under open air conditions.

Mineral oil fractions having a medium to high boiling point, such as kerosine or diesel oil, and coal tar oils and oils of vegetable or animal origin, aliphatic, cyclic and aromatic hydrocarbons, eg. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water, are suitable for the preparation of directly sprayable solutions, emulsions, pastes or oil dispersions.

Aqueous application forms can be prepared from emulsion concentrates, pastes, wettable powders or oil dispersions by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredients, wetting agents, adherents, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and alkali metal and alkaline earth metal salts thereof, salts of sulfated fatty alcohol glycol ethers, condensates of sulfonated naphthalene and naphthalene derivatives of formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active ingredients together with a solid carrier.

The formulations contain in general from 0.01 to 95, preferably from 0.1 to 90, % by weight of the active ingredient. The active ingredients are used in this case in a purity of from 90 to 100%, preferably from 95 to 100% (according to NMR spectrum).

Examples of formulations are:

I. 5 parts by weight of a novel compound are thoroughly mixed with 95 parts by weight of finely divided kaolin. A dusting agent which contains 5% by weight of the active ingredient is obtained in this manner.

II. 30 parts by weight of a novel compound are thoroughly mixed with a mixture of 92 parts by weight of silica gel powder and 8 parts by weight of liquid paraffin, which was sprayed onto the surface of the silica gel. A formulation of the active ingredient having good adhesion (active ingredient content 23% by weight) is obtained in this manner.

III. 10 parts by weight of a novel compound are dissolved in a mixture which consists of 90 parts by weight of xylene, 6 parts by weight of the adduct of from 8 to 10 mol of ethylene oxide with 1 mol of N-monoethanololeamide, 2 parts by weight of the calcium salt of dodecylbenzenesulfonic acid and 2 parts by weight of the adduct of 40 mol of ethylene oxide with 1 mol of castor oil (active ingredient content 9% by weight).

IV. 20 parts by weight of a novel compound are dissolved in a mixture which consists of 60 parts by weight of cyclohexanone, 30 parts by weight of isobutanol, 5 parts by weight of the adduct of 7 mol of ethylene oxide with 1 mol of isooctylphenol and 5 parts by weight of the adduct of 40 mol of ethylene oxide with 1 mol of castor oil (active ingredient content 16% by weight).

V. 80 parts by weight of a novel compound are thoroughly mixed with 3 parts by weight of the sodium salt of diisobutylnaphthalene-alpha-sulfonic acid, 10 parts by weight of the sodium salt of a lignosulfonic acid obtained from a sulfite waste liquor and 7 parts by weight of silica gel powder, and the mixture is milled in a hammer mill (active ingredient content 80% by weight).

VI. 90 parts by weight of a novel compound are mixed with 10 parts by weight of N-methyl-α-pyrrolidone, and a solution which is suitable for use in the form of very small drops is obtained (active ingredient content 90% by weight).

VII. 20 parts by weight of a novel compound are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

VIII. 20 parts by weight of a novel compound are thoroughly mixed with 3 parts by weight of the sodium salt of diisobutylnaphthalene-α-sulfonic acid, 17 parts by weight of the sodium salt of a lignosulfonic acid obtained from a sulfite waste liquor and 60 parts by weight of silica gel powder, and the mixture is milled in a hammer mill. By finely distributing the mixture in 20,000 parts by weight of water, a spray liquor which comprises 0.1% by weight of the active ingredient is obtained.

Granules, for example coated, impregnated and homogeneous granules, can be prepared by binding the active ingredients to solid carriers. Solid carriers are, for example, mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, eg. ammonium sulfate, ammonium phosphate, ammonium nitrate and ureas, and vegetable products, such as grain flour, bark meal, wood meal and nutshell meal, cellulosic powders, and other solid carriers.

Oils of various types, herbicides, fungicides, other pesticides and bactericides may be added to the active ingredients, if necessary only immediately before use (tank mix). These agents may be admixed with the novel agents in a weight ratio of from 1:10 to 10:1.

EXAMPLES OF SYNTHESES

The methods described in the following examples of syntheses were used with appropriate modification of the starting compounds to obtain further compounds I. The compounds thus obtained are shown in the subsequent tables, together with the physical data.

1. Synthesis of

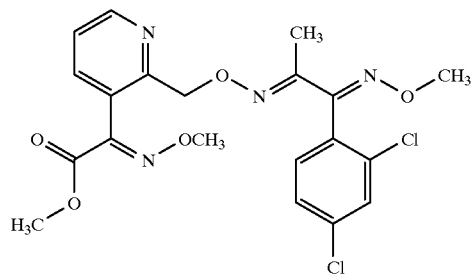

a) 2-Methyl-3-formylpyridinecyanhydrin

A mixture of 33 g (0.5 mol) of KCN and 26 g (0.5 mol) of $NH_4Cl$ in 200 ml of water and 30 g (0.24 mol) of 2-methyl-3-formylpyridine (Chem. Pharm. Bull. 42 (1994), 1941; J. Med. Chem. 32 (1989), 583; J. Heterocycl. Chem. 28 (1991), 1315; J. Org. Chem. 43 (1978), 324) in 200 ml of diethyl ether is stirred for 2 hours at room temperature, the product crystallizing out. The solid is filtered off with suction, washed with methyl t-butyl ether and dried in a stream of nitrogen (yield: 19.3 g (54%); m.p.=139° C.).

$^1$H-NMR (DMSO-$d_6$; δ in ppm): 8.5 (d, broad, 1H, pyridyl); 7.9 (d, broad, 1H, pyridyl);
7.3 (dd, 1H, pyridyl; 7.2 (s, broad, 1H, OH); 5.9 (s, 1H, CH); 2.55 (s, 3H, $CH_3$).

b) Methyl (2-methylpyrid-3-yl)-α-hydroxyacetate 15 g (0.4 mol) of gaseous hydrogen chloride are passed into a solution of 22 g (0.15 mol) of 2-methyl-3-formylpyridinecyanohydrin (Example 1a) in 250 ml of methanol. The reaction mixture is stirred overnight at room temperature and is then evaporated down under reduced pressure. The residue is taken up in 200 ml of water and refluxed for 1 hour. Thereafter, the reaction mixture is cooled to room temperature, neutralized with $NaHCO_3$ solution and extracted with methylene chloride. The combined organic phases are dried over $MgSO_4$ and evaporated down. The residue is purified by column chromatography with cyclohexane/ethyl acetate mixtures. 3.0 g (11%) of the title compound are obtained as a pale oil.

$^1$H-NMR ($CDCl_3$; δ in ppm): 8.35 (d, broad, 1H, pyridyl); 7.7 (d, broad, 1H, pyridyl); 7.15 (dd, 1H, pyridyl); 5.4 (s, 1H, CH); 4.5 (s, very broad, 1H, OH); 3.75 (s, 3H, $OCH_3$); 2.6 (s, 3H, $CH_3$).

c) Methyl (2-methylpyrid-3-yl)-glyoxylate

A pinch of tetramethylpyridine N-oxide and 10 ml of 12.5% strength sodium hypochlorite solution are added to a stirred mixture of 3 g (16 mmol) of methyl (2-methylpyrid-3-yl)-α-hydroxyacetate (Example 1b) in 20 ml of methylene chloride and 0.5 g (3.5 mmol) of $Na_2HPO_4$, 0.6 g (5 mmol) of $NaH_2PO_4$ and 0.2 g (1.6 mmol) of KBr in 20 ml of water. Stirring is carried out for 1 hour at room temperature, after which the organic phase is separated off and evaporated down. 2.2 g (77%) of the title compound are obtained as residual yellow oil.

$^1$H-NMR ($CDCl_3$; δ in ppm): 8.7 (d, broad, 1H, pyridyl), 8.05 (d, broad, 1H, pyridyl); 7.3 (dd, 1H, pyridyl); 4.0 (s, 3H, $OCH_3$); 2.8 (s, 3H, $CH_3$).

d) Trans-O-methyloxime of methyl (2-methylpyrid-3-yl)-glyoxylate

A mixture of 2.2 g (12 mmol) of methyl (2-methylpyrid-3-yl)glyoxylate (Example 1c) and 1.5 g (18 mmol) of o-methylhydroxylamine hydrochloride in 20 ml of methanol is stirred overnight at room temperature. The reaction mixture is then evaporated down. The residue is taken up in methylene chloride and extracted with a little water. The organic phase is dried over MgSO$_4$ and evaporated down. The residue is purified by column chromatography with cyclohexane/ethyl acetate mixtures. 1.8 g (73%) of the title compound are obtained as a pale oil.

$^1$H-NMR (CDCl$_3$, δ in ppm): 8.55 (d, broad, 1H, pyridyl); 7.45 (d, broad, 1H, pyridyl), 7.2 (dd, 1H, pyridyl); 4.1 (s, 3H, OCH$_3$); 3.9 (s, 3H, OCH$_3$); 2.45 (s, 3H, CH$_3$).

e) Trans-O-methyloxime of methyl (2-bromomethylpyrid-3-yl)-glyoxylate

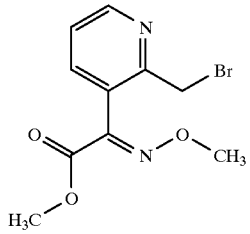

A mixture of 1.8 g (8.7 mmol) of the trans-O-methyloxime of methyl (2-methylpyrid-3-yl) glyxolate, 1.7 g (9.6 mmol) of N-bromosuccinimide and a pinch of azobisisobutyronitrile in 30 ml of CCl$_4$ is exposed to a 300 W UV lamp for about 4 hours, the reaction mixture warming up to the reflux temperature. The reaction mixture is then diluted with methylene chloride. The organic phase is extracted with water, dried over MgSO$_4$ and evaporated down. The residue is purified by column chromatography with cyclohexane/ethyl acetate mixtures. 1.1 g (44%) of the title compound are obtained as a pale oil.

$^1$H-NMR (CDCl$_3$; δ in ppm): 8.65 (d, broad, 1H, pyridyl); 7.55 (d, broad, 1H, pyridyl); 7.3 (t, broad, 1H, pyridyl); 4.4 (s, 2H, CH$_2$Br); 4.1 (s, 3H, OCH$_3$); 3.9 (s, 3H, OCH$_3$).

f) 2-Oximino-1-(2',4'-dichlorophenyl)propan-1-one 81 ml of a saturated solution of hydrogen chloride in ether are added to a mixture of 60 g (0.296 mol) of 2,4-dichloropropiophenone in 500 ml of toluene at from −10 to −20° C., and a solution of 33.3 g (0.323 mol) of 2,4-dichloropropiophenone in 150 ml of ether are then added at the same temperature. The reaction mixture is then stirred for 4 hours at −10° C. and for 14 hours at room temperature. Thereafter, the reaction mixture is extracted with ice water and then five times with 1N NaOH. The combined alkaline phases are acidified to pH 5 with 20% strength sulfuric acid, the product crystallizing out. The solid is filtered off and dissolved in methylene chloride and the organic phase is dried over MgSO$_4$ and evaporated down. 63.1 g (42%) of the title compound are obtained as a residual pale solid.

$^1$H-NMR (CDCl$_3$, δ in ppm): 8.8 (s, 1H, OH); 7.4 (s, 1H, phenyl); 7.3 (m, 2H, phenyl); 2.1 (s, 3H, CH$_3$).

g) 1-Methoximino-2-oximino-1-(2',4'-dichlorophenyl) propane

A mixture of 4.7 g (20 mmol) of 2-oximino-1-(2',4'-dichlorophenyl)propan-1-one (Example 1f), 2.5 g (30 mmol) of O-methylhydroxylamine hydrochloride and 4.8 g (60 mmol) of pyridine is stirred overnight at room temperature and then for 8 hours at 50° C. Thereafter, the reaction mixture is evaporated down and the residue is taken up in methylene chloride. The organic phase is washed with dilute hydrochloric acid and water, dried over MgSO$_4$ and evaporated down. The residue crystallizes and is stirred thoroughly with hexane. 3 g (57%) of the title compound are obtained as a colorless solid.

$^1$H-NMR (CDCl$_3$, δ in ppm): 8.25 (s, 1H, OH); 7.4 (S, 1H, phenyl); 7.25 (d, broad, 1H, phenyl); 7.0 (d, 1H, phenyl); 3.9 (s, 3H, OCH$_3$); 2.15 (s, 3H, CH$_3$).

h) Synthesis of

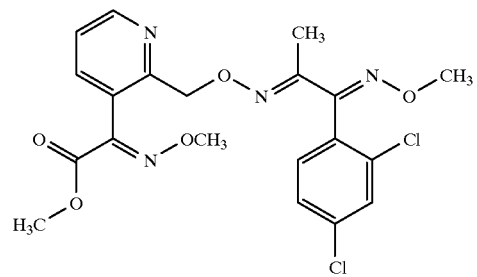

0.12 g (5 mmol) of sodium hydride is added to a mixture of 1 g (3.8 mmol) of 1-methoximino-2-oximino-1-(2',4'-dichlorophenyl)propane (Example 1g) in 20 ml of dimethylformamide. Stirring is carried out until the evolution of gas is complete, after which 1.1 g (3.8 mmol) of the trans-O-methyloxime of methyl (2-bromomethylpyrid-3-yl)-glyoxylate (Example 1e) are added. Stirring is carried out for 1 hour at room temperature, the reaction mixture is then diluted with water and the aqueous phase is extracted three times with methyl tert-butyl ether. The combined organic phases are dried over MgSO$_4$ and evaporated down. The residue is purified by column chromatography with cyclohexane/ethyl acetate mixtures. The product crystallizes and is stirred thoroughly with hexane. 0.35 g (20%) of the title compound is obtained as a colorless solid (m.p.=111° C.).

$^1$H-NMR (CDCl$_3$, δ in ppm): 8.55 (s, broad, 1H, pyridyl); 7.55 (d, broad, 1H; pyridyl); 7.35 (s, broad, 1H, phenyl), 7.3 (dd, 1H, pyridyl); 7.15 (d, broad, 1H, phenyl); 6.9 (d, 1H, phenyl); 5.05 (s, 2H, OCH$_2$); 4.05 (s, 3H, OCH$_3$); 3.9 (s, 3H, OCH$_3$); 3.85 (s, 3H, OCH$_3$); 2.15 (s, 3H, CH$_3$).

Examples of the action against harmful fungi

The fungicidal action of the compounds of the formula I were demonstrated by the following experiments:

The active ingredients were prepared as a 10% strength emulsion in a mixture of 70% by weight of cyclohexanone, 20% by weight of Nekanil® LN (Lutensol® AP6, wetting agent having an emulsifying and dispersing action and based on ethoxylated alkylphenols) and 10% by weight of Emulphor® EL (Emulan® EL, emulsifier based on ethoxylated fatty alcohols) and were diluted with water to give the desired concentration.

A) Activity Against Wheat Mildew

Leaves of wheat seedlings of the Frühgold variety, grown in pots, were sprayed with aqueous spray liquor prepared using a stock solution of 10% of active ingredient, 63% of cyclohexanone and 27% of emulsifier and, 24 hours after the spray coating had dried on, was sprayed with spores of wheat mildew (Erysiphe graminis var. tritici). The test plants were then placed in a greenhouse at from 20 to 22° C. and from 75 to 80% relative humidity. After 7 days, the extent of mildew development was determined visually in % infestation of the total leaf area.

In this test, the plants treated with 250 ppm of compounds No. I.2, I.3, I.4, I.6, I.7, I.8 and I.9 showed not more than 15% infestation, whereas the untreated plants exhibited 75% infestation.

B) Activity Against *Plasmopara viticola*

Leaves of potted vines of the Müller-Thurgau variety were sprayed with aqueous spray liquor prepared using a stock solution of 10% of active ingredient, 63% of cyclohexanone and 27% of emulsifier. In order to be able to assess the long-term action of the substances, the plants were placed in a greenhouse for 7 days after the spray coating had dried on. Only then were the leaves inoculated with an aqueous zoospore suspension of *Plasmopara viticola*. The vines were then placed first in a water vapor-saturated chamber at 24° C. for 48 hours and then in a greenhouse at from 20 to 30° C. for 5 days. After this time, the plants were again placed in a humid chamber for 16 hours to accelerate the sporangiophore discharge. The extent of development of infestation on the lower surfaces of the leaves was then determined visually.

In this test, the plants treated with 250 ppm of compounds No. 1, I.2, I.3, I.4, I.6 and I.9 showed not more than 15% infestation, whereas the untreated plants exhibited 70% infestation.

Examples of the action against animal pests

The action of the compounds of the general formula I against animal pests was demonstrated by the following experiments:

The active ingredients were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifying and dispersing action and based on ethoxylated alkylphenols) and 10% by weight of Emulphor® EL (Emulan® EL, emulsifier based on ethoxylated fatty alcohols)

and were diluted with acetone in the case of a) and with water in the case of b) to give the desired concentration.

After completion of the experiments, the lowest concentration in each case at which the compounds still caused 80–100% inhibition or mortality compared with untreated control experiments was determined (action threshold or minimum concentration).

We claim:

1. A pyridylacetic acid compound of the formula I

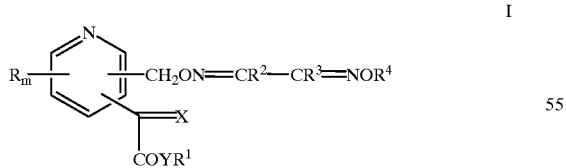

where

X is $NOCH_3$, $CHOCH_3$, $CHCH_3$ or $CHCH_2CH_3$;

Y is oxygen or NR';

R' is hydrogen or $C_1$–$C_4$-alkyl;

R is cyano, nitro, trifluoromethyl, halogen, $C_1$–$C_4$-alkyl or $C_1$–$C_4$-alkoxy;

m is 0, 1 or 2, and the radicals R may be different when m is 2;

$R^1$ is hydrogen or $C_1$–$C_4$-alkyl;

$R^2$ is hydrogen, cyano, nitro, hydroxyl, amino, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino or di-$C_1$–$C_4$-alkylamino;

$R^3$ is hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N-$C_2$–$C_6$-alkenyl-N-$C_1$–$C_6$-alkylamino, $C_2$–$C_6$-alkynyl, $C_2$–$C_6$-alkynyloxy, $C_2$–$C_6$-alkenylthio, $C_2$–$C_6$-alkynylamino or N-$C_2$–$C_6$-alkynyl-N-$C_1$–$C_6$-alkylamino, where the hydrocarbon radicals of these groups may be partly or completely halogenated or may carry from one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio or hetaryl-$C_1$–$C_4$-alkylthio, where the cyclic radicals in turn may be partially or completely halogenated and/or may carry from one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^a)$—$A_n$—$R^b$;

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino or N-hetaryl-N-$C_1$–$C_6$-alkylamino, where the cyclic radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, C(=NOR$^a$)—A$_n$—R$^b$ or NR$^f$—CO—D—R$^g$;

$R^4$ is hydrogen, $C_1$–$C_{10}$-alkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkenylcarbonyl or $C_1$–$C_{10}$alkylsulfonyl, where these radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy or hetarylthio, where the cyclic groups in turn may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or C(=NOR$^a$)—A$_n$—R$^b$;

$C_3$–$C_6$-cycloalkyl, aryl, arylcarbonyl, arylsulfonyl, hetaryl, hetarylcarbonyl or hetarylsulfonyl, where these radicals may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, C(=NOR$^a$)—A$_n$—R$^b$ or NR$^f$—CO—D—R$^g$;

A is oxygen, sulfur or nitrogen and the nitrogen carries hydrogen or $C_1$–$C_6$-alkyl;

D is a direct bond, oxygen or NR$^h$;

n is 0 or 1;

R$^a$ and R$^b$ are each hydrogen or $C_1$–$C_6$-alkyl;

R$^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy or $C_1$–$C_6$-alkoxycarbonyl;

R$^g$, R$^h$ independently of one another, are each hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl or hetaryl-$C_1$–$C_6$-alkyl;

and salts thereof.

2. A compound of the formula I as claimed in claim 1, in which $R^2$ is hydrogen, hydroxyl, cyclopropyl, halogen, $C_1$–$C_4$-alkyl, $C_1$–$C_4$-alkoxy or $C_1$–$C_4$-alkylthio;

$R^3$ is hydrogen, hydroxyl, halogen, cyclopropyl, cyclohexyl, $C_1$–$C_4$-alkyl, $C_1$–$C_4$-alkoxy, $C_1$–$C_4$-alkylthio, aryl or hetaryl, where these groups may be partially or completely halogenated or may carry from one to 3 of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl or hetaryloxy;

$R^4$ is hydrogen, $C_1$–$C_{10}$alkyl, $C_3$–$C_6$-cycloalkyl, $C_2$–$C_{10}$-alkenyl, $C_2$–$C_{10}$-alkynyl, $C_1$–$C_{10}$alkylcarbonyl, $C_2$–$C_{10}$-alkenylcarbonyl, $C_3$–$C_{10}$-alkenylcarbonyl or $C_1$–$C_{10}$alkylsulfonyl, where these groups may be partially or completely halogenated or may carry from one to 3 of the following groups:

cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy or hetarylthio, where the aromatic and heteroaromatic radicals in turn may be partially or completely halogenated or may carry from one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or C(=NOR$^a$)—A$_n$—R$^b$;

aryl, hetaryl, arylcarbonyl, hetarylcarbonyl, arylsulfonyl or hetarylsulfonyl, where these groups may be partially or completely halogenated or may carry from one to 3 of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^a)$—$A_n$—$R^b$.

3. A compound of the formula I as claimed in claim 1, in which Y is NR' and X is $NOCH_3$.

4. A compound of the formula I as claimed in claim 1, in which m is 0.

5. A compound of the formula I as claimed in claim 1, in which $R^1$ is methyl.

6. A process for the preparation of a compound of the formula I as claimed in claim 1, in which $R^2$ is not halogen, wherein a benzyl compound of the formula II

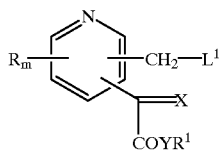

II where $L^1$ is a nucleophilically replaceable leaving group, is reacted with a hydroximine of the formula III $R^4ON=C(R^3)—C(R^2)=NOH$   III.

7. A process for the preparation of a compound of the formula I as claimed in claim 1, in which $R^2$ and $R^3$ are not halogen, wherein a benzyl compound of the formula II as claimed in claim 1 is reacted with a dihydroximine of the formula IV $HON=C(R^3)—C(R^2)=NOH$   IV to give a compound of the formula V

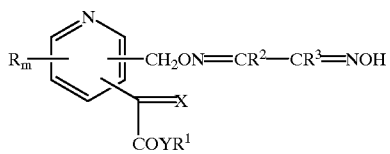

V and V is then reacted with a compound of the formula VI

   VI where $L^2$ is a nucleophilically replaceable leaving group, to give I.

8. A process for the preparation of a compound of the formula I as claimed in claim 1, in which $R^2$ is not halogen, wherein a benzyl derivative of the formula II as claimed in claim 1 is reacted with a carbonylhydroximine of the formula VII $O=C(R^3)—C(R^2)=NOH$   VII to give a compound of the formula VIII

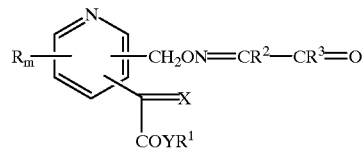

VIII and VIII is then reacted either a) first with hydroxylamine or its salt and then with a compound of the formula VI ($R^4$—$L^2$) as claimed in claim 7 or b) with a hydroxylamine or a hydroxylammonium salt of the formula IXa or IXb, respectively $R^4$—$ONH_2$   IXa $R^4$—$ONH_3^\oplus$ $Q^\ominus$   IXb where $Q^\ominus$ is an anion of an acid, to give I.

9. A process for the preparation of a compound I as claimed in claim 1, in which Y is oxygen (IA), wherein a methylpyridinecarboxylate of the formula X

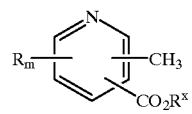

X where $R^x$ is $C_1$–$C_4$-alkyl, is converted into the corresponding methylenepyridinecarboxylate of the formula XI

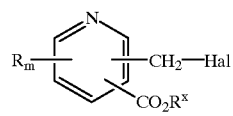

XI

XI is then converted into the corresponding pyridinecarboxylate of the formula XII by reaction with a hydroximine of the formula III $R^4ON=C(R3—C(R^2)=NOH$   III

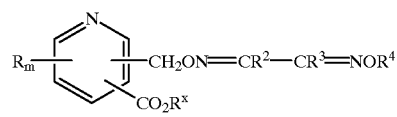

XII

XII is reduced to the alcohol XIII

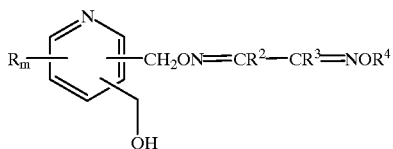
XIII

XIII is oxidized to the pyridinealdehyde XIV

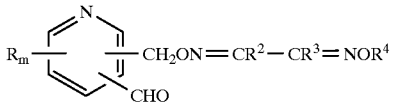
XIV

XIV is converted into the cyanhydrin XV

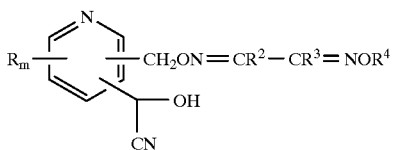
XV

XV is then hydrolyzed to the corresponding mandelate XVI

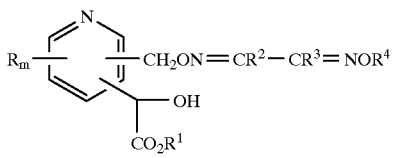
XVI

XVI is oxidized to the α-keto ester XVII

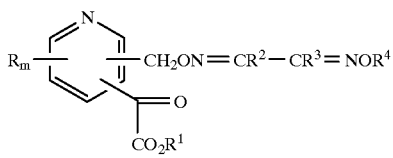
XVII and XVII is then converted either
  a) with O-methylhydroxylamine (H$_2$NOCH$_3$) or an O-methylhydroxylammonium salt, or
  b) with an ethylene-Wittig or -Wittig-Horner reagent, or
  c) with a methoxy-Wittig or -Wittig-Horner reagent
into the corresponding pyridylacetate IA.

10. A process for the preparation of a compound I in which Y is NR'(IB), wherein the corresponding pyridylacetate of the formula IA as claimed in claim 9 is reacted with an amine of the formula XVIII

HNR'R$^1$  XVIII.

11. A process for the preparation of a compound I as claimed in claim 1, wherein a hydroxylamine compound of the formula IIa

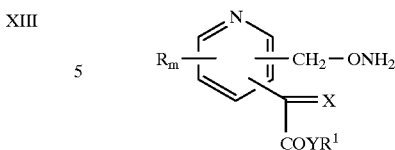
IIa is reacted with a carbonyl compound of the formula VIIa

O=C(R$^2$)—C(R$^3$)=NOR$^4$  VIIa.

12. A process for the preparation of a compound I as claimed in claim 1, in which Y is oxygen (IA), wherein a methylpyridinecarboxylate of the formula X

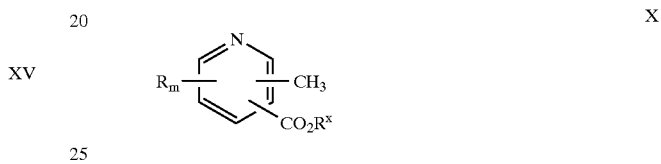
X where R$^x$ is C$_1$–C$_4$-alkyl, is reduced to the alcohol of the formula XIIIa

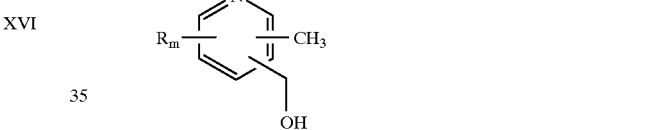
XIIIa

XIIIa is oxidized to the pyridinealdehyd XIVa into the corresponding pyridylacetate XVIIIa, XVIIIb or XVIIIc, respectively

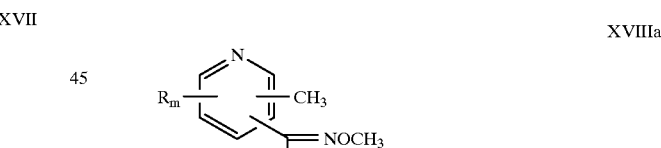
XVIIIa

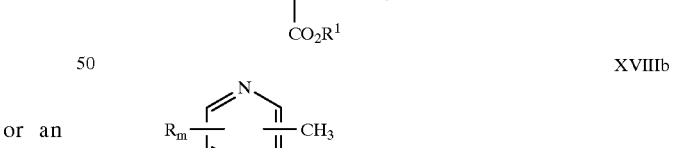
XVIIIb

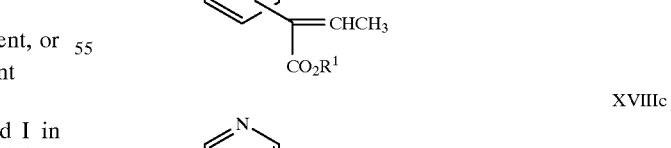
XVIIIc

XVIIIa, XVIIIb or XVIIIc is then halogenated to give the benzyl halide XIXa, XIXb or XIXc, respectively

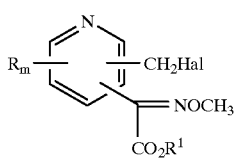

XIXa

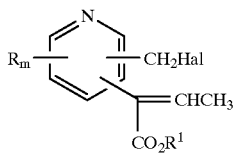

XIXb

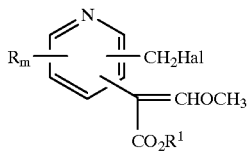

XIXc where Hal is chlorine or bromine, and XIXa, XIXb or XIXc is then converted into the corresponding pyridylacetate IA by reaction with a hydroximine of the formula III $$R^4ON=C(R3-C(R^2))=NOH \qquad III.$$

13. A compound of the formula II as claimed in claim 6.

14. A compound of the formula VIII as claimed in claim 8.

15. A compound of the formula XII, XIII, XIV, XV, XVI or XVII as claimed in claim 9.

16. A compound of the formula IIa as claimed in claim 11.

17. A compound of the formula XVIIIa

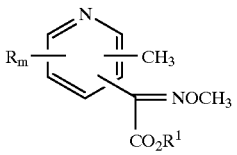

XVIIIa wherein $R^1$ is methyl and R is cyano, nitro, trifluoromethyl, halogen, $C_{1-4}$-alkyl or $C_{1-4}$-alkoxy; and m is 0, 1 or 2, and the radicals R may be different when m is 2.

18. A pesticide or fungicide containing a solvent or carrier and an effective amount of a compound of the formula I as claimed in claim 1.

19. A pesticide as claimed in claim 18 for controlling animal pests from the class consisting of the insects, arachnids or nematodes.

20. A method for controlling animal pests or harmful fungi, wherein the pests or harmful fungi, their habitat, or the plants, surfaces, materials or spaces to be kept free from them are treated with an effective amount of a compound of the formula I as claimed in claim 1.

* * * * *

UNITED STATES PATENT AND TRADEMARK OFFICE
CERTIFICATE OF CORRECTION

PATENT NO.: 5,965,587

DATED: October 12, 1999

INVENTOR(S): MUELLER et al.

It is certified that error appears in the above-identified patent and that said Letters Patent is hereby corrected as shown below:

Col. 126, claim 1, line 12, delete "alkenylthio" and substitute --alkynylthio--.

Col. 126, claim 1, line 48, delete "cycloalyl" and substitute --cycloalkyl--.

Col. 131, claim 11, line 66, delete "compound" and substitute --derivative--.

Signed and Sealed this

Eleventh Day of April, 2000

Attest:

Q. TODD DICKINSON

Attesting Officer

Director of Patents and Trademarks